United States Patent
Hanselmann et al.

(10) Patent No.: US 10,150,734 B2
(45) Date of Patent: Dec. 11, 2018

(54) SOLID FORMS OF 2-(5-(3-FLUOROPHENYL)-3-HYDROXYPICOLINAMIDO)ACETIC ACID, COMPOSITIONS, AND USES THEREOF

(71) Applicant: Akebia Therapeutics, Inc., Cambridge, MA (US)

(72) Inventors: Roger Hanselmann, Branford, CT (US); Anne Luong, Mississauga (CA)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/004,034

(22) Filed: Jan. 22, 2016

(65) Prior Publication Data

US 2016/0214939 A1    Jul. 28, 2016

Related U.S. Application Data

(60) Provisional application No. 62/205,096, filed on Aug. 14, 2015, provisional application No. 62/106,765, filed on Jan. 23, 2015.

(51) Int. Cl.
C07D 213/81    (2006.01)

(52) U.S. Cl.
CPC .................. *C07D 213/81* (2013.01)

(58) Field of Classification Search
None
See application file for complete search history.

(56) References Cited

U.S. PATENT DOCUMENTS

| | | | |
|---|---|---|---|
| 3,655,679 A | 4/1972 | Tsung-Ying et al. |
| 3,703,582 A | 11/1972 | Shen et al. |
| 3,894,920 A | 7/1975 | Kondo et al. |
| 4,016,287 A | 4/1977 | Ebhardt et al. |
| 5,397,799 A | 3/1995 | Kress et al. |
| 5,405,613 A | 4/1995 | Rowland et al. |
| 5,607,954 A | 3/1997 | Weidmann et al. |
| 5,610,172 A | 3/1997 | Weidmann et al. |
| 5,620,995 A | 4/1997 | Wiedmann et al. |
| 5,620,996 A | 4/1997 | Weidmann et al. |
| 5,658,933 A | 8/1997 | Wiedmann et al. |
| 5,719,164 A | 2/1998 | Weidmann et al. |
| 5,726,305 A | 3/1998 | Weidmann et al. |
| 6,020,350 A | 2/2000 | Wiedmann et al. |
| 6,093,730 A | 7/2000 | Weidmann et al. |
| 6,159,379 A | 12/2000 | Means et al. |
| 6,420,427 B1 | 7/2002 | Takahashi et al. |
| 6,566,088 B1 | 5/2003 | McKnight et al. |
| 6,589,758 B1 | 7/2003 | Zhu |
| 7,183,287 B2 | 2/2007 | Durley |
| 7,588,924 B2 | 9/2009 | Evdokimov et al. |
| 7,811,595 B2 | 10/2010 | Kawamoto et al. |
| 8,050,873 B2 | 11/2011 | Evdokimov et al. |
| 8,124,582 B2 | 2/2012 | Guenzler-Pukall et al. |
| 8,323,671 B2 | 12/2012 | Wu et al. |
| 8,343,952 B2 | 1/2013 | Wu et al. |
| 8,512,972 B2 | 8/2013 | Evdokimov et al. |
| 8,530,404 B2 | 9/2013 | Seeley et al. |
| 8,598,210 B2 | 12/2013 | Kawamoto et al. |
| 8,772,895 B2 | 7/2014 | Lu et al. |
| 8,865,748 B2 | 10/2014 | Shalwitz et al. |
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 2002/0192737 A1 | 12/2002 | Kaelin, Jr. et al. |
| 2003/0153503 A1 | 8/2003 | Klaus et al. |
| 2003/0176317 A1 | 9/2003 | Guenzler-Pukall et al. |
| 2004/0235082 A1 | 11/2004 | Fourney et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0105899 A1 | 5/2007 | Suzuki et al. |
| 2007/0154482 A1 | 7/2007 | Sukhatme et al. |
| 2007/0203174 A1 | 8/2007 | Klimko et al. |
| 2007/0213335 A1 | 9/2007 | Fitch et al. |
| 2007/0299086 A1 | 12/2007 | Kawamoto et al. |
| 2008/0124740 A1 | 5/2008 | Evkokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2009/0240475 A1 | 9/2009 | Evdokimov et al. |
| 2010/0021423 A1 | 1/2010 | Brameld et al. |

(Continued)

FOREIGN PATENT DOCUMENTS

| CA | 2098158 | 6/1993 |
|---|---|---|
| CA | 2253282 | 11/1997 |

(Continued)

OTHER PUBLICATIONS

Morissette et al. In Advanced Drug Delivery Reviews 56 (2004) 275-300.*
Morissette et al. in Drug Delivery Reviews, 56 (2004) 275-300 (Year: 2004).*
Brittain et al., 2009, "Polymorphism in Pharmaceutical Solids." Drugs and the Pharmaceutical Sciences. $2^{nd}$ Edition, Edited by Brittain H.G., 2009, vol. 192, pp. 333-335.
Ivanisevic et al., 2011, "Uses of X-Ray Powder Diffraction in the Pharmaceutical Industry." Pharmaceutical Formulation & Quality. Aug./Sep. 2011, pp. 30-33.
PubChem Open Chemistry Database Compound Name: SCHEMBL3484399 (CID 49848485); Retrieved on Mar. 15, 2016 from internet: https://pubchem.ncbi.nlm.nih.gov/compound/49848485.

(Continued)

*Primary Examiner* — Dennis Heyer
(74) *Attorney, Agent, or Firm* — Proskauer Rose LLP; Fangli Chen

(57) ABSTRACT

Provided herein are solid forms comprising 2-(5-(3-fluorophenyl)-3-hydroxypicolinamido)acetic acid, methods of making the solid forms, methods of their use for the treatment of various diseases and/or disorders and pharmaceutical compositions comprising the solid forms.

17 Claims, 109 Drawing Sheets

(56) References Cited

U.S. PATENT DOCUMENTS

| | | |
|---|---|---|
| 2010/0331303 A1 | 12/2010 | Kawamoto et al. |
| 2010/0331374 A1 | 12/2010 | Wu et al. |
| 2011/0305776 A1 | 12/2011 | Ho et al. |
| 2012/0282627 A1 | 11/2012 | Evdokimov et al. |
| 2012/0309977 A1 | 12/2012 | Lanthier et al. |
| 2012/0316204 A1* | 12/2012 | Shalwitz ............... C07D 213/81 514/346 |
| 2012/0329836 A1 | 12/2012 | Marsh et al. |
| 2013/0022974 A1 | 1/2013 | Chinnaiyan et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp et al. |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0199434 A1 | 7/2016 | Eubank et al. |
| 2016/0214939 A1 | 7/2016 | Hanselmann et al. |
| 2016/0339005 A1 | 11/2016 | Shalwitz et al. |
| 2017/0105981 A1 | 4/2017 | Clay et al. |
| 2017/0258773 A1 | 9/2017 | Copp et al. |

FOREIGN PATENT DOCUMENTS

| | | |
|---|---|---|
| EP | 0650960 | 5/1995 |
| EP | 0650961 | 5/1995 |
| EP | 2044005 | 10/2010 |
| JP | H09221476 | 8/1997 |
| JP | 2001-48786 | 2/2001 |
| JP | 2007-194072 | 11/2006 |
| JP | 2010-527378 | 11/2009 |
| WO | WO 2016/118858 | 7/1916 |
| WO | WO 2016/153996 | 9/1916 |
| WO | WO 2016/161094 | 10/1916 |
| WO | WO 2006/138511 | 12/1916 |
| WO | WO 1996/022021 | 7/1996 |
| WO | WO 1997/041103 | 11/1997 |
| WO | WO 1997/044333 | 11/1997 |
| WO | WO 1999/048870 | 11/1999 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2003/097040 | 11/2003 |
| WO | WO 2004/019868 | 3/2004 |
| WO | WO 2004/035812 | 4/2004 |
| WO | WO 2004/048383 | 6/2004 |
| WO | WO 2004/108121 | 12/2004 |
| WO | WO 2005/007192 | 1/2005 |
| WO | WO 2005/115984 | 12/2005 |
| WO | WO 2005/118836 | 12/2005 |
| WO | WO 2006/019831 | 2/2006 |
| WO | WO 2006/030977 | 3/2006 |
| WO | WO 2006/114213 | 11/2006 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/136990 | 11/2007 |
| WO | WO 2007/150011 | 12/2007 |
| WO | WO 2008/002576 | 1/2008 |
| WO | WO 2008/089051 | 7/2008 |
| WO | WO 2008/089052 | 7/2008 |
| WO | WO 2009/020119 | 8/2008 |
| WO | WO 2008/130508 | 10/2008 |
| WO | WO 2008/130527 | 10/2008 |
| WO | WO 2008/137060 | 11/2008 |
| WO | WO 2008/141731 | 11/2008 |
| WO | WO 2008/144266 | 11/2008 |
| WO | WO 2009/019656 | 2/2009 |
| WO | WO 2009/035534 | 3/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2009/111337 | 9/2009 |
| WO | WO 2010/029577 | 3/2010 |
| WO | WO 2010/113942 | 10/2010 |
| WO | WO 2011/057112 | 11/2010 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2014/168986 | 10/2014 |
| WO | WO 2014/200773 | 12/2014 |
| WO | WO 2015/023967 | 2/2015 |
| WO | WO 2015/073779 | 5/2015 |
| WO | WO 2015/112831 | 7/2015 |

OTHER PUBLICATIONS

PubChem Open Chemistry Database Compound Name: ZEADCOHJERWFOI-UHFFFAOYSA-M (CID 71491828); Retrieved on Mar. 21, 2016 from internet: https://pubchem.ncbi.nlm.nih.gov/compound/71491828.

Vippagunta et al., 2001, "Crystalline solids." Adv Drug Deliv Rev. 48(1):3-26.

"Akebia closes $41 million series C—Proceeds to support phase 2b trial and phase 3 prepartions for promising anemia candidate", 2013, retrieved from the internet: <http://files.shareholder.com/downloads/AMDA-2MD7AT/0x0x733748/5e5822e6-2bcd-4969-ab79-0d298fee5066/733748.pdf.

"Hippuric acid sodium salt", Science Lab.com: Chemicals & Laboratory Equipment; retrieved from the internet at <http://web.archive.org/web/20041107121553/http://www.sciencelab.com/page/S/PVAR/10415/SLH2620> on Mar. 11, 2010.

"Standards of Medical Care in Diabetes—2006", 2006, Diabetes Care, 29: s4-s42.

Acker et al., 2005, "Genetic evidence for a tumor suppressor role of HIF-2α", Cancer Cell, 8:131-141.

Alesso et al., 2003, "Improving resins for solid phase synthesis: incorporation of 1-[2-(2-methoxyethoxy) ethoxy]4-vinyl-benzene" Tetrahedron: 59: 7163-7169.

Altschul et al., 1997, "Gapped BLAST and PSI-BLAST: A New Generation of Protein Database Search Programs," Nucleic Acids Res., 25(27): 3389-3402.

Anderson et al., 1979, "Antileukemic Activity of Derivatives of 1,2-Dimethyl-3,4-bis(hydroxymethyl)-5-phenylpyrrole Bis(N-methylcarbamate)", J. Med. Chem., 22(8): 977-980.

Anderson et al., 2012, "Practical process research and development: a guide for organic chemists", p. 331.

Annex et al., 2005, "Growth Factor-Induced Therapeutic Angiogenesis in the Heart: Protein Therapy," Cardiovascular Research, 65(3): 649-655.

Ardelt et al., 2005, "Estradiol Regulates Angiopoietin-1 mRNA Expression Through Estrogen Receptor-α in a Rodent Experimental Stroke Model," Stroke, 36: 337-341.

Auerbach et al., 2003, "Angiogenesis Assays: A Critical Overview," Clinical Chemistry, 49: 32-40.

Barany et al., 1987, "Solid-phase Peptide Synthesis: A Silver Anniversary Report," Int. J. Peptide Protein Res., 30( 6): 705-739.

Bartlett et al., Apr. 1989, "Caveat: A Program to Facilitate the Structure-derived Design of Biologically Active Molecules", Molecular Recognition in Chemical and Biological Problems, Special Pub., Royal Chem. Soc., 78: 182-196.

(56) References Cited

OTHER PUBLICATIONS

Böhm, 1992, "The Computer Program LUDI: A New Method for the Novo Design of Enzyme Inhibitors," J. Computer-Aided Molecular Design, 6: 61-78.
Branden et al., 1999, "Introduction to Protein Structure Second Edition," Garland Publishing, Inc., New York: 374-375.
Burger, 1991, "Isosterism and biososterism in drug design", Progress in Drug Research, Birkhauser Verlag.
Bussolino, 1997, "Molecular Mechanisms of Blood Vessel Formation," Trends Biochem. Sci., 22(7): 251-256.
Byrn et al., 1995, "Pharmaceutical Solids: A Strategic Approach to Regularity Considerations", Pharmaceutical Research, 12(7): 945-954.
CAS Registry Nos. 1261813-98-2, 1261613-86-8, and 1261518-21-1. Chemcats, 2011.
Catrina et al., 2004, "Hyperglycemia Regulates Hypoxia-Inducible Factor-1a Protein Stability and Function," Diabetes 53: 3226-3232.
Carey, 2006, Organic Chemistry 6th Ed., McGraw Hill, Chapter 19: 839-840.
Cheeseright, 2009, "The Identification of Bioisosteres as Drug Development Candidates", Innovations in Pharmaceutical Technology, issue 28.
Cherng, 2002, "Synthesis of substituted pryidines by the reactions of halopyridines with sulfur, oxygen and carbon nucleophiles under focused microwave irradition", Tetrahedron, Jun. 10, 2002, 58(24): 4931-4935.
Clinicaltrials.gov: archive: NCT01235936 Nn 2012_09_30[online]. U.S. National Institute of Health, Aug. 30, 2012; retrieved from the internet at <http:clinicaltrials.gov/archive/NCT01235936/2012_09_30> on Aug. 30, 2012.
Cousins, "Retina Today", Oct. 2009, 2 pages; retrieved from the internet at <http://reinatoday.com/2009/10/1009_12.php>.
Costello et al., 2012, "Evidence for changes in RREB-1, ZIP3, and zinc in the early development of pancreatic adenocarcinoma", J Gastrointest Canc, 43: 570-578.
Cunliffe et al., 1992, "Novel Inhibitors of Prolyl4-Hydroxylase. 3. Inhibition by the Substrate Analogue N-Oxaloglycine and Its Derivatives," J. Med. Chem. 35: 2652-2658.
Demetriades et al., 2012, "Dynamic combinatinatorial chemistry employing embryonic boronic acids/boronate esters leads to potent oxygenase inhibitors", Angewandte Chemie, International Edition, May 25, 2012, 51(27): 6672-6675.
Designation of Inventors filed on entry into EP Regional Phase of EP Pat. No. 2044005.
Dranoff, 2003, "GM-CSF-secreting melanoma vaccines", Oncogene, 22: 3188-3192.
Elson et al., 2001, "Induction of hypervascularity without leakage or inflammation in transgenic mice overexpressing hypoxia-inducible factor-1α," Genes & Dev., 15: 2520-2532.
Elvidge et al., 2006, "Concordant Regulation of Gene Expression by Hypoxia and 2-Oxoglutarate-dependent Dioxygenase Inhibition", J. Biol. Chem., 281(22): 15215-15226.
Emerson et al., 2007, "Emerging Therapies for the Treatment of Neovascular Age-Related Macular Degeneration and Diabetic Macular Edema", Biodrugs, 2007, vol. 21. No. 4, pp. 345-257.
Enoch et al., 2006, "ABC of wound healing. Non-surgical and drug treatments", BMJ, 332(7546):332:900-3.
European Patent Office, Interlocutory Decision in Opposition Proceedings date May 3, 2013 for European Patent No. 2044005, 76 pages.
European Patent Office, Minutes of the Oral Proceedings Before the Opposition Division dated May 3, 2013 for European Patent No. 2044005, 6 pages.
Extract from USPTO patent assignment database regarding U.S. Appl. No. 11/821,936.
Favier et al., 2007, "HIF2α reduces growth rate but promotes angiogenesis in a mouse model of neuroblastoma", BMC Cancer, 7:139: 1-10.
Flower, 1999, "Modelling G-protein-coupled receptors for drug design," Biochimica et Biophysica Acta, 1422: 207-234.

Folkman et al., 1995, "Tumor Angiogenesis," The Molecular Basis of Cancer, Mendelsohn et al., eds., W. B. Saunders, Chapter 10: 206-232.
Franklin et al., Nov. 1991, "Approaches to the Design of Anti-Fibrotic Drugs," Biochem. Soc. Trans., 19(4): 812-5.
Gaunt, 1998, "Rational Design of Benzyl-Type Protecting Groups Allows Sequential Deprotection of Hydroxyl Groups by Catalytic Hydrogenolysis", 63(13): 4172-4173.
Gavhane et al., 2011, "Solid tumors: Facts, challenges, and solutions", International Journal of Pharma Sciences and Research, 2(1): 1-12.
Goodford, 1985, "A Computational Procedure for Determining Energetically Favorable Binding Sites on Biologically Important Macromolecules," J. Med. Chem., 28(7): 849-857.
Goodsell et al., 1990, "Automated Docking of Substrates to Proteins by Simulated Annealing", Proteins: Structure, Function, and Genetics, 8: 195-202.
Greer et. al., 2012 "The updated biology of hypoxia inducible factor", EMBO J. 31: 2448-2460.
Guillory, 1999, "Generation of polymorphs, hydrates, solvates, and amorphous solids", HG Brittain (Ed.), Polymorphism in Pharmaceutical Solids, V. 95, Marcel Dekker, New York: 183-226.
Hardcastle et al., 2005, "Discovery of Potent Chromen-4-one Inhibitors of the DNA-Dependent Protein Kinase (DNA-PK) Using a Small-Molecule Library Approach", J. of Medicinal Chem., 48(24): 7829-7846.
Hoeksema et al., 1982, "Structure of Rubradirin", J. of American Chem. Society, 104(19): 5173-5181.
Hu et al., 2003, "Differential Roles of Hypoxia-Inducible Factor 1α (HIF-1α) and HIF-2α in Hypoxic Gene Regulation", Mol. Cell. Biol., 23: 9361-9374.
Ingersoll et al. "Hippuric Acid", Organic Syntheses, CV 2, 328; retrieved from the internet at <http:web.archive.org/web20020724135719/http://orgsyn.org/orgsyn/prepContent.asp?prep=cv2p0328> on Mar. 11, 2010.
International Preliminary Report on Patentability dated Dec. 10, 2013 for PCT/US2012/40833.
International Search Report dated May 8, 2008 for PCT/US2007/014832.
International Search Report and Written Opinion dated Aug. 29, 2012 for PCT/US2012/40833.
International Search Report and Written Opinion dated Apr. 20, 2015 for PCT/US2015/12634.
International Union of Pure and Applied Chemistry, Glossary of Class Names of Organic Compounds and Reactive Intermediates Based on Structure, Pure & D Appl. Chern., 67(8/9): 1307-1375 (1995).
Ivan et al., 2002, "Biochemical purification and pharmacological inhibition of a mammalian prolyl hydroxylase acting on hypoxia-inducible factor," Proceedings of the National Academy of Science, 99(21): 13459-13464.
Ivan et al., 2001, "HIFα Targeted for VHL-Mediated Destruction by Proline Hydroxylation: Implications for O2 Sensing", Science, 292: 464-468.
Iyoda et al., 1990, "Homocoupling of aryl halides using nickel(II) complex and zinc in the presence of Et4NI. An efficient method for the synthesis of biaryls and bipyridines", Bull. Chem. Soc. Jpn., 63(1): 80-87.
Jaakkola et al., 2001, "Targeting of HIF-α to the von Hippel-Lindau Ubiquitylation Complex by O2-Regulated Prolyl Hydroxylation," Science, 292: 468-472.
Jones et al., 1995, "Molecular Recognition of Receptor Sites Using a Genetic Algorithm with a Description of Desolvation", J. Mol. Biol., 245: 43-53.
Kaelin, 2005, "Proline Hydroxylation and Gene Expression," Annual Rev. Biochem., 74: 115-125.
Karuppagounder et. al., 2012 "Hypoxia-inducible factor prolyl hydroxylase inhibition: robust new target or another big bust for stroke therapeutics?", J. Cereb. Blood F. Met., 32: 1347-1361.
Kawashima et al., 1987, "Suppressive effect of quinolinic acid and hippuric acid on bone marrow erythroid growth and lymphocyte blast formation in uremia", Advances in Experimental Medicine and Biology, 223: 69-72.

(56) References Cited

OTHER PUBLICATIONS

Ke and Costa, 2006, "Hypoxia-Inducible Factor-1 (HIF-1)", Molecular Pharmacology, 70(5): 1469-1480.
Khandhadia et al., 2012, "Neurodegenerative Diseases", edited by Shamim I. Ahmed, Published by Landes Biosciences and Springer Science + Business Media, Chapter 2: 15-36.
Kietzmann et al., 2001, "Perivenous expression of the mRNA of the three hypoxia-inducible factor α-subunits, HIF1α, HIF2α and HIF3α, in rat liver", Biochem. J., 354: 531-537.
Kim et al., 2015, "Recent advances in developing inhibitors for hypoxia-inducible factor prolyl hydroxylases and their therapeutic implications", Molecules, 20: 20551-20568.
Krantz, 1991, "Erythropoietin," Blood, 77: 419-434.
Kuntz et al., 1982, "A Geometric Approach to Macromolecule-Ligand Interactions," J. Mol. Biol., 161: 269-288.
Kurti et al., 2005, "Strategic applications of named reactions in organic synthesis", El Sevior: 448-449.
Langsetmo et al., 2006, "Inhibition of HIF-Prolyl Hydroxylases with FG-4539 is Neuroprotective in a Mouse Model of Permanent Focal Ischemia", International Stroke Conference, Kissimmee Florida, Presentation No. 427.
Lee et al., 2003, "Structure of Human FIH-1 Reveals a Unique Active Site Pocket and Interaction Sites for HIF-1 and von Hippel Lindau", JBC, 278: 7558-7563.
Li et al., 2000, "PR39, A Peptide Regulator of Angiogenesis," Nat Med., 6(1): 49-55.
Lima and Barreiro, 2005, "Bioisosterism: A Useful Strategy for Molecular Modification and Drug Design", Current Medicinal Chemistry, 12: 23-49.
Liu et al., Jun. 2011, "Hypoxia Induces Genomic DNA Demethylation through the Activation of HIF-1alpha and Transcriptional Upregulation of MAT2A in Hepatoma Cells", Mol. Cancer Ther., 10: 1113-1123.
Mancini et al., 2003, "Effect of Erythropoietin on Exercise Capacity in Patients with Moderate to Severe Chronic Heart Failure", Circulation, 107: 294-299.
McDonough et al., 2006, "Cellular Oxygen Sensing: Crystal Structure of Hypoxia-Inducible Factor Prolyl Hydroxylase (PHD2)", PNAS, 103(26): 9814-9819.
Miranker et al., 1991, "Functionality Maps of Binding Sites: A Multiple Copy Simultaneous Search Method", Proteins: Structure, Function and Genetics, 11: 29-34.
Morissette et al., 2004, "High-throughput crystallization: polymorphs, salts, co-crystals and solvates of pharmaceutical solids", Advanced Drug Delivery Reviews, 56: 275-300.
Myerson, 2002, Handbook of Industrial Crystallization, p. 249.
Nielsen et. al., 2010, "Antiangiogenic therapy for Breast Cancer", Breast Cancer Res. 12: 209-227.
Nguyen et al., 2001, "Cellular Interactions in Vascular Growth and Differentiation", Int. Review of Cytology, 204: 1-48.
Nishibata et al., 1991, "Automatic Creation of Drug Candidate Structures Based on Receptor Structure. Starting Point for Artificial Lead Generation", Tetrahedron, 47( 43): 8985-8990.
Nowak et al., 2006, "Age-related macular degeneration (AMD): pathogenesis and therapy", Pharmacological Reports, 58: 353-363.
O'Reilly et al., 1994, "Angiostatin: A Novel Angiogenesis Inhibitor that Mediates the Suppression of Metastases by a Lewis Lung Carcinoma", Cell, 79: 315-328.
O'Reilly et al., 1997, "Endostatin: An Endogenous Inhibitor of Angiogenesis and Tumor Growth", Cell, 88: 277-285.
Online Abstract showing publication date of McDonough et al. (2006) as Jun. 16, 2006.
Pasqualetti et al., 2000, "Circadian rhythm of serum erythropoietin in myelodysplastic syndromes", European Review for Medical and Pharmacological Sciences, 4: 111-115.
PCT Request Form dated Jun. 26, 2007 for PCT/US2007/014832.
Pergola et al, 2016, "Vadadustat, a novel oral HIF stabilizer, provides effective anemia treatment in nondialysis-dependent chronic kidney disease", 90: 1115-1122.

Peyssonnaux et al., 2005, "HIF-1α Expression Regulates the Bactericidal Capacity of Phagocytes", J. Clinical Invest., 115(7): 1806-1815.
Piyamongkol et al., 2010, "Amido-3-hydroxypyridin-4-ones as Iron (III) Ligands", Chemistry A European Journal, 16: 6374-6381.
Prabhakar et. al., 2012 "Adaptive and Maladaptive Cardiorespiratpiy Responses to Continuous and Intermittent Hypoxia Mediated by Hypoxia-Inducible Factors 1 and 2", Physiol. Rev., 92: 967-1003.
Qian et al., 2013, "A Randomized, Double-Blind, Placebo Controlled Trial of FG-4592 for Correction of Anemia in Subjects with Chronic Kidney Disease in China," Oral Abstract FR-OR011, J. Am. Soc. Nephrol., 24: 38A.
Qunibi et al., 2011, "A randomized controlled trial comparing intravenous ferric carboxymaltose with oral iron for treatment of iron deficiency of non-dialysis-dependent chronic kidney disease patients", Nephrol Dial Transplant, 26(5): 1599-1607.
Rahtu-Korpela et al., 2014, "HIF Prolyl 4-Hydroxylase-2 Inhibition Improves Glucose and Lipid Metabolism and Protects Against Obesity and Metabolic Dysfunction," Diabetes 63: 3324-3333.
Rankin et. al., 2007, "Hypoxia-inducible factor-2 (HIF-2) regulates hepatic erythropoietin in vivo" J. Clin. Invest. 117:1069-1076.
Ratcliffe et al., 2007, "HIF-1 and HIF-2: working alone or together in hypoxia?" J. Clin. Inv., 117(4):862-865.
Redondo et al., 2000, "Vascular endothelial growth factor (VEGF) and melanoma. N-Acetylcysteine downregulates VEGF production in vitro", Cytokine, 12(4):374-378.
Request for Correction of Inventorship at USPTO regarding U.S. Appl. No. 11/821,936.
Roda et al., 2012, "Stabilization of HIF-2a induces sVEGFR-1 production from tumor-associated macrophages and decreases tumor growth in a murine melanoma model", J. Immunology, 189: 3168-3177.
Schelhass and Waldmann, 1996, "Protecting Group Strategies in Organic Synthesis", Chem. Int. Ed. Engl., 36: 2056-2083.
Schoneberg et al., 1999, "Structural Basis of G Protein-Coupled Receptor Function," Molecular and Cellular Endocrinology, 151: 181-193.
Search Report dated Apr. 28, 2011 for European Pat. App. No. 11000872.9.
Semenza et al., 1994, "Transcriptional Regulation of Genes Encoding Glycolytic Enzymes by Hypoxia-Inducible Factor 1", J. Biol. Chem., 269: 23757-23763.
Semenza et al., 1994, "Regulation of Erythropoietin Production: New Insights into Molecular Mechanisms of Oxygen Homeostasis", Hematol. Oncol. Clin. North Am., 8: 863-884.
Semenza, 2000, "HIF-1 and human disease: one highly involved factor", Genes & Development, 14: 1983-1991.
Semenza, 2002, "Signal Transduction to Hypoxia-inducible Factor 1", Biochem. Pharmacol, 64: 993-998.
Sexton, 1999, "Recent advances in our understanding of peptide hormone receptors and RAMPS", Current Opinion in Drug Discovery and Development, 2(5): 440-448.
Seymour et al., 2011, "Decision T 0777/08 of the Boards of Appeal of the European Patent Office", retrieved from the internet: <http://www.epo.org/law-practice/case-law-appeals/pdf/t080777exl.pdf> on Dec. 19, 2017.
Sheehan, 1996, "3-Hydroxypicolinic Acid and Some of its Derivatives", J. Organic Chemistry 31(3): 636-638.
Siddiq, 2005, "Hypoxia-inducible factor prolyl 4-hydroxylase inhibition", J. of Biological Chemistry, 280(50): 41732-41743.
Sowter et al., 2003 "Predominant Role of Hypoxia-Inducible Transcription Factor (Hif)-1α versus (Hif)-2α in Regulation of the Transcriptional Response to Hypoxia", Cancer Res. 63: 6130-6134.
Sporn and Suh, 2000, "Chemoprevention of cancer", Carcinogenesis, 21(3): 525-530.
Stille, J. K., 1986, Angew. Chem., Int. Ed. Engl., vol. 25: 508.
Stohlawetz et al., 2000, "Effects of erythropoietin on platelet reactivity and thrombopoiesis in humans", Blood, 95(9): 2983-2989.
Sutter, 2000, "Hypoxia-inducible factor 1 alpha protein expression is controlled by oxygen-regulated ubiquitination that is disrupted by deletions and missense mutations", PNAS, 97(9): 4748-4753.

(56) References Cited

OTHER PUBLICATIONS

Teicher et al., 1994, "Potentiation of Cytotoxic Cancer Therapies by TNP-470 Alone and with other Anti-Angiogenic Agents", Int. J. Cancer, 57: 920-925.

Thoppil and Bishayee, 2011, "Terpenoids as potential chemopreventive and therapeutic agents in liver cancer", World J. Hepatol., 3(9): 228-249.

Thornber, 1979, "Isosterism and Molecular Modification in Drug Design", Progress Drug Res., vol. 37: 563-580.

Tzschucke et al., 2004, "Fluorous-Silica-Supported Perfluoro-Tagged Palladium Complexes Catalyze Suzuki Coupling in Water", Helvetica Chimica Acta; 87: 2882-2889.

Variankaval et al., 2008, "From form to unction: crystallization of active pharmaceutical ingredients", AICHE Journal, Jul. 2008, 54(7): 1682-1688.

Vickerstaffe et al., 2004, "Fully Automated Polymer-Assisted Synthesis of 1,5-Biaryl Pyrazoles", J. Comb. Chem., 6:332-33.

Vincent et al., 2000, "Angiogenesis is Induced in a Rabbit Model of Hindlimb Ischemia by Naked DNA Encoding an HIF-1a/VP16 Hybrid Transcription Factor", Circulation, 102: 2255-2261.

Wade et al., 2006, "Organic Chemistry", 6th ED., Pearson Prentice Hall, US: 780-781.

Warnecke et al., 2003, "Activation of the Hypoxia-Inducible Factor Pathway and Stimulation of Angiogenesis by Application of Prolyl Hydroxylase Inhibitors", FASEB Journal, 17: 1186-1188.

Warshakoon et al., 2006, "Design and synthesis of substituted pyridine derivatives as HIF-1alpha prolyl hydroxylase inhibitors", Bioorganic & Medicinal Chemistry Letters, 16: 5616-5620.

Wax et al., 1996, "SM-20 is a Novel20-kd Protein Whose Expression in the Arterial Wall is Restricted to Smooth Muscle", Lab. Invest., 74(4): 797-808.

Weidner et al., 1991, "Tumor Angiogenesis and Metastasis—Correlation in Invasive Breast Carcinoma", New Eng. J. Med., 324(1): 1-8.

Wiesener et al., 2003 "Widespread hypoxia-inducible expression of HIF-2alpha in distinct cell populations of different organs." FASEB J.17(2): 271-3.

Wright et al., 2003, "Activation of the Prolyl Hydroxylase Oxygen-Sensor Results in Induction of GLUT1, Heme Oxygenase-1, and Nitric-Oxide Synthase Proteins and Confers Protection from Metabolic Inhibition to Cardiomyocytes", J. Bio. Chem., 278(22): 20235-20239.

Wu et. al., 2010 "A systems biology perspective on sVEGFR1: its biological function, pathogenic role and therapeutic use", J. Cell. Mol. Med. 14:528-552.

Yang et al., 2012, "Desmoplakin acts as a tumor suppressor by inhibition of the Wnt/beta-catenin signaling pathway in human lung cancer", Carcinogenesis, 33(10): 1863-1870.

\* cited by examiner

DVS analysis, Filtration, Hemi-Calcium Salt (with extra peaks)

DVS analysis, Mono-Sodium Salt Filtration, Pattern C

DVS analysis, Filtration, Bis-Sodium Salt Pattern D

SOLID FORMS OF 2-(5-(3-FLUOROPHENYL)-3-HYDROXYPICOLINAMIDO)ACETIC ACID, COMPOSITIONS, AND USES THEREOF

This application claims the benefit of U.S. Provisional Application No. 62/205,096, filed Aug. 14, 2015, and U.S. Provisional Application No. 62/106,765, filed Jan. 23, 2015, the entire contents of each of which are incorporated herein by reference.

1. FIELD OF THE INVENTION

Provided herein are solid forms of 2-(5-(3-fluorophenyl)-3-hydroxypicolinamido)acetic acid, methods of making the solid forms, methods of their use for the treatment of various diseases or symptoms thereof, and pharmaceutical compositions thereof.

2. BACKGROUND OF THE INVENTION

The identification and selection of a solid form for making a pharmaceutical composition is complex, given that a change in solid form may affect a variety of physical and chemical properties, which may provide benefits or drawbacks in processing, maintaining, storage, formulation, stability and bioavailability, among other important pharmaceutical characteristics. Potential pharmaceutical solids include crystalline solids, amorphous solids, and mixtures thereof. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (See, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms for making a pharmaceutical composition include single-component and multiple-component solids. Single-component solids consist essentially of the pharmaceutical Compound 1 in the absence of other compounds. Variety among single-component crystalline materials may potentially arise from the phenomenon of polymorphism, wherein multiple three-dimensional arrangements exist for a particular pharmaceutical compound (See, e.g., S. R. Byrn et al., Solid State Chemistry of Drugs, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (See S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (See, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (See, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Nobel Prize winner Dr. Judah Folkman first proposed in 1971 that all cancer tumors were angiogenesis-dependent and therefore targeting angiogenesis was a potential means for treating cancer. Angiogenesis is the growth of new capillaries from pre-existent microvasculature. A wide range of pathological conditions, from atherosclerosis to cancer, are associated with either excessive or deficient angiogenesis.

It is now widely accepted that tumor growth beyond a few cubic millimeters cannot occur without the induction of a new vascular supply. Therefore, inhibition of new vasculature (antiangiognosis) can provide a non-chemotherapy or non-radiation therapy approach to the treatment of cancer by denying tumors the nutrient supply necessary for the tumors to grow. Although normally quiescent, endothelial cells are responsible for the formation of new vasculature in response to various stimuli. These stimuli can have their genesis in many forms.

The endothelial cells which form new vascular networks in tumors respond to angiogenic stimuli produced by the tumor itself. The best known of these stimuli is vascular endothelial growth factor (VEGF). Found to be ubiquitous in human tumors, increasing levels of VEGF correlate with an increasing rate of tumor growth. Therefore, suppression of VEGF represents a method for controlling the growth rate of tumors (primary and metastatic) and offers a possible means for shrinking existing tumors.

3. SUMMARY OF THE INVENTION

Provided herein are solid forms of Compound 1:

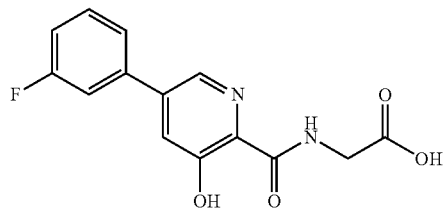

having the name 2-(5-(3-fluorophenyl)-3-hydroxypicolinamido)acetic acid, including tautomers thereof. Also provided are methods of preparing, isolating and characterizing the solid forms. 2-(5-(3-fluorophenyl)-3-hydroxypicolinamido)acetic acid ("Compound 1") is disclosed in United States Patent Application Publication No. 2007/0299086, published Dec. 27, 2007, United States Patent Application Publication No. 2012/0329836, published Dec. 27, 2012 and International Patent Application Publication No. WO 2012/170442, published Dec. 13, 2012, the entireties of which are incorporated by reference herein.

Provided herein are pharmaceutical compositions and dosage units comprising a solid form of Compound 1. In certain embodiments, the pharmaceutical compositions and dosage units comprise a solid form of Compound 1 and a pharmaceutically acceptable diluent, excipient or carrier.

Provided herein are methods for treating or preventing cancer, compromising administering an effective amount of a solid form of Compound 1 to a patient having cancer.

Provided herein are methods for decreasing vascular endothelial growth factor (VEGF) in a cell in vitro, in vivo or ex vivo, comprising contacting the cell with an effective amount of a solid form of Compound 1.

Provided herein are methods for increasing secretion of soluble vascular endothelial growth factor receptor-1 (sVEGF-1) in a cell in vitro, in vivo or ex vivo, comprising contacting the cell with an effective amount of a solid form of Compound 1.

Provided herein are methods for stabilizing hypoxia inducible factor-2 alpha (HIF-2a) in a cell in vitro, in vivo or ex vivo, comprising contacting the cell with an effective amount of a solid form of Compound 1.

4. BRIEF DESCRIPTION OF THE FIGURES

5. DETAILED DESCRIPTION

5.1 Definitions

Figure 1:
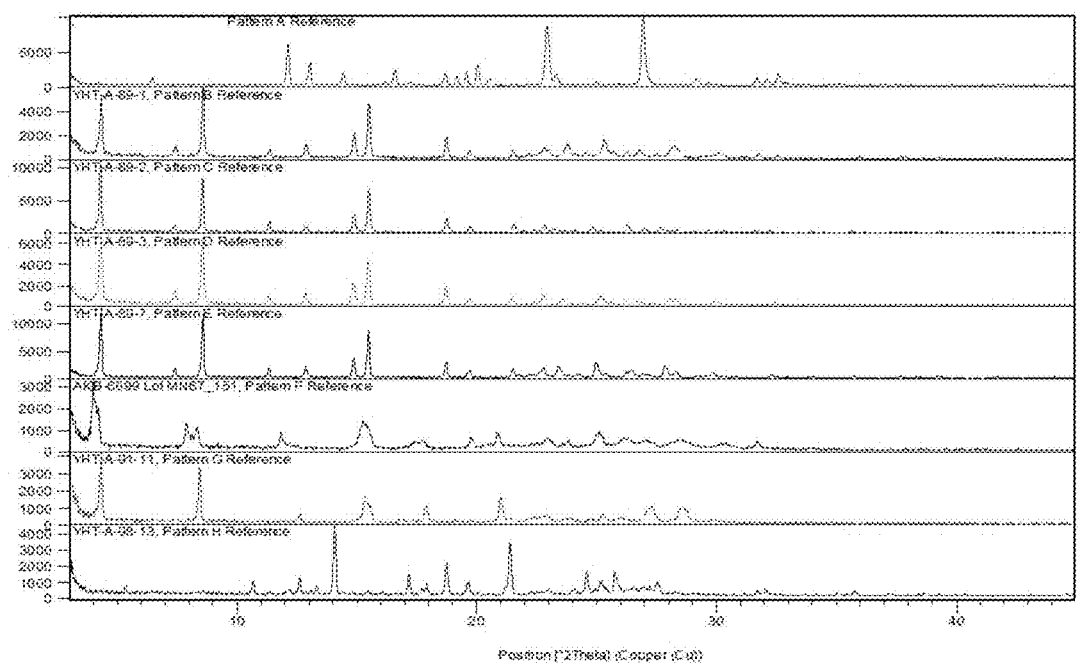
FIG. 1 depicts an overlay of X-ray powder diffractogram (XRPD) patterns of Forms A, B, C, D, E, F, G and H of Compound 1.

As used herein, the terms "prevent", "preventing" and "prevention" are art-recognized, and when used in relation to a condition, such as a local recurrence, a disease or any other medical condition, such as those described herein, is well understood in the art, and includes administration of a compound, such as a solid form of Compound 1, which reduces the frequency of, or delays the onset of, symptoms of a medical condition in a patient relative to a patient which does not receive the composition.

As used herein, the terms "treat", "treating" and "treatment" refer to the reversing, reducing, or arresting the symptoms, clinical signs, and underlying pathology of a disease condition, such as those described herein, in manner to improve or stabilize a subject's condition. The terms "treat" and "treatment" also refer to the eradication or amelioration of the disease or symptoms associated with the disease. In certain embodiments, such terms refer to minimizing the spread or worsening of the disease by the administration of a solid form of Compound 1 to a patient with such a disease.

As used herein, the term "hydrate" means 5-(3-fluorophenyl)-3-hydroxypyridine-2-carbonyl]amino}acetic acid or a pharmaceutically acceptable salt thereof, that further includes a stoichiometric or non-stoichiometric amount of water bound by non-covalent intermolecular forces.

As used herein, the term "solvate" means 5-(3-fluorophenyl)-3-hydroxypyridine-2-carbonyl]amino}acetic acid or a pharmaceutically acceptable salt thereof, that further includes a stoichiometric or non-stoichiometric amount of a solvent, other than water, bound by non-covalent intermolecular forces.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively.

The terms "solid form," "solid forms" and related terms, when used herein to refer to Compound 1, refer to a physical form comprising Compound 1 which is not predominantly in a liquid or a gaseous state. Crystal forms are examples of solid forms. In one embodiment, the solid form is Form A. In another embodiment, the solid form is Form B. In another embodiment, the solid form is Form C. In another embodiment, the solid form is Form D. In another embodiment, the solid form is Form E. In another embodiment, the solid form is Form F. In another embodiment, the solid form is Form G. In another embodiment, the solid form is Form H. In one embodiment, the solid form is Salt I. In one embodiment, the solid form is Salt II. In one embodiment, the solid form is Salt III. In one embodiment, the solid form is Salt IV. In one embodiment, the solid form is Salt V. In one embodiment, the solid form is Salt VI.

The term "crystalline" and related terms used herein, when used to describe a substance, component, product, or form, means that the substance, component or product is substantially crystalline as determined by X-ray diffraction. See, e.g., Remington's Pharmaceutical Sciences, 22nd ed., Pharmaceutical Press, (2012); *The United States Pharmacopoeia,* 30th ed., (2011).

The term "crystal form," "crystalline form" and related terms herein refer to a crystalline solid form comprising a chemical compound, and may refer to a particular single-component or multiple-component crystal form, including, but not limited to, a polymorph, a solvate, a hydrate or other molecular complex, a salt, a solvate of a salt, a hydrate of a salt, or other molecular complex of a salt, or a polymorph thereof.

The terms "polymorphs," "polymorphic forms" and related terms herein refer to two or more crystal forms that comprise the same molecule, molecules or ions. Different polymorphs may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by polymorphs affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Techniques for characterizing crystal forms and amorphous forms include, but are not limited to, thermal gravimetric analysis (TGA), melting point, differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy (e.g., polaraized light microscopy), hot stage optical microscopy, scanning electron microscopy (SEM), electron crystallography, dynamic vapor sorption (DVS), and quantitative analysis, particle size analysis (PSA), surface area analysis, solubility studies and dissolution studies.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, more specifically within 10%, more specifically within 5%, of the specified dose, amount, or weight percent.

As used herein, and unless otherwise specified, the terms "about" and "approximately," when used in connection with a numeric value or range of values, which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary, in particular embodiments, within 20%, 10%, 9%, 8%, 7%, 6%, 5%, 4%, 3%, 2%, 1.5%, 1%, 0.5%, or 0.25% of the recited value or range of values. With respect to XRPD, values given are ±0.2 degrees 2 theta.

As used herein, and unless otherwise specified, a crystalline that is "pure," i.e., substantially free of other crystalline or amorphous solids, contains less than about 10% by weight of one or more other crystalline or amorphous solids, less than about 5% by weight of one or more other crystalline or amorphous solids, less than about 3% by weight of one or more other crystalline or amorphous solids, or less than about 1% by weight of one or more other crystalline or amorphous solids.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, an "effective amount" refers to that amount of Compound 1 or a pharmaceutically acceptable salt, solvate or hydrate thereof sufficient to provide a therapeutic benefit in the treatment of the disease or to delay or minimize symptoms associated with the disease, such as any disease or condition described herein.

The terms "subject" and "patient," unless otherwise specified, are defined herein to include animals such as mammals, including, but not limited to, primates (e.g., humans), cows, sheep, goats, horses, dogs, cats, rabbits, rats, mice and the like. In specific embodiments, the patient or patient is a human. In certain embodiments, the patient has a disease or condition as described herein.

"VEGF-dependent cancer," "VEGF dependent cancers," "VEGF-dependent tumor" or "VEGF dependent tumors" refers to cancers that rely on VEGF to proliferate.

5.2 Compound 1

The solid forms (e.g., Form A, Form B, Form C, Form D, Form E, Form F, Form G, Form H, Salt I, Salt II, Salt III, Salt IV, Salt V, Salt VI, Salt VII, Salt VIII, Salt IX and Salt X), formulations and methods of use provided herein relate to Compound 1:

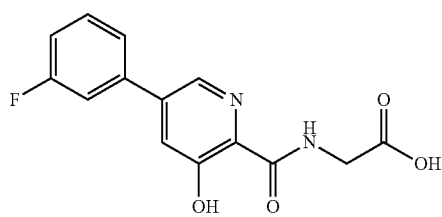

having the name 2-(5-(3-fluorophenyl)-3-hydroxypicolinamido)acetic acid, including tautomers thereof.

In certain embodiments, Form A, Form B, Form C, Form D, Form E, Form F, Form G and Form H of Compound 1 exist in the following zwitterionic form:

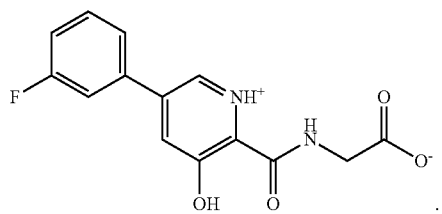 [SMILES: O=C([O-])CNC(=O)c1[nH+]cc(-c2cccc(F)c2)cc1O]

Compound 1 can be prepared using reagents and methods known in the art, including the methods provided in United States Patent Application Publication No. 2007/0299086, published Dec. 27, 2007, United States Patent Application Publication 2012/0329836, published Dec. 27, 2012 and International Patent Application Publication No. WO 2012/170442, published Dec. 13, 2012, the entireties of which are incorporated by reference herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms of Compound 1

In certain embodiments, provided herein are solid forms of Compound 1. In certain embodiments, the solid form is crystalline. In certain embodiments, the solid form is a single-component solid form. In certain embodiments, the solid form is a solvate. In certain embodiments, the solid form is anhydrous. In certain embodiments, the solid form is Form A, Form B, Form C, Form D, Form E, Form F, Form G, Form H, Salt I, Salt II, Salt III, Salt IV, Salt V, Salt VI, Salt VII, Salt VIII, Salt IX or Salt X.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form A, Form B, Form C, Form D, Form E, Form F, Form G, Form H, Salt I, Salt II, Salt III, Salt IV, Salt V, Salt VI, Salt VII, Salt VIII, Salt IX and Salt X of Compound 1) may be characterized using a number of methods known to a person skilled in the art, including, but not limited to, X-ray powder diffraction (XRPD), microscopy (e.g., scanning electron microscopy (SEM)) and thermal analysis (e.g., thermal gravimetric analysis (TGA) and differential scanning calorimetry (DSC)). The particle size and size distribution of the solid form provided herein may be determined by conventional methods, such as laser light scattering technique.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ(see United State Pharmacopoeia, page 2228 (2003)).

5.3.1 Form A of Compound 1

In certain embodiments, provided herein is Form A of Compound 1.

In one embodiment, Form A is a solid form of Compound 1. In one embodiment, Form A is anhydrous. In another embodiment, Form A is crystalline.

In certain embodiments, Form A is prepared by single solvent fast cooling crystallization, single solvent slow cooling crystallization, binary solvent fast cooling crystallization or binary solvent slow cooling crystallization experiments (see Table 1-Table 10).

In one embodiment, provided herein are methods for preparing Form A of Compound 1 comprising single solvent fast cooling crystallization comprising the steps of: (1) dissolving Compound 1 (e.g., approximately 10-55 mg) with a minimum amount of solvents (e.g., from about 0.25 mL to about 14.0 mL) at a first temperature (e.g., from about 30° C. to about 90° C.); (2) filtering the hot solution; (3) cooling the solution to a second temperature (e.g., from about −5° C. to about 10° C.) for a period of time (e.g., from about 6 hours to about 72 hours); (4) isolating the resulting solids; and (5) evaporating the samples without precipitation to dryness and collecting the resulting solids. See Table 1. In certain embodiments, the solvent is THF, MIBK or MTBE.

In one embodiment, provided herein are methods for preparing Form A of Compound 1 comprising single solvent fast cooling crystallization comprising the steps of: (1) dissolving Compound 1 (e.g., approximately 30-35 mg) with a minimum amount of solvents (e.g., up to about 7.0 mL) at a first temperature (e.g., about 50 or 70° C.); (2) filtering the hot solution (e.g., filtering through a 0.45 μm syringe filter); (3) cooling the solution to a second temperature (e.g., about 4° C.) for a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 1. In certain embodiments, the solvent is THF, MIBK or MTBE.

In one embodiment, provided herein are methods for preparing Form A of Compound 1 comprising single solvent slow cooling crystallization comprising the steps of: (1) dissolving Compound 1 (e.g., approximately 10-55 mg) with a minimum amount of solvents (e.g, from about 0.25 mL to about 14.0 mL) at a first temperature (e.g., from about 30° C. to about 90° C.); (2) filtering the hot solution; (3) cooling the hot solution to ambient temperature at a rate (e.g., from about 5° C./hr to about 40° C./hr) and allowing to equilibrate at ambient temperature over a period of time (e.g., from about 6 hours to about 72 hours); (4) isolating the resulting solids; and (5) evaporating the samples without precipitation to dryness and collecting the resulting solids. See Table 2. In certain embodiments, the solvent is THF or MTBE.

In one embodiment, provided herein are methods for preparing Form A of Compound 1 comprising single solvent slow cooling crystallization comprising the steps of: (1) dissolving Compound 1 (e.g., approximately 30-35 mg) with a minimum amount of solvents (e.g, up to about 7.0 mL) at a first temperature (e.g., about 50 or 70° C.); (2) filtering the hot solution (e.g., filtering through a 0.45 μm syringe filter); (3) cooling the hot solution to ambient temperature at a rate (e.g., about 20° C./hr) and allowing to equilibrate at ambient temperature over a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 2. In certain embodiments, the solvent is THF or MTBE.

In one embodiment, provided herein are methods for preparing Form A of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form. See Table 3, Table 5, Table 7 and Table 9. In certain embodiments, the solvent is MeOH, EtOH, IPA, acetone, DMSO, DMF, NMP, IPAc, MIBK or MTBE. In certain embodiments, the co-solvent is water, toluene, heptane or cyclohexane.

In one embodiment, provided herein are methods for preparing Form A of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form. See Table 3, Table 5, Table 7 and Table 9. In certain embodiments, the solvent is MeOH, EtOH, IPA, acetone, DMSO, DMF, NMP, IPAc, MIBK or MTBE. In certain embodiments, the co-solvent is water, toluene, heptane or cyclohexane.

In one embodiment, provided herein are methods for preparing Form A of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form. See Table 4, Table 6, Table 8 and Table 10. In certain embodiments, the solvent is acetone, DMF, NMP, MeCN, IPAc, MIBK or MTBE. In certain embodiments, the co-solvent is water, toluene, heptane or cyclohexane.

In one embodiment, provided herein are methods for preparing Form A of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form. See Table 4, Table 6, Table 8 and Table 10. In certain embodiments, the solvent is acetone, DMF, NMP, MeCN, IPAc, MIBK or MTBE. In certain embodiments, the co-solvent is water, toluene, heptane or cyclohexane.

In one embodiment, provided herein is Form A prepared by stirring Form G in a solvent for a period of time. See Table 13. In one embodiment, the solvent is IPAc/heptane (e.g., about 1:2 (V:V)) or toluene. In one embodiment, the solvent is acetone/water (e.g., about 1:2 (V:V)). In one embodiment, the period of time is from about 1 day to about 7 days (e.g., about 1 day or about 7 days).

Figure 11:
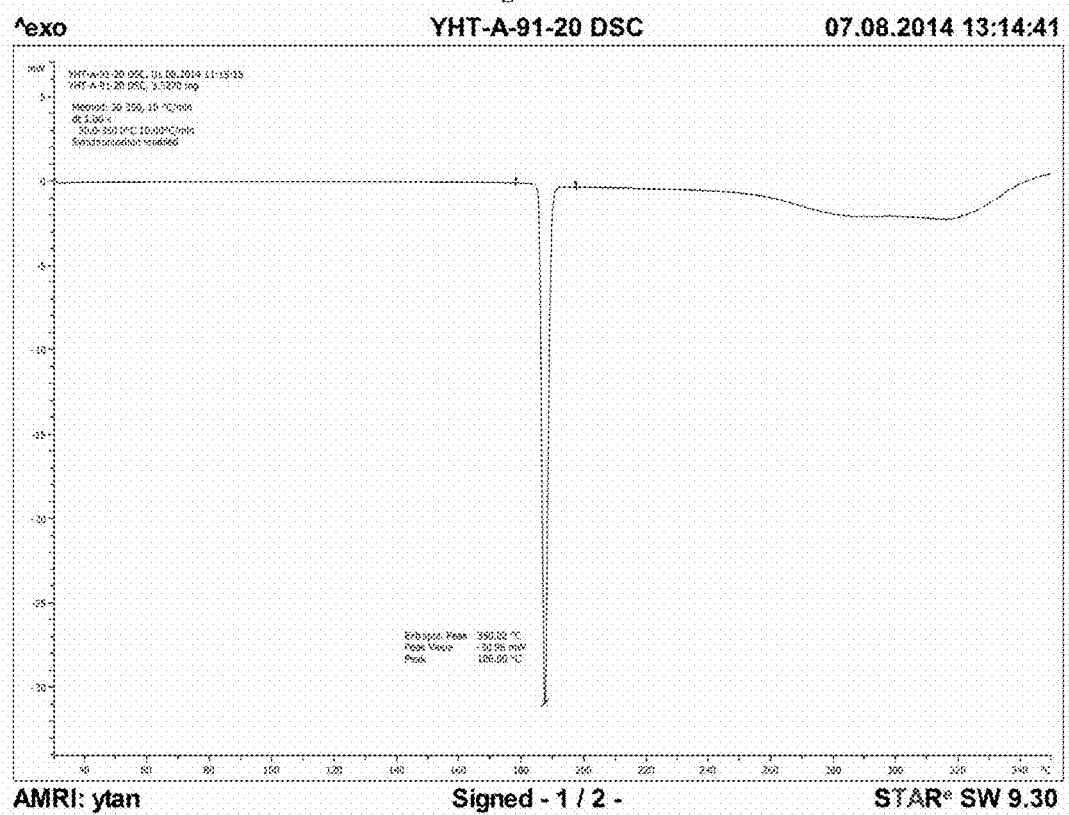
FIG. 11 depicts a DSC thermogram of Form A of Compound 1.

In one embodiment, provided herein is Form A having a DSC thermogram substantially as depicted in FIG. 11. In certain embodiments, the crystalline form exhibits a DSC thermogram comprising an endothermic event with a maximum at about 186° C. when heated from approximately 30° C. to approximately 230° C.

Figure 12:
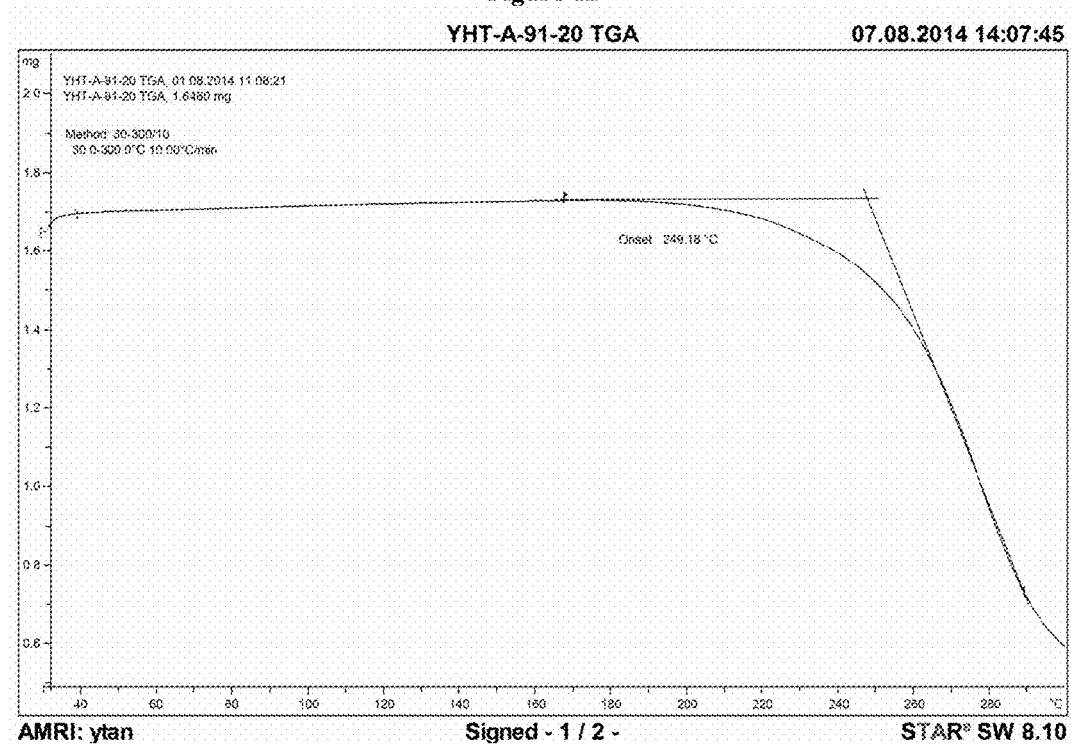
FIG. 12 depicts a TGA thermogram of Form A of Compound 1.

In one embodiment, provided herein is Form A having a TGA thermogram corresponding substantially to the representative TGA thermogram as depicted in FIG. 12. In certain embodiments, the crystalline form exhibits a TGA thermogram comprising no mass loss before about 155° C. when heated from approximately 30° C. to approximately 300° C. The TGA thermogram further comprises a decomposition event with an onset temperature at approximately 249.2° C. when heated from approximately 30° C. to approximately 300° C. Thus, in certain embodiments, the crystalline form has no mass loss at a temperature lower than about 100° C.

In one embodiment, provided herein is moderately hygroscopic Form A having about 0% weight moisture uptake at 60% RH and about 6.1% weight moisture uptake at 90% RH. See FIG. 13.

In certain embodiments, a solid form provided herein, e.g., Form A, is substantially crystalline, as indicated by, e.g., X-ray powder diffraction measurements. In one embodiment, Form A has an X-ray powder diffraction pattern substantially as shown in FIG. 2.

Figure 2:
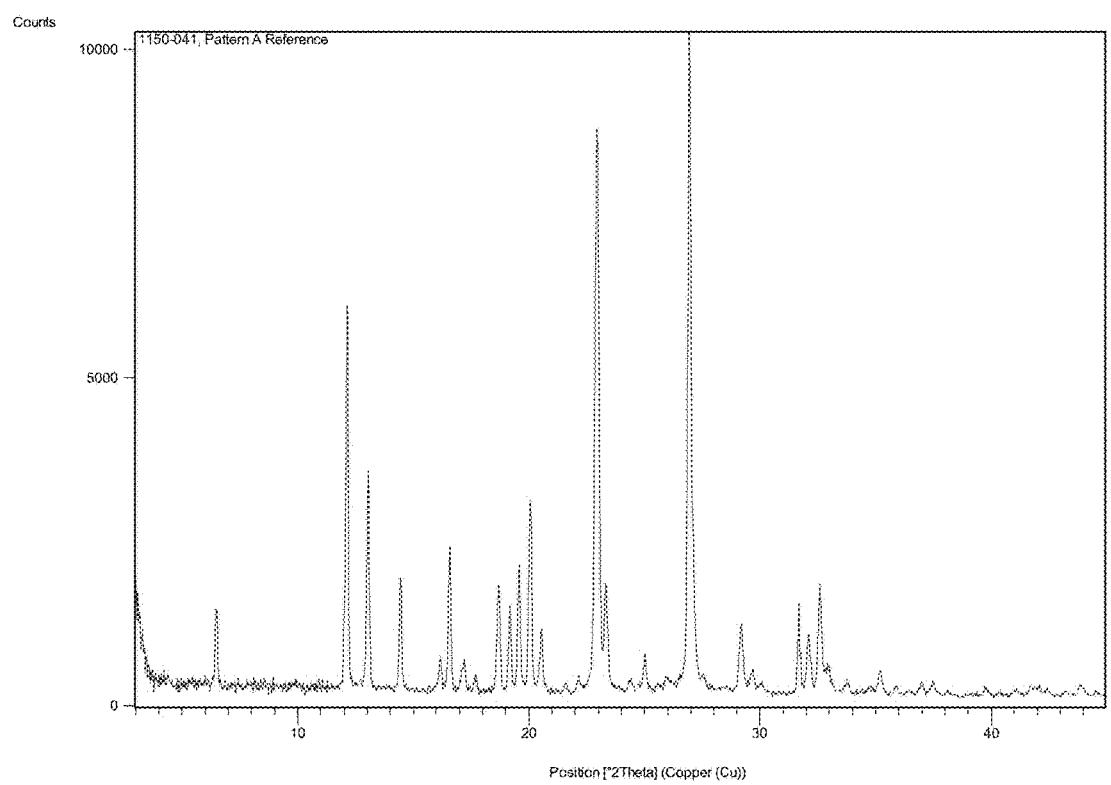
FIG. 2 depicts an XRPD pattern of Form A of Compound 1.

In one embodiment, Form A has one or more characteristic X-ray powder diffraction peaks at approximately 3.73, 3.86, 4.24, 4.39, 5.46, 5.58, 5.77, 6.01, 6.49, 6.86, 7.27, 7.40, 7.83, 8.13, 8.56, 8.67, 8.80, 8.93, 9.91, 10.09, 10.23, 10.41, 11.07, 12.14, 13.05, 14.45, 15.67, 16.20, 16.60, 17.21, 17.70, 18.71, 19.19, 19.59, 20.08, 20.54, 21.60, 22.15, 22.97, 23.34, 24.37, 25.02, 25.55, 25.93, 26.92, 27.55, 29.20, 29.70, 30.10, 31.68, 32.13, 32.59, 33.00, 33.77, 34.18, 34.67, 35.19, 35.88, 36.40, 36.99, 37.46, 38.08, 39.74, 40.38, 40.96, 41.76, 42.12, 42.45, 43.26, 43.87 or 44.52° 2θ as depicted in FIG. 2. In a specific embodiment, Form A has one, two, three, four, five, six, seven or eight characteristic X-ray powder diffraction peaks at approximately 12.14, 13.05, 14.45, 16.60, 19.59, 20.08, 22.97 or 26.92° 2θ. In another embodiment, Form A has one, two, three or four characteristic X-ray powder diffraction peaks at approximately 12.14, 13.05, 22.97 or 26.92° 2θ. In another embodiment, Form A has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, sixty-six, sixty-seven, sixty-eight, sixty-nine, seventy or seventy-one characteristic X-ray powder diffraction peaks as set forth in Table 20.

In certain embodiments, a solid form provided herein, e.g., Form A, is substantially crystalline, as indicated by, e.g., X-ray powder diffraction measurements. In one embodiment, Form A has an X-ray powder diffraction pattern substantially as shown in FIG. 2. In one embodiment, Form A has one or more characteristic X-ray powder diffraction peaks at approximately 3.7, 3.9, 4.2, 4.4, 5.5, 5.6, 5.8, 6.0, 6.5, 6.9, 7.3, 7.4, 7.8, 8.1, 8.6, 8.7, 8.8, 8.9, 9.9, 10.1, 10.2, 10.4, 11., 12.1, 13., 14.5, 15.7, 16.2, 16.6, 17.2, 17.7, 18.7, 19.2, 19.6, 20.1, 20.5, 21.6, 22.2, 23.0, 23.3, 24.4, 25.0, 25.6, 25.9, 26.9, 27.6, 29.2, 29.7, 30.1, 31.7, 32.1, 32.6, 33.0, 33.8, 34.2, 34.7, 35.2, 35.9, 36.4, 37.0, 37.5, 38.1, 39.7, 40.4, 41.0, 41.8, 42.1, 42.5, 43.3, 43.9 or 44.5° 2θ as depicted in FIG. 2. In a specific embodiment, Form A has one, two, three, four, five, six, seven or eight characteristic X-ray powder diffraction peaks at approximately 12.1, 13.1, 14.5, 16.6, 19.6, 20.1, 23.0 or 26.9° 2θ. In another embodiment, Form A has one, two, three or four characteristic X-ray powder diffraction peaks at approximately 12.1, 13.1, 23.0 or 26.9° 2θ. In another embodiment, Form A has one, two, three, four, five or six characteristic X-ray powder diffraction peaks at approximately 12.1, 13.1, 16.6, 20.1, 23.0 or 26.9° 2θ. In another embodiment, Form A has one, two or three characteristic X-ray powder diffraction peaks at approximately 12.1, 23.0 or 26.9° 2θ. In another embodiment, Form A has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, sixty-six, sixty-seven, sixty-eight, sixty-nine, seventy or seventy-one characteristic X-ray powder diffraction peaks as set forth in Table 20.

In still another embodiment, Form A is substantially pure. In certain embodiments, the substantially pure Form A is substantially free of other solid forms, e.g., Forms B, C, D, E, F, G or H. In certain embodiments, the purity of the substantially pure Form A is no less than about 95%, no less than about 96%, no less than about 97%, no less than about 98%, no less than about 98.5%, no less than about 99%, no less than about 99.5%, or no less than about 99.8%.

5.3.2 Form B of Compound 1

In certain embodiments, provided herein is Form B of Compound 1.

In one embodiment, Form B is a solid form of Compound 1. In one embodiment, Form B is anhydrous. In one embodiment, Form B is an anhydrous solid form of Compound 1 retaining residual solvent. In one embodiment, Form B is an anhydrous solid form of Compound 1 retaining residual MEK. In another embodiment, Form B is crystalline.

In certain embodiments, Form B is prepared by single solvent fast cooling crystallization, single solvent slow cooling crystallization, binary solvent fast cooling crystallization or binary solvent slow cooling crystallization experiments (see Table 1-Table 10).

In one embodiment, provided herein are methods for preparing Form B of Compound 1 comprising single solvent fast cooling crystallization comprising the steps of: (1) dissolving Compound 1 (e.g., approximately 10-55 mg) with a minimum amount of solvents (e.g., from about 0.25 mL to about 14.0 mL) at a first temperature (e.g., from about 30° C. to about 90° C.); (2) filtering the hot solution; (3) cooling the solution to a second temperature (e.g., from about −5° C. to about 10° C.) for a period of time (e.g., from about 6 hours to about 72 hours); (4) isolating the resulting solids; and (5) evaporating the samples without precipitation to dryness and collecting the resulting solids. See Table 1. In certain embodiments, the solvent is MeOH, THF or acetone.

In one embodiment, provided herein are methods for preparing Form B of Compound 1 comprising single solvent fast cooling crystallization comprising the steps of: (1) dissolving Compound 1 (e.g., approximately 30-35 mg) with a minimum amount of solvents (e.g., up to about 7.0 mL) at a first temperature (e.g., about 50 or 70° C.); (2) filtering the hot solution (e.g., filtering through a 0.45 µm syringe filter); (3) cooling the solution to a second temperature (e.g., about 4° C.) for a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 1. In certain embodiments, the solvent is MeOH, THF or acetone.

In one embodiment, provided herein are methods for preparing Form B of Compound 1 comprising single solvent slow cooling crystallization comprising the steps of: (1) dissolving Compound 1 (e.g., approximately 10-55 mg) with a minimum amount of solvents (e.g, from about 0.25 mL to about 14.0 mL) at a first temperature (e.g., from about 30° C. to about 90° C.); (2) filtering the hot solution; (3) cooling the hot solution to ambient temperature at a rate (e.g., from about 5° C./hr to about 40° C./hr) and allowing to equilibrate at ambient temperature over a period of time (e.g., from about 6 hours to about 72 hours); (4) isolating the resulting solids; and (5) evaporating the samples without precipitation to dryness and collecting the resulting solids. See Table 2. In certain embodiments, the solvent is MeOH, MeCN, THF, acetone or MIBK.

In one embodiment, provided herein are methods for preparing Form B of Compound 1 comprising single solvent slow cooling crystallization comprising the steps of: (1) dissolving Compound 1 (e.g., approximately 30-35 mg) with a minimum amount of solvents (e.g, up to about 7.0 mL) at a first temperature (e.g., about 50 or 70° C.); (2) filtering the hot solution (e.g., filtering through a 0.45 µm syringe filter); (3) cooling the hot solution to ambient temperature at a rate (e.g., about 20° C./hr) and allowing to equilibrate at ambient temperature over a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 2. In certain embodiments, the solvent is MeOH, MeCN, THF, acetone or MIBK.

In one embodiment, provided herein are methods for preparing Form B of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3). In certain embodiments, the solvent is THF. In certain embodiments, the co-solvent is water.

In one embodiment, provided herein are methods for preparing Form B of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3). In certain embodiments, the solvent is THF. In certain embodiments, the co-solvent is water.

In one embodiment, provided herein are methods for preparing Form B of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 4 and Table 6). In certain embodiments, the solvent is MeOH, MEK, MIBK or DMF. In certain embodiments, the co-solvent is water or toluene.

In one embodiment, provided herein are methods for preparing Form B of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3)

adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 4 and Table 6). In certain embodiments, the solvent is MeOH, MEK, MIBK or DMF. In certain embodiments, the co-solvent is water or toluene.

Figure 16:
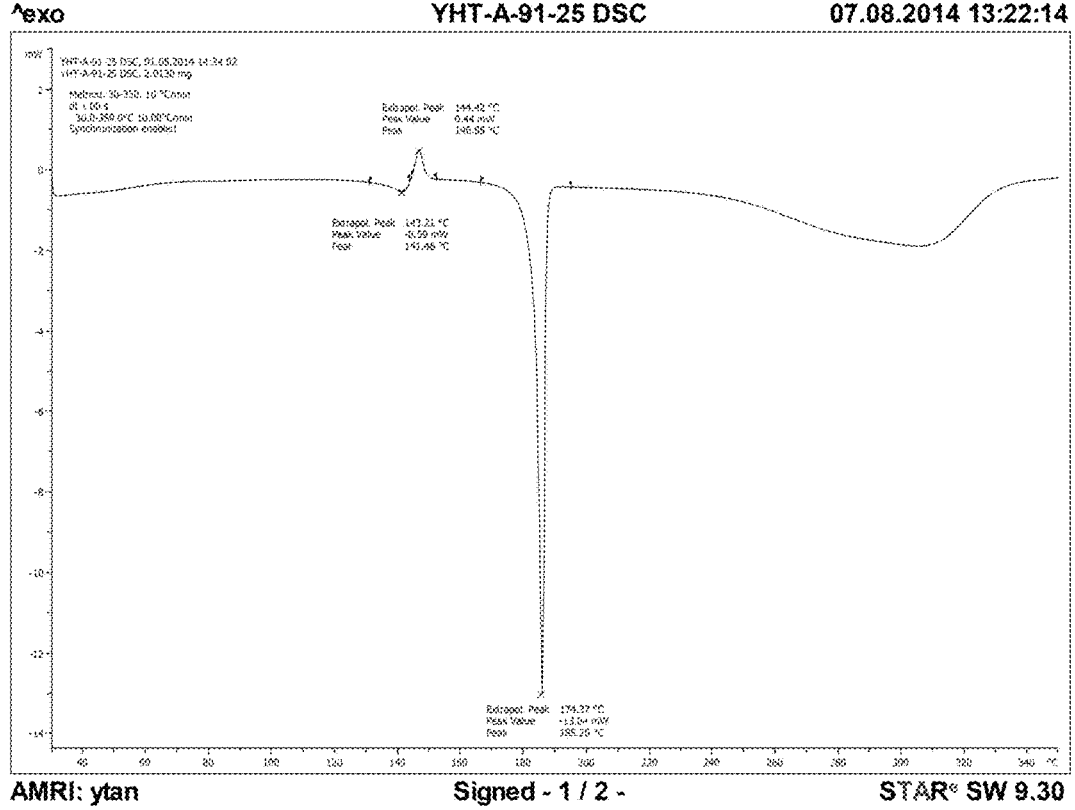
FIG. 16 depicts a DSC thermogram of Form B of Compound 1.

In one embodiment, provided herein is Form B having a DSC thermogram substantially as depicted in FIG. 16. In certain embodiments, the crystalline form exhibits a DSC thermogram comprising an endothermic event with a maximum at about 141.5° C. when heated from approximately 30° C. to approximately 230° C. In one embodiment, the DSC thermogram further comprises an endothermic event with a maximum at about 185.2° C. when heated from approximately 30° C. to approximately 230° C. In one embodiment, the DSC thermogram further comprises an exothermic event with a maximum at about 146.9° C. when heated from approximately 30° C. to approximately 230° C.

Figure 17:
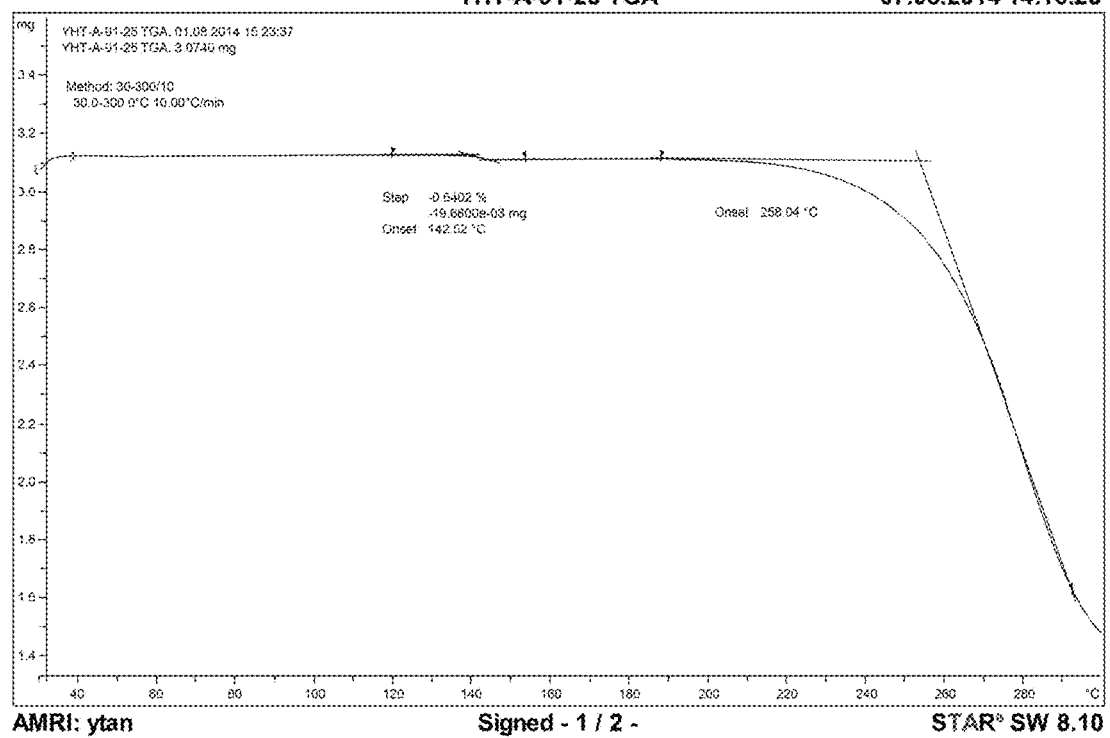
FIG. 17 depicts a TGA thermogram of Form B of Compound 1.

In one embodiment, provided herein is Form B having a TGA thermogram corresponding substantially to the representative TGA thermogram as depicted in FIG. 17. In certain embodiments, the crystalline form exhibits a TGA thermogram comprising about 0.64% mass loss before about 155° C. when heated from approximately 30° C. to approximately 300° C. The TGA thermogram further comprises a decomposition event with an onset temperature at approximately 258.0° C. when heated from approximately 30° C. to approximately 300° C.

In one embodiment, provided herein is Form B that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 3:
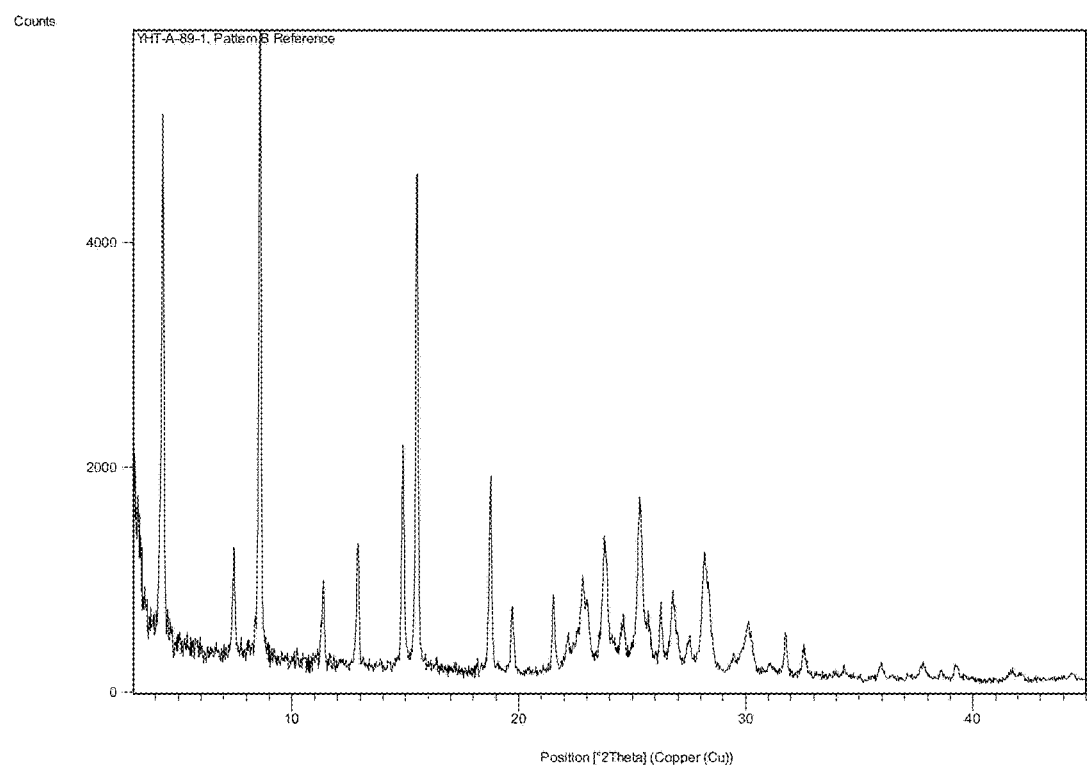
FIG. 3 depicts an XRPD pattern of Form B of Compound 1.

In certain embodiments, a solid form provided herein, e.g., Form B, is substantially crystalline, as indicated by, e.g., X-ray powder diffraction measurements. In one embodiment, Form B has an X-ray powder diffraction pattern substantially as shown in FIG. 3. In one embodiment, Form B has one or more characteristic X-ray powder diffraction peaks at approximately 4.34, 7.46, 8.61, 11.37, 12.90, 14.89, 15.50, 18.76, 19.71, 21.52, 22.15, 22.81, 23.03, 23.77, 24.60, 25.29, 25.73, 26.23, 26.76, 27.49, 28.17, 30.10, 31.76, 32.57, 34.34, 35.94, 37.74, 38.63, 39.27, 41.75, 42.20 or 44.45° 2θ as depicted in FIG. 3. In a specific embodiment, Form B has one, two, three, four, five, six, seven or eight characteristic X-ray powder diffraction peaks at approximately 4.34, 8.61, 12.90, 14.89, 15.50, 18.76, 23.77 or 25.29° 2θ. In another embodiment, Form B has one, two, three or four characteristic X-ray powder diffraction peaks at approximately 4.34, 8.61, 14.89 or 15.50° 2θ. In another embodiment, Form B has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two characteristic X-ray powder diffraction peaks as set forth in Table 21.

In certain embodiments, a solid form provided herein, e.g., Form B, is substantially crystalline, as indicated by, e.g., X-ray powder diffraction measurements. In one embodiment, Form B has an X-ray powder diffraction pattern substantially as shown in FIG. 3. In one embodiment, Form B has one or more characteristic X-ray powder diffraction peaks at approximately 4.3, 7.5, 8.6, 11.4, 12.9, 14.9, 15.5, 18.8, 19.7, 21.5, 22.2, 22.8, 23.0, 23.8, 24.6, 25.3, 25.7, 26.2, 26.8, 27.5, 28.2, 30.1, 31.8, 32.6, 34.3, 35.9, 37.7, 38.6, 39.3, 41.8, 42.2 or 44.5° 2θ as depicted in FIG. 3. In a specific embodiment, Form B has one, two, three, four, five, six, seven or eight characteristic X-ray powder diffraction peaks at approximately 4.3, 8.6, 12.9, 14.9, 15.5, 18.8, 23.8 or 25.3° 2θ. In another embodiment, Form B has one, two, three or four characteristic X-ray powder diffraction peaks at approximately 4.3, 8.6, 14.9 or 15.5° 2θ. In another embodiment, Form B has one, two, three, four, five, six or seven characteristic X-ray powder diffraction peaks at approximately 4.3, 8.6, 12.9, 14.9, 15.5, 18.8 or 25.3° 2θ. In another embodiment, Form B has one, two, three, four, five or six characteristic X-ray powder diffraction peaks at approximately 4.3, 8.6, 14.9, 15.5, 18.8 or 25.3° 2θ. In another embodiment, Form B has one, two, three or four characteristic X-ray powder diffraction peaks at approximately 4.3, 8.6, 15.5 or 25.3° 2θ. In another embodiment, Form B has one, two or three characteristic X-ray powder diffraction peaks at approximately 4.3, 8.6 or 15.5° 2θ. In another embodiment, Form B has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two characteristic X-ray powder diffraction peaks as set forth in Table 21.

In still another embodiment, Form B is substantially pure. In certain embodiments, the substantially pure Form B is substantially free of other solid forms, e.g., Forms A, C, D, E, F, G or H. In certain embodiments, the purity of the substantially pure Form B is no less than about 95%, no less than about 96%, no less than about 97%, no less than about 98%, no less than about 98.5%, no less than about 99%, no less than about 99.5%, or no less than about 99.8%.

5.3.3 Form C of Compound 1

In certain embodiments, provided herein is Form C of Compound 1.

In one embodiment, Form C is a solid form of Compound 1. In one embodiment, Form C is anhydrous. In one embodiment, Form C is an anhydrous solid form of Compound 1 retaining residual solvent. In one embodiment, Form C is an anhydrous solid form of Compound 1 retaining residual EtOH. In another embodiment, Form C is crystalline.

In certain embodiments, Form C is prepared by single solvent fast cooling crystallization, single solvent slow cooling crystallization, binary solvent fast cooling crystallization or binary solvent slow cooling crystallization experiments (see Table 1-Table 10).

In one embodiment, provided herein are methods for preparing Form C of Compound 1 comprising single solvent fast cooling crystallization comprising the steps of: (1) dissolving Compound 1 (e.g., approximately 10-55 mg) with a minimum amount of solvents (e.g., from about 0.25 mL to about 14.0 mL) at a first temperature (e.g., from about 30° C. to about 90° C.); (2) filtering the hot solution; (3) cooling the solution to a second temperature (e.g., from about −5° C. to about 10° C.) for a period of time (e.g., from about 6 hours to about 72 hours); (4) isolating the resulting solids; and (5) evaporating the samples without precipitation to dryness and collecting the resulting solids. See Table 1. In certain embodiments, the solvent is EtOH or IPAc.

In one embodiment, provided herein are methods for preparing Form C of Compound 1 comprising single solvent fast cooling crystallization comprising the steps of: (1) dissolving Compound 1 (e.g., approximately 30-35 mg) with a minimum amount of solvents (e.g., up to about 7.0 mL) at a first temperature (e.g., about 50 or 70° C.); (2) filtering the hot solution (e.g., filtering through a 0.45 μm syringe filter); (3) cooling the solution to a second temperature (e.g., about 4° C.) for a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 1. In certain embodiments, the solvent is EtOH or IPAc.

In one embodiment, provided herein are methods for preparing Form C of Compound 1 comprising single solvent slow cooling crystallization comprising the steps of: (1) dissolving Compound 1 (e.g., approximately 10-55 mg) with a minimum amount of solvents (e.g, from about 0.25 mL to about 14.0 mL) at a first temperature (e.g., from about 30° C. to about 90° C.); (2) filtering the hot solution; (3) cooling the hot solution to ambient temperature at a rate (e.g., from about 5° C./hr to about 40° C./hr) and allowing to equilibrate at ambient temperature over a period of time (e.g., from about 6 hours to about 72 hours); (4) isolating the resulting solids; and (5) evaporating the samples without precipitation to dryness and collecting the resulting solids. See Table 2. In certain embodiments, the solvent is EtOH or IPAc.

In one embodiment, provided herein are methods for preparing Form C of Compound 1 comprising single solvent slow cooling crystallization comprising the steps of: (1) dissolving Compound 1 (e.g., approximately 30-35 mg) with a minimum amount of solvents (e.g, up to about 7.0 mL) at a first temperature (e.g., about 50 or 70° C.); (2) filtering the hot solution (e.g., filtering through a 0.45 μm syringe filter); (3) cooling the hot solution to ambient temperature at a rate (e.g., about 20° C./hr) and allowing to equilibrate at ambient temperature over a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 2. In certain embodiments, the solvent is EtOH or IPAc.

In one embodiment, provided herein are methods for preparing Form C of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3, Table 5 and Table 9). In certain embodiments, the solvent is EtOH. In certain embodiments, the co-solvent is water, toluene or cyclohexane.

In one embodiment, provided herein are methods for preparing Form C of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3, Table 5 and Table 9). In certain embodiments, the solvent is EtOH. In certain embodiments, the co-solvent is water, toluene or cyclohexane.

In one embodiment, provided herein are methods for preparing Form C of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 10). In certain embodiments, the solvent is EtOH, EtOAc or IPAc. In certain embodiments, the co-solvent is cyclohexane.

In one embodiment, provided herein are methods for preparing Form C of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 10). In certain embodiments, the solvent is EtOH, EtOAc or IPAc. In certain embodiments, the co-solvent is cyclohexane.

Figure 19:
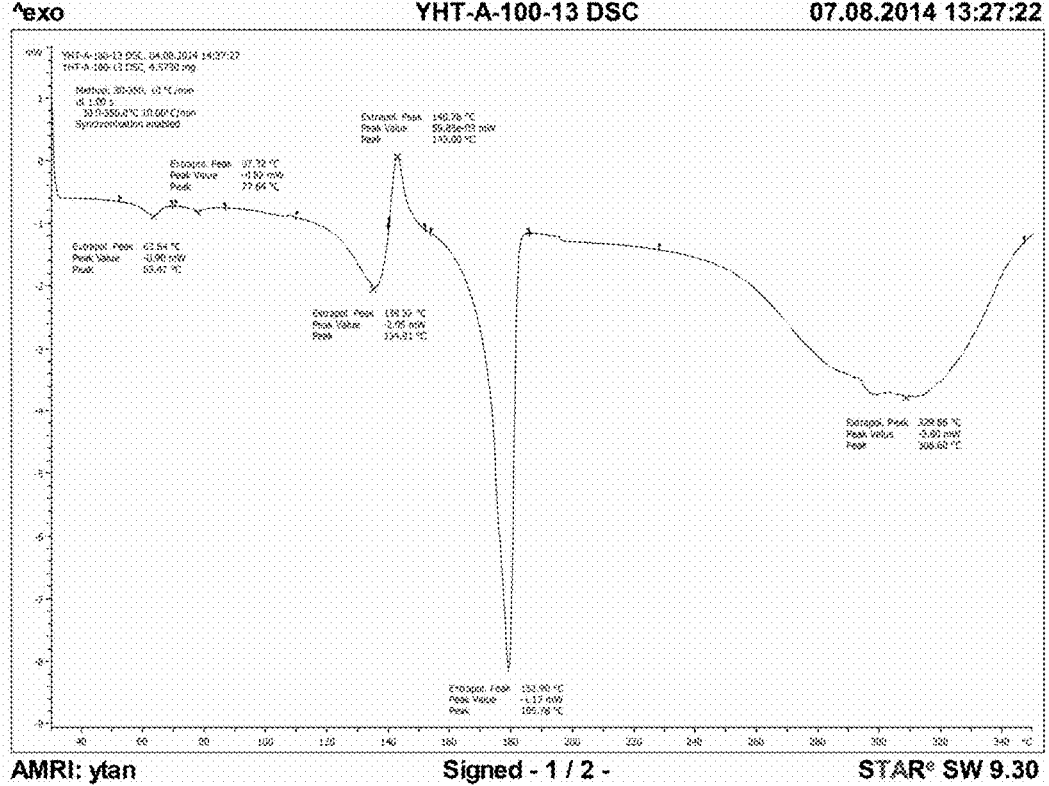
FIG. 19 depicts a DSC thermogram of Form C of Compound 1.

In one embodiment, provided herein is Form C having a DSC thermogram substantially as depicted in FIG. 19. In certain embodiments, the crystalline form exhibits a DSC thermogram comprising an endothermic event with a maximum at about 63.5° C. when heated from approximately 30° C. to approximately 230° C. In one embodiment, the DSC thermogram further comprises an endothermic event with a maximum at about 77.6° C. when heated from approximately 30° C. to approximately 230° C. In one embodiment, the DSC thermogram further comprises an endothermic event with a maximum at about 134.9° C. when heated from approximately 30° C. to approximately 230° C. In one embodiment, the DSC thermogram further comprises an endothermic event with a maximum at about 185.8° C. when heated from approximately 30° C. to approximately 230° C. In one embodiment, the DSC thermogram further comprises an exothermic event with a maximum at about 143.0° C. when heated from approximately 30° C. to approximately 230° C.

Figure 20:
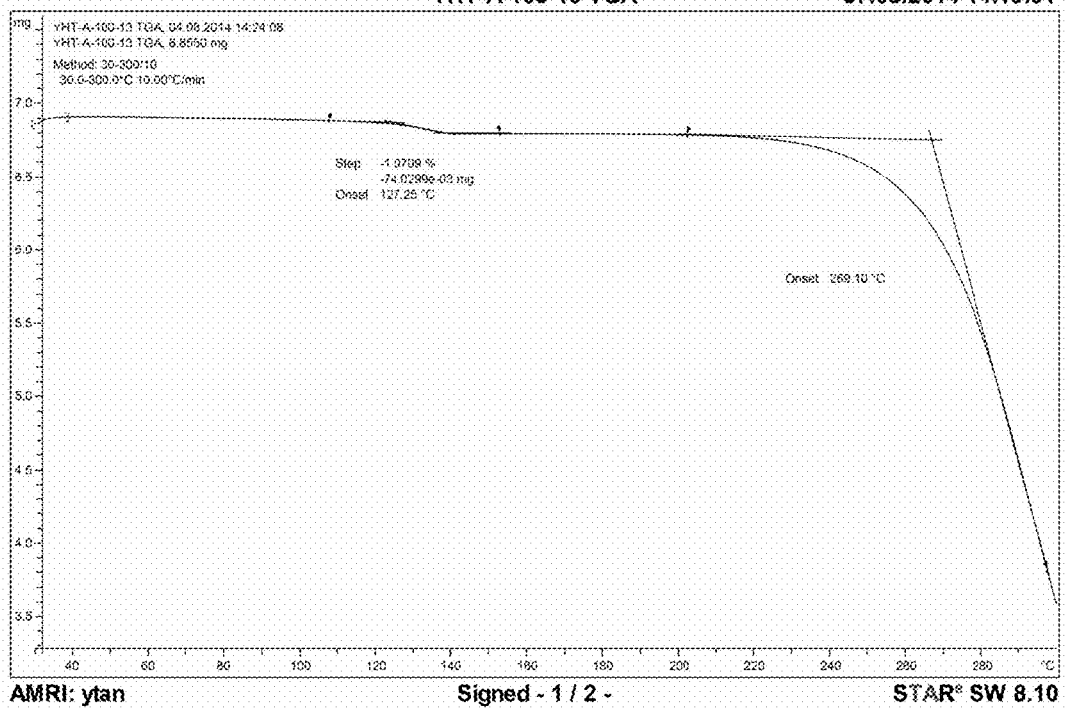
FIG. 20 depicts a TGA thermogram of Form C of Compound 1.

In one embodiment, provided herein is Form C having a TGA thermogram corresponding substantially to the representative TGA thermogram as depicted in FIG. 20. In certain embodiments, the crystalline form exhibits a TGA thermogram comprising about 1.08% mass loss before about 150.0° C. when heated from approximately 30° C. to approximately 300° C. The TGA thermogram further comprises a decomposition event with an onset temperature at approximately 269.1° C. when heated from approximately 30° C. to approximately 300° C.

In one embodiment, provided herein is Form C that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 4:
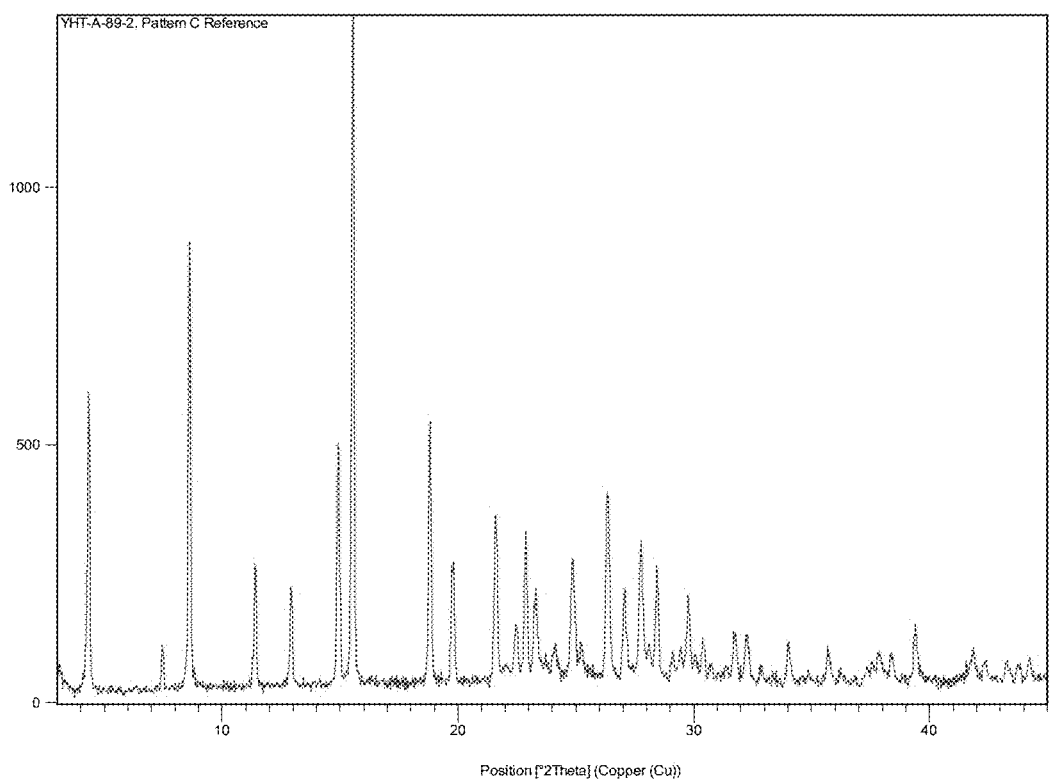
FIG. 4 depicts an XRPD pattern of Form C of Compound 1.

In certain embodiments, a solid form provided herein, e.g., Form C, is substantially crystalline, as indicated by, e.g., X-ray powder diffraction measurements. In one embodiment, Form C has an X-ray powder diffraction pattern substantially as shown in FIG. 4. In one embodiment, Form C has one or more characteristic X-ray powder diffraction peaks at approximately 3.09, 4.35, 7.46, 8.63, 11.41, 12.93, 14.94, 15.55, 18.80, 19.78, 21.60, 22.51, 22.89, 23.31, 24.10, 24.87, 25.25, 26.34, 27.07, 27.77, 28.10, 28.45, 29.09, 29.43, 29.75, 30.37, 30.73, 31.77, 32.24, 32.86, 34.02, 35.67, 37.86, 38.39, 39.35, 41.85, 42.35, 43.28, 43.74 or 44.24° 2θ as depicted in FIG. 4. In a specific embodiment, Form C has one, two, three, four, five, six, seven or eight characteristic X-ray powder diffraction peaks at approximately 4.35, 8.63, 11.41, 12.93, 14.94, 15.55, 18.80 or 21.60° 2θ. In another embodiment, Form C has one, two, three or four characteristic X-ray powder diffraction peaks at approximately 4.35, 8.63, 14.94 or 15.55° 2θ. In another embodiment, Form C has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine or forty characteristic X-ray powder diffraction peaks as set forth in Table 22.

In certain embodiments, a solid form provided herein, e.g., Form C, is substantially crystalline, as indicated by, e.g., X-ray powder diffraction measurements. In one embodiment, Form C has an X-ray powder diffraction pattern substantially as shown in FIG. 4. In one embodiment, Form C has one or more characteristic X-ray powder diffraction peaks at approximately 3.1, 4.4, 7.5, 8.6, 11.4, 12.9, 14.9, 15.6, 18.8, 19.8, 21.6, 22.5, 22.9, 23.3, 24.1, 24.9, 25.3, 26.3, 27.1, 27.8, 28.1, 28.5, 29.1, 29.4, 29.8, 30.4, 30.7, 31.8, 32.2, 32.9, 34.0, 35.7, 37.9, 38.4, 39.4, 41.9, 42.4, 43.3, 43.7 or 44.2° 2θ as depicted in FIG. 4. In a specific embodiment, Form C has one, two, three, four, five, six, seven or eight characteristic X-ray powder diffraction peaks at approximately 4.4, 8.6, 11.4, 12.9, 14.9, 15.6, 18.8 or 21.6° 2θ. In another embodiment, Form C has one, two, three or four characteristic X-ray powder diffraction peaks at approximately 4.4, 8.6, 14.9 or 15.6° 2θ. In another embodiment, Form C has one, two, three, four, five or six characteristic X-ray powder diffraction peaks at approximately 4.4, 8.6, 11.4, 14.9, 15.6 or 18.8° 2θ. In another embodiment, Form C has one, two, three or four characteristic X-ray powder diffraction peaks at approximately 4.4, 8.6, 11.4 or 15.6° 2θ. In another embodiment, Form C has one, two or three characteristic X-ray powder diffraction peaks at approximately 4.4, 8.6 or 15.6° 2θ. In another embodiment, Form C has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine or forty characteristic X-ray powder diffraction peaks as set forth in Table 22.

In still another embodiment, Form C is substantially pure. In certain embodiments, the substantially pure Form C is substantially free of other solid forms, e.g., Forms A, B, D, E, F, G or H. In certain embodiments, the purity of the substantially pure Form C is no less than about 95%, no less than about 96%, no less than about 97%, no less than about 98%, no less than about 98.5%, no less than about 99%, no less than about 99.5%, or no less than about 99.8%.

5.3.4 Form D of Compound 1

In certain embodiments, provided herein is Form D of Compound 1.

In one embodiment, Form D is a solid form of Compound 1. In one embodiment, Form D is anhydrous. In another embodiment, Form D is crystalline.

In certain embodiments, Form D is prepared by single solvent fast cooling crystallization, single solvent slow cooling crystallization, binary solvent fast cooling crystallization or binary solvent slow cooling crystallization experiments (see Table 1-Table 10).

In one embodiment, provided herein are methods for preparing Form D of Compound 1 comprising single solvent fast cooling crystallization comprising the steps of: (1) dissolving Compound 1 (e.g., approximately 10-55 mg) with a minimum amount of solvents (e.g., from about 0.25 mL to about 14.0 mL) at a first temperature (e.g., from about 30° C. to about 90° C.); (2) filtering the hot solution; (3) cooling the solution to a second temperature (e.g., from about −5° C. to about 10° C.) for a period of time (e.g., from about 6 hours to about 72 hours); (4) isolating the resulting solids; and (5) evaporating the samples without precipitation to dryness and collecting the resulting solids. See Table 1. In certain embodiments, the solvent is IPA, 1-BuOH, MeCN or EtOAc.

In one embodiment, provided herein are methods for preparing Form D of Compound 1 comprising single solvent fast cooling crystallization comprising the steps of: (1) dissolving Compound 1 (e.g., approximately 30-35 mg) with a minimum amount of solvents (e.g., up to about 7.0 mL) at a first temperature (e.g., about 50 or 70° C.); (2) filtering the hot solution (e.g., filtering through a 0.45 μm syringe filter); (3) cooling the solution to a second temperature (e.g., about 4° C.) for a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 1. In certain embodiments, the solvent is IPA, 1-BuOH, MeCN or EtOAc.

In one embodiment, provided herein are methods for preparing Form D of Compound 1 comprising single solvent slow cooling crystallization comprising the steps of: (1) dissolving Compound 1 (e.g., approximately 10-55 mg) with a minimum amount of solvents (e.g, from about 0.25 mL to about 14.0 mL) at a first temperature (e.g., from about 30° C. to about 90° C.); (2) filtering the hot solution; (3) cooling the hot solution to ambient temperature at a rate (e.g., from about 5° C./hr to about 40° C./hr) and allowing to equilibrate at ambient temperature over a period of time (e.g., from about 6 hours to about 72 hours); (4) isolating the resulting solids; and (5) evaporating the samples without precipitation to dryness and collecting the resulting solids. See Table 2. In certain embodiments, the solvent is IPA, EtOAc or MEK.

In one embodiment, provided herein are methods for preparing Form D of Compound 1 comprising single solvent slow cooling crystallization comprising the steps of: (1) dissolving Compound 1 (e.g., approximately 30-35 mg) with a minimum amount of solvents (e.g, up to about 7.0 mL) at a first temperature (e.g., about 50 or 70° C.); (2) filtering the hot solution (e.g., filtering through a 0.45 µm syringe filter); (3) cooling the hot solution to ambient temperature at a rate (e.g., about 20° C./hr) and allowing to equilibrate at ambient temperature over a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 2. In certain embodiments, the solvent is IPA, EtOAc or MEK.

In one embodiment, provided herein are methods for preparing Form D of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3, Table 5, Table 7 and Table 9). In certain embodiments, the solvent is MeOH, MeCN, n-Propanol, 1-BuOH, THF, 2-MeTHF, EtOAc, IPA, IPAc, acetone, MEK or MIBK. In certain embodiments, the co-solvent is water, toluene, heptane or cyclohexane.

In one embodiment, provided herein are methods for preparing Form D of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3, Table 5, Table 7 and Table 9). In certain embodiments, the solvent is MeOH, MeCN, n-Propanol, 1-BuOH, THF, 2-MeTHF, EtOAc, IPA, IPAc, acetone, MEK or MIBK. In certain embodiments, the co-solvent is water, toluene, heptane or cyclohexane.

In one embodiment, provided herein are methods for preparing Form D of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form. (see Table 4, Table 6, Table 8 and Table 10). In certain embodiments, the solvent is n-propanol, 1-BuOH, MeOH, MeCN, THF, acetone, MEK or MIBK. In certain embodiments, the co-solvent is water, toluene, heptane or cyclohexane.

In one embodiment, provided herein are methods for preparing Form D of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 4, Table 6, Table 8 and Table 10). In certain embodiments, the solvent is n-propanol, 1-BuOH, MeOH, MeCN, THF, acetone, MEK or MIBK. In certain embodiments, the co-solvent is water, toluene, heptane or cyclohexane.

In one embodiment, provided herein is Form D having a DSC thermogram substantially as depicted in FIG. 11. In certain embodiments, the crystalline form exhibits a DSC thermogram comprising an endothermic event with a maximum at about 185.2° C. when heated from approximately 30° C. to approximately 230° C. In one embodiment, the DSC thermogram further comprises an exothermic event with a maximum at about 118.7° C. when heated from approximately 30° C. to approximately 230° C.

In one embodiment, provided herein is Form D having a TGA thermogram corresponding substantially to the representative TGA thermogram as depicted in FIG. 12. In certain embodiments, the crystalline form exhibits a TGA thermogram comprising no mass loss before about 155° C. when heated from approximately 30° C. to approximately 300° C. The TGA thermogram further comprises a decomposition event with an onset temperature at approximately 259.8° C. when heated from approximately 30° C. to approximately 300° C. Thus, in certain embodiments, the crystalline form has no mass loss at a temperature lower than about 100° C.

In one embodiment, provided herein is slightly hygroscopic Form D having about 0.7% weight moisture uptake at 60% RH and about 1.0% weight moisture uptake at 90% RH. See FIG. 24.

In one embodiment, provided herein is Form D that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 5:
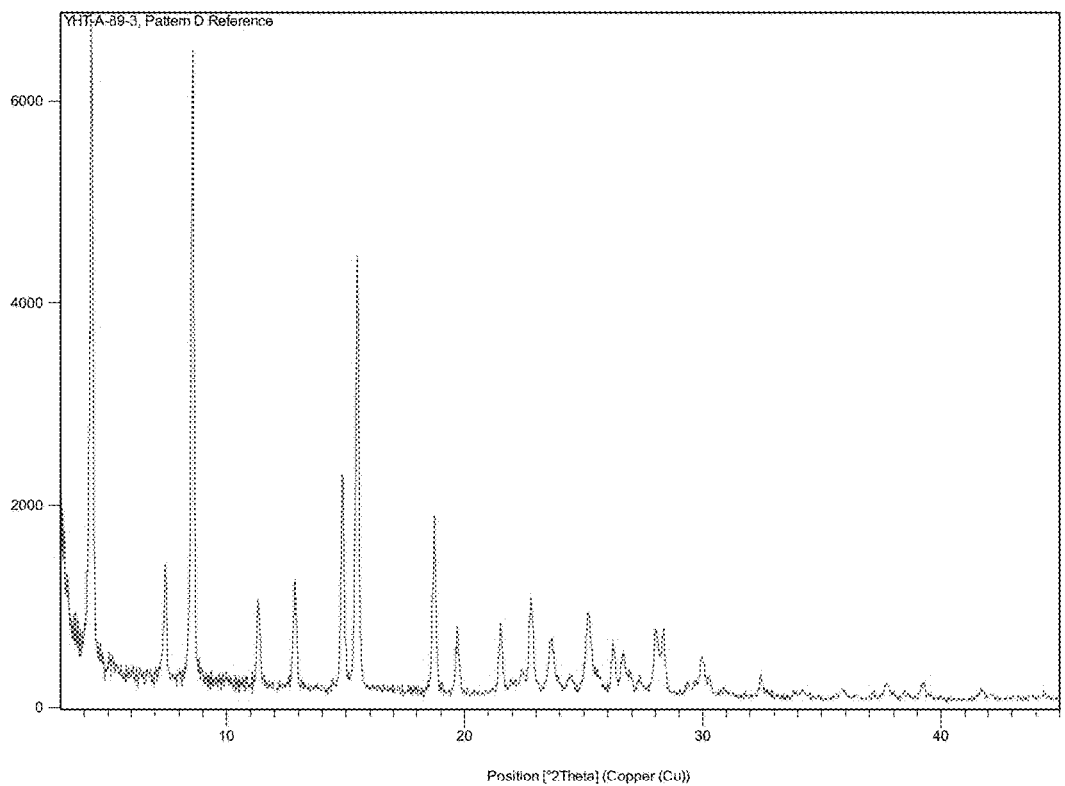
FIG. 5 depicts an XRPD pattern of Form D of Compound 1.

In certain embodiments, a solid form provided herein, e.g., Form D, is substantially crystalline, as indicated by, e.g., X-ray powder diffraction measurements. In one embodiment, Form D has an X-ray powder diffraction pattern substantially as shown in FIG. 5. In one embodiment, Form D has one or more characteristic X-ray powder diffraction peaks at approximately 4.32, 7.44, 8.59, 11.31, 12.85, 14.85, 15.49, 18.72, 19.71, 21.51, 22.40, 22.75, 23.62, 24.48, 25.17, 26.19, 26.68, 26.96, 27.32, 27.98, 28.35, 29.34, 29.98, 30.30, 32.44, 34.07, 35.81, 37.16, 37.69, 38.44, 39.25, 41.71, 42.19 or 44.35° 2θ as depicted in FIG. 5. In a specific embodiment, Form D has one, two, three, four, five, six, seven or eight characteristic X-ray powder diffraction peaks at approximately 4.32, 7.44, 8.59, 11.31, 12.85, 14.85, 15.49 or 18.72° 2θ. In another embodiment, Form D has one, two, three or four characteristic X-ray powder diffraction peaks at approximately 4.32, 8.59, 14.85 or 15.49° 2θ. In another embodiment, Form D has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three or thirty-four characteristic X-ray powder diffraction peaks as set forth in Table 23.

In certain embodiments, a solid form provided herein, e.g., Form D, is substantially crystalline, as indicated by, e.g., X-ray powder diffraction measurements. In one embodiment, Form D has an X-ray powder diffraction pattern substantially as shown in FIG. 5. In one embodiment, Form D has one or more characteristic X-ray powder diffraction peaks at approximately 4.3, 7.4, 8.6, 11.3, 12.9, 14.9, 15.5, 18.7, 19.7, 21.5, 22.4, 22.8, 23.6, 24.5, 25.2, 26.2, 26.7, 27.0, 27.3, 28.0, 28.4, 29.3, 30.0, 30.3, 32.4, 34.1, 35.8, 37.2, 37.7, 38.4, 39.3, 41.7, 42.2 or 44.4° 2θ as depicted in FIG. 5. In a specific embodiment, Form D has one, two, three, four, five, six, seven or eight characteristic X-ray powder diffraction peaks at approximately 4.3, 7.4, 8.6, 11.3, 12.9, 14.9, 15.5 or 18.7° 2θ. In another embodiment, Form D has one, two, three or four characteristic X-ray powder diffraction peaks at approximately 4.3, 8.6, 14.9 or 15.5° 2θ. In another embodiment, Form D has one, two, three, four, five, six or seven characteristic X-ray powder diffraction peaks at approximately 4.3, 7.4, 8.6, 12.9, 14.9, 15.5 or 18.7° 2θ. In another embodiment, Form D has one, two, three, four, five or six characteristic X-ray powder diffraction peaks at approximately 4.3, 8.6, 12.8, 14.9, 15.5 or 18.7° 2θ. In another embodiment, Form D has one, two, three or four characteristic X-ray powder diffraction peaks at approximately 4.3, 7.4, 8.6 or 15.5° 2θ. In another embodiment, Form D has one, two or three characteristic X-ray powder diffraction peaks at approximately 4.3, 8.6 or 15.5° 2θ. In another embodiment, Form D has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three or thirty-four characteristic X-ray powder diffraction peaks as set forth in Table 23.

In still another embodiment, Form D is substantially pure. In certain embodiments, the substantially pure Form D is substantially free of other solid forms, e.g., Forms A, B, C, E, F, G and H. In certain embodiments, the purity of the substantially pure Form D is no less than about 95%, no less than about 96%, no less than about 97%, no less than about 98%, no less than about 98.5%, no less than about 99%, no less than about 99.5%, or no less than about 99.8%.

5.3.5 Form E of Compound 1

In certain embodiments, provided herein is Form E of Compound 1.

In one embodiment, Form E is a solid form of Compound 1. In one embodiment, Form E is anhydrous. In one embodiment, Form E is an anhydrous solid form of Compound 1 retaining residual solvent. In one embodiment, Form E is an anhydrous solid form of Compound 1 retaining residual EtOAc. In another embodiment, Form E is crystalline.

In certain embodiments, Form E is prepared by single solvent fast cooling crystallization, single solvent slow cooling crystallization, binary solvent fast cooling crystallization or binary solvent slow cooling crystallization experiments (see Table 1-Table 10).

In one embodiment, provided herein are methods for preparing Form E of Compound 1 comprising single solvent fast cooling crystallization comprising the steps of: (1) dissolving Compound 1 (e.g., approximately 10-55 mg) with a minimum amount of solvents (e.g., from about 0.25 mL to about 14.0 mL) at a first temperature (e.g., from about 30° C. to about 90° C.); (2) filtering the hot solution; (3) cooling the solution to a second temperature (e.g., from about −5° C. to about 10° C.) for a period of time (e.g., from about 6 hours to about 72 hours); (4) isolating the resulting solids; and (5) evaporating the samples without precipitation to dryness and collecting the resulting solids. See Table 1. In certain embodiments, the solvent is 2-MeTHF, MEK or n-Propanol.

In one embodiment, provided herein are methods for preparing Form E of Compound 1 comprising single solvent fast cooling crystallization comprising the steps of: (1) dissolving Compound 1 (e.g., approximately 30-35 mg) with a minimum amount of solvents (e.g., up to about 7.0 mL) at a first temperature (e.g., about 50 or 70° C.); (2) filtering the hot solution (e.g., filtering through a 0.45 μm syringe filter); (3) cooling the solution to a second temperature (e.g., about 4° C.) for a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 1. In certain embodiments, the solvent is 2-MeTHF, MEK or n-Propanol.

In one embodiment, provided herein are methods for preparing Form E of Compound 1 comprising single solvent slow cooling crystallization comprising the steps of: (1) dissolving Compound 1 (e.g., approximately 10-55 mg) with a minimum amount of solvents (e.g, from about 0.25 mL to about 14.0 mL) at a first temperature (e.g., from about 30° C. to about 90° C.); (2) filtering the hot solution; (3) cooling the hot solution to ambient temperature at a rate (e.g., from about 5° C./hr to about 40° C./hr) and allowing to equilibrate at ambient temperature over a period of time (e.g., from about 6 hours to about 72 hours); (4) isolating the resulting solids; and (5) evaporating the samples without precipitation to dryness and collecting the resulting solids. See Table 2. In certain embodiments, the solvent is 1-BuOH, 2-MeTHF or n-Propanol.

In one embodiment, provided herein are methods for preparing Form E of Compound 1 comprising single solvent slow cooling crystallization comprising the steps of: (1) dissolving Compound 1 (e.g., approximately 30-35 mg) with a minimum amount of solvents (e.g, up to about 7.0 mL) at a first temperature (e.g., about 50 or 70° C.); (2) filtering the hot solution (e.g., filtering through a 0.45 μm syringe filter); (3) cooling the hot solution to ambient temperature at a rate (e.g., about 20° C./hr) and allowing to equilibrate at ambient temperature over a period of time (e.g., about 24 hours); (4) isolating the resulting solids (e.g., isolating by vacuum filtration); and (5) evaporating the samples without precipitation to dryness (e.g., evaporating under a gentle stream of nitrogen) and collecting the resulting solids. See Table 2. In certain embodiments, the solvent is 1-BuOH, 2-MeTHF or n-Propanol.

In one embodiment, provided herein are methods for preparing Form E of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3, Table 5, Table 7 and Table 9). In certain embodiments, the solvent is IPA, MEK, n-Propanol, EtOH, 1-BuOH, IPA, THF, 2-MeTHF or EtOAc. In certain embodiments, the co-solvent is toluene, heptane or cyclohexane.

In one embodiment, provided herein are methods for preparing Form E of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3, Table 5, Table 7 and Table 9). In certain embodiments, the solvent is IPA, MEK, n-Propanol, EtOH, 1-BuOH, IPA, THF, 2-MeTHF or EtOAc. In certain embodiments, the co-solvent is toluene, heptane or cyclohexane.

In one embodiment, provided herein are methods for preparing Form E of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 4, Table 6, Table 8 and Table 10). In certain embodiments, the solvent is EtOH, THF, IPA, 2-MeTHF, EtOAc, n-Propanol, 1-BuOH or MIBK. In certain embodiments, the co-solvent is water, toluene, heptane or cyclohexane.

In one embodiment, provided herein are methods for preparing Form E of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 4, Table 6, Table 8 and Table 10). In certain embodiments, the solvent is EtOH, THF, IPA, 2-MeTHF, EtOAc, n-Propanol, 1-BuOH or MIBK. In certain embodiments, the co-solvent is water, toluene, heptane or cyclohexane.

Figure 27:
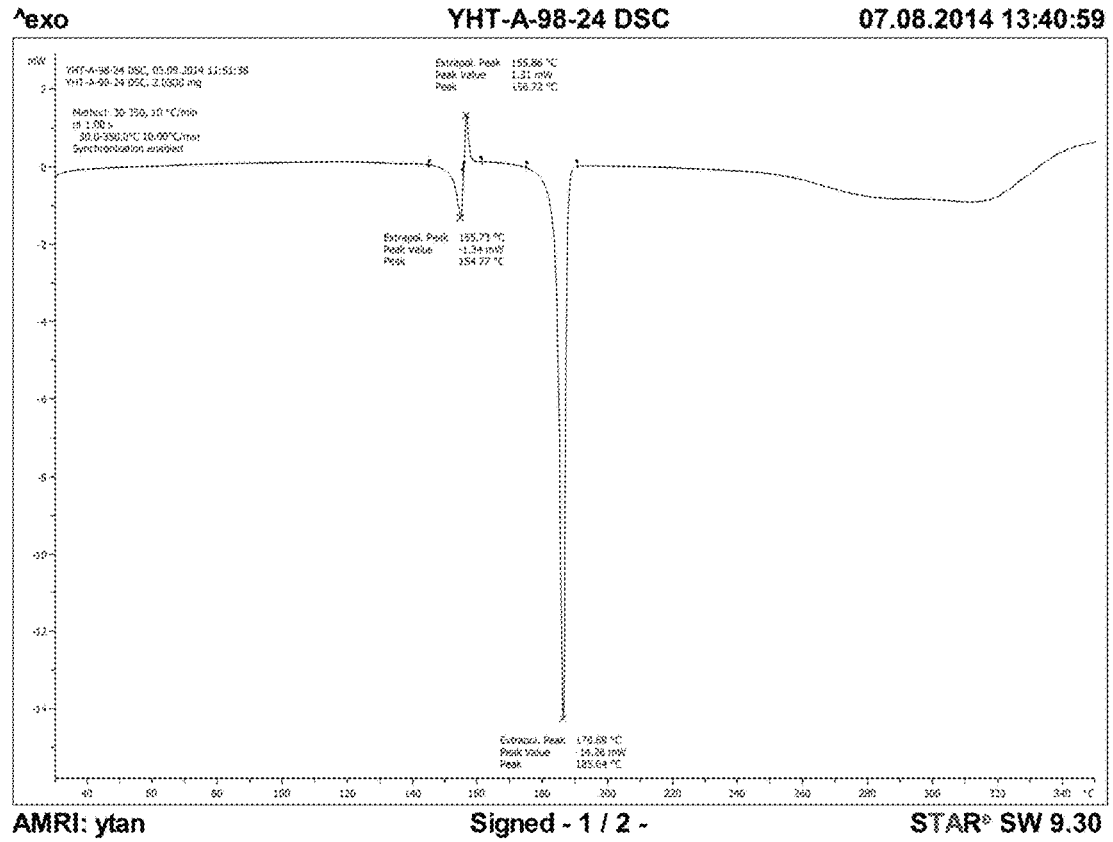
FIG. 27 depicts a DSC thermogram of Form E of Compound 1.

In one embodiment, provided herein is Form E having a DSC thermogram substantially as depicted in FIG. 27. In certain embodiments, the crystalline form exhibits a DSC thermogram comprising an endothermic event with a maximum at about 154.8° C. when heated from approximately 30° C. to approximately 230° C. In one embodiment, the DSC thermogram further comprises an endothermic event with a maximum at about 185.6° C. when heated from approximately 30° C. to approximately 230° C. In one embodiment, the DSC thermogram further comprises an exothermic event with a maximum at about 156.7° C. when heated from approximately 30° C. to approximately 230° C.

Figure 28:
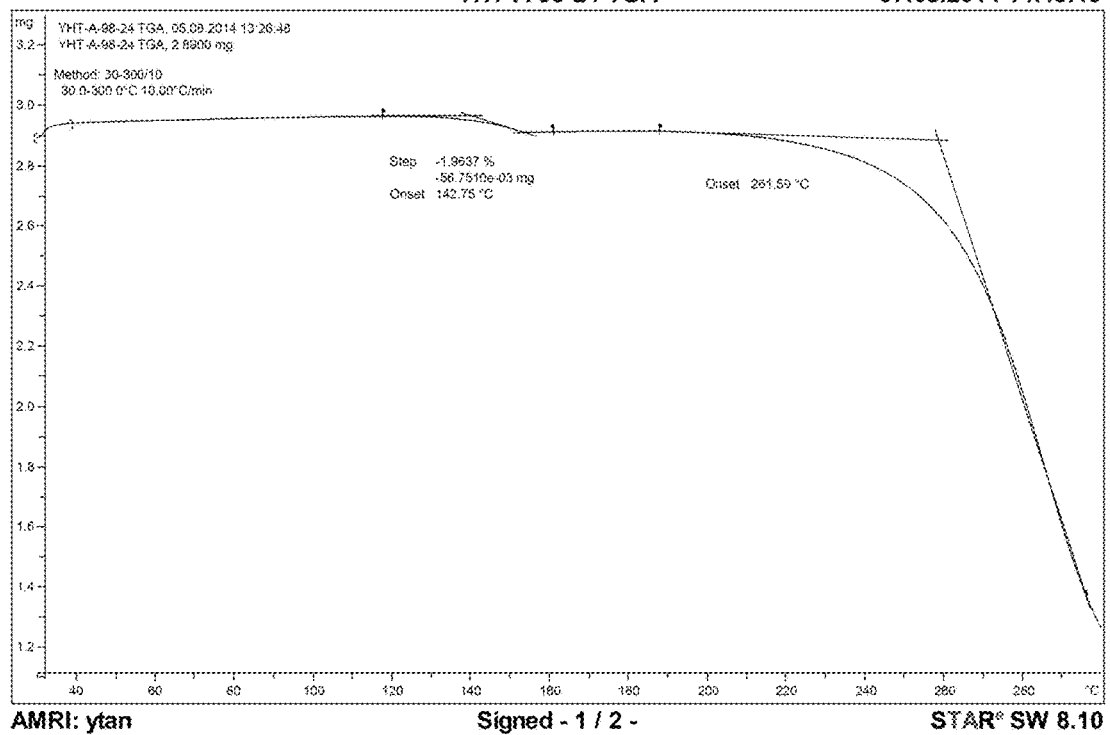
FIG. 28 depicts a TGA thermogram of Form E of Compound 1.

In one embodiment, provided herein is Form E having a TGA thermogram corresponding substantially to the representative TGA thermogram as depicted in FIG. 28. In certain embodiments, the crystalline form exhibits a TGA thermogram comprising about 1.96% mass loss before about 165.0° C. when heated from approximately 30° C. to approximately 300° C. The TGA thermogram further comprises a decomposition event with an onset temperature at approximately 261.6° C. when heated from approximately 30° C. to approximately 300° C.

In one embodiment, provided herein is Form E that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 6:
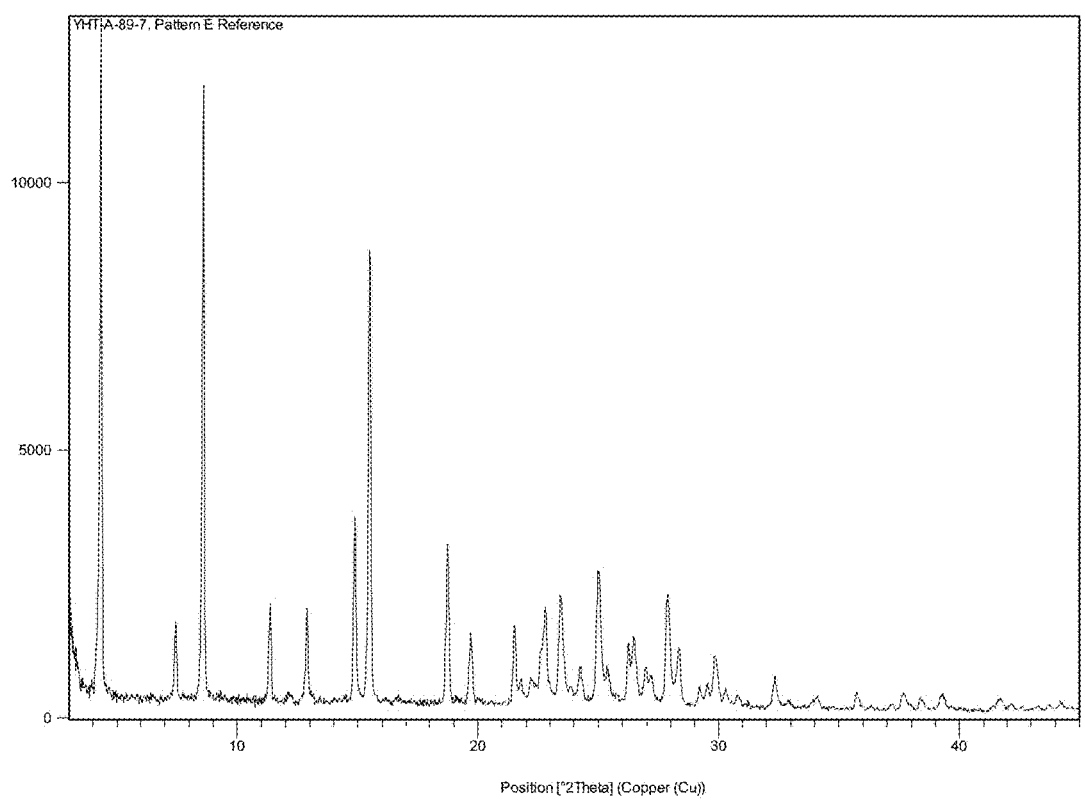
FIG. 6 depicts an XRPD pattern of Form E of Compound 1.

In certain embodiments, a solid form provided herein, e.g., Form E, is substantially crystalline, as indicated by, e.g., X-ray powder diffraction measurements. In one embodiment, Form E has an X-ray powder diffraction pattern substantially as shown in FIG. 6. In one embodiment, Form E has one or more characteristic X-ray powder diffraction peaks at approximately 4.33, 4.66, 5.42, 5.73, 5.99, 6.16, 6.29, 6.50, 7.46, 8.61, 9.32, 10.07, 10.78, 10.93, 11.37, 12.17, 12.89, 13.45, 14.45, 14.89, 15.50, 16.66, 18.74, 19.73, 20.04, 20.56, 21.53, 21.80, 22.19, 22.57, 22.81, 23.45, 23.87, 24.23, 24.97, 25.35, 26.24, 26.47, 26.96, 27.24, 27.85, 28.36, 29.19, 29.57, 29.85, 30.30, 30.81, 31.25, 32.34, 32.93, 34.10, 34.77, 35.74, 36.36, 37.23, 37.71, 38.36, 39.28, 40.74, 41.66, 42.19, 42.61, 43.29, 43.71 or 44.18° 2θ as depicted in FIG. 6. In a specific embodiment, Form E has one, two, three, four, five, six, seven or eight characteristic X-ray powder diffraction peaks at approximately 4.33, 8.61, 14.89, 15.50, 18.74, 23.45, 24.97 or 27.85° 2θ. In another embodiment, Form E has one, two, three or four characteristic X-ray powder diffraction peaks at approximately 4.33, 8.61, 14.89 or 15.50° 2θ. In another embodiment, Form E has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four or sixty-five characteristic X-ray powder diffraction peaks as set forth in Table 24.

In certain embodiments, a solid form provided herein, e.g., Form E, is substantially crystalline, as indicated by, e.g., X-ray powder diffraction measurements. In one embodiment, Form E has an X-ray powder diffraction pattern substantially as shown in FIG. 6. In one embodiment, Form E has one or more characteristic X-ray powder diffraction peaks at approximately 4.3, 4.7, 5.4, 5.7, 6.0, 6.2, 6.3, 6.5, 7.5, 8.6, 9.3, 10.1, 10.8, 10.9, 11.4, 12.2, 12.9, 13.5, 14.5, 14.9, 15.5, 16.7, 18.7, 19.7, 20.0, 20.6, 21.5, 21.8, 22.2, 22.6, 22.8, 23.5, 23.9, 24.2, 25.0, 25.4, 26.2, 26.5, 27.0, 27.2, 27.9, 28.4, 29.2, 29.6, 29.9, 30.3, 30.8, 31.3, 32.3, 32.9, 34.1, 34.8, 35.7, 36.4, 37.2, 37.7, 38.4, 39.3, 40.7, 41.7, 42.2, 42.6, 43.3, 43.7 or 44.2° 2θ as depicted in FIG. 6. In a specific embodiment, Form E has one, two, three, four, five, six, seven or eight characteristic X-ray powder diffraction peaks at approximately 4.3, 8.6, 14.9, 15.5, 18.7, 23.5, 25.0 or 27.9° 2θ. In another embodiment, Form E has one, two, three or four characteristic X-ray powder diffraction peaks at approximately 4.3, 8.6, 14.9 or 15.5° 2θ. In another embodiment, Form E has one, two, three, four, five, six or seven characteristic X-ray powder diffraction peaks at approximately 4.3, 8.6, 14.9, 15.5 18.7, 25.0 or 27.9° 2θ. In another embodiment, Form E has one, two, three, four, five or six characteristic X-ray powder diffraction peaks at approximately 4.3, 8.6, 14.9, 15.5 18.7 or 25.0° 2θ. In another embodiment, Form E has one, two, three or four characteristic X-ray powder diffraction peaks at approximately 4.3, 8.6, 15.5 or 27.9° 2θ. In another embodiment, Form E has one, two or three characteristic X-ray powder diffraction peaks at approximately 4.3, 8.6 or 15.5° 2θ. In another embodiment, Form E has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four or sixty-five characteristic X-ray powder diffraction peaks as set forth in Table 24.

In still another embodiment, Form E is substantially pure. In certain embodiments, the substantially pure Form E is substantially free of other solid forms, e.g., Forms A, B, C, D, F, G and H. In certain embodiments, the purity of the substantially pure Form E is no less than about 95%, no less than about 96%, no less than about 97%, no less than about 98%, no less than about 98.5%, no less than about 99%, no less than about 99.5%, or no less than about 99.8%.

5.3.6 Form F of Compound 1

In certain embodiments, provided herein is Form F.

In one embodiment, Form F is a solid form of Compound 1. In one embodiment, Form F is a hydrate solid form of Compound 1. In another embodiment, Form F is crystalline.

In certain embodiments, Form F is prepared by binary solvent fast cooling crystallization or binary solvent slow cooling crystallization experiments (see Table 3 and Table 4).

In one embodiment, provided herein are methods for preparing Form F of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about −5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3). In certain embodiments, the solvent is THF, n-Propanol or MIBK. In certain embodiments, the co-solvent is water.

In one embodiment, provided are methods for preparing Form F of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3). In certain embodiments, the solvent is THF, n-Propanol or MIBK. In certain embodiments, the co-solvent is water.

In one embodiment, provided herein are methods for preparing Form F of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooling the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 4). In certain embodiments, the solvent is THF. In certain embodiments, the co-solvent is water.

In one embodiment, provided herein are methods for preparing Form F of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 4). In certain embodiments, the solvent is THF. In certain embodiments, the co-solvent is water.

Figure 30:
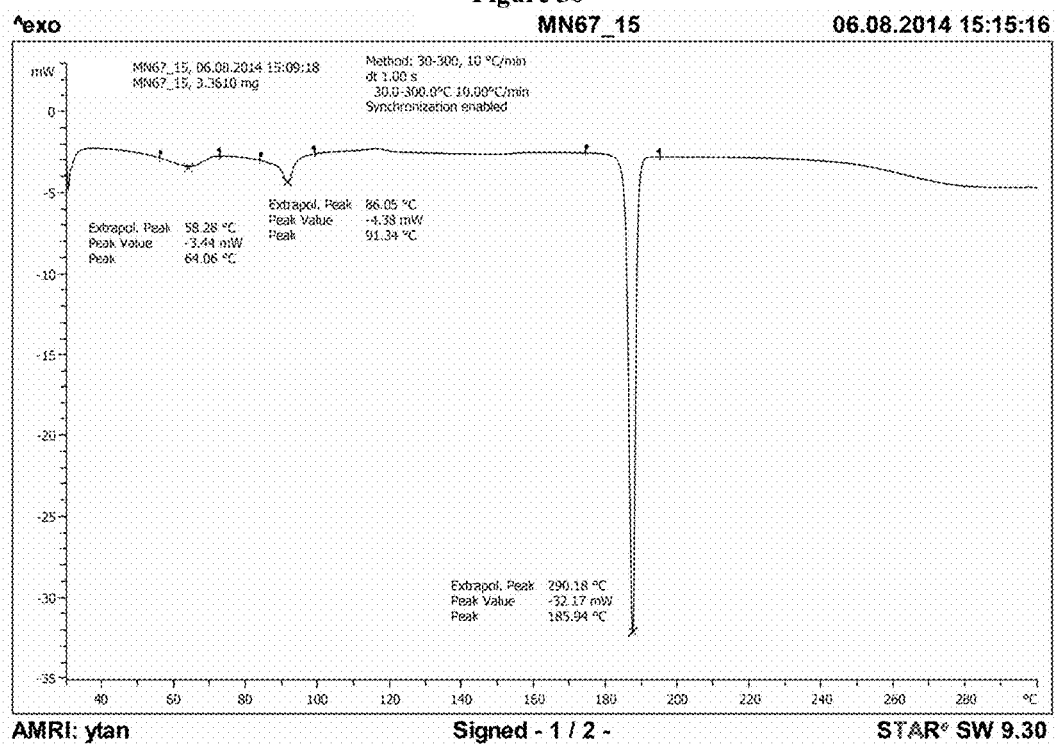
FIG. 30 depicts a DSC thermogram of Form F of Compound 1.

In one embodiment, provided herein is Form F having a DSC thermogram substantially as depicted in FIG. 30. In certain embodiments, the crystalline form exhibits a DSC thermogram comprising an endothermic event with a maximum at about 64.1° C. when heated from approximately 30° C. to approximately 230° C. In one embodiment, the DSC thermogram further comprises an endothermic event with a maximum at about 91.3° C. when heated from approximately 30° C. to approximately 230° C. In one embodiment, the DSC thermogram further comprises an endothermic event with a maximum at about 185.9° C. when heated from approximately 30° C. to approximately 230° C.

Figure 31:
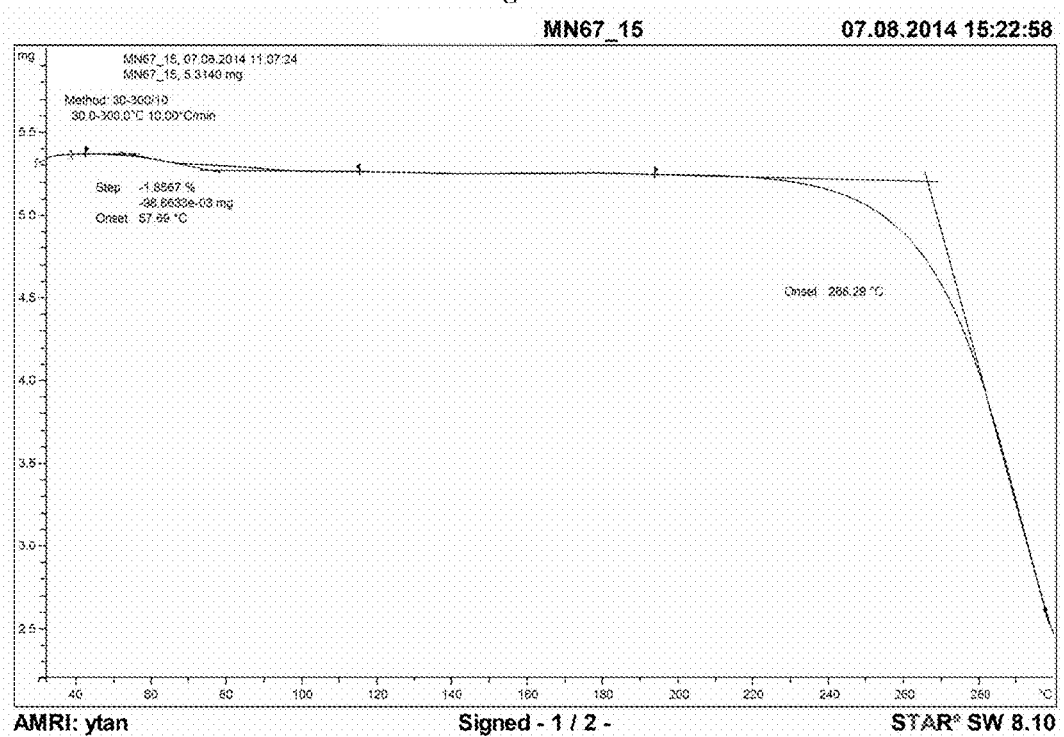
FIG. 31 depicts a TGA thermogram of Form F of Compound 1.

In one embodiment, provided herein is Form F having a TGA thermogram corresponding substantially to the representative TGA thermogram as depicted in FIG. 31. In certain embodiments, the crystalline form exhibits a TGA thermogram comprising about 1.86% mass loss before about 110.0° C. when heated from approximately 30° C. to approximately 300° C. The TGA thermogram further comprises a decomposition event with an onset temperature at approximately 268.3° C. when heated from approximately 30° C. to approximately 300° C.

In one embodiment, provided herein is Form F that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 7:
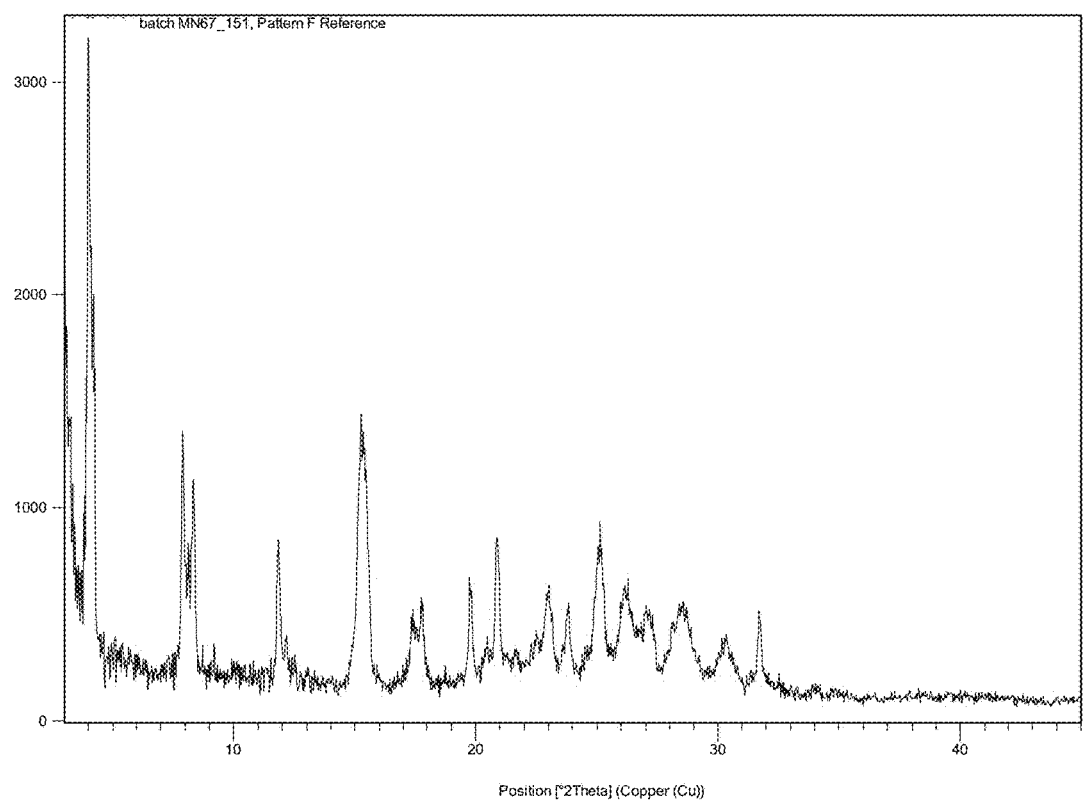
FIG. 7 depicts an XRPD pattern of Form F of Compound 1.

In certain embodiments, a solid form provided herein, e.g., Form F, is substantially crystalline, as indicated by, e.g., X-ray powder diffraction measurements. In one embodiment, Form F has an X-ray powder diffraction pattern substantially as shown in FIG. 7. In one embodiment, Form F has one or more characteristic X-ray powder diffraction peaks at approximately 3.99, 4.23, 7.89, 8.36, 11.81, 15.21, 15.44, 17.39, 17.79, 19.78, 20.87, 22.98, 23.83, 25.17, 26.10, 27.15, 28.53, 30.30, 31.71 or 34.06° 2θ as depicted in FIG. 7. In a specific embodiment, Form F has one, two, three, four, five, six, seven or eight characteristic X-ray powder diffraction peaks at approximately 3.99, 4.23, 7.89, 8.36, 15.21, 15.44, 20.87 or 25.17° 2θ. In another embodiment, Form F has one, two, three or four characteristic X-ray powder diffraction peaks at approximately 3.99, 4.23, 7.89 or 15.21° 2θ. In another embodiment, Form F has one, two, three, four, five, six, seven, eight, nine, ten, eleven, twelve, thirteen, fourteen, fifteen, sixteen, seventeen, eighteen, nineteen or twenty characteristic X-ray powder diffraction peaks as set forth in Table 25.

In certain embodiments, a solid form provided herein, e.g., Form F, is substantially crystalline, as indicated by, e.g., X-ray powder diffraction measurements. In one embodiment, Form F has an X-ray powder diffraction pattern substantially as shown in FIG. 7. In one embodiment, Form F has one or more characteristic X-ray powder diffraction peaks at approximately 4.0, 4.2, 7.9, 8.4, 11.8, 15.2, 15.4, 17.4, 17.8, 19.8, 20.9, 23.0, 23.8, 25.2, 26.1, 27.2, 28.5, 30.3, 31.7 or 34.1° 2θ as depicted in FIG. 7. In a specific embodiment, Form F has one, two, three, four, five, six, seven or eight characteristic X-ray powder diffraction peaks at approximately 4.0, 4.2, 7.9, 8.4, 15.2, 15.4, 20.9 or 25.2° 2θ. In another embodiment, Form F has one, two, three or four characteristic X-ray powder diffraction peaks at approximately 4.0, 4.2, 7.9 or 15.2° 2θ. In another embodiment, Form F has one, two, three, four, five or six characteristic X-ray powder diffraction peaks at approximately 4.0, 4.2, 7.9, 8.4, 15.2 or 15.4° 2θ. In another embodiment, Form F has one, two or three characteristic X-ray powder diffraction peaks at approximately 4.0, 4.2 or 15.2° 2θ. In another embodiment, Form F has one, two, three, four, five, six, seven, eight, nine, ten, eleven, twelve, thirteen, fourteen, fifteen, sixteen, seventeen, eighteen, nineteen or twenty characteristic X-ray powder diffraction peaks as set forth in Table 25.

In still another embodiment, Form F is substantially pure. In certain embodiments, the substantially pure Form F is substantially free of other solid forms, e.g., Forms A, B, C, D, E, G and H. In certain embodiments, the purity of the substantially pure Form F is no less than about 95%, no less than about 96%, no less than about 97%, no less than about 98%, no less than about 98.5%, no less than about 99%, no less than about 99.5%, or no less than about 99.8%.

5.3.7 Form G of Compound 1

In certain embodiments, provided herein is Form G.

In one embodiment, Form G is a solid form of Compound 1. In one embodiment, Form G is anhydrous. In another embodiment, Form G is crystalline.

In certain embodiments, Form G is prepared by binary solvent fast cooling crystallization or binary solvent slow cooling crystallization experiments (see Table 3 and Table 4).

In one embodiment, provided herein are methods for preparing Form G of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3). In certain embodiments, the solvent is MEK, MIBK or 2-MeTHF. In certain embodiments, the co-solvent is water.

In one embodiment, provided herein are methods for preparing Form G of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) cooling the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 4). In certain embodiments, the solvent is IPA or 2-MeTHF. In certain embodiments, the co-solvent is water.

Figure 33:
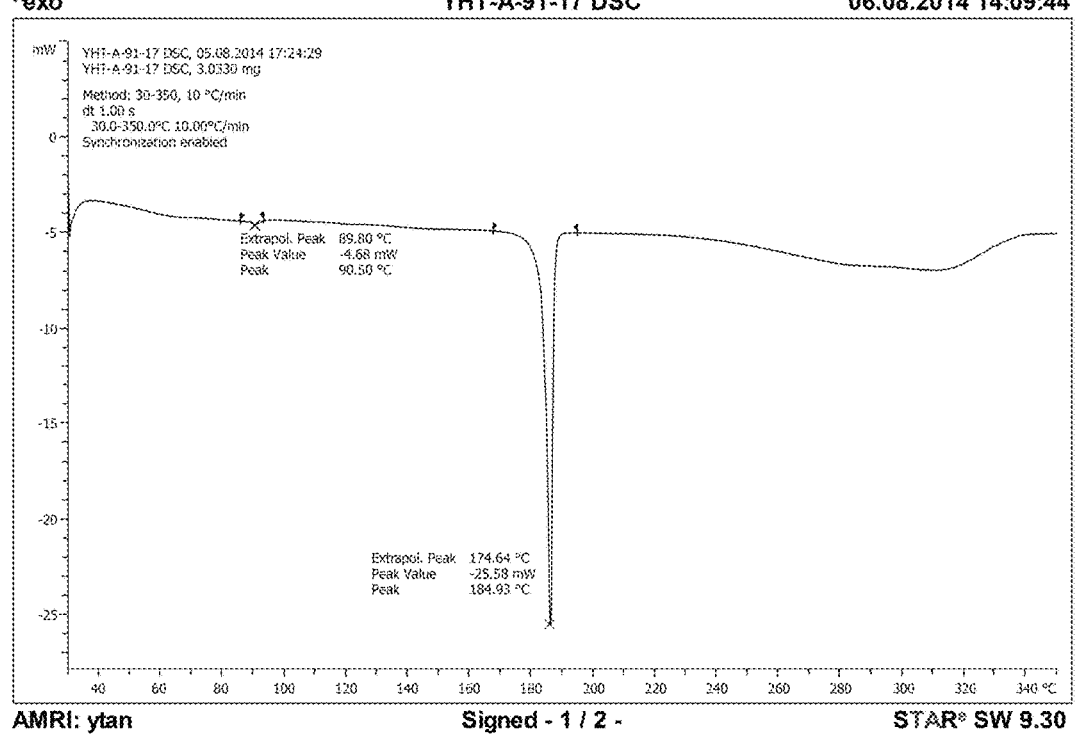
FIG. 33 depicts a DSC thermogram of Form G of Compound 1.

In one embodiment, provided herein is Form G having a DSC thermogram substantially as depicted in FIG. 33. In certain embodiments, the crystalline form exhibits a DSC thermogram comprising an endothermic event with a maximum at about 90.5° C. when heated from approximately 30° C. to approximately 230° C. In one embodiment, the DSC thermogram further comprises an endothermic event with a maximum at about 184.9° C. when heated from approximately 30° C. to approximately 230° C.

Figure 34:
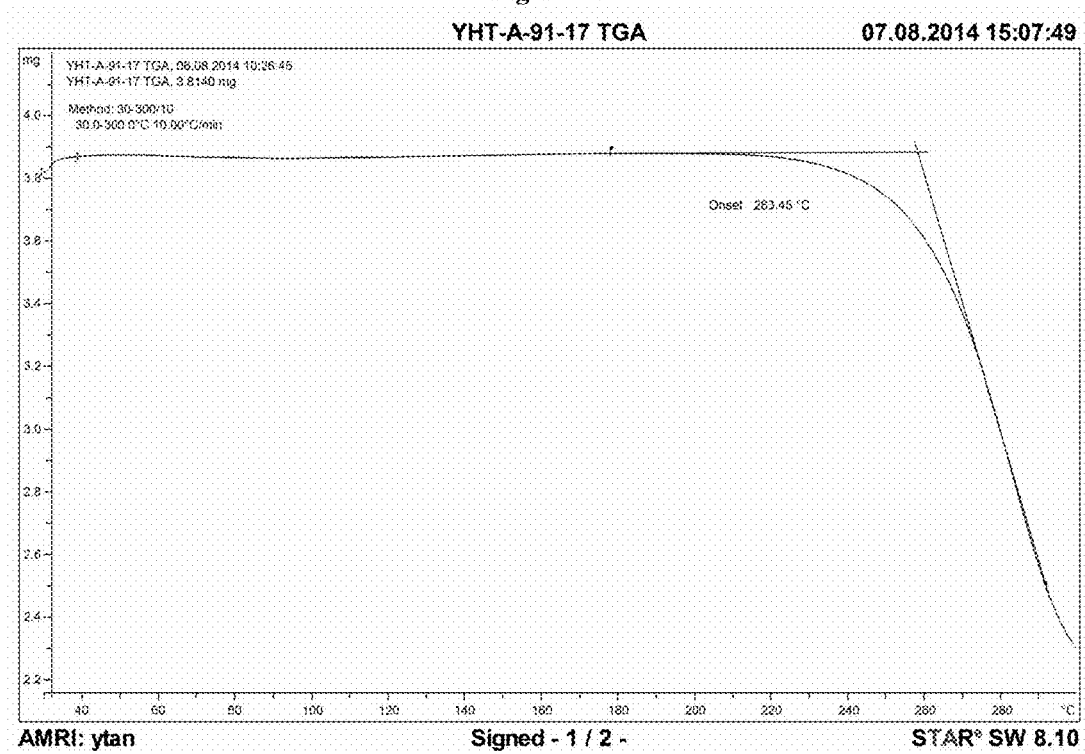
FIG. 34 depicts a TGA thermogram of Form G of Compound 1.

In one embodiment, provided herein is Form G having a TGA thermogram corresponding substantially to the representative TGA thermogram as depicted in FIG. 34. In certain embodiments, the crystalline form exhibits a TGA thermogram comprising no mass loss before about 110.0° C. when heated from approximately 30° C. to approximately 300° C. The TGA thermogram further comprises a decomposition event with an onset temperature at approximately 263.5° C. when heated from approximately 30° C. to approximately 300° C.

In one embodiment, provided herein is Form G that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

In one embodiment, provided herein is slightly hygroscopic Form G having about 0.4% weight moisture uptake at 60% RH and about 7.1% weight moisture uptake at 90% RH. See FIG. 35.

Figure 8:
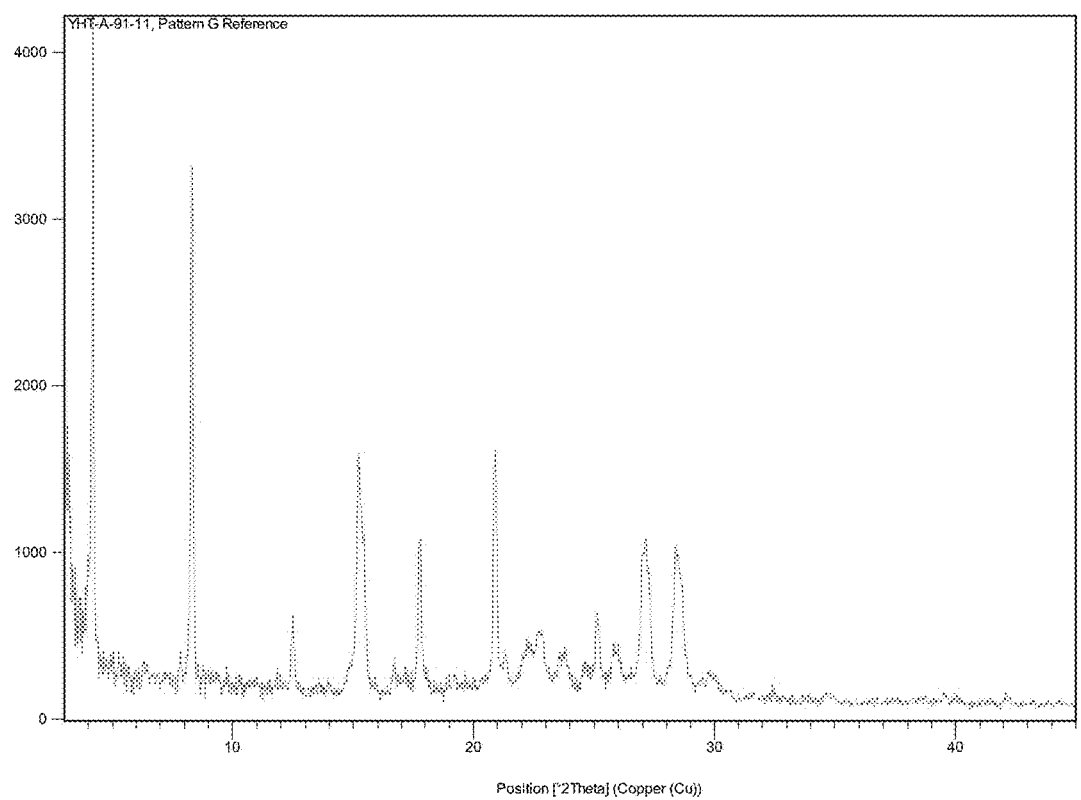
FIG. 8 depicts an XRPD pattern of Form G of Compound 1.

In certain embodiments, a solid form provided herein, e.g., Form G, is substantially crystalline, as indicated by, e.g., X-ray powder diffraction measurements. In one embodiment, Form G has an X-ray powder diffraction pattern substantially as shown in FIG. 8. In one embodiment, Form G has one or more characteristic X-ray powder diffraction peaks at approximately 4.19, 8.33, 12.47, 15.19, 15.44, 16.67, 17.81, 19.26, 20.87, 21.33, 22.18, 22.86, 23.71, 24.59, 25.09, 25.89, 27.00, 28.36, 28.63, 29.87, 32.45, 34.70, 39.53 or 42.08° 2θ as depicted in FIG. 8. In a specific embodiment, Form G has one, two, three, four, five, six, seven or eight characteristic X-ray powder diffraction peaks at approximately 4.19, 8.33, 15.19, 15.44, 17.81, 20.87, 27.00 or 28.36° 2θ. In another embodiment, Form G has one, two, three or four characteristic X-ray powder diffraction peaks at approximately 4.19, 8.33, 15.19 or 20.87° 2θ. In another embodiment, Form G has one, two, three, four, five, six, seven, eight, nine, ten, eleven, twelve, thirteen, fourteen, fifteen, sixteen, seventeen, eighteen, nineteen, twenty, twenty-one, twenty-two, twenty-three or twenty-four characteristic X-ray powder diffraction peaks as set forth in Table 26.

In certain embodiments, a solid form provided herein, e.g., Form G, is substantially crystalline, as indicated by, e.g., X-ray powder diffraction measurements. In one embodiment, Form G has an X-ray powder diffraction pattern substantially as shown in FIG. 8. In one embodiment, Form G has one or more characteristic X-ray powder diffraction peaks at approximately 4.2, 8.3, 12.5, 15.2, 15.4, 16.7, 17.8, 19.3, 20.9, 21.3, 22.2, 22.9, 23.7, 24.6, 25.1, 25.9, 27.0, 28.4, 28.6, 29.9, 32.5, 34.7, 39.5 or 42.1° 2θ as depicted in FIG. 8. In a specific embodiment, Form G has one, two, three, four, five, six, seven or eight characteristic X-ray powder diffraction peaks at approximately 4.2, 8.3, 15.2, 15.4, 17.8, 20.9, 27.0 or 28.4° 2θ. In another embodiment, Form G has one, two, three or four characteristic X-ray powder diffraction peaks at approximately 4.2, 8.3, 15.2 or 20.9° 2θ. In another embodiment, Form G has one, two, three, four, five or six characteristic X-ray powder diffraction peaks at approximately 4.2, 8.3, 15.2, 15.4, 17.8 or 20.9° 2θ. In another embodiment, Form G has one, two or three characteristic X-ray powder diffraction peaks at approximately 4.2, 8.3 or 15.2° 2θ. In another embodiment, Form G has one, two, three, four, five, six, seven, eight, nine, ten, eleven, twelve, thirteen, fourteen, fifteen, sixteen, seventeen, eighteen, nineteen, twenty, twenty-one, twenty-two, twenty-three or twenty-four characteristic X-ray powder diffraction peaks as set forth in Table 26.

In still another embodiment, Form G is substantially pure. In certain embodiments, the substantially pure Form G is substantially free of other solid forms, e.g., Forms A, B, C, D, E, F and H. In certain embodiments, the purity of the substantially pure Form G is no less than about 95%, no less than about 96%, no less than about 97%, no less than about 98%, no less than about 98.5%, no less than about 99%, no less than about 99.5%, or no less than about 99.8%.

5.3.8 Form H of Compound 1

In certain embodiments, provided herein is Form H.

In one embodiment, Form H is a solid form of Compound 1. In one embodiment, Form H is a solvate of Compound 1. In one embodiment, Form H is a DMSO solvate of Compound 1. In one embodiment, Form H is a mono-DMSO solvate of Compound 1. In another embodiment, Form H is crystalline.

In certain embodiments, Form H is prepared by binary solvent fast cooling crystallization or binary solvent slow cooling crystallization experiments (see Table 3 and Table 4).

In one embodiment, provided herein are methods for preparing Form H of Compound 1 comprising binary solvent fast cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) placing the solution at a second temperature (e.g., from about –5° C. to about 10° C.) for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 3 and Table 5). In certain embodiments, the solvent is DMSO. In certain embodiments, the co-solvent is toluene.

In one embodiment, provided herein are methods for preparing Form H of Compound 1 comprising binary solvent fast cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 µm syringe filter); (3) adding a co-solvent; (4) placing the solution at a second temperature (e.g., about 4° C.) for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 3 and Table 5). In certain embodiments, the solvent is DMSO. In certain embodiments, the co-solvent is toluene.

In one embodiment, provided herein are methods for preparing Form H of Compound 1 comprising binary solvent slow cooling crystallization comprising the steps of: (1) dissolving Compound 1 (e.g., about 10-55 mg) with a minimum amount of solvents (e.g., from about 0.25 mL to about 14.0 mL) at a first temperature (e.g., from about 30° C. to about 90° C.); (2) filtering the hot solution; (3) adding a co-solvent; (4) cooled the solution to ambient temperature at a rate (e.g., from about 5° C./hr to about 40° C./hr) and allowing to equilibrate at ambient temperature for a period of time (e.g., from about 6 hours to about 72 hours); (5) isolating the resulting solids; and (6) evaporating the samples without precipitation to dryness and collecting the resulting solids. All obtained solids were analyzed by XRPD to determine the solid form (see Table 6). In certain embodiments, the solvent is DMSO. In certain embodiments, the co-solvent is toluene.

In one embodiment, provided herein are methods for preparing Form H of Compound 1 comprising binary solvent slow cooling crystallization comprising the steps of: (1) dissolving Compound 1 (e.g., about 30-35 mg) with a minimum amount of solvents (e.g., up to 7.0 mL) at a first temperature (e.g., about 50 or 70° C.); (2) filtering the hot solution (e.g., filtering through a 0.45 μm syringe filter); (3) adding a co-solvent; (4) cooled the solution to ambient temperature at a rate (e.g., about 20° C./hr) and allowing to equilibrate at ambient temperature for a period of time (e.g., about 24 hours); (5) isolating the resulting solids (e.g., isolating by vacuum filtration); and (6) evaporating the samples without precipitation to dryness (e.g., evaporating under a gentle stream of nitrogen gas) and collecting the resulting solids. All obtained solids were analyzed by XRPD to determine the solid form (see Table 6). In certain embodiments, the solvent is DMSO. In certain embodiments, the co-solvent is toluene.

Figure 38:
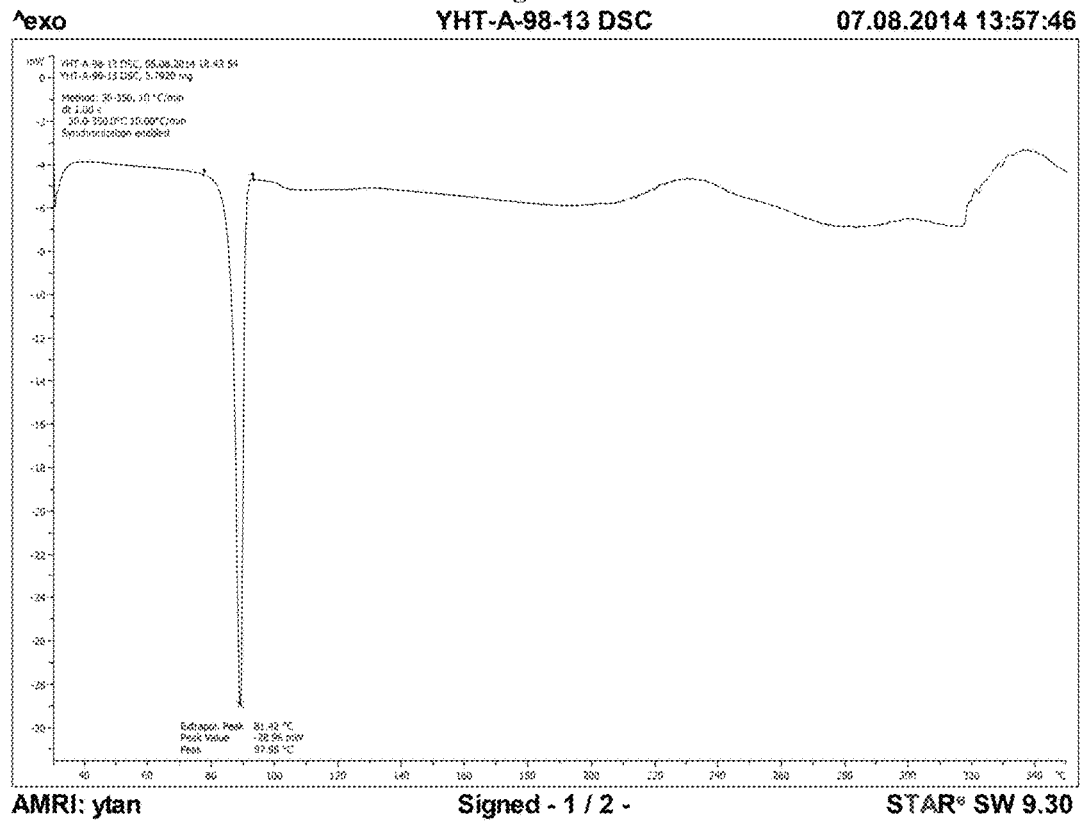
FIG. 38 depicts a DSC thermogram of Form H of Compound 1.

In one embodiment, provided herein is Form H having a DSC thermogram substantially as depicted in FIG. 38. In certain embodiments, the crystalline form exhibits a DSC thermogram comprising an endothermic event with a maximum at about 88.0° C. when heated from approximately 30° C. to approximately 230° C.

Figure 39:
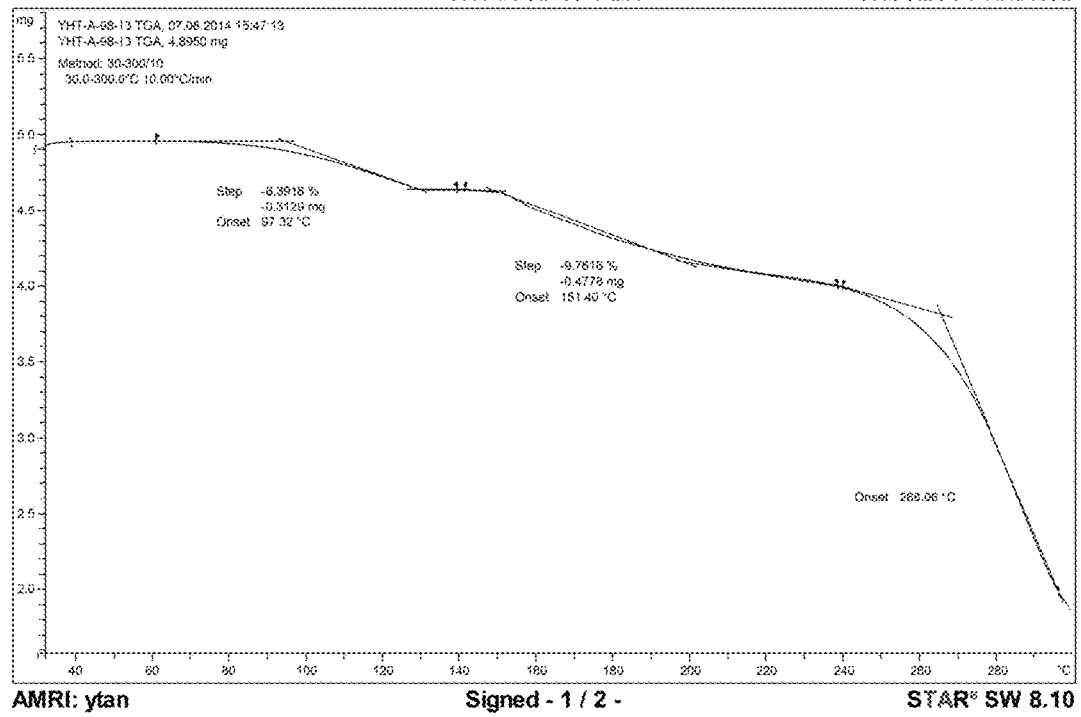
FIG. 39 depicts a TGA thermogram of Form H of Compound 1.

In one embodiment, provided herein is Form H having a TGA thermogram corresponding substantially to the representative TGA thermogram as depicted in FIG. 39. In certain embodiments, the crystalline form exhibits a TGA thermogram comprising about 6.4% mass loss before about 140° C. when heated from approximately 30° C. to approximately 300° C.

In certain embodiments, the TGA thermogram further comprises about 9.8% mass loss before about 240° C. when heated from approximately 30° C. to approximately 300° C. The TGA thermogram further comprises a decomposition event with an onset temperature at approximately 268.1° C. when heated from approximately 30° C. to approximately 300° C.

In one embodiment, provided herein is Form H that can be converted to Form A after being stirred in a solvent for a period of time. See Table 13. In one embodiment, the solvent is IPAc/heptane (e.g., about 1:2 (V:V)) or toluene. In one embodiment, the period of time is from about 1 day to about 7 days (e.g., about 1 day or about 7 days).

Figure 9:
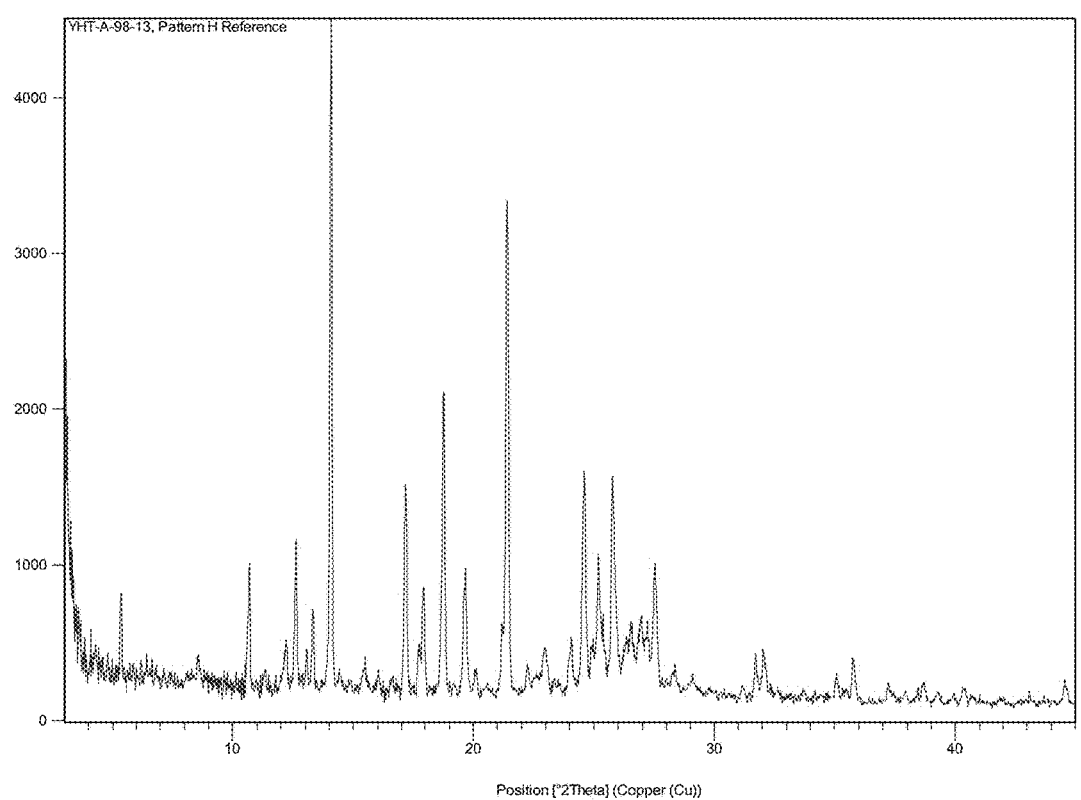
FIG. 9 depicts an XRPD pattern of Form H of Compound 1.

In certain embodiments, a solid form provided herein, e.g., Form H, is substantially crystalline, as indicated by, e.g., X-ray powder diffraction measurements. In one embodiment, Form H has an X-ray powder diffraction pattern substantially as shown in FIG. 9. In one embodiment, Form H has one or more characteristic X-ray powder diffraction peaks at approximately 3.07, 5.35, 8.56, 10.69, 12.20, 12.62, 13.08, 13.32, 14.08, 15.46, 16.04, 17.18, 17.69, 17.93, 18.76, 19.69, 20.14, 21.19, 21.40, 22.22, 22.99, 24.02, 24.59, 25.18, 25.75, 26.55, 26.93, 27.53, 28.32, 29.07, 31.19, 31.72, 32.05, 33.70, 35.09, 35.76, 37.23, 37.94, 38.67, 39.26, 39.96, 40.36, 43.14 or 44.56° 2θ as depicted in FIG. 9. In a specific embodiment, Form H has one, two, three, four, five, six, seven or eight characteristic X-ray powder diffraction peaks at approximately 3.07, 12.62, 14.08, 17.18, 18.76, 21.40, 24.59 or 25.75° 2θ. In another embodiment, Form H has one, two, three or four characteristic X-ray powder diffraction peaks at approximately 14.08, 18.76, 21.40 or 24.59° 2θ. In another embodiment, Form H has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three or forty-four characteristic X-ray powder diffraction peaks as set forth in Table 27.

In certain embodiments, a solid form provided herein, e.g., Form H, is substantially crystalline, as indicated by, e.g., X-ray powder diffraction measurements. In one embodiment, Form H has an X-ray powder diffraction pattern substantially as shown in FIG. 9. In one embodiment, Form H has one or more characteristic X-ray powder diffraction peaks at approximately 3.1, 5.4, 8.6, 10.7, 12.2, 12.6, 13.1, 13.3, 14.1, 15.5, 16.0, 17.2, 17.7, 17.9, 18.8, 19.7, 20.1, 21.2, 21.4, 22.2, 23.0, 24.0, 24.6, 25.2, 25.8, 26.6, 26.9, 27.5, 28.3, 29.1, 31.2, 31.7, 32.1, 33.7, 35.1, 35.8, 37.2, 37.9, 38.7, 39.3, 40.0, 40.4, 43.1 or 44.6° 2θ as depicted in FIG. 9. In a specific embodiment, Form H has one, two, three, four, five, six, seven or eight characteristic X-ray powder diffraction peaks at approximately 3.1, 12.6, 14.1, 17.2, 18.8, 21.4, 24.6 or 25.8° 2θ. In another embodiment, Form H has one, two, three or four characteristic X-ray powder diffraction peaks at approximately 14.1, 18.8, 21.4 or 24.6 °2θ. In another embodiment, Form H has one, two, three, four, five or six characteristic X-ray powder diffraction peaks at approximately 14.1, 17.2, 18.8, 21.4, 24.6 or 25.7° 2θ. In another embodiment, Form H has one, two or three characteristic X-ray powder diffraction peaks at approximately 14.1, 18.8 or 21.4° 2θ. In another embodiment, Form H has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three or forty-four characteristic X-ray powder diffraction peaks as set forth in Table 27.

In still another embodiment, Form H is substantially pure. In certain embodiments, the substantially pure Form H is substantially free of other solid forms, e.g., Forms A, B, C, D, E, F and G. In certain embodiments, the purity of the substantially pure Form H is no less than about 95%, no less than about 96%, no less than about 97%, no less than about 98%, no less than about 98.5%, no less than about 99%, no less than about 99.5%, or no less than about 99.8%.

5.4 Salts of Compound 1

In certain embodiments, provided herein are salts of Compound 1. In one embodiment, the salt is crystalline.

The salts provided herein (e.g., Salt I, Salt II, Salt III, Salt IV, Salt V and Salt VI of Compound 1) may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), dynamic vapor sorption (DVS), thermal gravimetric analysis (TGA), and hot-stage microscopy), spectroscopy (e.g., infrared, Raman, and solid-state nuclear magnetic resonance), high performance liquid chromatography (HPLC), and proton nuclear magnetic resonance ($^1$H NMR) spectrum. The particle size and size distribution of the salt provided herein may be determined by conventional methods, such as laser light scattering technique.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ(see United State Pharmacopoeia, page 2228 (2003)).

In certain embodiments, provided herein is a method for making a salt of Compound 1, comprising 1) dissolving Compound 1 in a solvent (e.g., CH$_3$OH, CH$_3$CN or acetone) to yield a mixture; 2) heating the mixture to an elevated temperature (e.g., about 30-70° C. or about 50° C.); 3) filtering the mixture at the elevated temperature to yield a solution; 4) adding a basic counter-ion solution (e.g., about 1 or 3 equivalents); 5) cooling the resulting mixture to a temperature (e.g., about 10-30° C. or about 25° C.); 6) collecting precipitation by filtration; and 7) evaporating the solution to yield a solid if no precipitation and collecting the solid. In certain embodiments, the solvent is CH$_3$OH, CH$_3$CN or acetone. In certain embodiments, the basic counter-ion is provided by calcium acetate hydrate, choline hydroxide, potassium hydroxide, sodium hydroxide in, 1-arginine, n-methyl-d-glucamine (meglumine), a mixture of magnesium nitrate and sodium hydroxide or a mixture of calcium nitrate and sodium hydroxide. In certain embodiments, the solvent of the basic counter-ion solution is water, CH$_3$OH or a mixture of water and CH$_3$OH.

5.4.1 Hemi-Calcium Salt of Compound 1 (Salt I)

In one embodiment, provided herein is a calcium salt of Compound 1. In one embodiment, provided herein is a hemi-calcium salt of Compound 1 ("Salt I"). In one embodiment, Salt I is crystalline. In one embodiment, Salt I is moderately hydroscopic. In one embodiment, Salt I is chemically stable.

In certain embodiments, provided herein is a method for making Salt I, comprising 1) dissolving Compound 1 in a solvent (e.g., CH$_3$OH) to yield a mixture; 2) heating the mixture to an elevated temperature (e.g., about 30-70° C.); 3) filtering the mixture at the elevated temperature to yield a solution; 4) contacting the mixture with a calcium acetate solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the calcium acetate solution is a solution of calcium acetate hydrate in water, methanol or a mixture of methanol and water (e.g., about 1:1).

In certain embodiments, provided herein is a method for making Salt I, comprising 1) dissolving Compound 1 in a solvent (e.g., CH$_3$OH) to yield a mixture; 2) heating the mixture to an elevated temperature (e.g., about 50° C.); 3) filtering the mixture at the elevated temperature with a 0.45 μm syringe filter to yield a solution; 4) contacting the mixture with a calcium acetate solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the calcium acetate solution is a solution of calcium acetate hydrate in water, methanol or a mixture of methanol and water (e.g., about 1:1).

Figure 49:
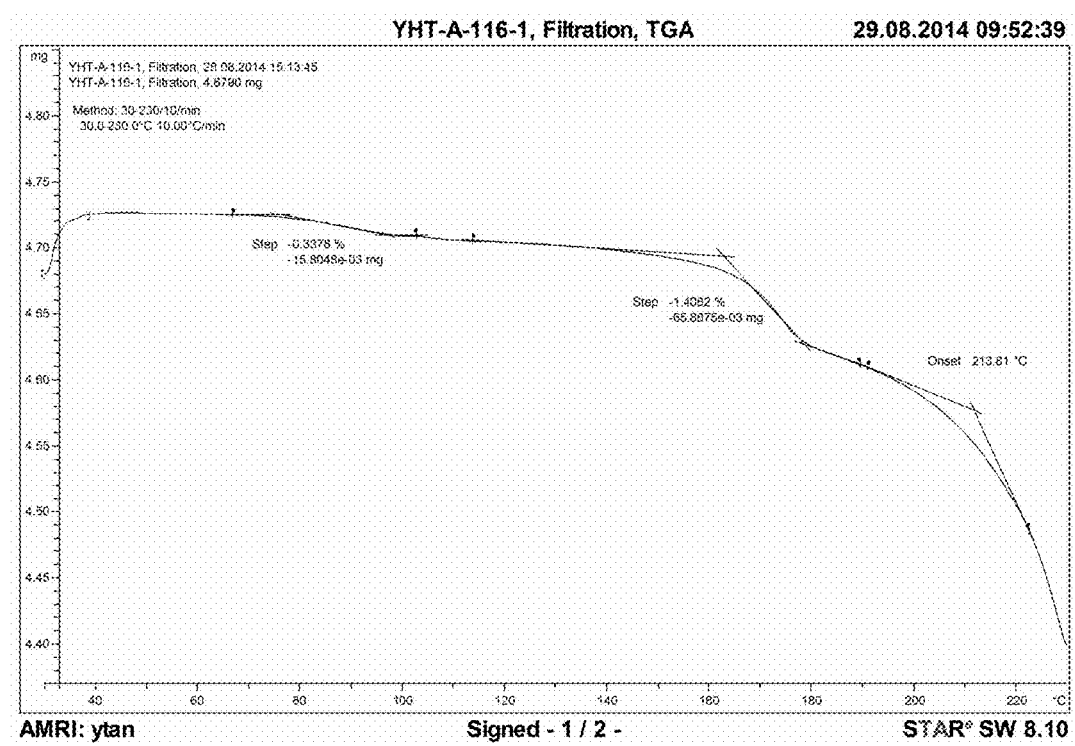
FIG. 49 depicts a TGA thermogram of Salt I of Compound 1.

In one embodiment, Salt I has a TGA thermogram corresponding substantially to the representative TGA thermogram as depicted in FIG. 49. In certain embodiments, Salt I exhibits a TGA thermogram comprising a total mass loss of approximately 0.34% of the total mass of the sample between approximately 65° C. and approximately 105° C. when heated from approximately 25° C. to approximately 230° C. In one embodiment, the TGA thermogram further comprises a total mass loss of approximately 1.41% of the total mass of the sample between approximately 140° C. and approximately 190° C. when heated from approximately 25° C. to approximately 230° C. In one embodiment, the TGA thermogram further comprises a decomposition event with onset temperature at approximately 213.8° C. when heated from approximately 25° C. to approximately 230° C.

Figure 48:
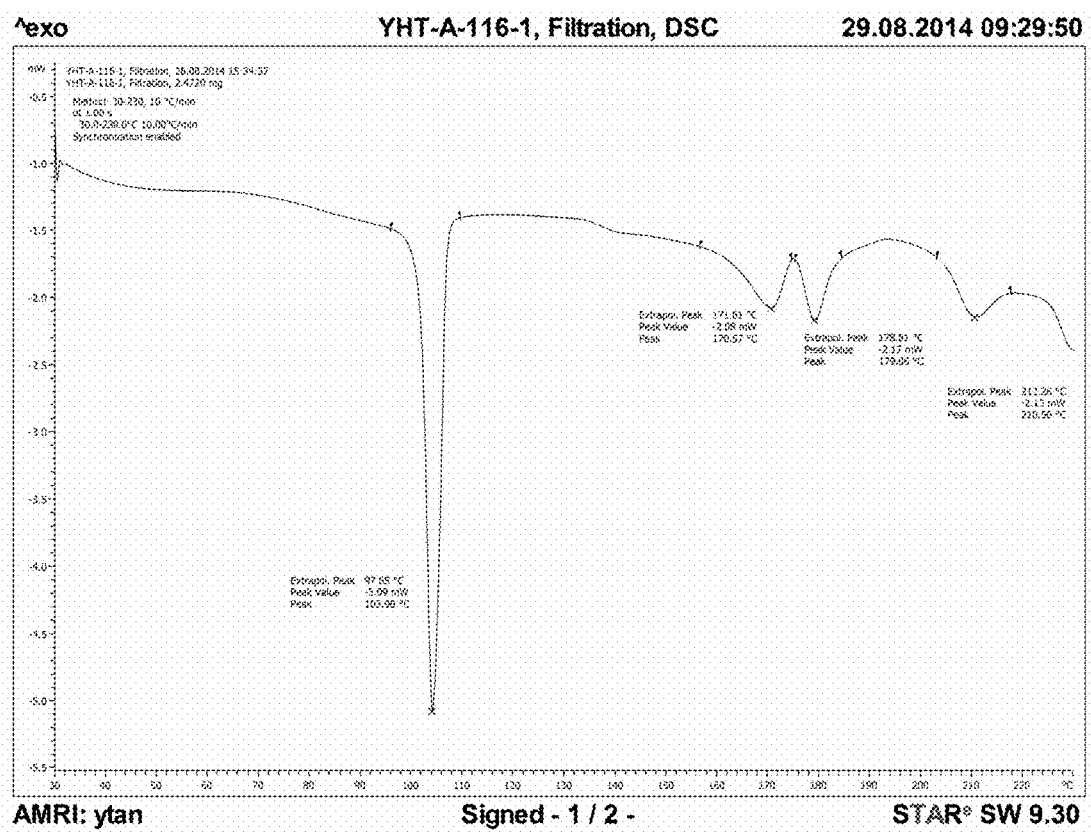
FIG. 48 depicts a DSC thermogram of Salt I of Compound 1.

In one embodiment, Salt I has a DSC thermogram as depicted in FIG. 48 comprising an endothermic event with a maximum at approximately 104.0° C. when heated from approximately 25° C. to approximately 230° C. In one embodiment, the DSC thermogram further comprises an endothermic event with a maximum at approximately 170.6° C. when heated from approximately 25° C. to approximately 230° C. In one embodiment, the DSC thermogram further comprises an endothermic event with a maximum at approximately 179.1° C. when heated from approximately 25° C. to approximately 230° C. In one embodiment, the DSC thermogram further comprises an endothermic event with a maximum at approximately 210.6° C. when heated from approximately 25° C. to approximately 230° C.

Figure 40:
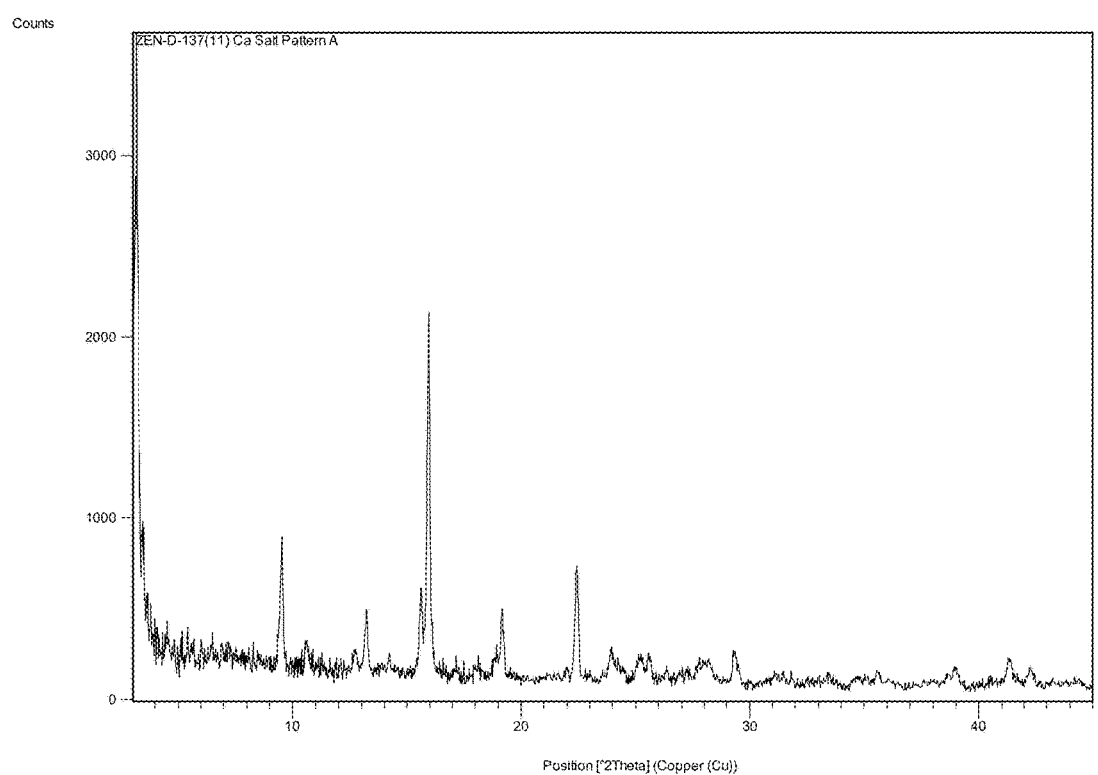
FIG. 40 depicts a XRPD Diffractogram of Salt I of Compound 1.

In certain embodiments, Salt I is substantially crystalline, as indicated by, e.g., X-ray powder diffraction measurements. In one embodiment, Salt I has an X-ray powder diffraction pattern substantially as shown in FIG. 40. In one embodiment, Salt I has one or more characteristic X-ray powder diffraction peaks at approximately 3.20, 4.09, 4.51, 4.85, 4.99, 5.19, 5.43, 5.69, 6.01, 6.49, 6.92, 7.21, 8.29, 8.47, 9.17, 9.53, 10.39, 10.58, 11.30, 11.87, 12.10, 12.23, 12.73, 13.23, 14.23, 15.60, 15.97, 17.21, 17.49, 18.08, 18.88, 19.15, 22.00, 22.41, 23.92, 25.25, 25.60, 26.35, 26.67, 27.76, 28.21, 29.29, 31.08, 31.46, 31.82, 33.44, 34.63, 35.58, 37.97, 38.65, 38.96, 41.35, 42.29 or 43.31° 2θ as depicted in FIG. 40. In a specific embodiment, Salt I has one, two, three, four, five, six, seven or eight characteristic X-ray powder diffraction peaks at approximately 3.20, 5.43, 9.53, 13.23, 15.60, 15.97, 19.15 or 22.41° 2θ. In another embodiment, Salt I has one, two, three or four characteristic X-ray powder diffraction peaks at approximately 3.20, 9.53, 15.97 or 22.41° 2θ. In another embodiment, Salt I has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three or fifty-four characteristic X-ray powder diffraction peaks as set forth in Table 38.

In certain embodiments, Salt I is substantially crystalline, as indicated by, e.g., X-ray powder diffraction measurements. In one embodiment, Salt I has an X-ray powder diffraction pattern substantially as shown in FIG. 40. In one embodiment, Salt I has one or more characteristic X-ray powder diffraction peaks at approximately 3.2, 4.1, 4.5, 4.9, 5.0, 5.2, 5.4, 5.7, 6.0, 6.5, 6.9, 7.2, 8.3, 8.5, 9.2, 9.5, 10.4, 10.6, 11.3, 11.9, 12.1, 12.2, 12.7, 13.2, 14.2, 15.6, 16.0, 17.2, 17.5, 18.1, 18.9, 19.2, 22.0, 22.4, 23.9, 25.3, 25.6, 26.4, 26.7, 27.8, 28.2, 29.3, 31.1, 31.5, 31.8, 33.4, 34.6, 35.6, 38.0, 38.7, 39.0, 41.4, 42.3 or 43.3° 2θ as depicted in FIG. 40. In a specific embodiment, Salt I has one, two, three, four, five, six, seven or eight characteristic X-ray powder diffraction peaks at approximately 3.2, 5.4, 9.5, 13.2, 15.6, 16.0, 19.2 or 22.4° 2θ. In another embodiment, Salt I has one, two, three or four characteristic X-ray powder diffraction peaks at approximately 3.2, 9.5, 16.0 or 22.4° 2θ. In another embodiment, Salt I has one, two, three, four, five or six characteristic X-ray powder diffraction peaks at approximately 3.2, 9.5, 15.6, 16.0, 19.2 or 22.4° 2θ. In another embodiment, Salt I has one, two or three characteristic X-ray powder diffraction peaks at approximately 3.2, 9.5 or 16.0° 2θ. In another embodiment, Salt I has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three or fifty-four characteristic X-ray powder diffraction peaks as set forth in Table 38.

5.4.2 Dihydrate Hemi-Calcium Salt of Compound 1 (Salt II)

In one embodiment, provided herein is a calcium salt of Compound 1. In one embodiment, provided herein is a hemi-calcium salt of Compound 1. In one embodiment, the hemi-calcium salt is a hydrate. In one embodiment, the hemi-calcium salt is a dihydrate ("Salt II"). In one embodiment, Salt II is crystalline. In one embodiment, Salt II is moderately hydroscopic. In one embodiment, Salt II is chemically stable.

In certain embodiments, provided herein is a method for making Salt II, comprising 1) dissolving Compound 1 in a solvent (e.g., acetone) to yield a mixture; 2) heating the mixture to an elevated temperature (e.g., about 30-70° C.); 3) filtering the mixture at the elevated temperature to yield a solution; 4) contacting the mixture with a calcium acetate solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the calcium acetate solution is a solution of calcium acetate hydrate in water, methanol or a mixture of methanol and water (e.g., about 1:1).

In certain embodiments, provided herein is a method for making Salt II, comprising 1) dissolving Compound 1 in a solvent (e.g., acetone) to yield a mixture; 2) heating the mixture to an elevated temperature (e.g., about 50° C.); 3) filtering the mixture at the elevated temperature with a 0.45 μm syringe filter to yield a solution; 4) contacting the mixture with a calcium acetate solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the calcium acetate solution is a solution of calcium acetate hydrate in water, methanol or a mixture of methanol and water (e.g., about 1:1).

Figure 54:
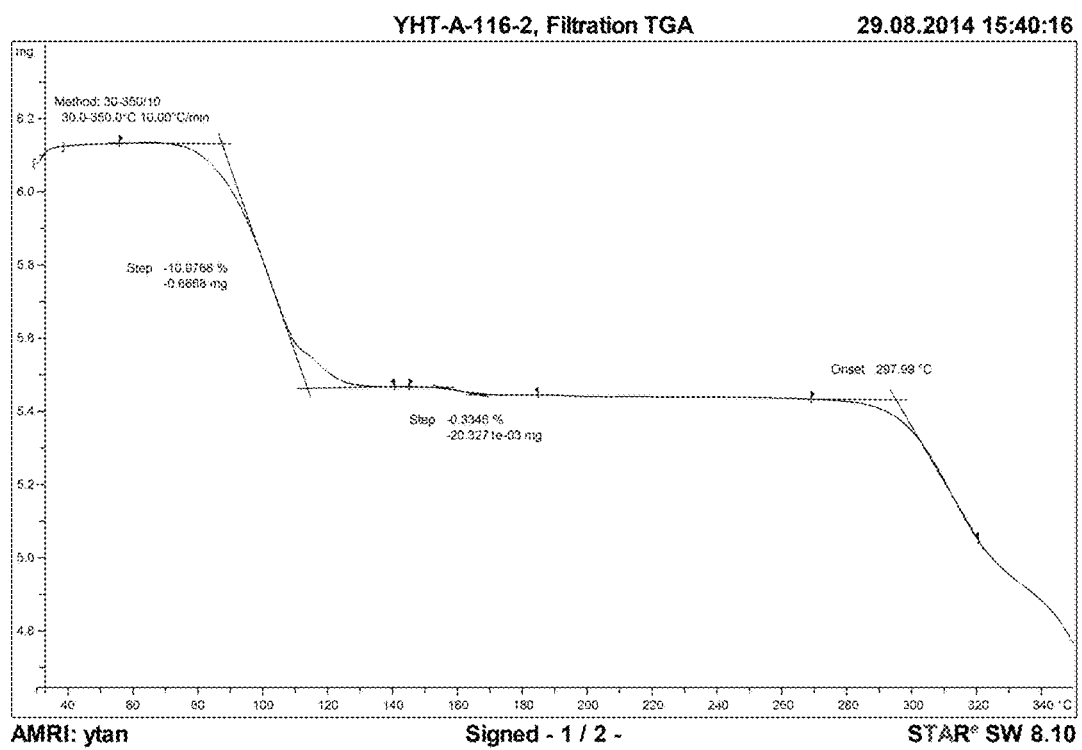
FIG. 54 depicts a TGA thermogram of Salt II of Compound 1.

In one embodiment, Salt II has a TGA thermogram corresponding substantially to the representative TGA thermogram as depicted in FIG. 54. In one embodiment, Salt II exhibits a TGA thermogram comprising a total mass loss of approximately 10.98% of the total mass of the sample between approximately 65° C. and approximately 140° C. when heated from approximately 25° C. to approximately 350° C. In one embodiment, the TGA thermogram further comprises a total mass loss of approximately 0.33% of the total mass of the sample between approximately 150° C. and approximately 180° C. when heated from approximately 25° C. to approximately 350° C. In one embodiment, the TGA thermogram further comprises a decomposition event with onset temperature at approximately 298° C. when heated from approximately 25° C. to approximately 350° C.

Figure 53:
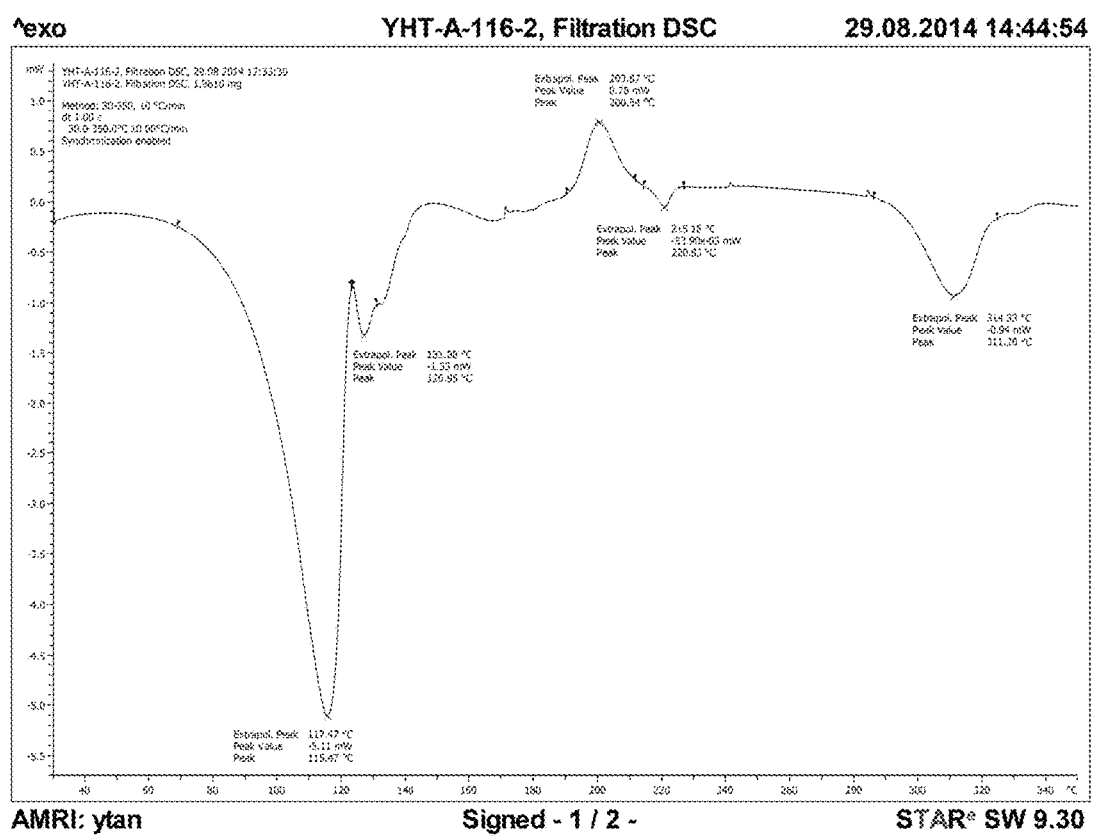
FIG. 53 depicts a DSC thermogram of Salt II of Compound 1.

In one embodiment, Salt II has a DSC thermogram as depicted in FIG. 53 comprising an endothermic event with a maximum at approximately 115.5° C. when heated from approximately 25° C. to approximately 350° C. In one embodiment, the DSC thermogram further comprises an endothermic event with a maximum at approximately 127.0° C. when heated from approximately 25° C. to approximately 350° C. In one embodiment, the DSC thermogram further comprises an exothermic event with a maximum at approximately 200.5° C. when heated from approximately 25° C. to approximately 350° C. In one embodiment, the DSC thermogram further comprises an endothermic event with a maximum at approximately 220.8° C. when heated from approximately 25° C. to approximately 350° C. In one embodiment, the DSC thermogram further comprises an endothermic event with a maximum at approximately 311.3° C. when heated from approximately 25° C. to approximately 350° C.

Figure 41:
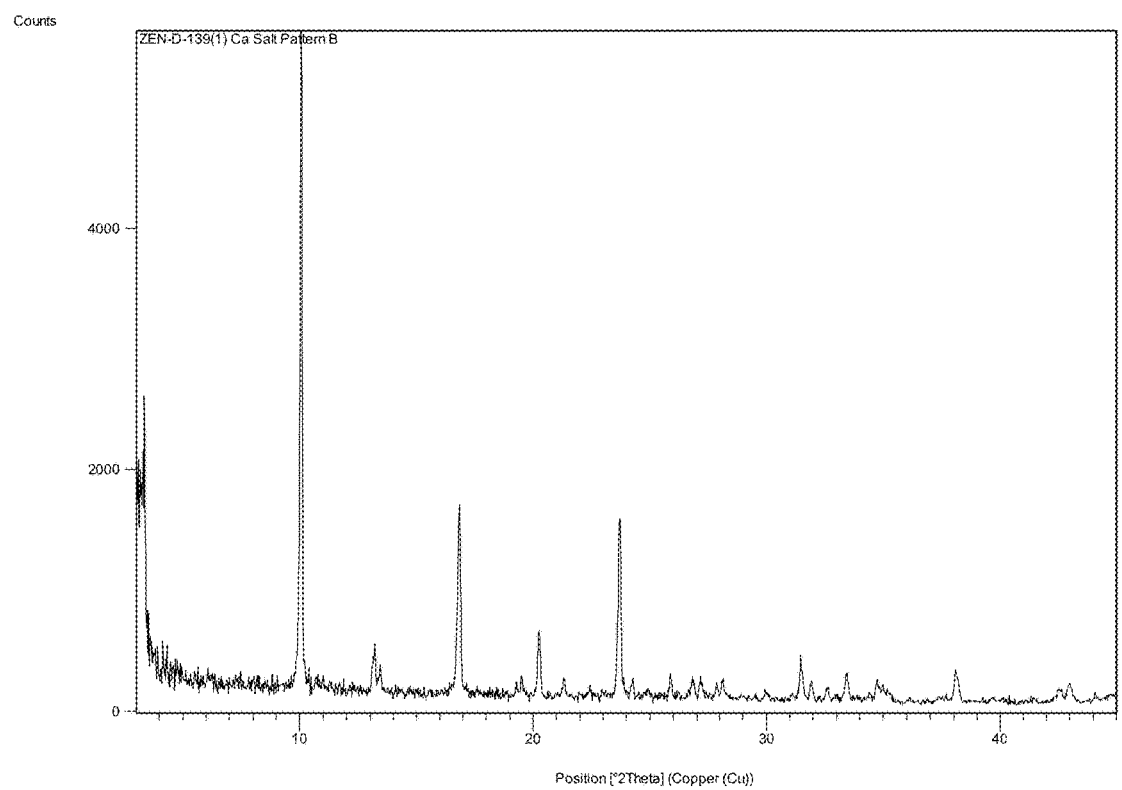
FIG. 41 depicts a XRPD Diffractogram of Salt II of Compound 1.

In certain embodiments, Salt II is substantially crystalline, as indicated by, e.g., X-ray powder diffraction measurements. In one embodiment, Salt II has an X-ray powder diffraction pattern substantially as shown in FIG. 41. In one embodiment, Salt II has one or more characteristic X-ray powder diffraction peaks at approximately 3.37, 3.81, 3.94, 4.15, 4.33, 4.59, 4.77, 5.12, 5.51, 6.07, 6.25, 7.27, 7.45, 7.82, 8.03, 8.56, 8.83, 10.07, 10.39, 10.71, 11.32, 11.56, 11.70, 13.21, 13.46, 14.10, 14.36, 15.32, 15.58, 16.86, 19.28, 19.51, 20.23, 20.68, 21.32, 22.41, 22.95, 23.71, 24.27, 24.90, 25.87, 26.21, 26.83, 27.15, 27.57, 27.85, 28.12, 28.95, 29.24, 29.53, 29.95, 31.08, 31.47, 31.90, 32.59, 32.97, 33.42, 34.73, 34.97, 35.25, 36.09, 38.09, 39.69, 41.35, 42.56, 42.94 or 44.06° 2θ as depicted in FIG. 41. In a specific embodiment, Salt II has one, two, three, four, five, six, seven or eight characteristic X-ray powder diffraction peaks at approximately 3.37, 10.07, 13.21, 16.86, 20.23, 23.71, 31.47 or 38.09° 2θ. In another embodiment, Salt II has one, two, three or four characteristic X-ray powder diffraction peaks at approximately 3.37, 10.07, 16.86 or 23.71° 2θ. In another embodiment, Salt II has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, sixty-six or sixty-seven characteristic X-ray powder diffraction peaks as set forth in Table 39.

In certain embodiments, Salt II is substantially crystalline, as indicated by, e.g., X-ray powder diffraction measurements. In one embodiment, Salt II has an X-ray powder diffraction pattern substantially as shown in FIG. 41. In one embodiment, Salt II has one or more characteristic X-ray powder diffraction peaks at approximately 3.4, 3.8, 3.9, 4.2, 4.3, 4.6, 4.8, 5.1, 5.5, 6.1, 6.3, 7.3, 7.5, 7.8, 8.0, 8.6, 8.8, 10.1, 10.4, 10.7, 11.3, 11.6, 11.7, 13.2, 13.5, 14.1, 14.4, 15.3, 15.6, 16.9, 19.3, 19.5, 20.2, 20.7, 21.3, 22.4, 23.0, 23.7, 24.3, 24.9, 25.9, 26.2, 26.8, 27.2, 27.6, 27.9, 28.1, 29.0, 29.2, 29.5, 30.0, 31.1, 31.5, 31.9, 32.6, 33.0, 33.4, 34.7, 35.0, 35.3, 36.1, 38.1, 39.7, 41.4, 42.6, 42.9 or 44.1° 2θ as depicted in FIG. 41. In a specific embodiment, Salt II has one, two, three, four, five, six, seven or eight characteristic X-ray powder diffraction peaks at approximately 3.4, 10.1, 13.2, 16.9, 20.2, 23.7, 31.5 or 38.1° 2θ. In another embodiment, Salt II has one, two, three or four characteristic X-ray powder diffraction peaks at approximately 3.4, 10.1, 16.9 or 23.7° 2θ. In another embodiment, Salt II has one, two, three, four, five or six characteristic X-ray powder diffraction peaks at approximately 3.4, 10.1, 13.2, 16.9, 20.2 or 23.7° 2θ. In another embodiment, Salt II has one, two or three characteristic X-ray powder diffraction peaks at approximately 10.1, 16.9 or 23.7° 2θ. In another embodiment, Salt II has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, sixty-six or sixty-seven characteristic X-ray powder diffraction peaks as set forth in Table 39.

5.4.3 Mono-Potassium Salt of Compound 1 (Salt III)

In one embodiment, provided herein is a potassium salt of Compound 1. In one embodiment, provided herein is a mono-potassium salt of Compound 1 ("Salt III"). In one embodiment, Salt III is crystalline. In one embodiment, Salt III is moderately hydroscopic. In one embodiment, Salt III is chemically stable. In one embodiment, Salt III has a tendency to form hydrates.

In certain embodiments, provided herein is a method for making Salt III, comprising 1) dissolving Compound 1 in a solvent (e.g., acetonitrile) to yield a mixture; 2) heating the mixture to an elevated temperature (e.g., about 30-70° C.); 3) filtering the mixture at the elevated temperature to yield a solution; 4) contacting the mixture with a potassium hydroxide solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the potassium hydroxide solution is a solution of potassium hydroxide in water, methanol or a mixture of methanol and water (e.g., about 1:1).

In certain embodiments, provided herein is a method for making Salt III, comprising 1) dissolving Compound 1 in a solvent (e.g., acetonitrile) to yield a mixture; 2) heating the mixture to an elevated temperature (e.g., about 50° C.); 3) filtering the mixture at the elevated temperature with a 0.45 μm syringe filter to yield a solution; 4) contacting the mixture with a potassium hydroxide solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the potassium hydroxide solution is a solution of potassium hydroxide in water, methanol or a mixture of methanol and water (e.g., about 1:1).

Figure 59:
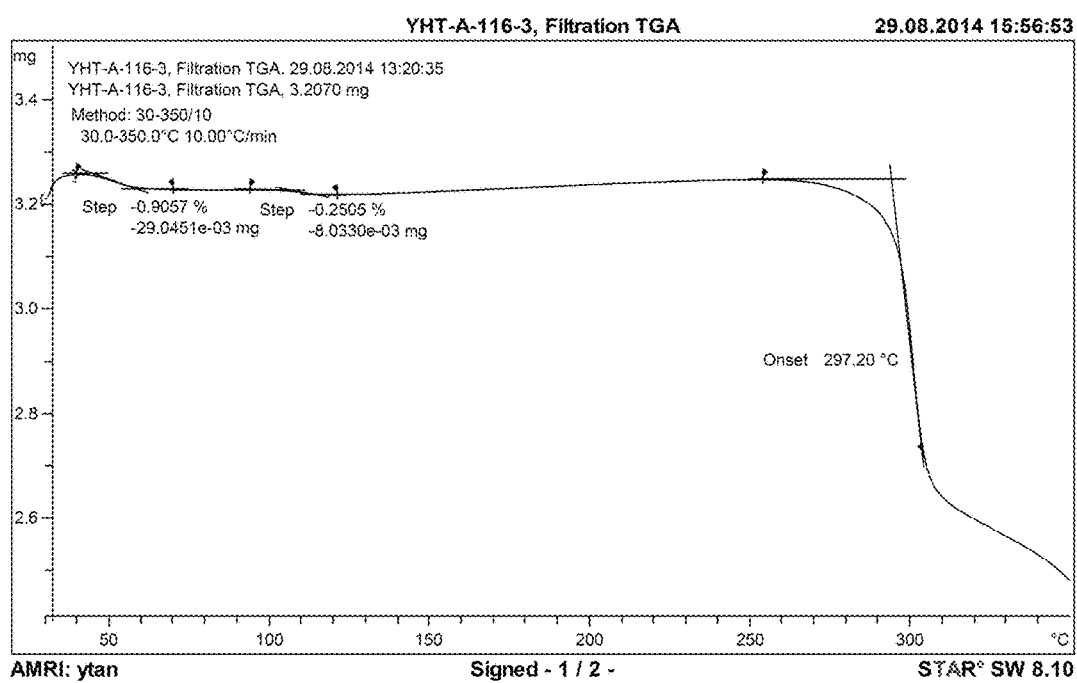
FIG. 59 depicts a TGA thermogram of Salt III of Compound 1.

In one embodiment, Salt III has a TGA thermogram corresponding substantially to the representative TGA thermogram as depicted in FIG. 59. In one embodiment, Salt III exhibits a TGA thermogram comprising a total mass loss of approximately 0.91% of the total mass of the sample between approximately 40° C. and approximately 70° C. when heated from approximately 25° C. to approximately 350° C. In one embodiment, the TGA thermogram further comprises a total mass loss of approximately 0.25% of the total mass of the sample between approximately 100° C. and approximately 120° C. when heated from approximately 25° C. to approximately 350° C. In one embodiment, the TGA thermogram further comprises a decomposition event with onset temperature at approximately 297.2° C. when heated from approximately 25° C. to approximately 350° C.

Figure 58:
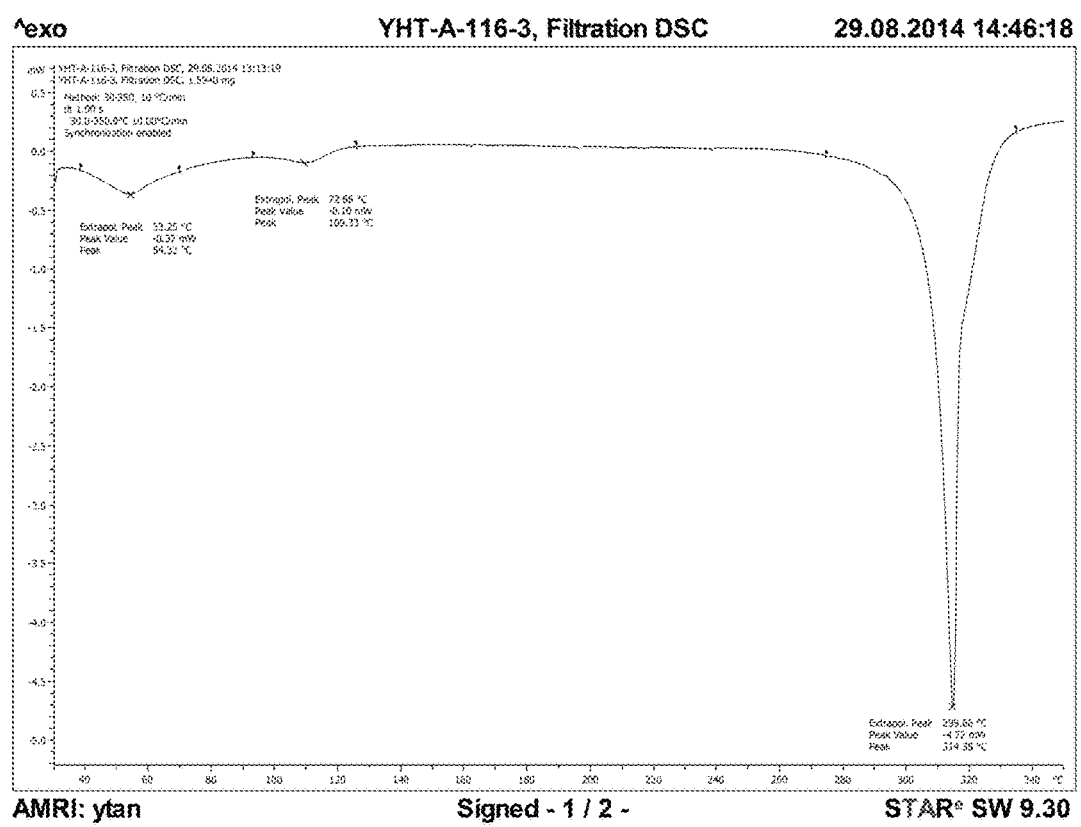
FIG. 58 depicts a DSC thermogram of Salt III of Compound 1.

In one embodiment, Salt III has a DSC thermogram as depicted in FIG. 58 comprising an endothermic event with a maximum at approximately 54.3° C. when heated from approximately 25° C. to approximately 350° C. In one embodiment, the DSC thermogram further comprises an endothermic event with a maximum at approximately 109.3° C. when heated from approximately 25° C. to approximately 350° C. In one embodiment, the DSC thermogram further comprises an endothermic event with a maximum at approximately 314.4° C. when heated from approximately 25° C. to approximately 350° C.

Figure 42:
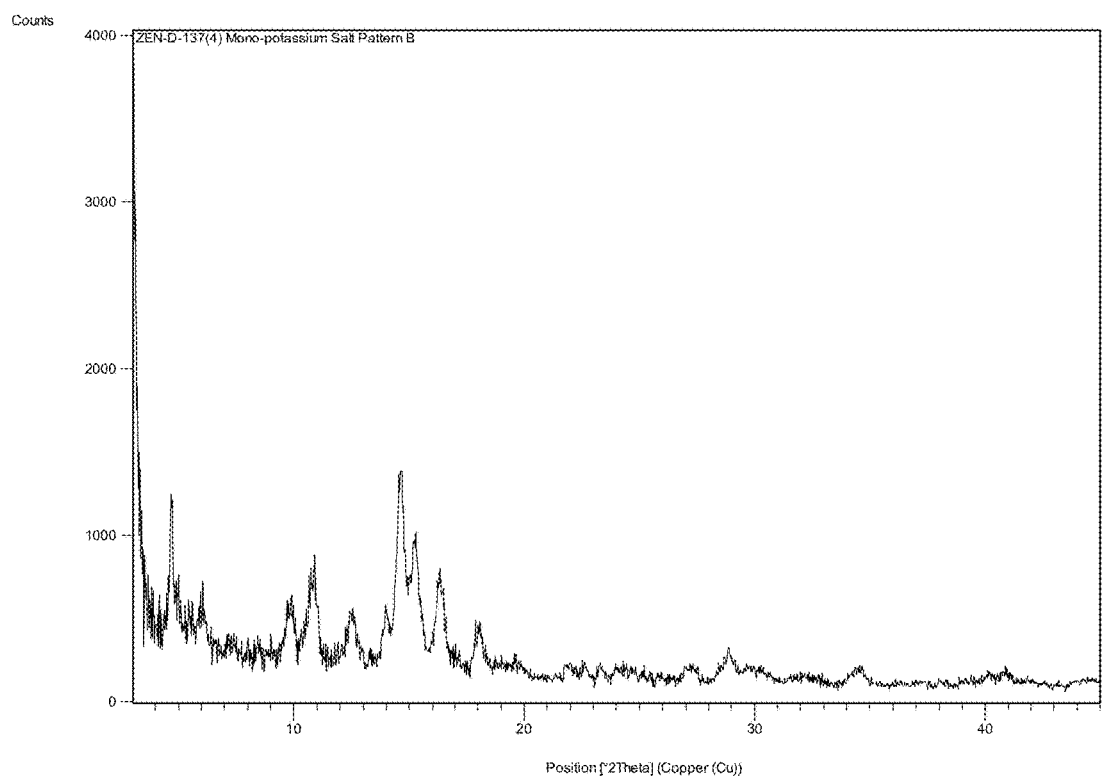
FIG. 42 depicts a XRPD Diffractogram of Salt III of Compound 1.

In certain embodiments, Salt III is substantially crystalline, as indicated by, e.g., X-ray powder diffraction measurements. In one embodiment, Salt III has an X-ray powder diffraction pattern substantially as shown in FIG. 42. In one embodiment, Salt III has one or more characteristic X-ray powder diffraction peaks at approximately 4.18, 4.71, 4.98, 5.61, 6.06, 6.41, 6.73, 7.14, 7.39, 8.01, 8.55, 8.78, 9.03, 9.73, 9.88, 10.72, 10.89, 11.76, 11.89, 12.48, 12.97, 13.29, 13.97, 14.54, 14.65, 15.18, 15.29, 16.35, 16.49, 17.01, 17.17, 18.09, 19.70, 21.78, 22.62, 23.13, 23.99, 24.44, 25.16, 25.44, 25.88, 27.37, 28.88, 29.93, 32.09, 34.55, 37.21, 40.15, 40.86 or 41.95° 2θ as depicted in FIG. 42. In a specific embodiment, Salt III has one, two, three, four, five, six, seven or eight characteristic X-ray powder diffraction peaks at approximately 4.71, 10.72, 10.89, 14.54, 14.65, 15.18, 15.29 or 16.35° 2θ. In another embodiment, Salt III has one, two, three or four characteristic X-ray powder diffraction peaks at approximately 4.71, 14.54, 14.65 or 15.29° 2θ. In another embodiment, Salt III has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine or fifty characteristic X-ray powder diffraction peaks as set forth in Table 40.

In certain embodiments, Salt III is substantially crystalline, as indicated by, e.g., X-ray powder diffraction measurements. In one embodiment, Salt III has an X-ray powder diffraction pattern substantially as shown in FIG. 42. In one embodiment, Salt III has one or more characteristic X-ray powder diffraction peaks at approximately 4.2, 4.7, 5.0, 5.6, 6.1, 6.4, 6.7, 7.1, 7.4, 8.0, 8.6, 8.8, 9.0, 9.7, 9.9, 10.7, 10.9, 11.8, 11.9, 12.5, 13.0, 13.3, 14.0, 14.5, 14.7, 15.2, 15.3, 16.4, 16.5, 17.0, 17.2, 18.1, 19.7, 21.8, 22.6, 23.1, 24.0, 24.4, 25.2, 25.4, 25.9, 27.4, 28.9, 29.9, 32.1, 34.6, 37.2, 40.2, 40.9 or 42.0° 2θ as depicted in FIG. 42. In a specific embodiment, Salt III has one, two, three, four, five, six, seven or eight characteristic X-ray powder diffraction peaks at approximately 4.7, 10.7, 10.9, 14.5, 14.6, 15.2, 15.3 or 16.4° 2θ. In another embodiment, Salt III has one, two, three or four characteristic X-ray powder diffraction peaks at approximately 4.7, 14.5, 14.7 or 15.3° 2θ. In another embodiment, Salt III has one, two, three, four, five or six characteristic X-ray powder diffraction peaks at approximately 4.7, 10.9, 14.5, 14.7, 15.2 or 15.3° 2θ. In another embodiment, Salt III has one, two or three characteristic X-ray powder diffraction peaks at approximately 14.5, 14.7 or 15.3° 2θ. In another embodiment, Salt III has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine or fifty characteristic X-ray powder diffraction peaks as set forth in Table 40.

5.4.4 Monohydrate Mono-Sodium Salt of Compound 1 (Salt IV)

In one embodiment, provided herein is a sodium salt of Compound 1. In one embodiment, provided herein is a mono-sodium salt of Compound 1. In one embodiment, the mono-sodium salt is a hydrate. In one embodiment, the mono-sodium salt is a mono-hydrate ("Salt IV"). In one embodiment, Salt IV is crystalline. In one embodiment, Salt IV is moderately hydroscopic. In one embodiment, Salt IV is chemically stable. In one embodiment, Salt IV is a stable hydrate.

In certain embodiments, provided herein is a method for making Salt IV, comprising 1) dissolving Compound 1 in a solvent (e.g., acetone) to yield a mixture; 2) heating the mixture to an elevated temperature (e.g., about 30-70° C.); 3) filtering the mixture at the elevated temperature to yield a solution; 4) contacting the mixture with a sodium hydroxide solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water (e.g., about 1:1).

In certain embodiments, provided herein is a method for making Salt IV, comprising 1) dissolving Compound 1 in a solvent (e.g., acetone) to yield a mixture; 2) heating the mixture to an elevated temperature (e.g., about 50° C.); 3) filtering the mixture at the elevated temperature with a 0.45 μm syringe filter to yield a solution; 4) contacting the mixture with a sodium hydroxide solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water (e.g., about 1:1).

Figure 64:
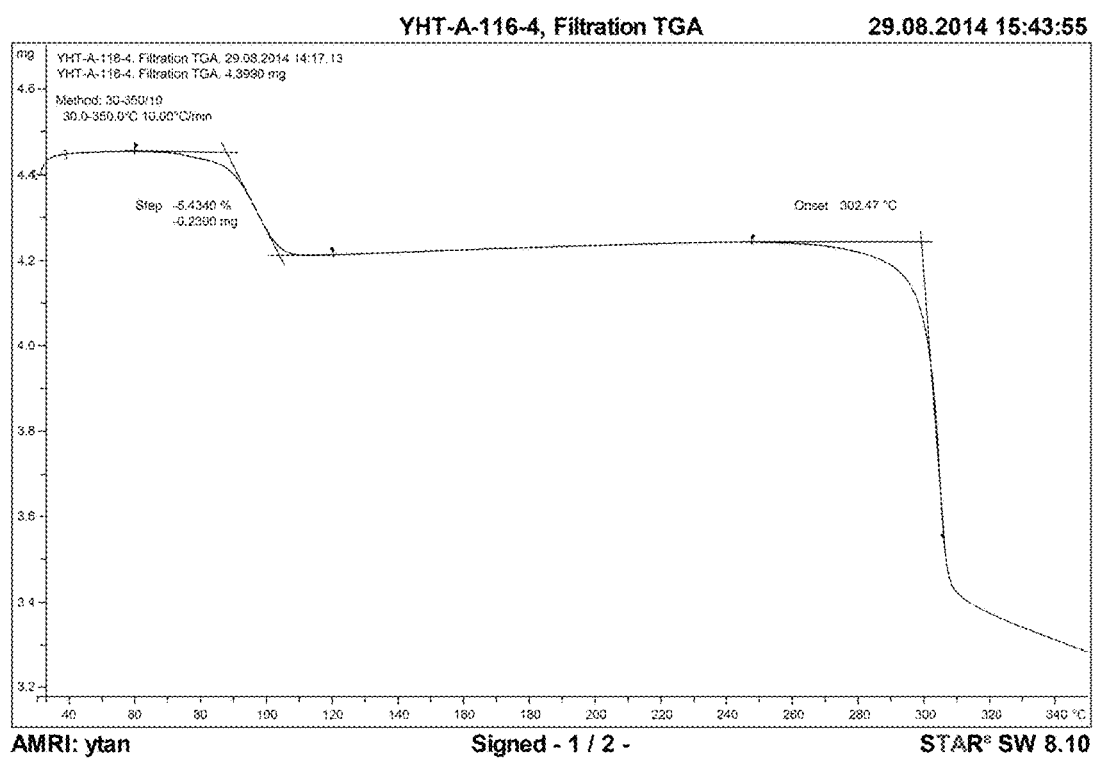
FIG. 64 depicts a TGA thermogram of Salt IV of Compound 1.

In one embodiment, Salt IV has a TGA thermogram corresponding substantially to the representative TGA thermogram as depicted in FIG. 64. In one embodiment, Salt IV exhibits a TGA thermogram comprising a total mass loss of approximately 5% of the total mass of the sample between approximately 60° C. and approximately 120° C. when heated from approximately 25° C. to approximately 350° C. In one embodiment, Salt IV exhibits a TGA thermogram comprising a total mass loss of approximately 5.43% of the total mass of the sample between approximately 60° C. and approximately 120° C. when heated from approximately 25° C. to approximately 350° C. In one embodiment, the TGA thermogram further comprises a decomposition event with onset temperature at approximately 302.5° C. when heated from approximately 25° C. to approximately 350° C.

Figure 63:
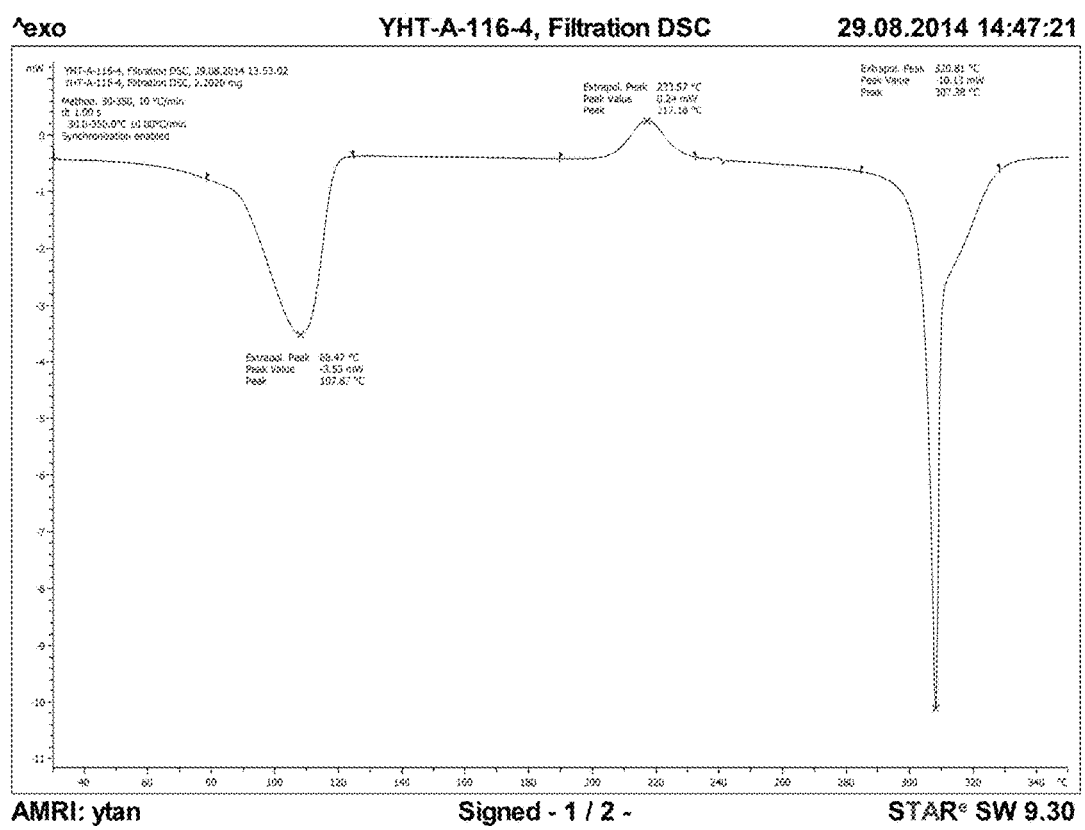
FIG. 63 depicts a DSC thermogram of Salt IV of Compound 1.

In one embodiment, Salt IV has a DSC thermogram as depicted in FIG. 63 comprising an endothermic event with a maximum at approximately 107.9° C. when heated from approximately 25° C. to approximately 350° C. In one embodiment, the DSC thermogram further comprises an exothermic event with a maximum at approximately 217.2° C. when heated from approximately 25° C. to approximately 350° C. In one embodiment, the DSC thermogram further comprises an endothermic event with a maximum at approximately 307.4° C. when heated from approximately 25° C. to approximately 350° C.

Figure 43:
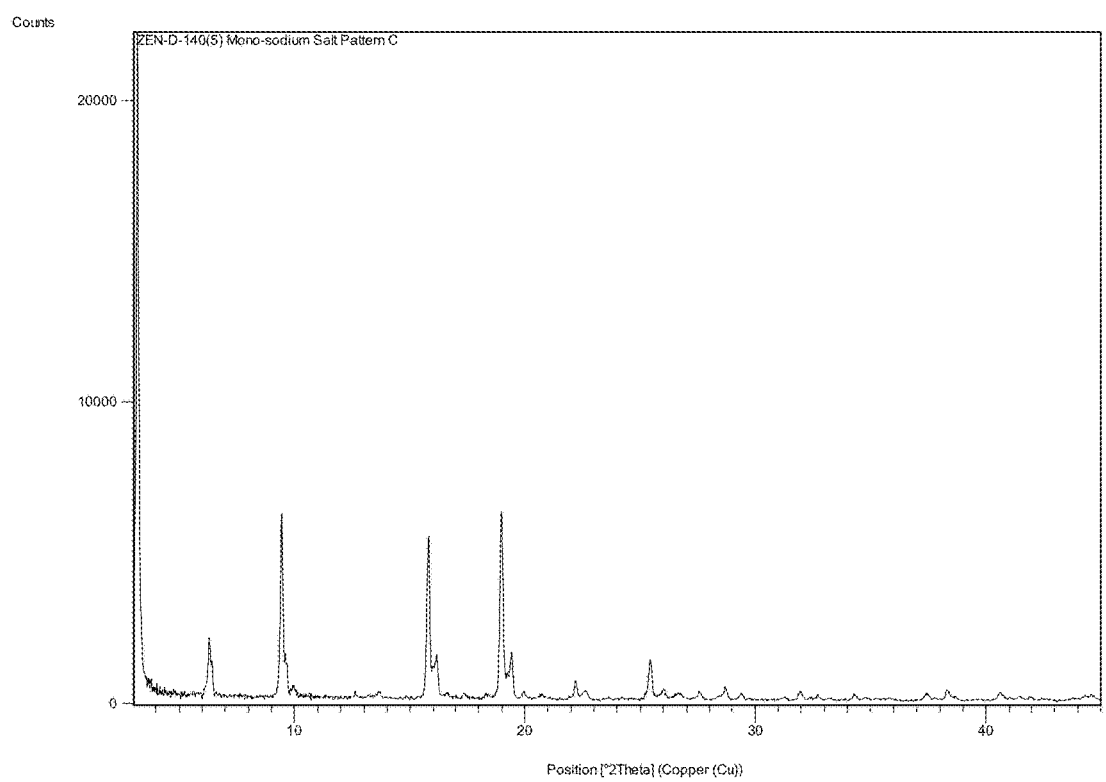
FIG. 43 depicts a XRPD Diffractogram of Salt IV of Compound 1.

In certain embodiments, Salt IV is substantially crystalline, as indicated by, e.g., X-ray powder diffraction measurements. In one embodiment, Salt IV has an X-ray powder diffraction pattern substantially as shown in FIG. 43. In one embodiment, Salt IV has one or more characteristic X-ray powder diffraction peaks at approximately 3.18, 4.17, 4.78, 5.23, 5.62, 5.86, 5.93, 6.29, 6.44, 6.74, 7.43, 9.45, 9.66, 9.94, 10.63, 11.83, 12.03, 12.62, 13.24, 13.61, 14.57, 14.85, 15.05, 15.80, 16.17, 16.68, 16.98, 17.37, 18.31, 19.00, 19.43, 19.94, 20.72, 22.20, 22.69, 23.63, 24.22, 25.42, 26.01, 26.70, 27.54, 28.35, 28.67, 29.39, 31.24, 31.97, 32.69, 33.18, 34.29, 34.73, 35.82, 37.41, 37.84, 38.27, 38.67, 39.65, 40.64, 41.02, 41.48, 41.90, 42.80, 43.80, 44.32 or 44.59° 2θ as depicted in FIG. 43. In a specific embodiment, Salt IV has one, two, three, four, five, six, seven or eight characteristic X-ray powder diffraction peaks at approximately 3.18, 6.29, 9.45, 15.80, 16.17, 19.00, 19.43 or 25.42° 2θ. In another embodiment, Salt IV has one, two, three or four characteristic X-ray powder diffraction peaks at approximately 3.18, 9.45, 15.80 or 19.00° 2θ. In another embodiment, Salt IV has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three or sixty-four characteristic X-ray powder diffraction peaks as set forth in Table 41.

In certain embodiments, Salt IV is substantially crystalline, as indicated by, e.g., X-ray powder diffraction measurements. In one embodiment, Salt IV has an X-ray powder diffraction pattern substantially as shown in FIG. 43. In one embodiment, Salt IV has one or more characteristic X-ray powder diffraction peaks at approximately 3.2, 4.2, 4.8, 5.2, 5.6, 5.9, 6.3, 6.4, 6.7, 7.4, 9.5, 9.7, 9.9, 10.6, 11.8, 12.0, 12.6, 13.2, 13.6, 14.6, 14.9, 15.1, 15.8, 16.2, 16.7, 17.0, 17.4, 18.3, 19.00, 19.4, 19.9, 20.7, 22.2, 22.7, 23.6, 24.2, 25.4, 26.0, 26.7, 27.5, 28.4, 28.7, 29.4, 31.2, 32.0, 32.7, 33.2, 34.3, 34.7, 35.8, 37.4, 37.8, 38.3, 38.7, 39.7, 40.6, 41.0, 41.5, 41.9, 42.8, 43.8, 44.3 or 44.6° 2θas depicted in FIG. 43. In a specific embodiment, Salt IV has one, two, three, four, five, six, seven or eight characteristic X-ray powder diffraction peaks at approximately 3.2, 6.3, 9.5, 15.8, 16.2, 19.0, 19.4 or 25.4° 2θ. In another embodiment, Salt IV has one, two, three or four characteristic X-ray powder diffraction peaks at approximately 3.2, 9.5, 15.8 or 19.0° 2θ. In another embodiment, Salt IV has one, two, three, four, five or six characteristic X-ray powder diffraction peaks at approximately 3.2, 6.3, 9.5, 15.8, 19.0 or 19.4° 2θ. In another embodiment, Salt IV has one, two or three characteristic X-ray powder diffraction peaks at approximately 3.2, 9.5 or 19.0° 2θ. In another embodiment, Salt IV has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three or sixty-four characteristic X-ray powder diffraction peaks as set forth in Table 41.

5.4.5 Monohydrate Bis-Sodium Salt of Compound 1 (Salt V)

In one embodiment, provided herein is a sodium salt of Compound 1. In one embodiment, provided herein is a bis-sodium salt of Compound 1. In one embodiment, the bis-sodium salt is a hydrate. In one embodiment, the bis-sodium salt is a mono-hydrate ("Salt V"). In one embodiment, Salt V is crystalline. In one embodiment, Salt V is moderately hygroscopic. In one embodiment, Salt V is an unstable hydrate.

In certain embodiments, provided herein is a method for making Salt V, comprising 1) dissolving Compound 1 in a solvent (e.g., acetone) to yield a mixture; 2) heating the mixture to an elevated temperature (e.g., about 30-70° C.); 3) filtering the mixture at the elevated temperature to yield a solution; 4) contacting the mixture with a sodium hydroxide solution (e.g., about 2-4 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water (e.g., about 1:1).

In certain embodiments, provided herein is a method for making Salt V, comprising 1) dissolving Compound 1 in a solvent (e.g., acetone) to yield a mixture; 2) heating the mixture to an elevated temperature (e.g., about 50° C.); 3) filtering the mixture at the elevated temperature with a 0.45 µm syringe filter to yield a solution; 4) contacting the mixture with a sodium hydroxide solution (e.g., about 3 equivalents); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water (e.g., about 1:1).

Figure 69:
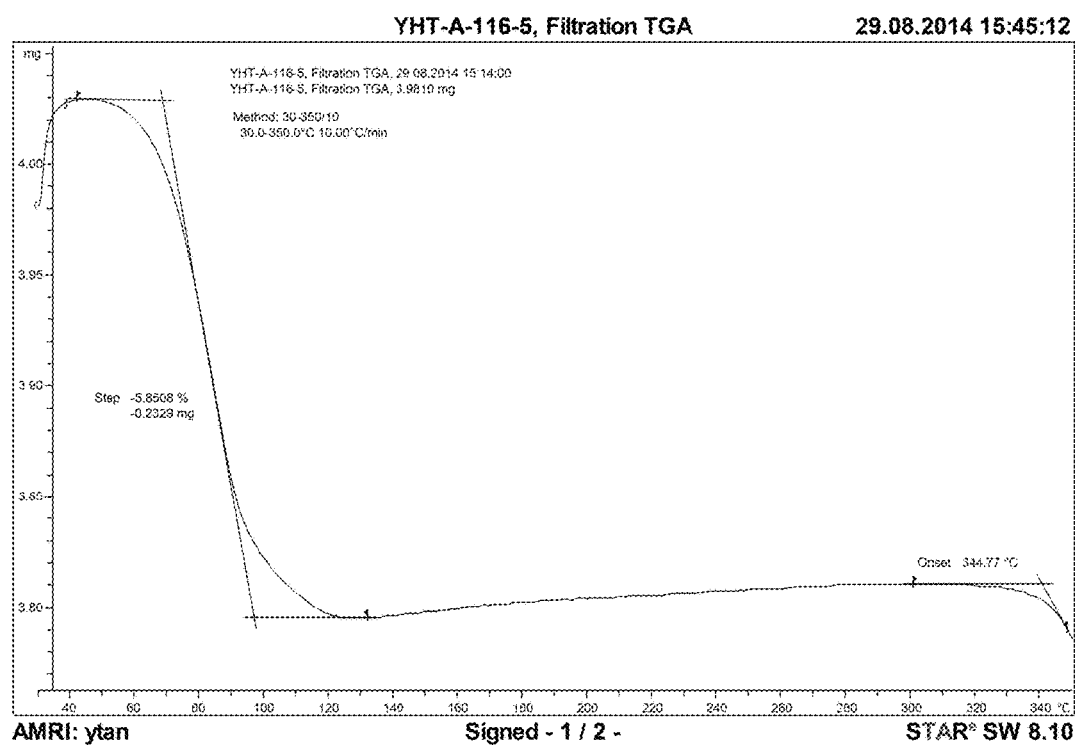
FIG. 69 depicts a TGA thermogram of Salt V of Compound 1.

In one embodiment, Salt V has a TGA thermogram corresponding substantially to the representative TGA thermogram as depicted in FIG. 69. In one embodiment, Salt V exhibits a TGA thermogram comprising a total mass loss of approximately 5.85% of the total mass of the sample between approximately 40° C. and approximately 130° C. when heated from approximately 25° C. to approximately 350° C. In one embodiment, the TGA thermogram further comprises a decomposition event with onset temperature at approximately 344.77° C. when heated from approximately 25° C. to approximately 350° C.

Figure 68:
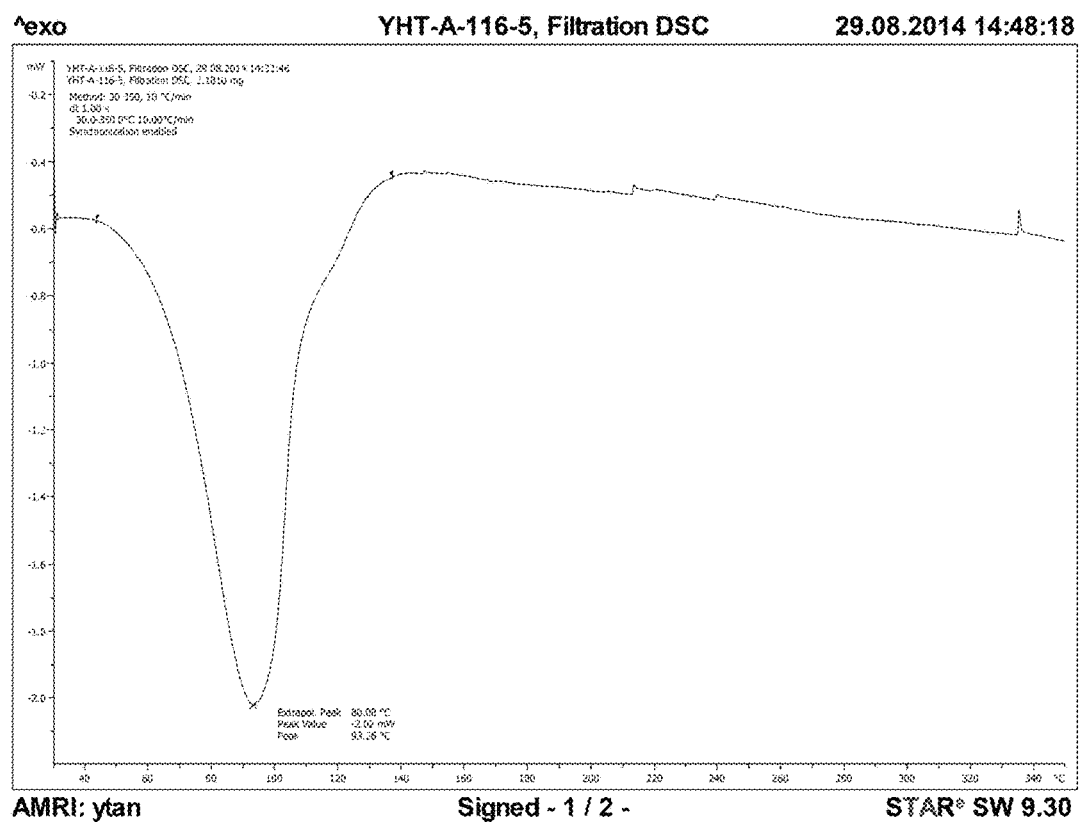
FIG. 68 depicts a DSC thermogram of Salt V of Compound 1.

In one embodiment, Salt V has a DSC thermogram as depicted in FIG. 68 comprising an endothermic event with a maximum at approximately 93.3° C. when heated from approximately 25° C. to approximately 350° C.

Figure 44:
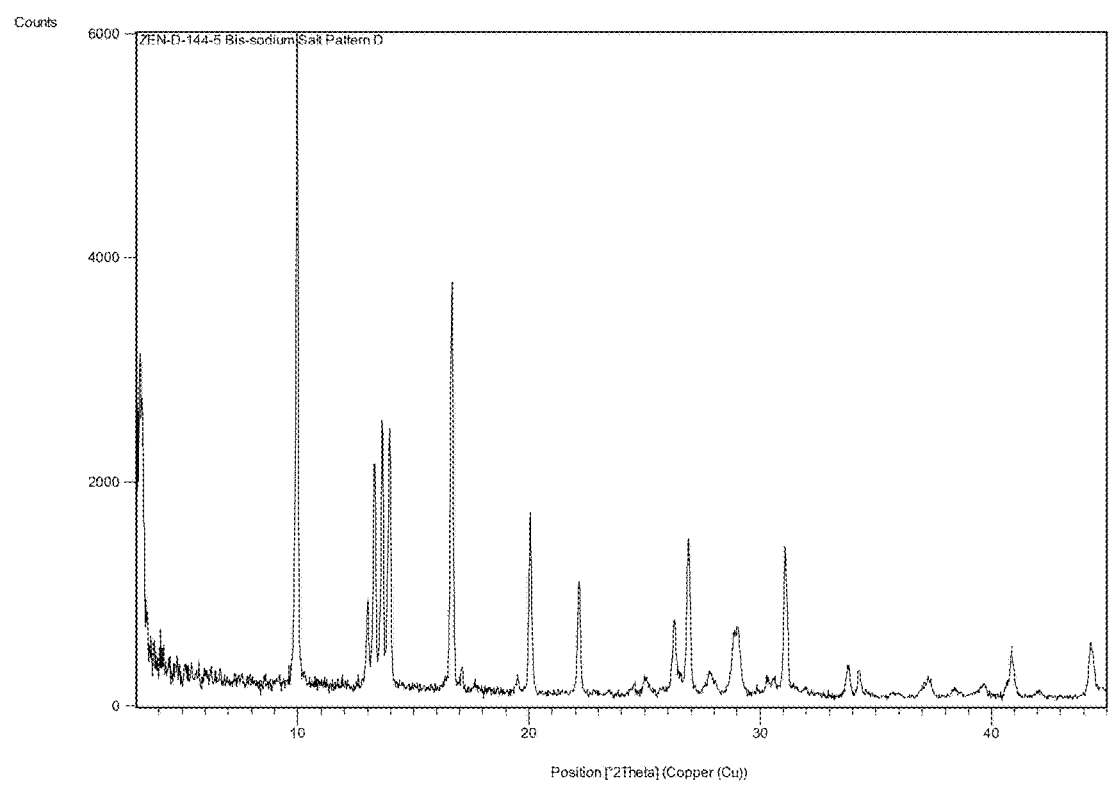
FIG. 44 depicts a XRPD Diffractogram of Salt V of Compound 1.

In certain embodiments, Salt V is substantially crystalline, as indicated by, e.g., X-ray powder diffraction measurements. In one embodiment, Salt V has an X-ray powder diffraction pattern substantially as shown in FIG. 44. In one embodiment, Salt V has one or more characteristic X-ray powder diffraction peaks at approximately 3.15, 3.33, 3.51, 3.65, 4.19, 4.45, 4.74, 5.09, 5.24, 5.40, 5.75, 6.00, 6.24, 6.43, 6.64, 7.29, 7.45, 7.58, 7.92, 8.57, 9.21, 9.39, 9.97, 13.02, 13.31, 13.64, 13.97, 16.69, 17.13, 17.65, 18.09, 18.65, 19.51, 20.06, 22.15, 22.50, 22.87, 23.41, 24.54, 25.01, 25.70, 26.29, 26.87, 27.81, 28.89, 29.06, 29.90, 30.29, 30.60, 31.08, 31.97, 32.21, 33.85, 34.24, 35.73, 37.31, 38.39, 39.71, 40.87, 42.01 or 44.30° 2θas depicted in FIG. 44. In a specific embodiment, Salt V has one, two, three, four, five, six, seven or eight characteristic X-ray powder diffraction peaks at approximately 3.15, 9.97, 13.31, 13.64, 13.97, 16.69, 20.06 or 26.87° 2θ. In another embodiment, Salt V has one, two, three or four characteristic X-ray powder diffraction peaks at approximately 9.97, 13.64, 13.97 or 16.69° 2θ. In another embodiment, Salt V has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty or sixty-one characteristic X-ray powder diffraction peaks as set forth in Table 42.

In certain embodiments, Salt V is substantially crystalline, as indicated by, e.g., X-ray powder diffraction measurements. In one embodiment, Salt V has an X-ray powder diffraction pattern substantially as shown in FIG. 44. In one embodiment, Salt V has one or more characteristic X-ray powder diffraction peaks at approximately 3.2, 3.3, 3.5, 3.7, 4.2, 4.5, 4.7, 5.1, 5.2, 5.4, 5.8, 6.0, 6.2, 6.4, 6.6, 7.3, 7.5, 7.6, 7.9, 8.6, 9.2, 9.4, 10.0, 13.0, 13.3, 13.6, 14.0, 16.7, 17.1, 17.7, 18.1, 18.7, 19.5, 20.1, 22.2, 22.5, 22.9, 23.4, 24.5, 25.0, 25.7, 26.3, 26.9, 27.8, 28.9, 29.1, 29.9, 30.3, 30.6, 31.1, 32.0, 32.2, 33.9, 34.2, 35.7, 37.3, 38.4, 39.7, 40.9, 42.0 or 44.3° 2θ as depicted in FIG. 44. In a specific embodiment, Salt V has one, two, three, four, five, six, seven or eight characteristic X-ray powder diffraction peaks at approximately 3.2, 10.0, 13.3, 13.6, 14.0, 16.7, 20.1 or 26.9° 2θ. In another embodiment, Salt V has one, two, three or four characteristic X-ray powder diffraction peaks at approximately 10.0, 13.6, 14.0 or 16.7° 2θ. In another embodiment, Salt V has one, two, three, four, five or six characteristic X-ray powder diffraction peaks at approximately 3.2, 10.0, 13.3, 13.6, 14.0 or 16.7° 2θ. In another embodiment, Salt V has one, two or three characteristic X-ray powder diffraction peaks at approximately 10.0, 13.6 or 16.7° 2θ. In another embodiment, Salt V has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty or sixty-one characteristic X-ray powder diffraction peaks as set forth in Table 42.

5.4.6 Anhydrous Mono-Sodium Salt of Compound 1 (Salt VI)

In one embodiment, provided herein is a sodium salt of Compound 1. In one embodiment, provided herein is a mono-sodium salt of Compound 1. In one embodiment, the mono-sodium salt is anhydrous ("Salt VI"). In one embodiment, Salt VI is crystalline. In one embodiment, Salt VI is slightly hydroscopic. In one embodiment, Salt VI is chemically stable.

In certain embodiments, provided herein is a method for making Salt VI, comprising 1) heating Salt IV of Compound 1 from a first temperature (e.g., about 160-200° C.) to a second temperature (e.g., about 240-280° C.) at a speed (e.g., about 10° C./minute); 2) holding the solid at the second temperature for a period of time (e.g., about 1-10 minutes); and 3) collecting the resulting solids.

In certain embodiments, provided herein is a method for making Salt VI, comprising 1) heating Salt IV of Compound 1 from a first temperature (e.g., about 180° C.) to a second temperature (e.g., about 260° C.) at a speed (e.g., about 10° C./minute); 2) holding the solid at the second temperature for a period of time (e.g., about 2 minutes); and 3) collecting the resulting solids.

Figure 75:
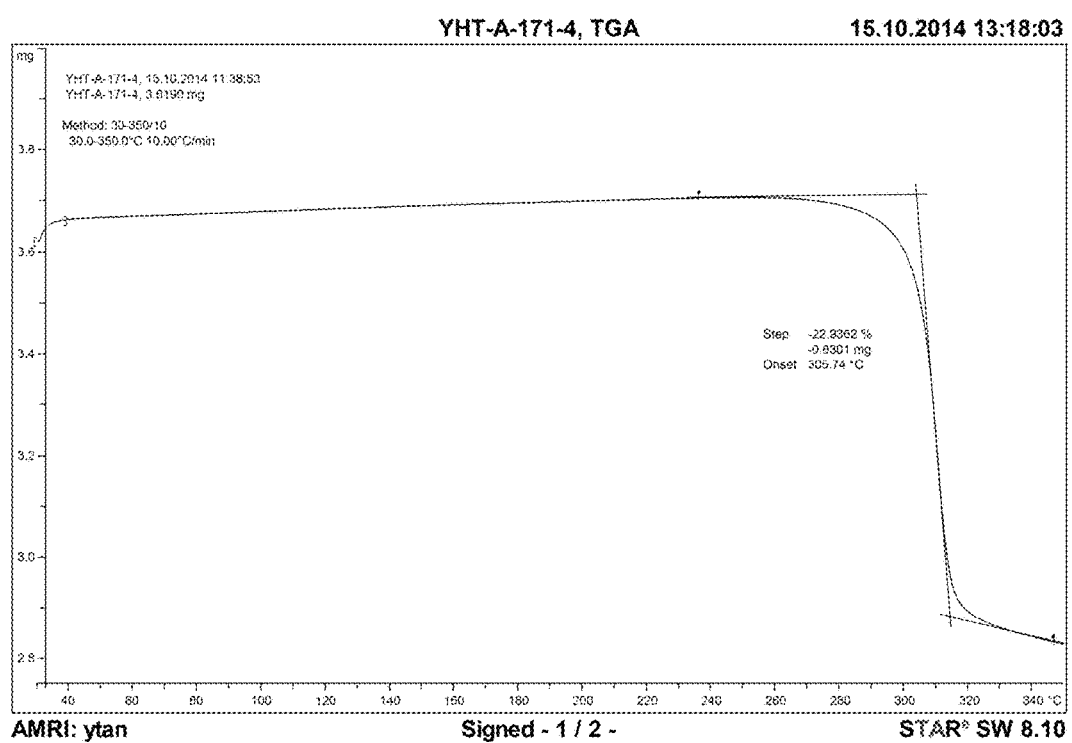
FIG. 75 depicts a TGA thermogram of Salt VI of Compound 1.

In one embodiment, Salt VI has a TGA thermogram corresponding substantially to the representative TGA thermogram as depicted in FIG. 75. In one embodiment, Salt VI exhibits a TGA thermogram comprising a decomposition event with onset temperature at approximately 305.7° C. when heated from approximately 25° C. to approximately 350° C.

Figure 74:
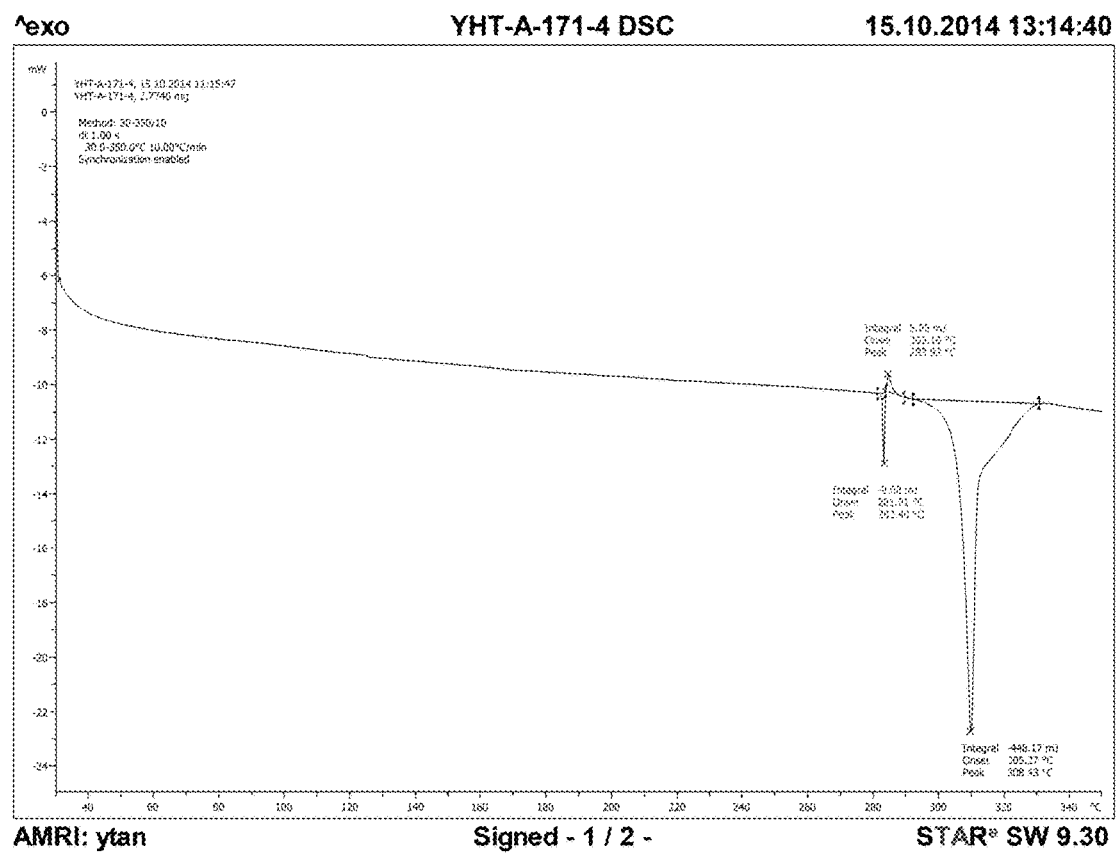
FIG. 74 depicts a DSC thermogram of Salt VI of Compound 1.

In one embodiment, Salt VI has a DSC thermogram as depicted in FIG. 74 comprising an endothermic event with a maximum at approximately 282.4° C. when heated from approximately 25° C. to approximately 350° C. In one embodiment, the DSC thermogram further comprises an exothermic event with a maximum at approximately 283.9° C. when heated from approximately 25° C. to approximately 350° C. In one embodiment, the DSC thermogram further comprises an endothermic event with a maximum at approximately 308.4° C. when heated from approximately 25° C. to approximately 350° C.

Figure 45:
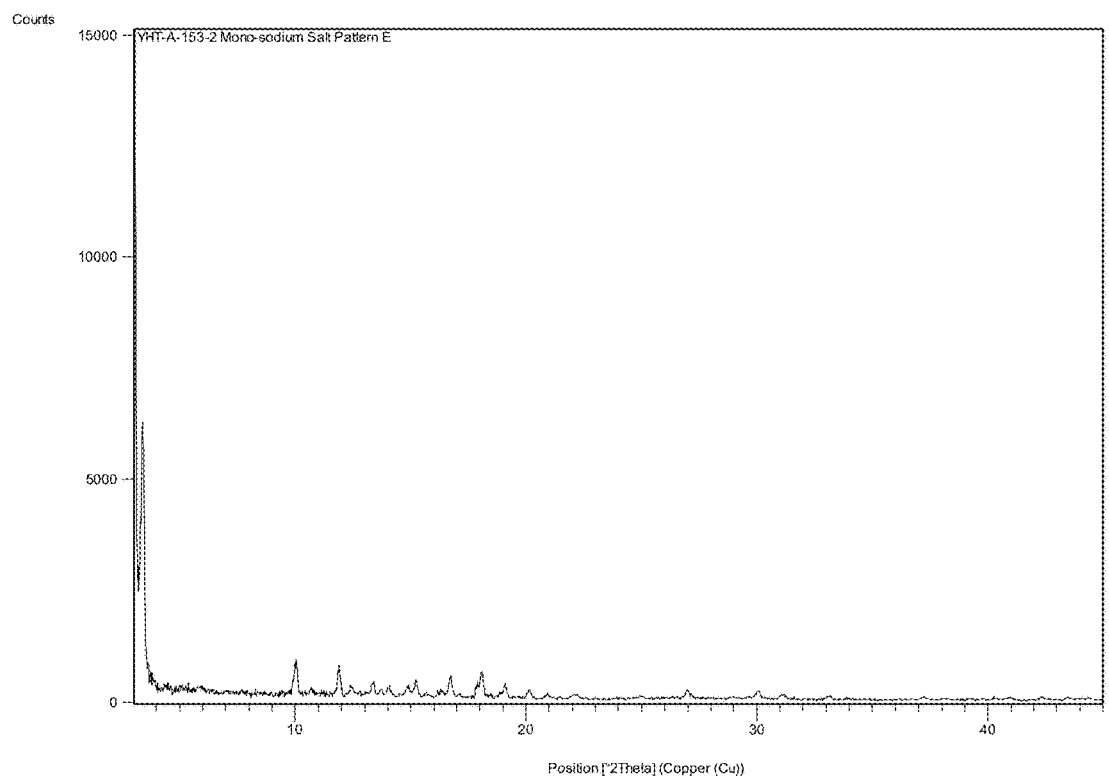
FIG. 45 depicts a XRPD Diffractogram of Salt VI of Compound 1.

In certain embodiments, Salt VI is substantially crystalline, as indicated by, e.g., X-ray powder diffraction measurements. In one embodiment, Salt VI has an X-ray powder diffraction pattern substantially as shown in FIG. 45. In one embodiment, Salt VI has one or more characteristic X-ray powder diffraction peaks at approximately 3.03, 3.39, 4.42, 4.63, 5.01, 5.40, 5.81, 6.23, 6.42, 7.06, 7.66, 8.96, 10.06, 10.68, 11.53, 11.89, 12.42, 13.40, 13.73, 14.04, 14.91, 15.22, 15.67, 16.33, 16.74, 17.10, 17.82, 18.11, 18.48, 19.07, 20.15, 20.94, 21.47, 22.05, 23.37, 24.03, 24.96, 26.38, 26.96, 28.88, 30.07, 31.04, 31.61, 33.20, 33.94, 34.87, 37.20, 38.13, 39.72, 40.29, 40.97, 42.35, 43.41 or 44.38° 2θ as depicted in FIG. 45. In a specific embodiment, Salt VI has one, two, three, four, five, six, seven or eight characteristic X-ray powder diffraction peaks at approximately 3.03, 3.39, 10.06, 11.89, 13.40, 15.22, 16.74 or 18.11° 2θ. In another embodiment, Salt VI has one, two, three or four characteristic X-ray powder diffraction peaks at approximately 3.03, 3.39, 10.06 or 11.89° 2θ. In another embodiment, Salt VI has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three or forty-four characteristic X-ray powder diffraction peaks as set forth in Table 43.

In certain embodiments, Salt VI is substantially crystalline, as indicated by, e.g., X-ray powder diffraction measurements. In one embodiment, Salt VI has an X-ray powder diffraction pattern substantially as shown in FIG. 45. In one embodiment, Salt VI has one or more characteristic X-ray powder diffraction peaks at approximately 3.0, 3.4, 4.4, 4.6, 5.0, 5.4, 5.8, 6.2, 6.4, 7.1, 7.7, 9.0, 10.1, 10.7, 11.5, 11.9, 12.4, 13.4, 13.7, 14.0, 14.9, 15.2, 15.7, 16.3, 16.7, 17.1, 17.8, 18.1, 18.5, 19.1, 20.2, 20.9, 21.5, 22.1, 23.4, 24.0, 25.0, 26.4, 27.0, 28.9, 30.1, 31.0, 31.6, 33.2, 33.9, 34.9, 37.2, 38.1, 39.7, 40.3, 41.0, 42.4, 43.4 or 44.4° 2θ as depicted in FIG. 45. In a specific embodiment, Salt VI has one, two, three, four, five, six, seven or eight characteristic X-ray powder diffraction peaks at approximately 3.0, 3.4, 10.1, 11.9, 13.4, 15.2, 16.7 or 18.1° 2θ. In another embodiment, Salt VI has one, two, three or four characteristic X-ray powder diffraction peaks at approximately 3.0, 3.4, 10.1 or 11.9° 2θ. In another embodiment, Salt VI has one, two, three, four, five or six characteristic X-ray powder diffraction peaks at approximately 3.0, 3.4, 10.1, 11.9, 16.7 or 18.1° 2θ. In another embodiment, Salt VI has one, two or three characteristic X-ray powder diffraction peaks at approximately 3.0, 3.4 or 10.1° 2θ. In another embodiment, Salt VI has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three or forty-four characteristic X-ray powder diffraction peaks as set forth in Table 43.

5.4.7 Hydrated Mono-Sodium Salt of Compound 1 (Salt VII)

In one embodiment, provided herein is a sodium salt of Compound 1. In one embodiment, provided herein is a mono-sodium salt of Compound 1. In one embodiment, the mono-sodium salt is a hydrate ("Salt VII"). In one embodiment, Salt VII is crystalline. In one embodiment, Salt VII is moderately hydroscopic. In one embodiment, Salt VII is chemically stable. In one embodiment, Salt VII is a stable hydrate.

In certain embodiments, provided herein is a method for making Salt VII, comprising 1) dissolving Compound 1 in a solvent (e.g., methanol) to yield a mixture; 2) heating the mixture to an elevated temperature (e.g., about 30-70° C.); 3) filtering the mixture at the elevated temperature to yield a solution; 4) contacting the mixture with a sodium hydroxide solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water.

In certain embodiments, provided herein is a method for making Salt VII, comprising 1) dissolving Compound 1 in a solvent (e.g., methanol) to yield a mixture; 2) heating the mixture to an elevated temperature (e.g., about 50° C.); 3) filtering the mixture at the elevated temperature with a 0.45 µm syringe filter to yield a solution; 4) contacting the mixture with a sodium hydroxide solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the sodium hydroxide solution is a solution of sodium hydroxide in water, methanol or a mixture of methanol and water.

Figure 87:
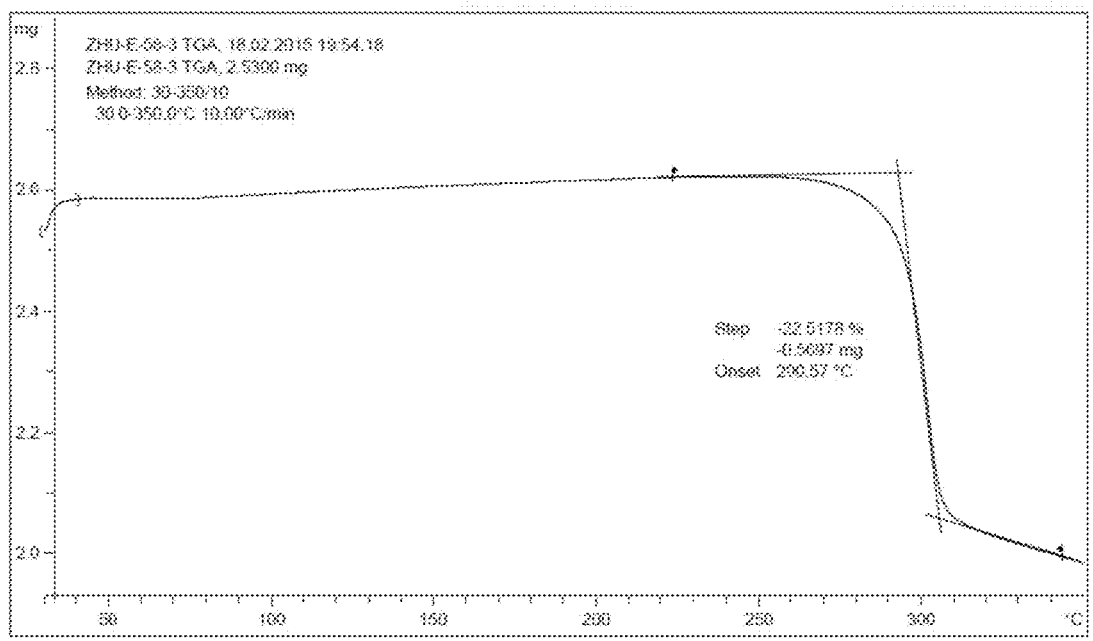
FIG. 87 depicts a TGA thermogram of Salt VII of Compound 1.

In one embodiment, Salt VII has a TGA thermogram corresponding substantially to the representative TGA thermogram as depicted in FIG. 87. In one embodiment, the TGA thermogram comprises a decomposition event with onset temperature at approximately 290.6° C. when heated from approximately 25° C. to approximately 350° C.

Figure 86:
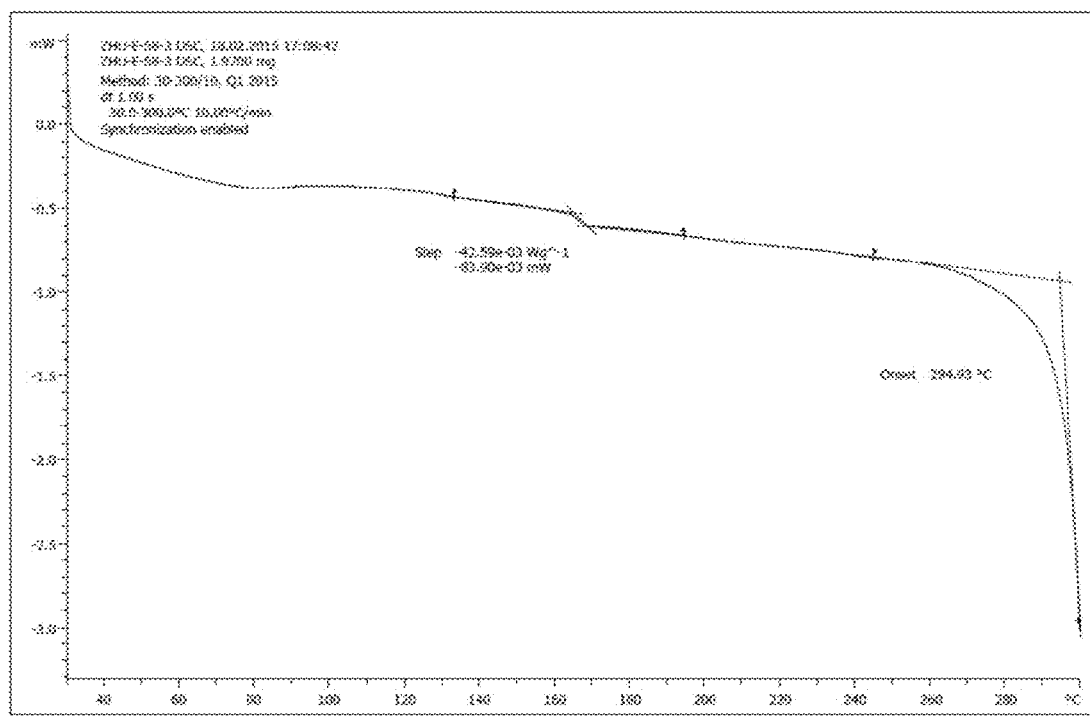
FIG. 86 depicts a DSC thermogram of Salt VII of Compound 1.

In one embodiment, Salt VII has a DSC thermogram as depicted in FIG. 86 comprising a broad transition event before approximately 90° C. when heated from approximately 25° C. to approximately 350° C. In one embodiment, the DSC thermogram further comprises a glass transition event at approximately 160° C. when heated from approximately 25° C. to approximately 350° C.

In certain embodiments, Salt VII is substantially crystalline, as indicated by, e.g., X-ray powder diffraction measurements. In one embodiment, Salt VII has an X-ray powder diffraction pattern substantially as shown in FIG. 43. In one embodiment, Salt VII has one or more characteristic X-ray powder diffraction peaks at approximately 3.40, 3.71, 4.08, 4.31, 4.95, 5.07, 5.33, 5.59, 6.11, 6.55, 6.95, 7.27, 7.60, 7.79, 8.49, 8.62, 9.54, 9.96, 10.87, 11.53, 11.88, 12.53, 12.78, 13.28, 13.64, 13.97, 14.31, 14.90, 15.48, 15.73, 16.37, 16.66, 18.02, 18.68, 20.03, 20.76, 20.96, 21.58, 22.15, 24.89, 25.46, 25.82, 26.83, 28.73, 29.35, 31.10, 32.28, 32.84, 33.75, 34.30, 37.27, 38.29, 38.86, 39.67, 40.80 or 44.33° 2θ as depicted in FIG. 43. In a specific embodiment, Salt VII has one, two, three, four, five, six, seven or eight characteristic X-ray powder diffraction peaks at approximately 3.40, 3.71, 9.96, 10.87, 14.90, 15.48, 15.73 or 16.66° 2θ. In another embodiment, Salt VII has one, two, three or four characteristic X-ray powder diffraction peaks at approximately 3.40, 9.96, 14.90 or 16.66° 2θ. In another embodiment, Salt VII has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, or fifty-six characteristic X-ray powder diffraction peaks as set forth in Table 44.

In certain embodiments, Salt VII is substantially crystalline, as indicated by, e.g., X-ray powder diffraction measurements. In one embodiment, Salt VII has an X-ray powder diffraction pattern substantially as shown in FIG. 43. In one embodiment, Salt VII has one or more characteristic X-ray powder diffraction peaks at approximately 3.4, 3.7, 4.1, 4.3, 5.0, 5.1, 5.3, 5.6, 6.1, 6.6, 7.0, 7.3, 7.6, 7.8, 8.5, 8.6, 9.5, 10.0, 10.9, 11.5, 11.9, 12.5, 12.8, 13.3, 13.6, 14.0, 14.3, 14.9, 15.5, 15.7, 16.4, 16.7, 18.0, 18.7, 20.0, 20.8, 21.0, 21.6, 22.2, 24.9, 25.5, 25.8, 26.8, 28.7, 29.4, 31.1, 32.3, 32.8, 33.8, 34.3, 37.3, 38.3, 38.9, 39.7, 40.8 or 44.3° 2θ as depicted in FIG. 43. In a specific embodiment, Salt VII has one, two, three, four, five, six, seven or eight characteristic X-ray powder diffraction peaks at approximately 3.4, 3.7, 10.0, 10.9, 14.9, 15.5, 15.7 or 16.7° 2θ. In another embodiment, Salt VII has one, two, three or four characteristic X-ray powder diffraction peaks at approximately 3.4, 10.0, 14.9 or 16.7° 2θ. In another embodiment, Salt VII has one, two, three, four, five or six characteristic X-ray powder diffraction peaks at approximately 3.4, 10.0, 10.9, 14.9, 15.5 or 16.7° 2θ. In another embodiment, Salt VII has one, two or three characteristic X-ray powder diffraction peaks at approximately 3.4, 10.0 or 14.9° 2θ. In another embodiment, Salt VII has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, or fifty-six characteristic X-ray powder diffraction peaks as set forth in Table 44.

5.4.8 Anhydrous Mono-Sodium Salt of Compound 1 (Salt VIII)

In one embodiment, provided herein is a sodium salt of Compound 1. In one embodiment, provided herein is a mono-sodium salt of Compound 1. In one embodiment, the mono-sodium salt is anhydrous ("Salt VIII"). In one embodiment, Salt VIII is crystalline. In one embodiment, Salt VIII is moderately hydroscopic. In one embodiment, Salt VIII is chemically stable.

In certain embodiments, provided herein is a method for making Salt VIII, comprising 1) stirring Salt IV of Compound 1 in a solvent (e.g., methanol) for a period of time (e.g., about 12 hours to about 48 hours) at a temperature (e.g., about 5° C. to about 45° C.); 2) collecting precipitation by filtration; and 3) in the absence of precipitation, evaporating the solution to yield a solid and collecting the solid.

In certain embodiments, provided herein is a method for making Salt VIII, comprising 1) stirring Salt IV of Compound 1 in a solvent (e.g., methanol) for a period of time (e.g., about 24 hours) at a temperature (e.g., about 25° C.);

2) collecting precipitation by filtration; and 3) in the absence of precipitation, evaporating the solution to yield a solid and collecting the solid.

Figure 94:
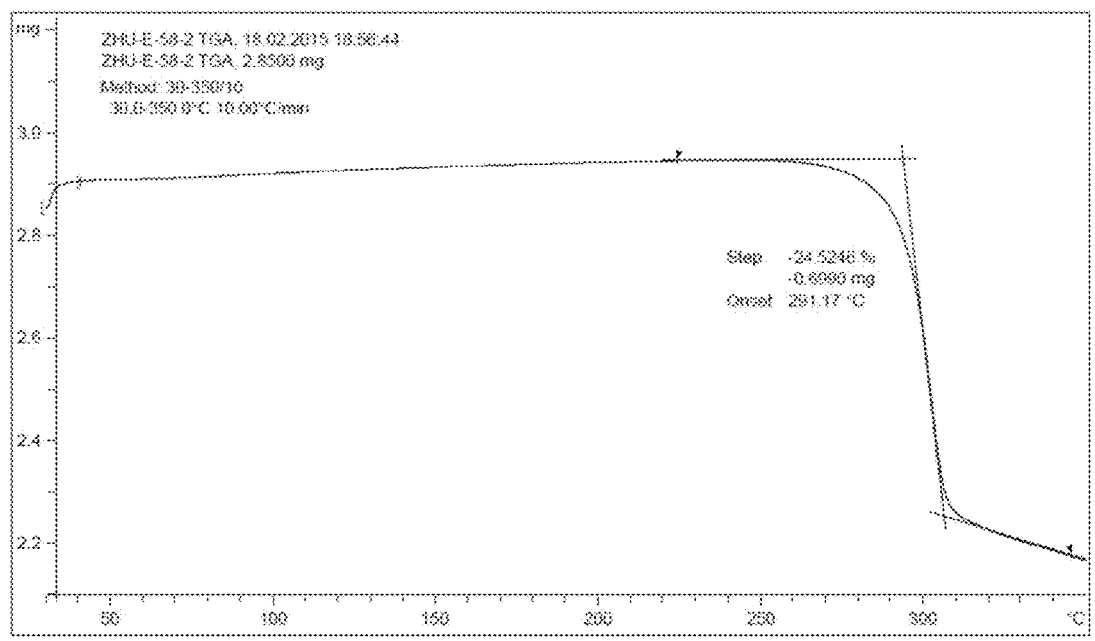
FIG. 94 depicts a TGA thermogram of Salt VIII of Compound 1.

In one embodiment, Salt VIII has a TGA thermogram corresponding substantially to the representative TGA thermogram as depicted in FIG. 94. In one embodiment, the TGA thermogram comprises a decomposition event with onset temperature at approximately 291.2° C. when heated from approximately 25° C. to approximately 350° C.

Figure 93:
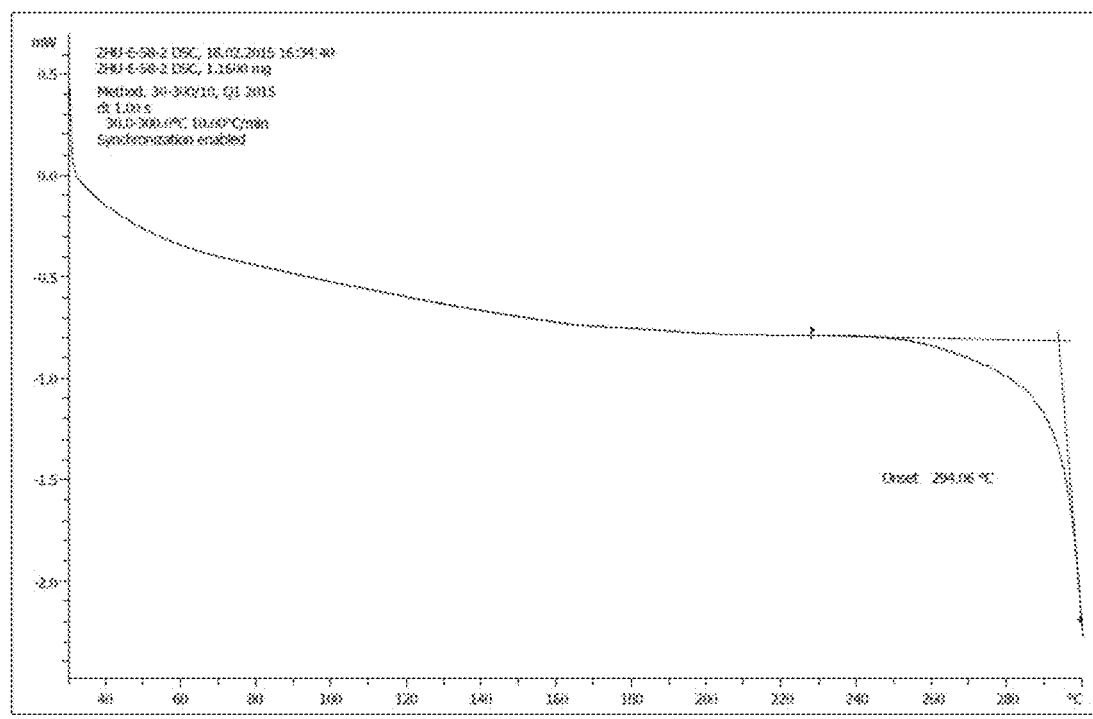
FIG. 93 depicts a DSC thermogram of Salt VIII of Compound 1.

In one embodiment, Salt VIII has a DSC thermogram as depicted in FIG. 93 comprising a decomposition event with onset temperature at approximately 294.0° C. when heated from approximately 25° C. to approximately 350° C.

Figure 91:
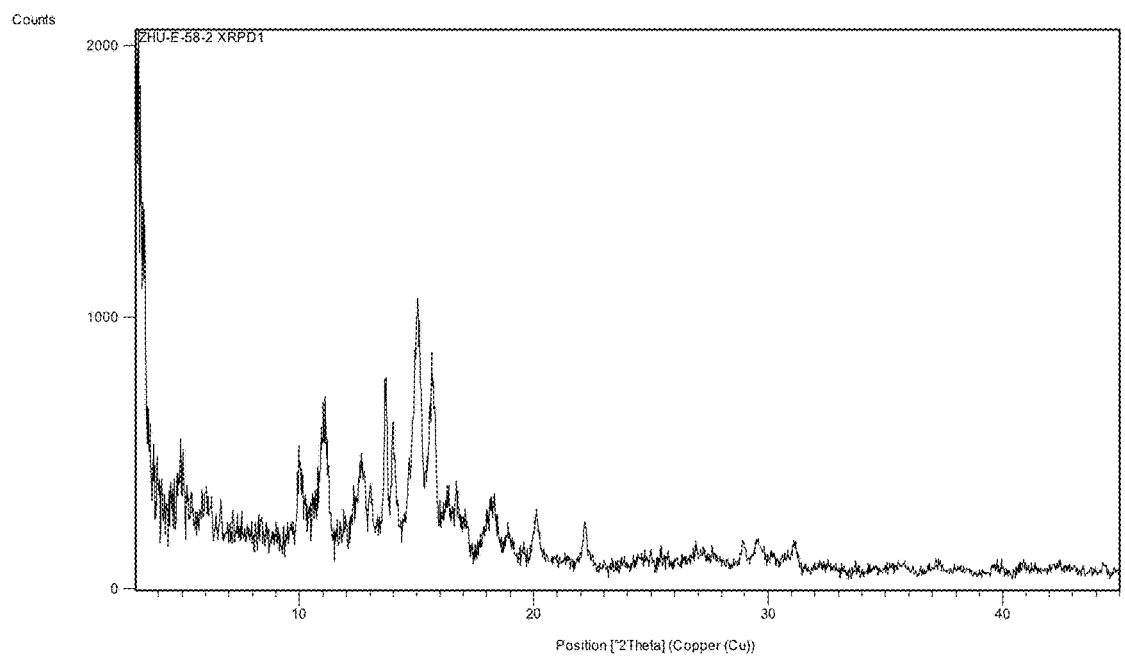
FIG. 91 depicts a XRPD Diffractogram of Salt VIII of Compound 1.

In certain embodiments, Salt VIII is substantially crystalline, as indicated by, e.g., X-ray powder diffraction measurements. In one embodiment, Salt VIII has an X-ray powder diffraction pattern substantially as shown in FIG. 91. In one embodiment, Salt VIII has one or more characteristic X-ray powder diffraction peaks at approximately 3.06, 3.39, 3.64, 3.79, 3.95, 4.54, 4.94, 5.07, 5.21, 5.40, 6.02, 6.27, 6.65, 7.18, 8.00, 8.37, 9.32, 10.00, 10.43, 11.04, 11.94, 12.72, 13.01, 13.71, 13.97, 14.66, 15.01, 15.65, 15.73, 16.34, 16.69, 17.14, 17.37, 18.31, 18.91, 19.57, 20.13, 22.17, 24.68, 25.02, 26.92, 28.96, 29.53, 31.12, 32.42, 33.47, 33.76, 34.58, 35.75, 37.25, 39.65, 40.87, 42.36, 43.42 or 44.34° 2θ as depicted in FIG. 91. In a specific embodiment, Salt VIII has one, two, three, four, five, six, seven or eight characteristic X-ray powder diffraction peaks at approximately 3.06, 3.39, 3.64, 13.71, 13.97, 15.01, 15.65 or 15.73° 2θ. In another embodiment, Salt VIII has one, two, three or four characteristic X-ray powder diffraction peaks at approximately 3.06, 3.39, 15.01 or 15.65° 2θ. In another embodiment, Salt VIII has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four or fifty-five characteristic X-ray powder diffraction peaks as set forth in Table 45.

In certain embodiments, Salt VIII is substantially crystalline, as indicated by, e.g., X-ray powder diffraction measurements. In one embodiment, Salt VIII has an X-ray powder diffraction pattern substantially as shown in FIG. 91. In one embodiment, Salt VIII has one or more characteristic X-ray powder diffraction peaks at approximately 3.1, 3.4, 3.6, 3.8, 4.0, 4.5, 4.9, 5.1, 5.2, 5.4, 6.0, 6.3, 6.7, 7.2, 8.0, 8.4, 9.3, 10.0, 10.4, 11.0, 11.9, 12.7, 13.0, 13.7, 14.0, 14.7, 15.0, 15.7, 15.7, 16.3, 16.7, 17.1, 17.4, 18.3, 18.9, 19.6, 20.1, 22.2, 24.7, 25.0, 26.9, 29.0, 29.5, 31.1, 32.4, 33.5, 33.8, 34.6, 35.8, 37.3, 39.7, 40.9, 42.4, 43.4 or 44.3° 2θ as depicted in FIG. 91. In a specific embodiment, Salt VIII has one, two, three, four, five, six, seven or eight characteristic X-ray powder diffraction peaks at approximately 3.1, 3.4, 3.6, 13.7, 14.0, 15.0, 15.7 or 15.7° 2θ. In another embodiment, Salt VIII has one, two, three or four characteristic X-ray powder diffraction peaks at approximately 3.1, 3.4, 15.0 or 15.7° 2θ. In another embodiment, Salt VIII has one, two, three, four, five or six characteristic X-ray powder diffraction peaks at approximately 3.1, 3.4, 13.7, 15.0, 15.6 or 15.7° 2θ. In another embodiment, Salt VIII has one, two or three characteristic X-ray powder diffraction peaks at approximately 3.1, 3.4 or 15.0° 2θ. In another embodiment, Salt VIII has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four or fifty-five characteristic X-ray powder diffraction peaks as set forth in Table 45.

5.4.9 Anhydrous Mono-Sodium Salt of Compound 1 (Salt IX)

In one embodiment, provided herein is a sodium salt of Compound 1. In one embodiment, provided herein is a mono-sodium salt of Compound 1. In one embodiment, the mono-sodium salt is anhydrous ("Salt IX"). In one embodiment, Salt IX is crystalline. In one embodiment, Salt IX is moderately hydroscopic. In one embodiment, Salt IX is chemically stable.

In certain embodiments, provided herein is a method for making Salt IX, comprising 1) dissolving Compound 1 in a solvent (e.g., acetone) to yield a mixture; 2) heating the mixture to an elevated temperature (e.g., about 30-70° C.); 3) filtering the mixture at the elevated temperature to yield a solution; 4) contacting the mixture with a sodium hydroxide solution (e.g., about 0.5-1.5 equivalents); 5) cooling the resulting mixture (e.g., to about 10-30° C.); 6) collecting precipitation by filtration; and 7) in the absence of precipitation, evaporating the solution to yield a solid and collecting the solid. In one embodiment, the sodium hydroxide solution is a solution of sodium hydroxide in water, acetone or a mixture of acetone and water.

In certain embodiments, provided herein is a method for making Salt IX, comprising 1) dissolving Compound 1 in a solvent (e.g., acetone) to yield a mixture; 2) heating the mixture to an elevated temperature (e.g., about 50° C.); 3) filtering the mixture at the elevated temperature with a 0.45 µm syringe filter to yield a solution; 4) contacting the mixture with a sodium hydroxide solution (e.g., about 1 equivalent); 5) cooling the resulting mixture (e.g., to about 25° C.) (e.g., at a speed of about 20° C./hour); 6) collecting precipitation by filtration; and 7) in the absence of precipitation, evaporating the solution to yield a solid and collecting the solid. In one embodiment, the sodium hydroxide solution is a solution of sodium hydroxide in water, acetone or a mixture of acetone and water.

Figure 101:
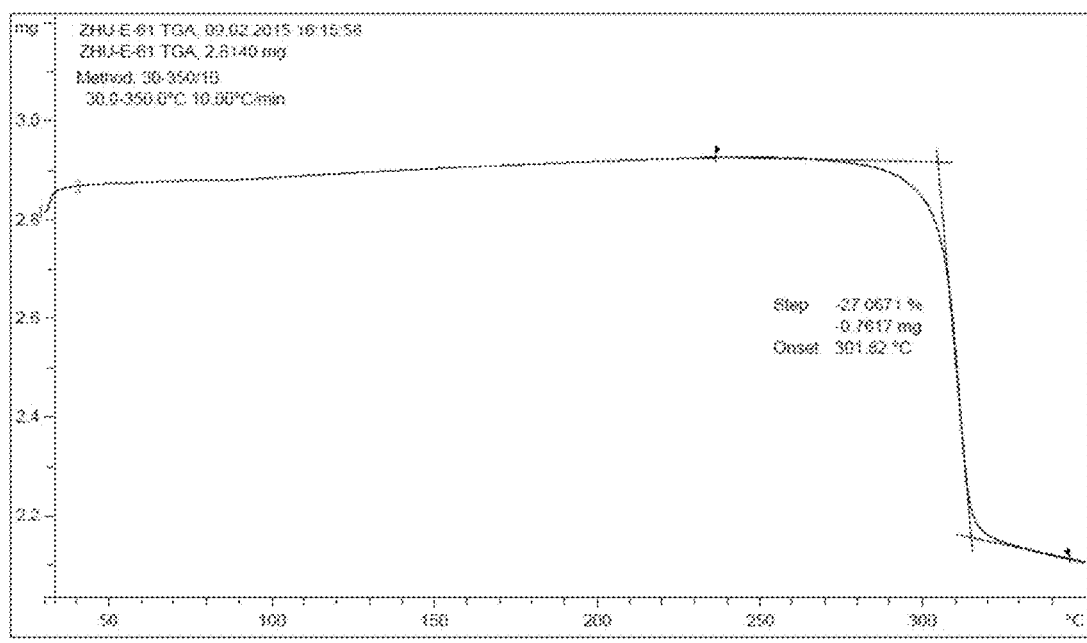
FIG. 101 depicts a TGA thermogram of Salt IX of Compound 1.

In one embodiment, Salt IX has a TGA thermogram corresponding substantially to the representative TGA thermogram as depicted in FIG. 101. In one embodiment, the TGA thermogram comprises a decomposition event with onset temperature at approximately 301.8° C. when heated from approximately 25° C. to approximately 350° C.

Figure 100:
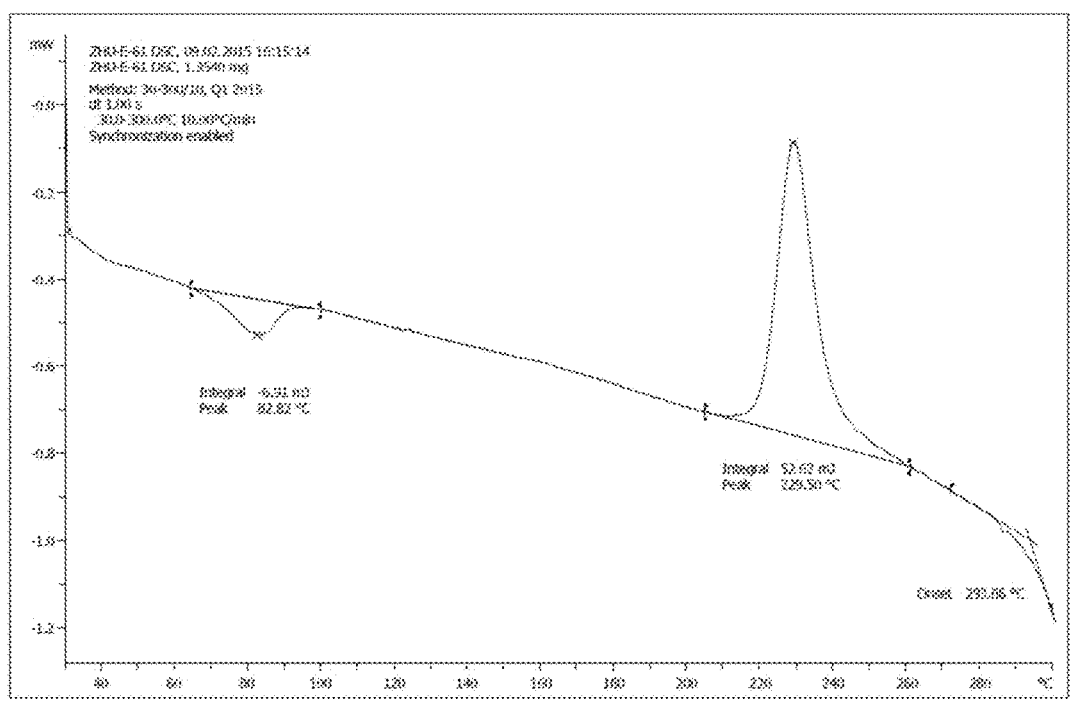
FIG. 100 depicts a DSC thermogram of Salt IX of Compound 1.

In one embodiment, Salt IX has a DSC thermogram as depicted in FIG. 100 comprising an endothermic event with a maximum at approximately 82.8° C. when heated from approximately 25° C. to approximately 350° C. In one embodiment, the DSC thermogram further comprises an exothermic event with a maximum at approximately 229.5° C. when heated from approximately 25° C. to approximately 350° C.

Figure 98:
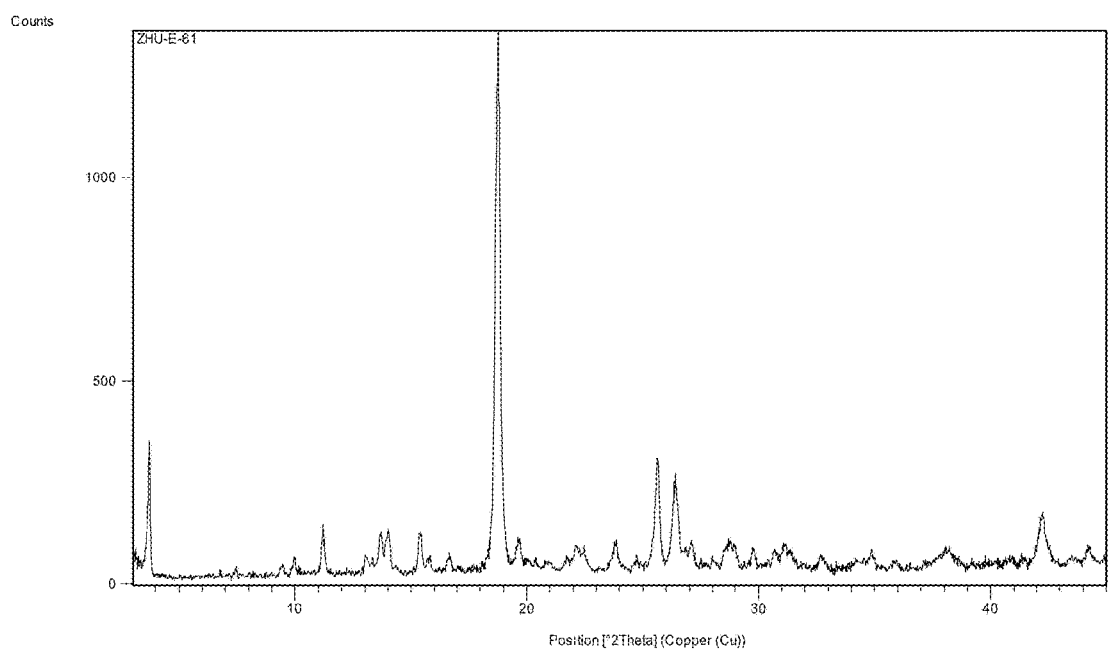
FIG. 98 depicts a XRPD Diffractogram of Salt IX of Compound 1.

In certain embodiments, Salt IX is substantially crystalline, as indicated by, e.g., X-ray powder diffraction measurements. In one embodiment, Salt IX has an X-ray powder diffraction pattern substantially as shown in FIG. 98. In one embodiment, Salt IX has one or more characteristic X-ray powder diffraction peaks at approximately 3.05, 3.19, 4.33, 4.57, 5.11, 5.25, 5.71, 6.32, 7.68, 7.88, 9.47, 9.93, 10.04, 12.63, 13.06, 13.69, 14.01, 14.89, 15.83, 16.31, 16.68, 17.39, 18.33, 19.01, 19.94, 20.72, 20.88, 22.12, 22.27, 22.60, 23.58, 24.21, 24.69, 25.47, 26.26, 26.62, 27.63, 28.42, 28.73, 29.44, 31.25, 31.90, 32.51, 33.23, 34.35, 35.85, 37.39, 38.30, 39.79, 40.61, 41.44, 41.96 or 44.56° 2θ as depicted in FIG. 98. In a specific embodiment, Salt IX has one, two, three, four, five, six, seven or eight characteristic X-ray powder diffraction peaks at approximately 3.05, 3.19, 6.32, 9.47, 13.69, 15.83, 19.01 or 25.47° 2θ. In another embodiment, Salt IX has one, two, three or four characteristic X-ray powder diffraction peaks at approximately 3.05, 3.19, 9.47 or 19.01° 2θ. In another embodiment, Salt IX has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two or fifty-three characteristic X-ray powder diffraction peaks as set forth in Table 46.

In certain embodiments, Salt IX is substantially crystalline, as indicated by, e.g., X-ray powder diffraction measurements. In one embodiment, Salt IX has an X-ray powder diffraction pattern substantially as shown in FIG. 98. In one embodiment, Salt IX has one or more characteristic X-ray powder diffraction peaks at approximately 3.1, 3.2, 4.3, 4.6, 5.1, 5.3, 5.7, 6.3, 7.7, 7.9, 9.5, 9.9, 10.0, 12.6, 13.1, 13.7, 14.0, 14.9, 15.8, 16.3, 16.7, 17.4, 18.3, 19.0, 19.9, 20.7, 20.9, 22.1, 22.3, 22.6, 23.6, 24.2, 24.7, 25.5, 26.3, 26.6, 27.6, 28.4, 28.7, 29.4, 31.3, 31.9, 32.5, 33.2, 34.4, 35.9, 37.4, 38.3, 39.8, 40.6, 41.4, 42.0 or 44.6° 2θ as depicted in FIG. 98. In a specific embodiment, Salt IX has one, two, three, four, five, six, seven or eight characteristic X-ray powder diffraction peaks at approximately 3.1, 3.2, 6.3, 9.5, 13.7, 15.8, 19.0 or 25.5° 2θ. In another embodiment, Salt IX has one, two, three or four characteristic X-ray powder diffraction peaks at approximately 3.1, 3.2, 9.5 or 19.0° 2θ. In another embodiment, Salt IX has one, two, three, four, five or six characteristic X-ray powder diffraction peaks at approximately 3.1, 3.2, 6.3, 9.5, 15.8 or 19.0° 2θ. In another embodiment, Salt IX has one, two or three characteristic X-ray powder diffraction peaks at approximately 3.2, 9.5 or 19.0° 2θ. In another embodiment, Salt IX has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two or fifty-three characteristic X-ray powder diffraction peaks as set forth in Table 46.

5.4.10 Hydrated Mono-Sodium Salt of Compound 1 (Salt X)

In one embodiment, provided herein is a sodium salt of Compound 1. In one embodiment, provided herein is a mono-sodium salt of Compound 1. In one embodiment, the mono-sodium salt is a hydrate ("Salt X"). In one embodiment, Salt X is crystalline. In one embodiment, Salt X is moderately hydroscopic. In one embodiment, Salt X is chemically unstable. In one embodiment, Salt X is an unstable hydrate.

In one embodiment, provided herein are methods for preparing Salt X of Compound 1 comprising binary solvent fast cooling crystallization comprising the steps of: (1) dissolving Salt IV of Compound 1 (e.g., about 100-300 mg) with a minimum amount of solvents (e.g., up to 7.0 mL) at a first temperature (e.g., about 50 or 70° C.); (2) adding a co-solvent (e.g., about 5-25 mL); (3) placing the solution at a second temperature (e.g., about 15-35° C.) for a period of time (e.g., about 12-48 hours); and (4) evaporating the samples without precipitation to dryness (e.g., evaporating under a gentle stream of nitrogen gas) and collecting the resulting solids. All obtained solids were analyzed by XRPD to determine the solid form (see Table 47). In certain embodiments, the solvent is water. In certain embodiments, the co-solvent is THF.

In one embodiment, provided herein are methods for preparing Salt X of Compound 1 comprising binary solvent fast cooling crystallization comprising the steps of: (1) dissolving Salt IV of Compound 1 (e.g., about 168 mg) with a minimum amount of solvents (e.g., about 4.3 mL) at a first temperature (e.g., about 60° C.); (2) adding a co-solvent (e.g., about 12.8 mL); (3) placing the solution at a second temperature (e.g., about 25° C.) for a period of time (e.g., about 24 hours); and (4) evaporating the samples without precipitation to dryness (e.g., evaporating under a gentle stream of nitrogen gas) and collecting the resulting solids. All obtained solids were analyzed by XRPD to determine the solid form (see Table 47). In certain embodiments, the solvent is water. In certain embodiments, the co-solvent is THF.

Figure 108:
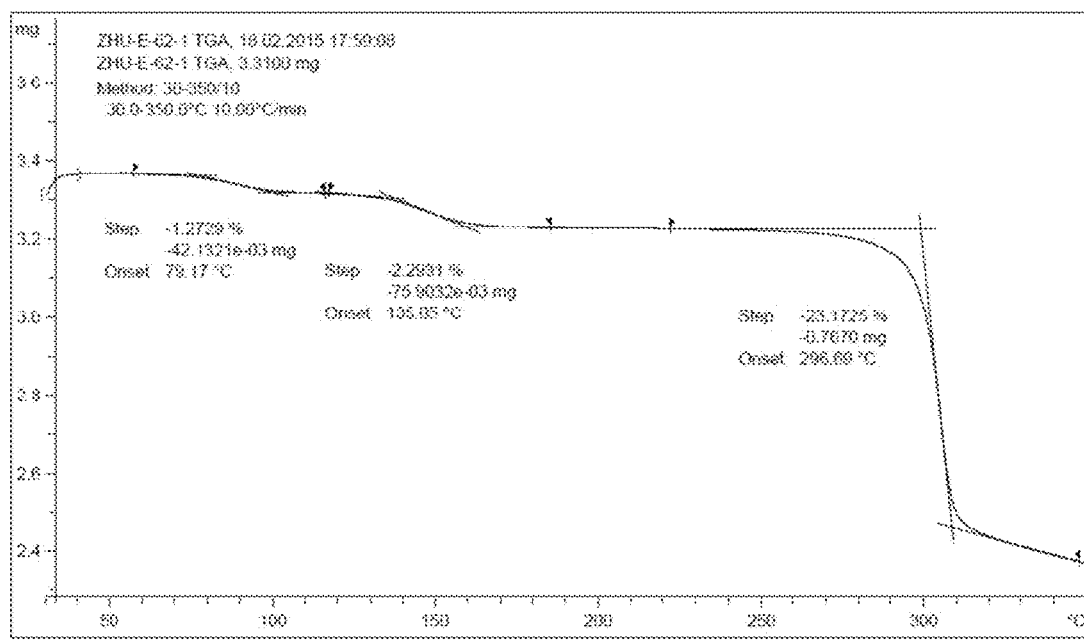
FIG. 108 depicts a TGA thermogram of Salt X of Compound 1.

In one embodiment, Salt X has a TGA thermogram corresponding substantially to the representative TGA thermogram as depicted in FIG. 108. In one embodiment, Salt X exhibits a TGA thermogram comprising a total mass loss of approximately 1.3% of the total mass of the sample between approximately 60° C. and approximately 120° C. when heated from approximately 25° C. to approximately 350° C. In one embodiment, Salt X exhibits a TGA thermogram comprising a total mass loss of approximately 2.3% of the total mass of the sample between approximately 120° C. and approximately 180° C. when heated from approximately 25° C. to approximately 350° C. In one embodiment, the TGA thermogram further comprises a decomposition event with onset temperature at approximately 296.7° C. when heated from approximately 25° C. to approximately 350° C.

Figure 107:
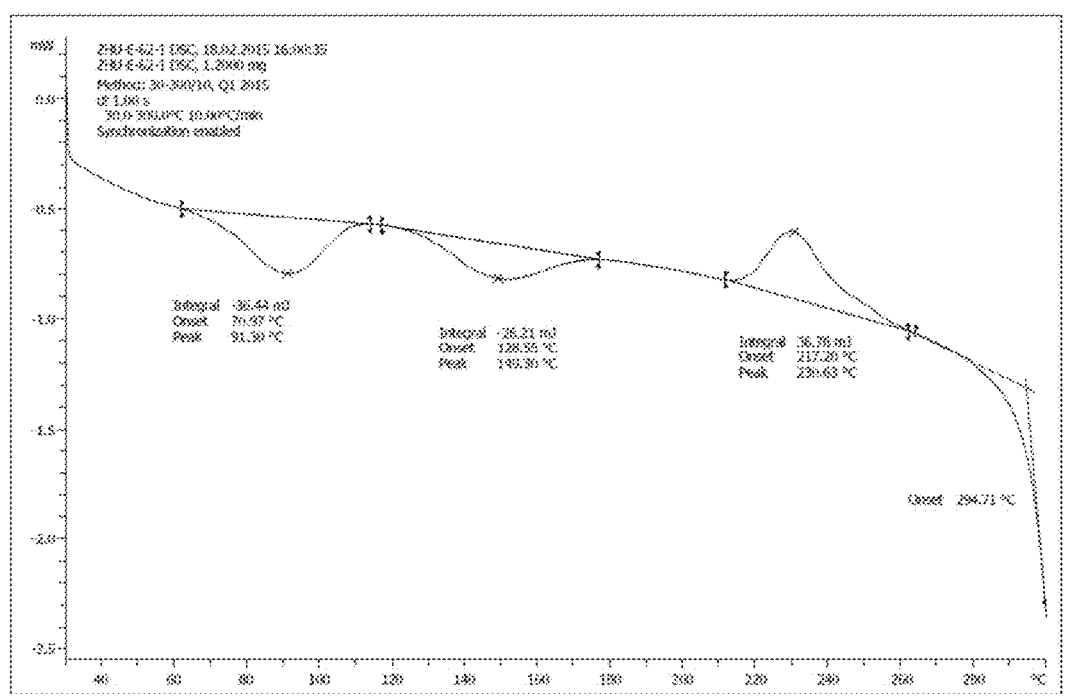
FIG. 107 depicts a DSC thermogram of Salt X of Compound 1.

In one embodiment, Salt IX has a DSC thermogram as depicted in FIG. 107 comprising an endothermic event with a maximum at approximately 91.3° C. when heated from approximately 25° C. to approximately 350° C. In one embodiment, the DSC thermogram further comprises an endothermic event with a maximum at approximately 149.3° C. when heated from approximately 25° C. to approximately 350° C. In one embodiment, the DSC thermogram further comprises an exothermic event with a maximum at approximately 230.6° C. when heated from approximately 25° C. to approximately 350° C.

Figure 105:
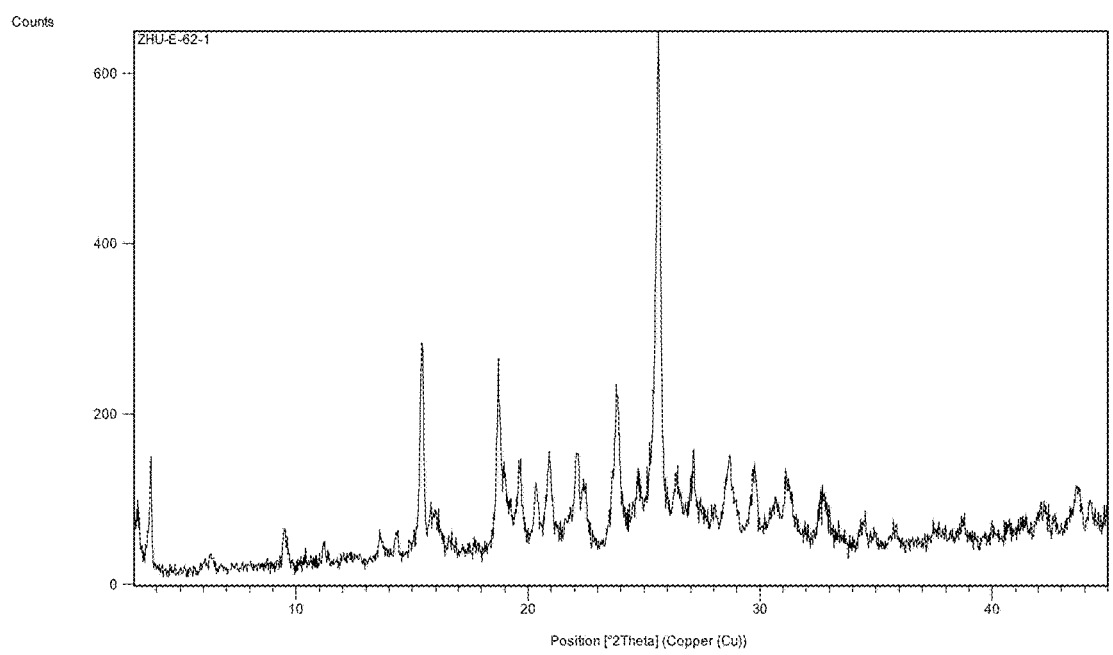
FIG. 105 depicts a XRPD Diffractogram of Salt X of Compound 1.

In certain embodiments, Salt X is substantially crystalline, as indicated by, e.g., X-ray powder diffraction measurements. In one embodiment, Salt X has an X-ray powder diffraction pattern substantially as shown in FIG. 105. In one embodiment, Salt X has one or more characteristic X-ray powder diffraction peaks at approximately 3.20, 3.74, 4.11, 4.23, 4.36, 4.59, 4.78, 5.03, 5.22, 5.43, 5.62, 5.88, 6.06, 6.28, 6.76, 7.24, 7.41, 7.83, 8.01, 9.50, 10.37, 11.01, 11.15, 11.38, 12.12, 12.75, 13.58, 14.37, 14.87, 15.06, 15.41, 15.78, 16.65, 18.71, 19.70, 20.35, 20.88, 22.16, 22.49, 23.83, 24.73, 25.62, 26.38, 27.11, 28.71, 29.79, 30.65, 31.15, 32.80, 34.52, 35.81, 37.64, 38.77, 41.35, 42.26, 43.70 or 44.25° 2θ as depicted in FIG. 105. In a specific embodiment, Salt X has one, two, three, four, five, six, seven or eight characteristic X-ray powder diffraction peaks at approximately 3.20, 3.74, 15.41, 18.71, 19.70, 22.16, 23.83 or 25.62° 2θ. In another embodiment, Salt X has one, two, three or four characteristic X-ray powder diffraction peaks at approximately 3.20, 3.74, 15.41 or 25.62° 2θ. In another embodiment, Salt X has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three or sixty-four characteristic X-ray powder diffraction peaks as set forth in Table 47.

In certain embodiments, Salt X is substantially crystalline, as indicated by, e.g., X-ray powder diffraction measurements. In one embodiment, Salt X has an X-ray powder diffraction pattern substantially as shown in FIG. 105. In one embodiment, Salt X has one or more characteristic X-ray powder diffraction peaks at approximately 3.2, 3.7, 4.1, 4.2, 4.4, 4.6, 4.8, 5.0, 5.2, 5.4, 5.6, 5.9, 6.1, 6.3, 6.8, 7.2, 7.4, 7.8, 8.0, 9.5, 10.4, 11.0, 11.2, 11.4, 12.1, 12.8, 13.6, 14.4, 14.9, 15.0, 15.4, 15.8, 16.7, 18.7, 19.7, 20.4, 20.9, 22.1, 22.5, 23.8, 24.7, 25.6, 26.4, 27.1, 28.7, 29.8, 30.7, 31.2, 32.8, 34.5, 35.8, 37.6, 38.8, 41.4, 42.3, 43.7 or 44.3° 2θ as depicted in FIG. 105. In a specific embodiment, Salt X has one, two, three, four, five, six, seven or eight characteristic X-ray powder diffraction peaks at approximately 3.2, 3.7, 15.4, 18.7, 19.7, 22.2, 23.8 or 25.6° 2θ. In another embodiment, Salt X has one, two, three or four characteristic X-ray powder diffraction peaks at approximately 3.2, 3.7, 15.4 or 25.6° 2θ. In another embodiment, Salt X has one, two, three, four, five or six characteristic X-ray powder diffraction peaks at approximately 3.2, 3.7, 15.4, 18.7, 23.8 or 25.6° 2θ. In another embodiment, Salt X has one, two or three characteristic X-ray powder diffraction peaks at approximately 3.2, 3.7 or 25.6° 2θ. In another embodiment, Salt X has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three or sixty-four characteristic X-ray powder diffraction peaks as set forth in Table 47.

5.5 Methods for Making Compound 1

By way of example and not limitation, Compound 1 can be prepared as outlined in Scheme 1, as well as in the examples set forth herein.

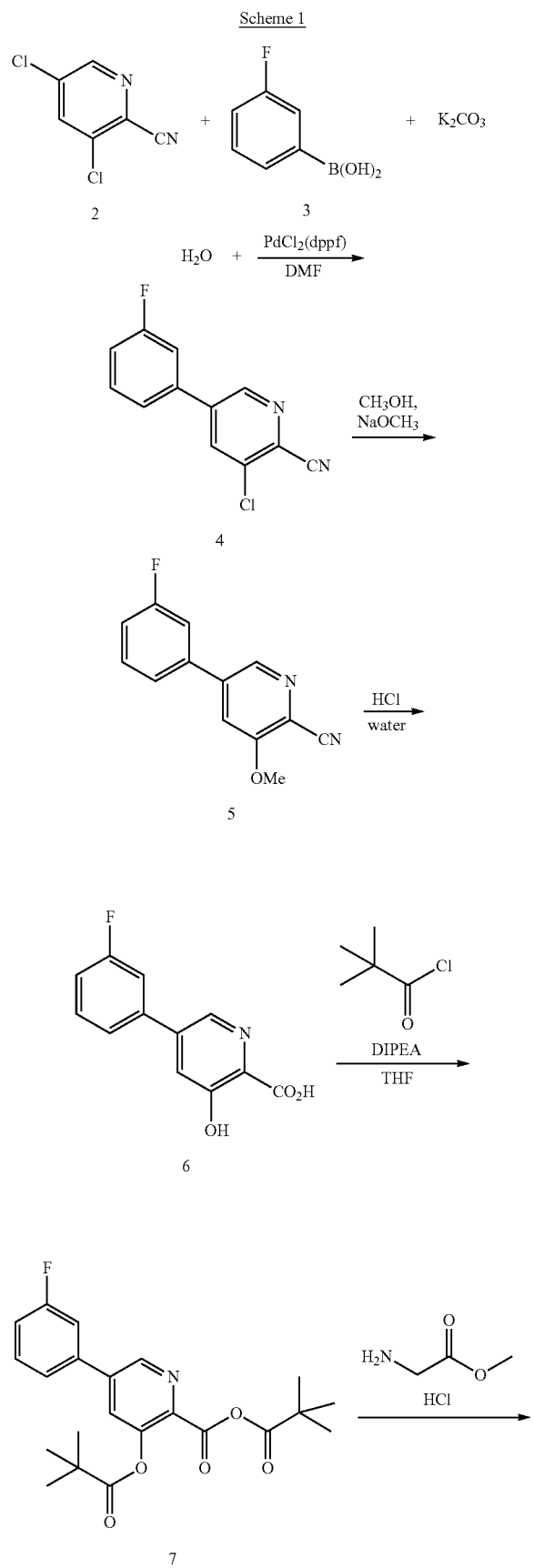

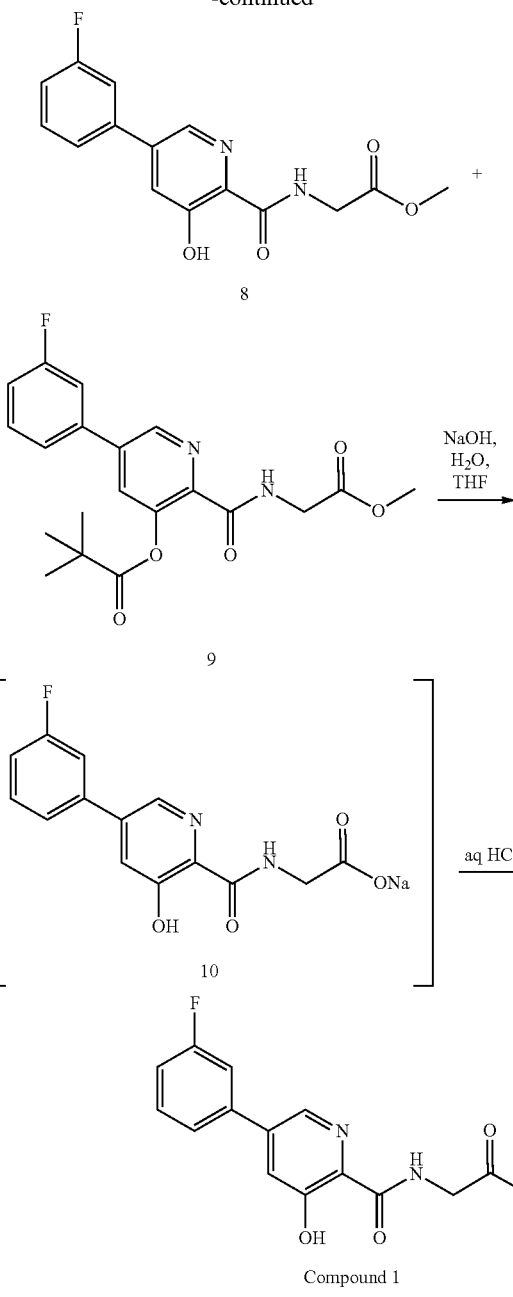

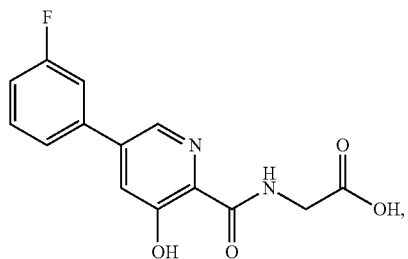

Provided are methods of preparing Compound 1 comprising contacting compound 10

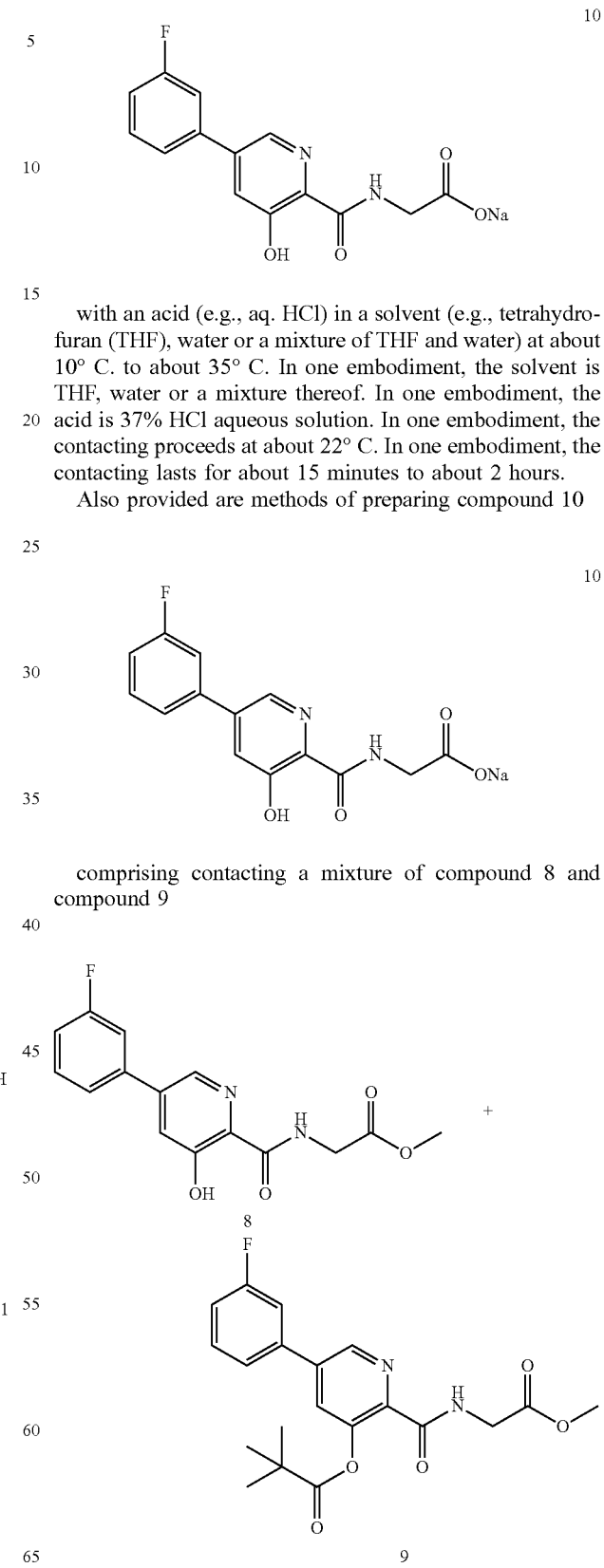

with an acid (e.g., aq. HCl) in a solvent (e.g., tetrahydrofuran (THF), water or a mixture of THF and water) at about 10° C. to about 35° C. In one embodiment, the solvent is THF, water or a mixture thereof. In one embodiment, the acid is 37% HCl aqueous solution. In one embodiment, the contacting proceeds at about 22° C. In one embodiment, the contacting lasts for about 15 minutes to about 2 hours.

Also provided are methods of preparing compound 10 comprising contacting a mixture of compound 8 and compound 9 with a base (e.g., NaOH) in a solvent (e.g., tetrahydrofuran (THF), water or THF/water) at about 10° C. to about 35° C. In some embodiments, the solvent is THF, water or a mixture thereof. In one embodiment, the base is NaOH. In one embodiment, the contacting proceeds at about 22° C. In one embodiment, the contacting lasts for about 1 hour to about 5 hours.

Also provided are methods of preparing a mixture of compound 8 and compound 9

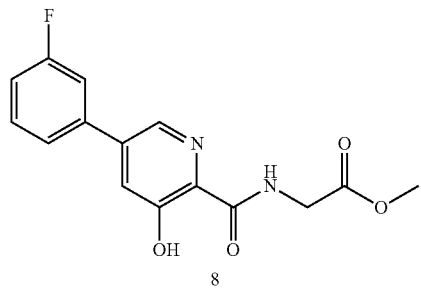

8

+

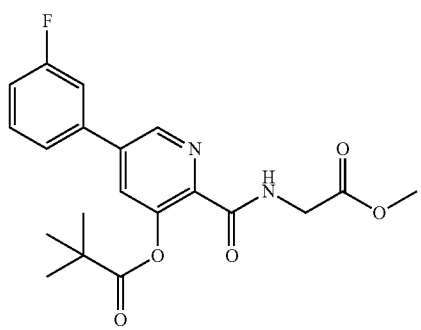

9 comprising contacting compound 7

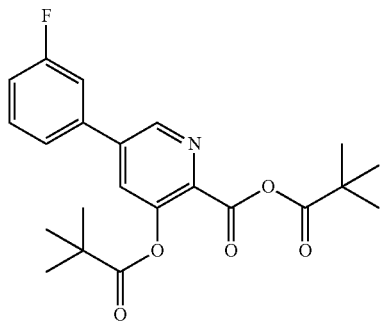

7 with glycine methyl ester HCl salt in a solvent (e.g., tetrahydrofuran (THF)) in the presence of a base (e.g., diisopropylethylamine) at about 10° C. to about 35° C. In some embodiments, the solvent is THF. In one embodiment, the base is diisopropylethylamine. In one embodiment, the contacting proceeds at about 22° C. In one embodiment, the contacting lasts for about 4 hours to about 16 hours.

Also provided are methods of preparing compound 7

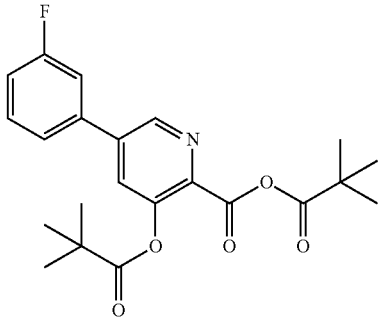

7 comprising contacting compound 6

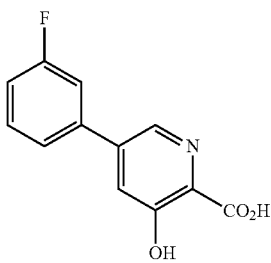

6 with trimethylacetyl chloride in a solvent (e.g., tetrahydrofuran (THF)) in the presence of a base (e.g., diisopropylethylamine) at about −10° C. to about 10° C. In some embodiments, the solvent is THF. In one embodiment, the base is diisopropylethylamine. In one embodiment, the contacting proceeds at about 3° C. In one embodiment, the contacting lasts for about 1 hours to about 3 hours.

Also provided are methods of preparing compound 6

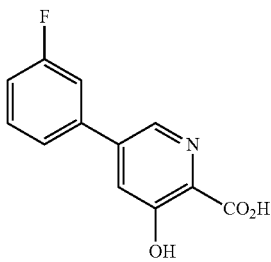

6 comprising contacting compound 5

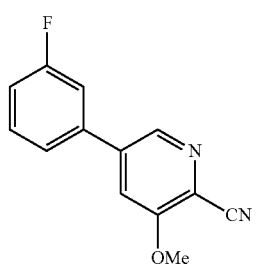

5 with an acid (e.g., 37% HCl aqueous solution) in a solvent (e.g., water) at about 60° C. to about 110° C. In one embodiment, the acid is 37% HCl aqueous solution. In one embodiment, the contacting proceeds at about 100° C. In one embodiment, the contacting lasts for about 10 hours to about 60 hours.

Also provided are methods of preparing compound 5

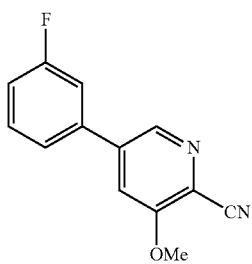

comprising contacting compound 4

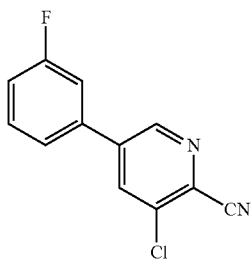

with a methoxide (e.g., sodium methoxide) in a solvent (e.g., methanol) at about 50° C. to about 90° C. In one embodiment, the methoxide is sodium methoxide. In one embodiment, the solvent is methanol. In one embodiment, the contacting proceeds at about 68° C. In one embodiment, the contacting lasts for about 6 hours to about 36 hours.

Also provided are methods of preparing compound 4

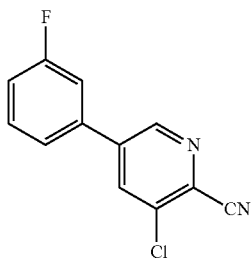

comprising contacting compound 2

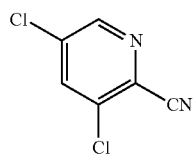

with (3-fluorophenyl)boronic acid and a catalyst (e.g., DCM adduct PdCl$_2$(dppf) and PdCl$_2$(dppf)) in a solvent (e.g., DMF, water or DMF/water) in the presence of a base (e.g., potassium carbonate) at about 25° C. to about 75° C. In certain embodiments, the catalyst is DCM adduct PdCl$_2$(dppf) or PdCl$_2$(dppf). In some embodiments, the solvent is DMF, water or a mixture thereof. In some embodiments, the base is potassium carbonate. In one embodiment, the contacting proceeds at about 50° C. In one embodiment, the contacting lasts for about 6 hours to about 36 hours.

5.6 Methods of Use

Provided herein are methods for treating or preventing cancer, comprising administering an effective amount of a solid form of Compound 1 to a patient having cancer.

Further provided herein are methods for preventing metastasis of malignant tumors or other cancerous cells, comprising administering an effective amount of a solid form of Compound 1 to a patient having a malignant tumor or cancerous cells.

Further provided herein are methods for reducing the rate of tumor growth or cancer cell growth, comprising administering an effective amount of a solid form of Compound 1 to a patient having a malignant tumor or cancerous cells.

Further provided herein are methods for decreasing tumor angiogenesis, comprising administering an effective amount of a solid form of Compound 1 to a patient having cancer.

Further provided herein are methods for stabilizing hypoxia inducible factor-2 alpha (HIF-2a), comprising administering an effective amount of a solid form of Compound 1 to a patient in need thereof.

Further provided herein are methods for decreasing vascular endothelial growth factor (VEGF) in a cell in vitro, in vivo or ex vivo, by inhibiting the binding of VEGF to vascular endothelial growth factor receptors (VEGFRs), comprising contacting the cell with an effective amount of a solid form of Compound 1. In one embodiment, the cell is a cancer cell. In another embodiment, the cell is a human cell. In as still further embodiment, the cell is a human cancer cell.

Further provided herein are methods for increasing secretion of soluble vascular endothelial growth factor receptor-1 (sVEGF-1) from a cell in vitro, in vivo or ex vivo, comprising contacting the cell with an effective amount of a solid form of Compound 1. In one embodiment, the cell is a tumor associated cell. In another embodiment, the cell is a human tumor associated cell. In as still further embodiment, the cell is a human cancer cell.

Further provided herein are methods for the treatment or prevention of cancer treatable or preventable by decreasing vascular endothelial growth factor (VEGF), comprising administering an effective amount of a solid form of Compound 1 to a patient having cancer treatable or preventable by decreasing VEGF.

Further provided herein are methods for the treatment or prevention of cancer treatable or preventable by increasing secretion of soluble vascular endothelial growth factor receptor-1 (sVEGF-1), comprising administering effective amount of a solid form of Compound 1 to a patient having cancer treatable or preventable by increasing sVEGF-1.

Further provided herein are methods for the treatment or prevention of cancer treatable or preventable by stabilizing hypoxia inducible factor-2 alpha (HIF-2a), comprising administering an effective amount of a solid form of Compound 1 to a patient having cancer treatable or preventable by stabilizing HIF-2a.

Further provided are methods for controlling, inhibiting or decreasing tumor growth in a patient, comprising administering effective amount of a solid form of Compound 1 to a patient having a tumor.

Further provided herein is the use of a solid form of Compound 1 for making a medicament for treating cancer.

Further provided herein is the use of a solid form of Compound 1 for making a medicament for the uses provided herein.

Provided herein is the use of a solid form of Compound 1 for treating or preventing cancer.

Further provided herein is the use of a solid form of Compound 1 for preventing metastasis of malignant tumors or other cancerous cells and for slowing tumor growth.

Further still provided herein is the use of a solid form of Compound 1 for decreasing tumor angiogenesis.

Further provided herein are methods for treating or preventing cancer, comprising administering to a patient having cancer an effective amount of a solid form of Compound 1 and an effective amount of one or more chemotherapeutic agents, wherein a solid form of Compound 1 and the one or more chemotherapeutic agents are administered in any order. Non-limiting examples of chemotherapeutic agents include taxol, IL-2, gemcitabine, erlotinib, doxil, irinortecan, and bevacizumab.

Further provided herein are methods for preventing metastasis of cancer cells, comprising administering to a patient having cancer an effective amount of a solid form of Compound 1 and an effective amount of one or more chemotherapeutic agents, wherein a solid form of Compound 1 and the one or more chemotherapeutic agents are administered in any order. Non-limiting examples of chemotherapeutic agents include taxol, IL-2, gemcitabine, erlotinib, doxil, irinortecan, and bevacizumab.

Further provided herein are methods for treating a patient diagnosed with cancer, comprising administering to a patient diagnosed with cancer an effective amount of a solid form of Compound 1 and an effective amount of one or more chemotherapeutic agents, wherein a solid form of Compound 1 and the one or more chemotherapeutic agents are administered in any order. Non-limiting examples of chemotherapeutic agents include taxol, IL-2, gemcitabine, erlotinib, doxil, irinortecan, and bevacizumab.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/:Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial;

Uterine Sarcoma; Vaginal Cancer; Vulvar Cancer; Waldenstrom Macroglobulinemia; and Wilms Tumor.

The cancer can be any cancer described herein, including VEGF-dependent cancers.

In certain embodiments, provided herein are methods of treating and/or preventing conditions of the eye wherein the methods comprise administering to a subject in need of treatment and/or prevention a solid form of Compound 1. Illustrative conditions of the eye include, but are not limited to, retinopathy (including diabetic retinopathy), radiation retinopathy, macular degeneration, age-related macular degeneration (including early, intermediate, and advanced stage age-related macular degeneration), Wet (exudative) age-related macular degeneration, specific genotypes associated with macular degeneration, cancer, solid or blood borne tumors, choroidal melanoma, sickle cell retinopathy, neovascularization, ocular neovascularization, subretinal neovascularization, vein occlusion, retinopathy of prematurity, chronic uveitis/vitritis, ocular trauma, ocular ischemia, retinal ischemia, Best's disease, chronic retinal detachment, diseases associated with rubeosis, Eales' disease proliferative vitreoretinopathy, familial exudative vitreoretinopathy, Stargardt's disease, presumed ocular histoplasmosis, hyperviscosity syndromes, myopia, post-laser complications, retinopathy of prematurity, infections causing a retinitis or choroiditis, optic pits, pars planitis, toxoplasmosis, choroidal neovascularization (including Type 1, 2, and 3 choroidal neovascularization), macular edema, cystoid macular edema, diabetic macular edema, ocular edema, glaucoma, neovascular glaucoma, surgery-induced edema, surgery-induced neovascularization, retinoschisis, retinal capillary occlusions, retinal angiomatous proliferation, vitreous hemorrhage, retinal neovascularization, polypoidal choroidal vasculopathy (juxtafoveal and subfovial), vitreomacular adhesion, geographic atrophy, retinal hypoxia, pathological myopia, dysregulated para-inflammation, chronic inflammation, chronic wound healing environment in the aging eye, carotid vacernous fistula, idiopathic occlusive arteriolitis, birdshot retinochoroidopathy, retinal vasculitis, incontinentia pigmenti, retinitis pigmentosa, tachyphylaxis, and limbal stem cell deficiency.

5.7 Pharmaceutical Compositions

Pharmaceutical compositions may be used in the preparation of individual, single unit dosage forms. Pharmaceutical compositions and dosage forms provided herein comprise a solid form of Compound 1.

In certain embodiment, pharmaceutical compositions and dosage forms comprise a solid form of Compound 1 and one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

Lactose-free compositions can comprise excipients that are well known in the art and are listed, for example, in the U.S. Pharmacopeia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

5.7.1 Oral Dosage Forms

Pharmaceutical compositions that are suitable for oral administration can be provided as discrete dosage forms, such as, but not limited to, tablets (e.g., chewable tablets), caplets, capsules, suspensions and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form. The binder or filler in pharmaceutical compositions is, in another embodiment, present in from about 20 to about 30 weight percent of the pharmaceutical composition or dosage form. The binder or filler in pharmaceutical compositions is, in another embodiment, present in about 24 weight percent of the pharmaceutical composition or dosage form.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof. In certain embodiments, POLOXAMER or PLURONIC, including, but not limited to POLOXAMER 188 NF, POLOXAMER 237 NF, POLOXAMER 338 NF, POLOXAMER 437 NF, and mixtures thereof, are surfactants.

In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 5 to about 9 weight percent of disintegrant, or from about 1 to about 5 weight percent of disintegrant, or from about 1 to about 7 weight percent of disintegrant, or about 7 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants and/or lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic colloidal silicon dioxide product sold by Cabot Co. of Boston, Mass.), and mixtures thereof. If used at all, glidants and/or lubricants may be used in an amount of less than about 1 weight percent of the pharmaceutical compositions or dosage forms into which they are incorporated.

In certain embodiments, an oral dosage form comprises the compound, silicified microcrystalline cellulose, sodium starch glycolate, a block copolymer of ethylene oxide and propylene oxide, sodium stearyl fumarate and colloidal silicon dioxide. In certain embodiments, an oral dosage form comprises a solid form of Compound 1 in an amount of about 5% to about 75% by weight, silicified microcrystalline cellulose in an amount of about 15% to about 85%, sodium starch glycolate in an amount of about 2% to about 10%, block copolymer of ethylene oxide and propylene oxide in an amount of about 2% to about 10%, sodium stearyl fumarate in an amount of 0.2% to about 2%, and colloidal silicon dioxide in an amount of about 0.2% to about 2% by weight of the oral dosage form.

In certain embodiments, an oral dosage form comprises the solid form of Compound 1, microcrystalline cellulose, isomalt, sodium starch glycolate, sodium lauryl sulfate, povidone, colloidal silicon dioxide, and magnesium stearate. In certain embodiments, an oral dosage form comprises a solid form of Compound 1 in an amount of about 40% to about 50%, microcrystalline cellulose in an amount of about 40% to about 50%, isomalt in an amount of 0% to about 5%, sodium starch glycolate in an amount of about 5% to about 10%, sodium lauryl sulfate in an amount of 0.2% to about 2%, povidone in an amount of about 2% to about 10%, colloidal silicon dioxide in an amount of 0.1% to about 1%, and magnesium stearate in an amount of about 0.1% to about 1% by weight of the oral dosage form.

In certain embodiments, the invention relates to unit dosage forms that comprise between about 100 mg and about 1,200 mg, about 200 mg and about 1,000 mg, about 400 mg and about 800 mg, or about 450 mg and about 600 mg of a solid form of Compound 1.

In certain embodiments, the invention relates to unit dosage forms that comprise about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150, or even about 1,200 mg of a solid form of Compound 1. In certain such embodiments, the unit dosage form is a capsule comprising about 40 mg, about 120 mg, about 185 mg, about 200 mg, about 250 mg, or about 400 mg of a solid form of Compound 1.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

6. EXAMPLES

The following examples are presented by way of illustration, not limitation. The following abbreviations are used in descriptions and examples:

ACN: Acetonitrile
AUC: Area under the curve
CI: Counter Ion
DMF: N,N-Dimethylformide
DMSO: Dimethylsulfoxide
DSC: Differential Scanning Calorimetry
DVS: Dynamic Vapor Sorption
EtOH: Ethanol
Evp: Evaporation
HPLC: High performance liquid chromatography
IC: Ion Chromatography
IPA: 2-Propanol
IPAc: Isopropyl Acetate
LCMS: Liquid Chromatography with Mass Spectroscopy
MEK: Methyl Ethyl Ketone
MeCN: Acetonitrile
MeOH: Methanol
MIBK: Methyl isoButyl Ketone
mp: Melting point
MS: Mass spectrometry
MTBE: tert-Butyl methyl ether
NMP: N-Methyl-2-pyrrolidone
NMR: Nuclear magnetic resonance
ppt: Precipitation
RH: Relative Humidity
RT: Room Temperature
SM: Compound 1
TGA: Thermogravimetric Analysis
THF: Tetrahydrofuran
XRPD: X-Ray Powder Diffraction

6.1 Summary of Polymorph Screen of Compound 1

Eight unique crystal forms (Forms A, B, C, D, E, F, G, and H) were prepared in the polymorph screen, including single solvent and binary solvent crystallization experiments, based on XRPD analysis. The characterization data indicated that Form A is a stable anhydrate polymorph. Forms B, C, D, and E showed high similarity with each other, with small differences between approximately 15 and 30° 2θ. Based on the DSC analysis, all four forms (B, C, D and E) showed similar endotherms at low temperature and recrystallization events at ~150.0° C. Characterization data showed that Form D is likely a metastable anhydrate polymorph. Forms B, C and E are likely either metastable anhydrate polymorph or solvent inclusion complexes, in which variable amount and type of organic solvents are retained and cause minor changes in crystal lattice. Form F is likely a metastable hydrate polymorph. Although Form G showed similarity to Form F, its TGA analysis did not show significant weight loss so it is possibly a metastable anhydrate polymorph. Form H is a mono-DMSO solvate, harvested when DMSO was used as primary solvent during re-crystallization experiment. Form A was found to be thermodynamically the most stable anhydrate polymorph.

6.1.1 Crystallization Experiments

Both fast cooling (refrigerating at 4° C., 24 hrs) and slow cooling (20° C./hr) approaches were used in attempt to generate crystals via single-solvent and binary solvent crystallization steps. Solvent crystallization experiments were performed as described in Sections 6.1.1.1 and 6.1.1.2 and summarized in Table 1-Table 10.

TABLE 1

Compound 1 single solvent fast cooling crystallization experiments (refrigerate at 4° C., 24 hrs), no precipitation formed.

| Cmpd 1 amount. (mg) | Solvent | Solvent Vol. (mL) | Temp. (° C.) | Solid form determined by XRPD |
|---|---|---|---|---|
| 33.0 | MeOH | 2.25 | 50.0 | B |
| 33.6 | EtOH | 2.63 | 50.0 | C |
| 32.5 | IPA | 4.81 | 50.0 | D |
| 31.2 | 1-BuOH | 4.91 | 50.0 | D + minor additional peaks |
| 32.8 | MeCN | 5.06 | 50.0 | D |
| 30.2 | THF | 3.08 | 50.0 | A + B |
| 32.2 | 2-MeTHF | 5.10 | 50.0 | E |
| 32.1 | EtOAc | 4.61 | 50.0 | D |
| 35.8 | IPAc | 4.50 | 50.0 | C |
| 32.9 | Acetone | 3.85 | 50.0 | B |
| 34.2 | MEK | 4.64 | 50.0 | E + minor additional peaks |
| 32.7 | MIBK | 6.00 | 50.0 | A + minor additional peaks |
| 35.1 | MTBE | 6.13 | 50.0 | A |
| 30.3 | DMSO | 1.04 | 50.0 | — |
| 31.6 | n-Propanol | 3.72 | 50.0 | E |

TABLE 2

Compound 1 single solvent slow cooling crystallization experiments (20° C./hr), no precipitation formed.

| Cmpd 1 amount. (mg) | Solvent | Solvent Vol. (mL) | Temp. (° C.) | Solid form by XRPD |
|---|---|---|---|---|
| 35.6 | MeOH | 2.25 | 50.0 | B |
| 32.8 | EtOH | 2.63 | 50.0 | C |
| 31.1 | IPA | 4.81 | 50.0 | D |
| 31.0 | 1-BuOH | 4.91 | 50.0 | E |
| 31.2 | MeCN | 5.06 | 50.0 | B |
| 34.7 | THF | 3.08 | 50.0 | A + B |
| 33.1 | 2-MeTHF | 5.10 | 50.0 | E |
| 32.0 | EtOAc | 4.61 | 50.0 | D |
| 33.2 | IPAc | 4.50 | 50.0 | C |
| 30.7 | Acetone | 3.85 | 50.0 | B |
| 32.1 | MEK | 4.64 | 50.0 | D |
| 30.0 | MIBK | 6.00 | 50.0 | B |
| 35.8 | MTBE | 6.13 | 50.0 | A + minor peak |
| 33.2 | DMSO | 1.04 | 50.0 | — |
| 35.3 | n-Propanol | 3.72 | 50.0 | E |

TABLE 3

Compound 1 binary solvent fast cooling crystallization experiments, water as co-solvent (refrigerate at 4° C., 24 hrs).

| Cmpd 1 amnt. (mg) | Primary Solvent | Temp. (° C.) | 1° solvent Vol. (mL) | Co-solvent Vol. (mL) | Precipitation/ Evaporation | Yield (mg) | Solid form by XRPD |
|---|---|---|---|---|---|---|---|
| 36.5 | MeOH | 50.0 | 2.5 | 3.0 | Precipitation | 3.99 | A + D |
| 32.8 | EtOH | 70.0 | 2.6 | 5.0 | Precipitation | 12.13 | A + C |
| 33.4 | IPA | 70.0 | 4.9 | 10.0 | Precipitation | 20.6 | A |
| 35.0 | MeCN | 70.0 | 5.4 | 10.0 | Precipitation | 13.49 | D |
| 31.3 | THF | 50.0 | 3.2 | 7.5 | Evaporation with N$_2$ | — | B + F |
| 32.5 | Acetone | 50.0 | 3.8 | 8.0 | Precipitation | 13.06 | A |
| 35.5 | DMSO | 70.0 | 1.2 | 1.0 | Precipitation | 20.86 | A |
| 30.1 | DMF | 70.0 | 1.1 | 2.0 | Precipitation | 7.86 | A |
| 33.9 | NMP | 70.0 | 1.3 | 2.0 | Precipitation | 15.46 | A |
| 34.2 | n-Propanol | 70.0 | 4.0 | 8.0 | Precipitation | 4.91 | D + F |
| 30.2 | MEK | 70.0 | 4.1 | 2.0 | Evaporation with N$_2$ | — | G |
| 31.5 | MIBK | 70.0 | 5.7 | 1.0 | Evaporation with N$_2$ | — | F + G |
| 31.8 | 2-MeTHF | 70.0 | 5.0 | 1.0 | Evaporation with N$_2$ | — | G |
| 32.5 | 1-BuOH | 70.0 | 5.1 | 5.0 | Evaporation with N$_2$ | — | D |

TABLE 4

Compound 1 binary solvent slow cooling crystallization experiments, water as co-solvent (20° C./hr).

| Cmpd 1 amnt. (mg) | Primary Solvent | Temp. (° C.) | 1° solvent Vol. (mL) | Co-solvent Vol. (mL) | Precipitation/ Evaporation | Yield (mg) | Solid form by XRPD |
|---|---|---|---|---|---|---|---|
| 32.6 | MeOH | 50.0 | 2.2 | 3.0 | Precipitation | 14.35 | A + B |
| 35.9 | EtOH | 70.0 | 2.8 | 5.0 | Precipitation | 12.1 | E |
| 35.1 | IPA | 70.0 | 5.2 | 10.0 | Evaporation with N$_2$ | — | G |
| 34.8 | MeCN | 70.0 | 5.4 | 10.0 | Precipitation | 12.86 | A |
| 36.7 | THF | 50.0 | 3.7 | 7.5 | Evaporation with N$_2$ | — | E + F |
| 36.3 | Acetone | 50.0 | 4.2 | 8.0 | Precipitation | 16.96 | A |
| 30.7 | DMSO | 70.0 | 1.1 | 1.0 | Evaporation with N$_2$ | — | Oily material |
| 32.2 | DMF | 70.0 | 1.2 | 2.0 | Precipitation | 2.66 | A |
| 33.5 | NMP | 70.0 | 1.3 | 2.0 | Precipitation | 11.16 | A |
| 34.0 | n-Propanol | 70.0 | 4.0 | 8.0 | Evaporation with N$_2$ | — | D |
| 31.6 | MEK | 70.0 | 4.3 | 2.0 | Evaporation with N$_2$ | — | B |
| 33.4 | MIBK | 70.0 | 6.0 | 1.0 | Evaporation with N$_2$ | — | B |
| 30.1 | 2-MeTHF | 70.0 | 4.8 | 1.0 | Evaporation with N$_2$ | — | G |

TABLE 4-continued

Compound 1 binary solvent slow cooling crystallization experiments, water as co-solvent (20° C./hr).

| Cmpd 1 amnt. (mg) | Primary Solvent | Temp. (° C.) | 1° solvent Vol. (mL) | Co-solvent Vol. (mL) | Precipitation/ Evaporation | Yield (mg) | Solid form by XRPD |
|---|---|---|---|---|---|---|---|
| 31.9 | 1-BuOH | 70.0 | 5.0 | 5.0 | Evaporation with N$_2$ | — | D |

TABLE 5

Compound 1 binary solvent fast cooling crystallization experiments, toluene as co-solvent (refrigerate at 4° C., 24 hrs), no precipitation formed.

| Cmpd 1 amnt. (mg) | Primary Solvent | Temp. (° C.) | 1° solvent Vol. (mL) | Co-solvent Vol. (mL) | Solid form by XRPD |
|---|---|---|---|---|---|
| 30.0 | MeOH | 50.0 | 2.0 | 4.0 | D + extra peak (5.475° 2θ) |
| 32.0 | EtOH | 70.0 | 2.5 | 5.0 | C |
| 35.0 | IPA | 70.0 | 5.2 | 10.0 | E |
| 31.3 | 1-BuOH | 70.0 | 4.9 | 9.5 | E + extra peak (4.984° 2θ) |
| 35.0 | MeCN | 70.0 | 5.4 | 10.8 | D |
| 31.0 | THF | 50.0 | 3.2 | 6.4 | D |
| 31.5 | 2-MeTHF | 70.0 | 5.0 | 10.0 | D |
| 33.2 | EtOAc | 70.0 | 4.7 | 9.6 | D |
| 31.1 | IPAc | 70.0 | 3.9 | 7.6 | D |
| 32.8 | Acetone | 50.0 | 3.9 | 7.6 | D |
| 32.6 | MEK | 70.0 | 4.4 | 8.8 | E |
| 31.2 | MIBK | 70.0 | 5.9 | 11.6 | D |
| 32.8 | DMSO | 70.0 | 1.1 | 2.2 | H |
| 31.1 | DMF | 70.0 | 1.1 | 2.2 | A + extra peaks (4.32, 15.4° 2θ) |
| 33.1 | NMP | 70.0 | 1.3 | 2.5 | Oily material |
| 32.0 | n-Propanol | 70.0 | 3.8 | 7.4 | E |

TABLE 6

Compound 1 binary solvent slow cooling crystallization experiments, toluene as co-solvent (20° C./hr), no precipitation formed.

| Cmpd 1 amnt. (mg) | Primary Solvent | Temp. (° C.) | 1° solvent Vol. (mL) | Co-solvent Vol. (mL) | Solid form by XRPD |
|---|---|---|---|---|---|
| 33.2 | MeOH | 50.0 | 2.3 | 4.4 | D |
| 31.1 | EtOH | 70.0 | 2.4 | 4.8 | E |
| 30.0 | IPA | 70.0 | 4.4 | 8.8 | E |
| 32.4 | 1-BuOH | 70.0 | 5.1 | 10.0 | E + extra peak (4.984° 2θ) |
| 30.4 | MeCN | 70.0 | 4.7 | 9.3 | D |
| 31.5 | THF | 50.0 | 3.2 | 6.4 | D |
| 30.4 | 2-MeTHF | 70.0 | 4.8 | 9.6 | E |
| 34.3 | EtOAc | 70.0 | 4.9 | 9.8 | E |
| 32.3 | IPAc | 70.0 | 4.0 | 8.0 | A |
| 30.0 | Acetone | 50.0 | 3.5 | 7.0 | D |
| 33.9 | MEK | 70.0 | 4.6 | 9.2 | D |
| 33.1 | MIBK | 70.0 | 6.0 | 12.0 | D |
| 34.3 | DMSO | 70.0 | 1.2 | 2.2 | H |
| 31.2 | DMF | 70.0 | 1.1 | 2.2 | A + B |
| 34.6 | NMP | 70.0 | 1.3 | 2.6 | Oily material |
| 33.5 | n-Propanol | 70.0 | 3.9 | 7.8 | E |

TABLE 7

Compound 1 binary solvent fast cooling crystallization experiments, heptane as co-solvent (refrigerate at 4° C., 24 hrs), no precipitation formed.

| Cmpd 1 amnt. (mg) | Primary Solvent | Temp. (° C.) | 1° solvent Vol. (mL) | Co-solvent Vol. (mL) | Solid form by XRPD |
|---|---|---|---|---|---|
| 32.0 | EtOH | 70.0 | 2.5 | 5.0 | E |
| 34.7 | IPA | 70.0 | 5.1 | 10.0 | D |
| 32.5 | 1-BuOH | 70.0 | 5.1 | 10.0 | E |
| 32.9 | THF | 50.0 | 3.4 | 6.7 | D |
| 33.8 | 2-MeTHF | 70.0 | 5.4 | 10.8 | D |
| 32.1 | EtOAc | 70.0 | 4.6 | 9.0 | D |
| 34.3 | IPAc | 70.0 | 4.3 | 8.6 | C |
| 32.1 | Acetone | 50.0 | 3.8 | 7.4 | D |
| 33.8 | MEK | 70.0 | 4.6 | 9.0 | D |
| 35.7 | MIBK | 70.0 | 6.5 | 12.5 | A + D |
| 32.7 | MTBE | 70.0 | 5.7 | 11.4 | A (with strong preferred orientation) |
| 34.0 | NMP | 70.0 | 1.3 | 2.5 | Oily material |
| 35.8 | n-Propanol | 70.0 | 4.2 | 8.4 | E |

TABLE 8

Compound 1 binary solvent slow cooling crystallization experiments, heptane as co-solvent (20° C./hr).

| Cmpd 1 amnt. (mg) | Primary Solvent | Temp. (° C.) | 1° solvent Vol. (mL) | Co-solvent Vol. (mL) | Precipitation/ Evaporation | Yield (mg) | Solid form by XRPD |
|---|---|---|---|---|---|---|---|
| 32.4 | EtOH | 70.0 | 2.5 | 5.0 | Evaporation with N$_2$ | — | E |
| 30.9 | IPA | 70.0 | 4.5 | 9.0 | Evaporation with N$_2$ | — | E |

TABLE 8-continued

Compound 1 binary solvent slow cooling crystallization experiments, heptane as co-solvent (20° C./hr).

| Cmpd 1 amnt. (mg) | Primary Solvent | Temp. (° C.) | 1° solvent Vol. (mL) | Co-solvent Vol. (mL) | Precipitation/ Evaporation | Yield (mg) | Solid form by XRPD |
|---|---|---|---|---|---|---|---|
| 33.9 | 1-BuOH | 70.0 | 5.3 | 10.5 | Evaporation with $N_2$ | — | E + extra peak (5.07° 2θ) |
| 30.4 | THF | 50.0 | 3.1 | 6.2 | Evaporation with $N_2$ | — | E |
| 33.0 | 2-MeTHF | 70.0 | 5.2 | 10.4 | Evaporation with $N_2$ | — | E |
| 31.9 | EtOAc | 70.0 | 4.6 | 9.0 | Evaporation with $N_2$ | — | E |
| 33.6 | IPAc | 70.0 | 4.2 | 8.4 | Precipitation | 20.57 | A |
| 32.6 | Acetone | 50.0 | 3.8 | 7.6 | Evaporation with $N_2$ | — | D |
| 35.2 | MEK | 70.0 | 4.8 | 9.4 | Evaporation with $N_2$ | — | D |
| 34.8 | MIBK | 70.0 | 6.3 | 12.6 | Precipitation | 13.01 | A |
| 33.1 | MTBE | 70.0 | 5.8 | 11.6 | Precipitation | 15.49 | A |
| 31.3 | NMP | 70.0 | 1.2 | 2.4 | Evaporation with $N_2$ | — | Oily material |
| 30.8 | n-Propanol | 70.0 | 3.6 | 7.2 | Evaporation with $N_2$ | — | E |

TABLE 9

Compound 1 binary solvent fast cooling crystallization experiments, cyclohexane as co-solvent (refrigerate at 4° C., 24 hrs), no precipitation formed.

| Cmpd 1 amnt. (mg) | Primary Solvent | Temp. (° C.) | 1° solvent Vol. (mL) | Co-solvent Vol. (mL) | Solid form by XRPD |
|---|---|---|---|---|---|
| 30.5 | EtOH | 70.0 | 2.4 | 4.8 | C |
| 33.0 | IPA | 70.0 | 4.9 | 9.8 | E |
| 33.4 | 1-BuOH | 70.0 | 5.2 | 10.4 | E |
| 31.2 | THF | 50.0 | 3.2 | 6.4 | E |
| 34.9 | 2-MeTHF | 70.0 | 5.5 | 11.0 | E |
| 30.4 | EtOAc | 70.0 | 4.4 | 8.8 | E |
| 30.5 | IPAc | 70.0 | 3.8 | 7.6 | A |
| 35.6 | Acetone | 50.0 | 4.2 | 8.4 | D |
| 30.1 | MEK | 70.0 | 4.1 | 8.2 | D |
| 32.4 | MIBK | 70.0 | 5.9 | 11.8 | D |
| 30.3 | NMP | 70.0 | 1.1 | 2.2 | Oily material |
| 30.0 | n-Propanol | 70.0 | 3.5 | 7.0 | E |

TABLE 10

Compound 1 binary solvent slow cooling crystallization experiments, cyclohexane as co-solvent (20° C./hr), no precipitation formed.

| Cmpd 1 amnt. (mg) | Primary Solvent | Temp. (° C.) | 1° solvent Vol. (mL) | Co-solvent Vol. (mL) | Solid form by XRPD |
|---|---|---|---|---|---|
| 34.2 | EtOH | 70.0 | 2.7 | 5.4 | C |
| 34.2 | IPA | 70.0 | 5.0 | 10.0 | E |
| 34.5 | 1-BuOH | 70.0 | 5.4 | 10.8 | E + extra peak (5.05° 2θ) |
| 33.5 | THF | 50.0 | 3.4 | 6.8 | E |
| 32.6 | 2-MeTHF | 70.0 | 5.2 | 10.4 | E |
| 31.9 | EtOAc | 70.0 | 4.6 | 9.2 | C |
| 32.6 | IPAc | 70.0 | 4.1 | 8.2 | A + C |
| 32.8 | Acetone | 50.0 | 3.9 | 7.8 | D |
| 30.8 | MEK | 70.0 | 4.2 | 8.4 | D |
| 30.0 | MIBK | 70.0 | 5.5 | 11.0 | E |
| 31.5 | NMP | 70.0 | 1.2 | 2.4 | Oily material |
| 31.3 | n-Propanol | 70.0 | 3.7 | 7.4 | E |

6.1.1.1 Single Solvent Crystallization

Single solvent crystallizations were conducted at 30-35 mg scale using the primary solvents listed in Table 1 and Table 2. The experiments employed fast and slow cooling profiles as described in Table 1 and Table 2. No precipitates were obtained for all single-solvent crystallization experiments. All 30 crystallization samples had to be evaporated to dryness under a gentle stream of nitrogen to obtain solid for XRPD analysis (Table 1 and Table 2). Five unique XRPD patterns (Forms A, B, C, D, and E, FIG. 1) were observed from 28 crystallization experiments. Forms A, B, C, D, and E were prepared. The remaining two experiments produced an oily material that was not suitable for XRPD analysis.

The method of single solvent fast cooling crystallization comprised the steps of: (1) placing approximately 30-35 mg of Compound 1 into 8 mL clear glass vials equipped with stir bars; (2) dissolving with a minimum amount of solvents (starting with 500 µL increment) at 50° C. (up to 7.0 mL); (3) filtering the hot solution through a 0.45 µm syringe filter into a clean preheated vial; (4) placing the vial in a refrigerator (4° C.) without stirring over 24 hours; (5) isolating the resulting solids by vacuum filtration; and (6) evaporating the samples without precipitation to dryness under a gentle stream of nitrogen. All obtained solids were analyzed by XRPD to determine the solid form. See Table 1.

The method of single solvent slow cooling crystallization comprised the steps of: (1) placing approximately 30-35 mg of Compound 1 into 8 mL clear glass vials equipped with stir bars; (2) dissolving with a minimum amount of solvents (starting with 500 µL increment) at 50° C. (up to 7.0 mL); (3) filtering the hot solution through a 0.45 µm syringe filter into a clean preheated vial; (4) cooling to ambient temperature at a rate of 20° C./hr and allowing to equilibrate with stirring at ambient temperature over 24 hours; (5) isolating the resulting solids by vacuum filtration; and (6) evaporating the samples without precipitation to dryness under a gentle stream of nitrogen. All obtained solids were analyzed by XRPD to determine the solid form. See Table 2.

6.1.1.2 Binary Solvent Crystallization

Binary solvent crystallizations were conducted at ~30 mg scale. A list of the chosen primary solvent systems is presented in Table 3-Table 10, respectively, to dissolve the Compound 1 at 50 or 70° C. Solvents such as $H_2O$, toluene, heptane and cyclohexane were used as co-solvents as described in Table 3-Table 10. Besides the six patterns (Forms A, B, C, D, E and F), two additional unique XRPD patterns (Forms G and H) were obtained from 110 binary solvent crystallization experiments. Forms A, B, C, D, E, F, G and H were prepared. A representative overlay of XRPD patterns of all eight forms is shown in FIG. 1.

The method of binary solvent fast cooling crystallization comprised the steps of: (1) placing approximately 30.0-35.0 mg of Compound 1 into 8 mL clear glass vials equipped with stir bars; (2) dissolving with a minimum amount of solvents (starting with 500 mL increment) at 50 or 70° C. (up to 7.0 mL); (3) filtering the hot solution through a 0.45 μm syringe filter into a clean preheated vial; (4) adding a co-solvent drop-wise; (5) placing the vials in a refrigerator (4° C.) without stirring over 24 hours; (6) isolating the resulting solids by vacuum filtration; and (7) evaporating the samples without precipitation to dryness under a gentle stream of nitrogen gas. All obtained solids were analyzed by XRPD to determine the solid form (see Table 3, Table 5, Table 7 and Table 9).

The method of binary solvent slow cooling crystallization comprised the steps of: (1) placing approximately 30.0-35.0 mg of Compound 1 into 8 mL clear glass vials equipped with stir bars; (2) dissolving with a minimum amount of solvents (starting with 500 mL increment) at 50 or 70° C. (up to 7.0 mL); (3) filtering the hot solution through a 0.45 μm syringe filter into a clean preheated vial; (4) adding a co-solvent drop-wise; (5) cooling the vial to ambient temperature at a rate of 20° C./hr and allowing to equilibrate with stirring at ambient temperature over 24 hours; (6) isolating the resulting solids by vacuum filtration; and (7) evaporating the samples without precipitation to dryness under a gentle stream of nitrogen gas. All obtained solids were analyzed by XRPD to determine the solid form (see Table 4, Table 6, Table 8 and Table 10).

Water as co-solvent:

Precipitations were isolated by filtration from 15 experiments out of 28 crystallization experiments (Table 3 and Table 4). For the remaining crystallization experiments, solids were obtained in most experiments after the solutions were evaporated to dryness under a gentle stream of nitrogen, followed by XRPD analysis. Five unique XRPD patterns (Forms A, B, D, E and G) and seven XRPD pattern mixtures were observed. Forms A, B, D, E and G were prepared.

Toluene as co-solvent:

No precipitates were obtained for all binary-solvent crystallizations in toluene (Table 5 and Table 6). All the solutions were evaporated to dryness under a gentle stream of nitrogen to obtain solids for XRPD analysis. In 32 crystallization experiments, five unique XRPD patterns (Forms A, C, D, E and H) and one pattern mixture were observed. Forms A, C, D, and E were prepared. New unique Form H was observed and prepared from DMSO/Toluene via both fast and slow cooling methods.

Heptane as co-solvent:

Precipitations were isolated by filtration from 3 experiments out of 26 crystallization experiments (Table 7 and Table 8). For the remaining crystallization samples, solids were obtained in most experiments after the solutions were evaporated to dryness under a gentle stream of nitrogen, followed by XRPD analysis. Four unique XRPD patterns (Forms A, C, D, and E) and one XRPD pattern mixture were observed. Forms A, C, D, and E were prepared.

Cyclohexane as co-solvent:

No precipitates were obtained for all binary-solvent crystallizations in cyclohexane (Table 9 and Table 10). All the solutions were evaporated to dryness under a gentle stream of nitrogen to obtain solids for XRPD analysis. In 24 crystallization experiments, four unique XRPD patterns (Forms A, C, D, and E) and one pattern mixture was observed. Forms A, C, D, and E were prepared.

6.1.2 Scale Up of Crystalline Forms D and G

Forms A, D and G were identified as potential anhydrate polymorphs and prepared for full characterization. The starting material was Form A. A series of experiments were performed to generate a sufficient quantity of Forms D and G materials for further characterization. Details of the experiments are summarized in Table 11.

TABLE 11

Scale up of crystalline Forms D and G with the slow cooling method (20° C./hr).

| Cmpd 1 amnt. (mg) | Primary Solvent | Temp. (° C.) | 1° solvent Vol. (mL) | Co-solvent | Co-solvent Vol. (mL) | Precipitation/ Evaporation | Yield (mg) | Solid form by XRPD |
|---|---|---|---|---|---|---|---|---|
| 60.7 | THF | 50.0 | 6.2 | Toluene | 12.0 | Evaporation with $N_2$ | — | D |
| 62.5 | MEK | 70.0 | 8.5 | Toluene | 17.0 | Evaporation with $N_2$ | — | D |
| 59.7 | IPA | 70.0 | 8.8 | Water | 17.5 | Precipitation | 30.2 | G |
| 61.4 | 2-MeTHF | 70.0 | 9.8 | Water | 12.0 | Evaporation with $N_2$ | — | G |

Form D material was scaled up using the binary solvent crystallizations method and conducted at ~60 mg scale (Table 11). Two batches of Form D materials were generated. Procedures utilized to generate these Form D materials followed the methods used for the two batches in intermediate scale experiments (Table 5 and Table 6).

The scale-up method of binary solvent slow cooling crystallization for preparation of Form D comprised the steps of: (1) placing approximately 60 mg of Compound 1 into 20 mL clear glass vials equipped with stir bars; (2) dissolving with a minimum amount of solvents (THF or MEK, starting with 500 mL increment) at 50 or 70° C.; (3) filtering the hot solution through a 0.45 μm syringe filter into a clean preheated vial; (4) adding a co-solvent (toluene); (5) cooling the vial to ambient temperature at a rate of 20° C./hr and allowing to equilibrate with stirring at ambient temperature over 5 hours; (6) isolating the resulting solids by vacuum filtration; and (7) evaporating the samples without precipitation to dryness under a gentle stream of nitrogen gas. All obtained solids were analyzed by XRPD to determine the solid form (Table 11).

Form G material was scaled up using binary solvent crystallizations method and conducted at ~60 mg scale (Table 11). Two batches of Form G materials were generated. Procedures utilized to generate these Form G materials followed the methods used for the two batches in intermediate scale experiments (Table 3 and Table 4).

The scale-up method of binary solvent slow cooling crystallization for preparation of Form G comprised the steps of: (1) placing approximately 60 mg of Compound 1 into 20 mL clear glass vials equipped with stir bars; (2) dissolving with a minimum amount of solvents (IPA or 2-MeTHF, starting with 500 mL increment) at 70° C.; (3) filtering the hot solution through a 0.45 μm syringe filter into a clean preheated vial; (4) adding a co-solvent (water); (5) cooling the vial to ambient temperature at a rate of 20° C./hr and allowing to equilibrate with stirring at ambient temperature over 5 hours; (6) isolating the resulting solids by vacuum filtration; and (7) evaporating the samples without precipitation to dryness under a gentle stream of nitrogen gas. All obtained solids were analyzed by XRPD to determine the solid form (Table 11).

6.1.3 Competitive Slurry Experiment of Forms A, D and G

To evaluate relative stability of the anhydrate polymorphs, competitive slurry experiments of Forms A, D and G were conducted as described in below and summarized in Table 12. In all three solvent systems, water, 1:2 v/v IPAc/heptane, and toluene, Form A was the final polymorph after equilibration for 8 days. Therefore, Form A is the most stable anhydrate polymorph among the three polymorphs at ambient temperature.

TABLE 12

Competitive slurry experiment of Forms A, D and G.

| Parent Materials | Weight (mg) | Solvent | Vol. (mL) | Tempt. (° C.) | Aliquot time point Day | Aliquot time point XRPD | Aliquot time point Day | Aliquot time point XRPD |
|---|---|---|---|---|---|---|---|---|
| Form A | 12.54 | Water | 1.0 | RT | 1 | A + D | 8 | A |
| Form D | 11.06 | | | | | | | |
| Form G | 12.00 | | | | | | | |
| Form A | 12.45 | IPAc/Heptane | 1.0 | RT | 1 | A | 8 | A |
| Form D | 12.88 | (1:2 V/V) | | | | | | |
| Form G | 12.34 | | | | | | | |
| Form A | 15.20 | Toluene | 1.0 | RT | 1 | A | 8 | A |
| Form D | 16.70 | | | | | | | |
| Form G | 14.75 | | | | | | | |

Slurry experiments were performed using the following procedure: a mixture of Form A (~12.0 mg, Compound 1), Form D (~12.0 mg) and Form G (~12.0 mg) were weighed into a 20.0 mL clear vial equipped with magnetic stir bars (Table 12). Water, IPAc/Heptane (1:2 V/V) and toluene were used as the solvent systems for these competitive slurry experiments. Three selected solvents, 1.0 mL, were added to achieve free-flowing slurry and allowed to equilibrate at room temperature.

6.1.4 Competitive Slurry Experiment of Forms A Through H

Competitive slurry experiment of all unique Forms A through H were also conducted as described below and summarized in Table 13. Again Form A was detected after one day and seven days equilibration, indicating that it is the most stable polymorph.

TABLE 13

Competitive slurry experiment of Forms A to H.

| Parent Materials | Weight (mg) | Solvent | Vol. (mL) | Tempt. (° C.) | Aliquot time point Day | Aliquot time point XRPD | Aliquot time point Day | Aliquot time point XRPD |
|---|---|---|---|---|---|---|---|---|
| Form A | 4.72 | IPAc/Heptane | 1.0 | RT | 1 | A | 7 | A |
| Form B | 3.01 | (1:2, V/V) | | | | | | |
| Form C | 1.13, 1.91 | | | | | | | |
| Form D | 1.65 or 1.70 | | | | | | | |

TABLE 13-continued

Competitive slurry experiment of Forms A to H.

| Parent Materials | Weight (mg) | Solvent | Vol. (mL) | Tempt. (° C.) | Aliquot time point Day | Aliquot time point XRPD | Aliquot time point Day | Aliquot time point XRPD |
|---|---|---|---|---|---|---|---|---|
| Form E | 3.23 | | | | | | | |
| Form F | 3.45 | | | | | | | |
| Form G | 3.43 | | | | | | | |
| Form H | 3.52 | | | | | | | |
| Form A | 4.95 | Toluene | 1.0 | RT | 1 | A | 7 | A |
| Form B | 3.32 | | | | | | | |
| Form C | 1.97, 1.80 | | | | | | | |
| Form D | 1.64 or 1.72 | | | | | | | |
| Form E | 3.60 | | | | | | | |
| Form F | 3.22 | | | | | | | |
| Form G | 3.25 | | | | | | | |
| Form H | 3.61 | | | | | | | |

Approximately 2 to 3 mg of materials from Forms A to H were weighed into a 20.0 mL clear vial equipped with magnetic stir bars (Table 13). IPAc/Heptane (1:2 V/V) and toluene were used as the solvent systems for these competitive slurry experiments. Two selected solvents, 1.0 mL, were added to achieve free-flowing slurry and allowed to equilibrate at room temperature. All slurries will be isolated via centrifuge filtration after one day and seven days of equilibration.

6.1.5 Single Form Slurry Experiments

Single form slurry experiments were conducted for Forms A, D and G in three solvents stems, water, 1:2 v/v IPAc/heptane, and toluene to evaluate their physical form stability as a single polymorph (Table 14). Form A remained unchanged at six day time point. Form G converted to Form A after three day time points. Form D remained unchanged for three days in water but converted to a mixture A and D at six days. In 1:2 IPAc/heptane and toluene, Form D converted to a mixture of A and D at three days and then Form A at six days. These results showed that Form G is a metastable polymorph and readily converts to Form A under slurry conditions at ambient temperature. Form D is also a metastable polymorph but its conversion to Form A is kinetically slower than Form G. The conversion was the slowest in water partly due to low solubility.

TABLE 14

| Single form slurry experiment of Forms A, D and G | | | | | | | | |
|---|---|---|---|---|---|---|---|---|
| Parent Materials | Weight (mg) | Solvent | Vol. (mL) | Tempt. (° C.) | Aliquot time point Day | Aliquot time point XRPD | Aliquot time point Day | Aliquot time point XRPD |
| Form A | 16.33 | Water | 1.0 | RT | 3 | A | 6 | A |
| Form A | 17.80 | IPAc/Heptane (1:2 V/V) | 1.0 | RT | 3 | A | 6 | A |
| Form A | 16.28 | Toluene | 1.0 | RT | 3 | A | 6 | A |
| Form D | 10.01 | Water | 1.0 | RT | 3 | D | 6 | A + D |
| Form D | 11.70 | IPAc/Heptane (1:2 V/V) | 1.0 | RT | 3 | A + D | 6 | A |
| Form D | 10.90 | Toluene | 1.0 | RT | 3 | A + D | 6 | A |
| Form G | 27.01 | Water | 1.0 | RT | 3 | A | 6 | A |
| Form G | 21.32 | IPAc/Heptane (1:2 V/V) | 1.0 | RT | 3 | A | 6 | A |
| Form G | 21.29 | Toluene | 1.0 | RT | 3 | A | 6 | A |

Approximately 10-20 mg of Forms A, D and G were weighed into 8 mL clear vials equipped with magnetic stir bars (Table 14). Water, IPAc/Heptane (1:2 V/V) and toluene were used as the solvent systems for these competitive slurry experiments. Three selected solvents, 1.0 mL, were added to achieve free-flowing slurry and allowed to equilibrate at room temperature. All slurries will be isolated via centrifuge filtration after three day and six days of equilibration.

Thermal stability experiments of Forms A, D and G were conducted and summarized in Table 15.

TABLE 15

Thermal Stability Experiments

| Parent Material | Weight (mg) | Tempt. (° C.) | Aliquot time point Day | XRPD | Aliquot time point Day | XRPD | Parent Material HPLC (% AUC) | HPLC (% AUC) |
|---|---|---|---|---|---|---|---|---|
| Form A | 27.0 | 60.0 | 1 | A | 7 | A | >99.9 | >99.9 |
| Form D | 26.5 | 60.0 | 1 | D | 7 | D | >99.9 | >99.9 |
| Form G | 27.3 | 60.0 | 1 | A + G | 7 | A | >99.3 | >99.9 |

6.1.6 Aqueous Solubility

Approximately 14-25 mg of Forms A, D and G were transferred to 20 mL vials equipped with magnetic stir bars. 1.0 mL of deionized water was added and the resulting free flowing slurry was allowed to equilibrate over 1 and 7 days period with stirring at room temperature. The slurries were filtered through 0.45 micron centrifuge filters and the resulting solids analyzed by XRPD (Table 16). The filtrates were analyzed by HPLC to determine solubility.

TABLE 16

Aqueous solubility of Forms A, D and G

| Initial form | Mass (mg) | DI H$_2$O vol. (mL) | Condition | Solid form by XRPD after 1 day | Solid form by XRPD after 7 day | Solubility (mg/mL) |
|---|---|---|---|---|---|---|
| A | 25.93 | 1.0 | free flowing | A | A | (0.0026)* |
| D | 13.88 | 1.0 | slurry was | A | A | (0.49)* |
| G | 21.94 | 1.0 | allowed to equilibrate with stirring at room temperature | A | A | 0.061 |

*Extrapolated values based on the standard curve (0.008-0.2 mg/mL).

6.2 Instrumentation

The vendor and model information of the instruments used for analysis are provided below in Table 17.

TABLE 17

Instrument vendors and models

| Instrument | Vendor/Model # |
|---|---|
| Differential Scanning Calorimeter | Mettler DSC1 |
| Thermal Gravimetric Analyzer | Mettler 851$^e$ TGA |
| X-Ray Powder Diffractometer | CubiX-Pro |
| Nuclear Magnetic Resonance Spectrometer | Bruker 500 MHz AVANCE |

6.2.1 Differential Scanning Calorimetry (DSC)

DSC analysis was performed on the sample "as is." Sample was weighed in an aluminum pan, covered with a pierced lid, and then crimped and analyzed from 30-230° C. at 10° C./min.

6.2.2 Thermal Gravimetric Analysis (TGA)

TGA was carried out on the sample "as is." Sample was weighed in an alumina crucible and analyzed from 30-300° C. at 10° C./min.

6.2.3 X-Ray Powder Diffraction

Samples were analyzed "as is." Sample was placed on Si zero-return ultra-micro sample holders. Analysis was performed using a 10 mm irradiated width and the following parameters were set within the hardware/software:

X-ray tube: Cu Kα, 45 kV, 40 mA

Detector: X'Celerator

ASS Primary Slit: Fixed 10

Divergence Slit (Prog): Automatic—5 mm irradiated length

Soller Slits: 0.02 radian

Scatter Slit (PASS): Automatic—5 mm observed length

Scan Range: 3.0-45.0°

Scan Mode: Continuous

Step Size: 0.02°

Time per Step: 10 s

Active Length: 2.54°

Following analysis the data was converted from adjustable to fixed slits using the X'Pert HighScore Plus software with the following parameters:

Fixed Divergence Slit Size: 1.00°, 1.59 mm

6.2.4 Nuclear Magnetic Resonance

Samples were dissolved in DMSO-d6 with 0.05% tetramethylsilane (TMS) for internal reference. $^1$H-NMR spectra were acquired at 500 MHz using 5 mm broadband (1H-X) Z gradient probe. A 30 degree pulse with 20 ppm spectral width, 1.0 s repetition rate, and 64 transients were utilized in acquiring the spectra.

Weight percent purity determination by $^1$H NMR using 1,4 Dimethoxybenzene in DMSO-d6 with 0.05% tetramethylsilane (TMS). Sample preparation, $^1$H-NMR spectra acquiring and sample purity was calculated accordingly.

6.2.5 Dynamic Vapour Sorption (DVS)

Dynamic vapour sorption experiment was carried out by first holding the sample at 40% RH and 25.0° C. until an equilibrium weight was reached or for a maximum of four hours. The sample was then subjected to an isothermal (at 25.0° C.) adsorption scan from 40 to 90% RH in steps of 10%. The sample was allowed to equilibrate to an asymptotic weight at each point for a maximum of four hours. Following adsorption, a desorption scan from 85 to 5% RH (at 25.0° C.) was run in steps of 10% again allowing a maximum of four hours for equilibration to an asymptotic weight. An adsorption scan was then performed from 0 to 40% RH in steps of 10%. The sample was then dried for no less than two hours at 60.0° C. and the resulting solid analyzed by XRPD.

6.2.6 HPLC

HPLC conditions are listed in Table 18.

TABLE 18

| HPLC conditions | |
| --- | --- |
| System: | Agilent 1100 Series HPLC |
| Column: | Agilent Zorbax SB-C18, (SN: USEG012031) 4.6 mm × 150 mm, 3.5 μm |
| Column Temperature: | 30.0° C. |
| Auto Sampler Temp: | Ambient |
| Flow Rate: | 1.0 mL/min. |
| Injection Volume: | 15.0 μL |
| Run Time: | 40 minutes |
| Detection: | 263 nm |
| Sample Preparation: | Standard reference: 1.0 mg/mL Dissolved 2.333 mg of Compound 1 in 2.333 mL of diluent and stirred at 25.0° C. for 10 minutes API aqueous solubility samples: Filtrates from aqueous solubility experiments |

TABLE 18-continued

| HPLC conditions | | | |
| --- | --- | --- | --- |
| Thermal Stability Experiments: | | | |
| | | API weight (mg) | Diluent volume (mL) |
| | Compound 1, Form A | 3.284 | 3.284 |
| | Compound 1, Form D | 3.549 | 3.549 |
| | Compound 1, Form G | 2.586 | 2.586 |
| Mobile Phases: | Dissolved polymorphs in diluent and stirred at 25.0° C. for 10 minutes A - 0.1% TEA and TFA in H$_2$O, adjusted pH to 1.3 using HCl solution B - 100% ACN | | |
| Diluent: | 50:50 (V/V) ACN:H$_2$O | | |

6.2.7 Characterization of Compound 1 Polymorphs

All unique XRPD forms of Compound 1 were characterized to evaluate their physical form and stability. Table 19 summarizes the characterization results for each polymorph of Compound 1. A stackplot of representative XRPD Patterns of Forms A, B, C, D, E, F, G and H is shown in FIG. 1. X-ray powder diffraction pattern and peak list of each unique polymorph are shown in FIG. 2-FIG. 9.

TABLE 19

Summary of Compound 1 Polymorphs.

| Solid form | DSC (° C.) | TGA (Weight loss) | NMR | Moisture Sorption | Comments |
| --- | --- | --- | --- | --- | --- |
| A | Endotherm at 186.0 | onset of decomposition at 249.2° C. | No detectable solvent, no degradation | 60% RH: 0% 90% RH: 6.1 wt % | Anhydrate |
| B | Endotherm at 141.5, 185.2 Exotherm at 146.9 | 0.64% @ 135-155° C., onset decomposition at 258.0° C. | No degradation, 0.48 wt % MEK | N/A | Metastable anhydrate (or possible inclusion complex) |
| C | Endotherm at 63.5, 77.6, 134.9, 185.8 Exotherm at 143.0 | 1.08% @ 120-150° C., onset decomposition at 269.1° C. | Additional NMR peaks 1.98 wt % EtOH | N/A | Metastable anhydrate (or possible inclusion complex) |
| D | Endotherm at 185.2 Exotherm at 118.7 | onset of decomposition at 259.8° C. | No detectable solvent, no degradation | 60% RH: 0.7% 90% RH: 1.0 wt % | Metastable anhydrate |
| E | Endotherm at 154.8, 185.6 Exotherm at 156.7 | 1.96% @ 130-165° C., onset decomposition at 261.6° C. | 1.66 wt % EtOAc, no degradation | N/A | Metastable anhydrate (or possible inclusion complex) |
| F | Endotherm at 64.1, 91.3, 185.9 | 1.86% @ 50-110° C., onset decomposition at 268.3° C. | No detectable solvent, no degradation | N/A | metastable hydrate |
| G | Endotherm at 90.5, 184.9 | onset of decomposition at 263.5° C. | No detectable solvent, no degradation | 60% RH: 0.4% 90% RH: 7.1 wt % | metastable anhydrate |
| H | Endotherm at 88.0 | 6.4% @ 70-140° C., 9.8% @ 145-240° C., onset decomposition at 268.1° C. | 18.9 wt % DMSO, no degradation | N/A | mono-DMSO solvate |

6.2.8 Form A of Compound 1

Figure 10:
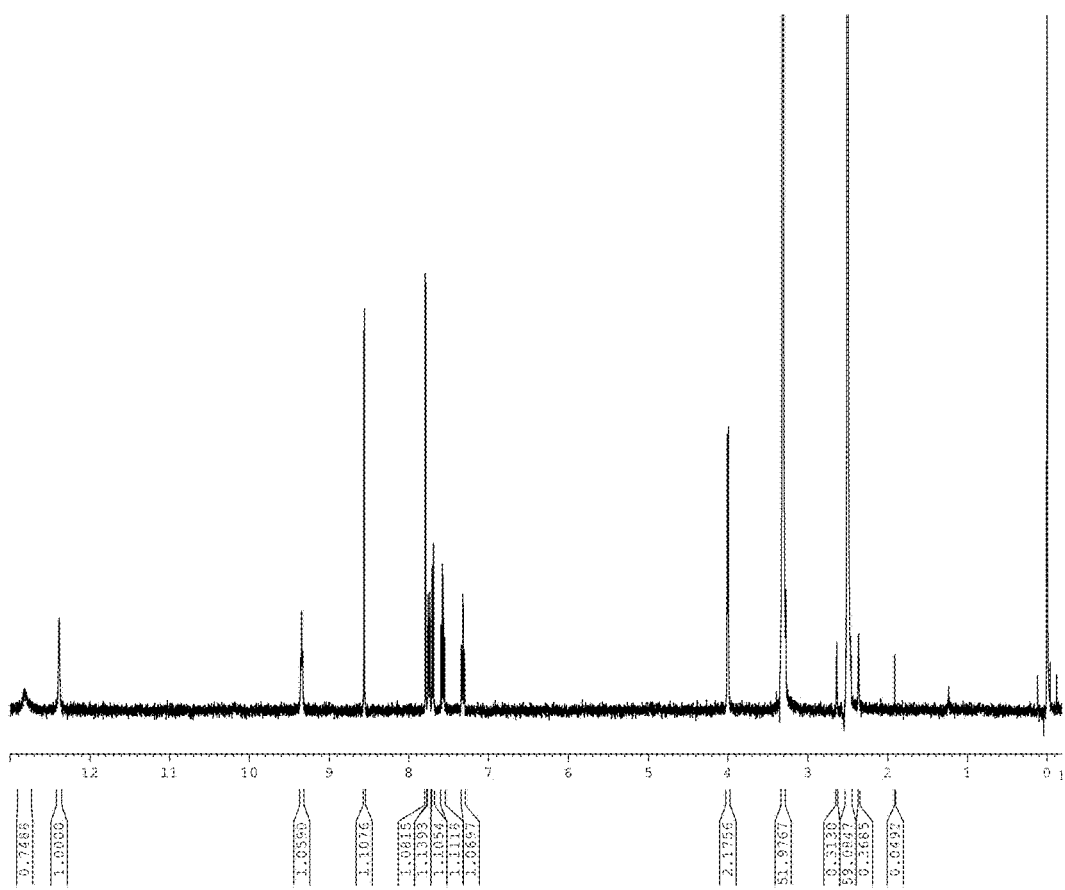
FIG. 10 depicts a $^1$H NMR spectrum of Form A of Compound 1.
Figure 13:
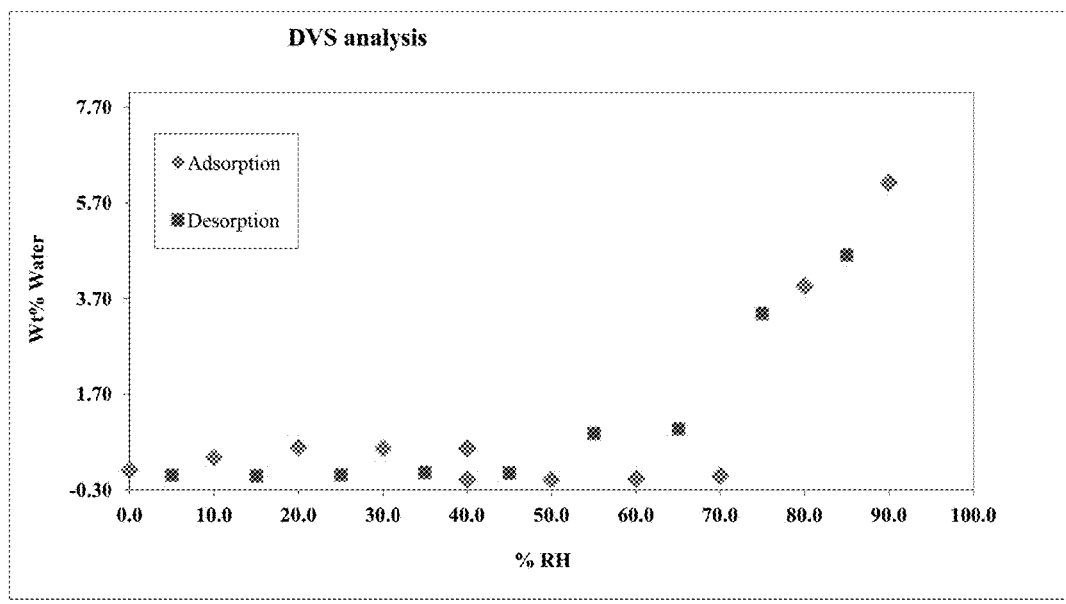
FIG. 13 depicts a DVS analysis of Form A of Compound 1.
Figure 14:
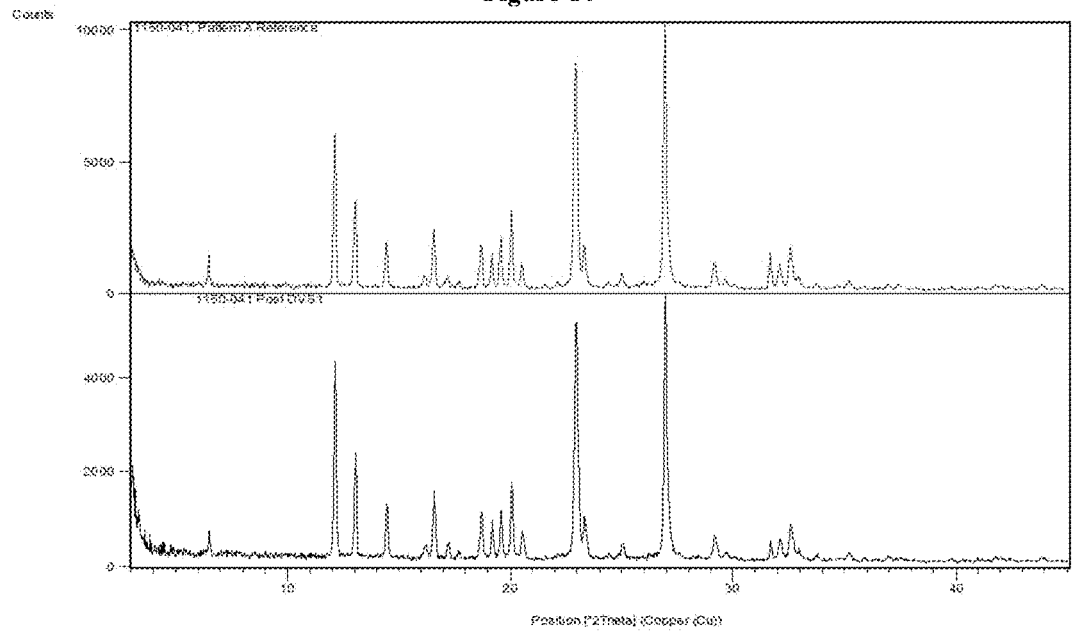
FIG. 14 depicts an XRPD pattern of post-DVS Form A of Compound 1.

Form A was harvested from the binary solvent recrystallization experiment using acetone as primary solvent and water as co-solvent (Table 3 and Table 4). Form A was also isolated in other single solvent and binary solvents recrystallization experiments in multiple solvent systems (Table 1-Table 10). The $^1$H NMR ($d_6$-DMSO) spectrum of Form A is provided in FIG. 10. Thermal analysis by DSC showed a single endothermic transition at 186.0° C. (FIG. 11). Further analysis by TGA indicated no weight loss before the onset of decomposition at 249.2° C. (FIG. 12). The material adsorbed 0 wt % moisture at 60% RH and 6.1 wt % moisture at 90% RH (FIG. 13). Although the material is moderately hygroscopic, no deliquescence was observed. The XRPD analysis of the post-DVS material after drying at 60° C. for 2 hours, recorded an XRPD pattern consistent with the starting material (FIG. 14). Aqueous solubility of Form A was determined to be 0.0026 mg/mL, which is extrapolated value based on the standard curve (Table 16).

In the single form and competitive slurry experiments, Form A was found to be the most stable polymorph at ambient temperature under all tested conditions. In addition, DSC did not show any noticeable endothermic event prior to 186° C. and TGA did not show any weight loss at low temperature range (<100.0° C.). No chemical and physical form changes were observed for Form A after storing the material at 60° C. for seven days (Table 15).

Characterization results of Form A are consistent with a stable anhydrate polymorph.

FIG. 2 provides an XRPD pattern of Form A. A list of X-Ray Diffraction Peaks for Form A is provided below in Table 20.

TABLE 20

X-Ray Diffraction Peaks for Form A

| Two-theta angle (°) | d Space (Å) | Relative Intensity (%) |
| --- | --- | --- |
| 3.73 | 23.68 | 0.99 |
| 3.86 | 22.92 | 1.14 |
| 4.24 | 20.86 | 2.46 |
| 4.39 | 20.13 | 1.24 |
| 5.46 | 16.19 | 1.25 |
| 5.58 | 15.85 | 0.78 |
| 5.77 | 15.31 | 1.04 |
| 6.01 | 14.70 | 1.21 |
| 6.49 | 13.61 | 11.74 |
| 6.86 | 12.89 | 0.62 |
| 7.27 | 12.16 | 0.63 |
| 7.40 | 11.94 | 0.26 |
| 7.83 | 11.29 | 0.77 |
| 8.13 | 10.88 | 0.98 |
| 8.56 | 10.34 | 0.85 |
| 8.67 | 10.20 | 0.57 |
| 8.80 | 10.05 | 0.44 |
| 8.93 | 9.91 | 1.18 |
| 9.91 | 8.92 | 1.34 |
| 10.09 | 8.76 | 0.79 |
| 10.23 | 8.65 | 0.01 |
| 10.41 | 8.50 | 0.17 |
| 11.07 | 7.99 | 1.37 |
| 12.14 | 7.29 | 58.99 |
| 13.05 | 6.78 | 33.11 |
| 14.45 | 6.13 | 17.61 |
| 15.67 | 5.66 | 0.64 |
| 16.20 | 5.47 | 4.48 |
| 16.60 | 5.34 | 19.83 |
| 17.21 | 5.15 | 4.65 |
| 17.70 | 5.01 | 2 |
| 18.71 | 4.74 | 15.15 |

TABLE 20-continued

X-Ray Diffraction Peaks for Form A

| Two-theta angle (°) | d Space (Å) | Relative Intensity (%) |
| --- | --- | --- |
| 19.19 | 4.63 | 12.76 |
| 19.59 | 4.53 | 19 |
| 20.08 | 4.42 | 28.19 |
| 20.54 | 4.33 | 9.63 |
| 21.60 | 4.11 | 1.1 |
| 22.15 | 4.01 | 2.09 |
| 22.97 | 3.87 | 84.6 |
| 23.34 | 3.81 | 15.95 |
| 24.37 | 3.65 | 1.22 |
| 25.02 | 3.56 | 6.03 |
| 25.55 | 3.49 | 0.72 |
| 25.93 | 3.44 | 1.66 |
| 26.92 | 3.31 | 100 |
| 27.55 | 3.24 | 1.69 |
| 29.20 | 3.06 | 10.29 |
| 29.70 | 3.01 | 3.15 |
| 30.10 | 2.97 | 1.34 |
| 31.68 | 2.82 | 11.82 |
| 32.13 | 2.79 | 8.52 |
| 32.59 | 2.75 | 16.15 |
| 33.00 | 2.71 | 2.88 |
| 33.77 | 2.65 | 1.79 |
| 34.18 | 2.62 | 0.43 |
| 34.67 | 2.59 | 0.64 |
| 35.19 | 2.55 | 3.41 |
| 35.88 | 2.50 | 1.01 |
| 36.40 | 2.47 | 0.33 |
| 36.99 | 2.43 | 1.57 |
| 37.46 | 2.40 | 1.86 |
| 38.08 | 2.36 | 0.68 |
| 39.74 | 2.27 | 0.84 |
| 40.38 | 2.23 | 0.39 |
| 40.96 | 2.20 | 0.79 |
| 41.76 | 2.16 | 1.44 |
| 42.12 | 2.15 | 1.48 |
| 42.45 | 2.13 | 0.83 |
| 43.26 | 2.09 | 0.54 |
| 43.87 | 2.06 | 1.84 |
| 44.52 | 2.03 | 0.81 |

6.2.9 Form B of Compound 1

Figure 15:
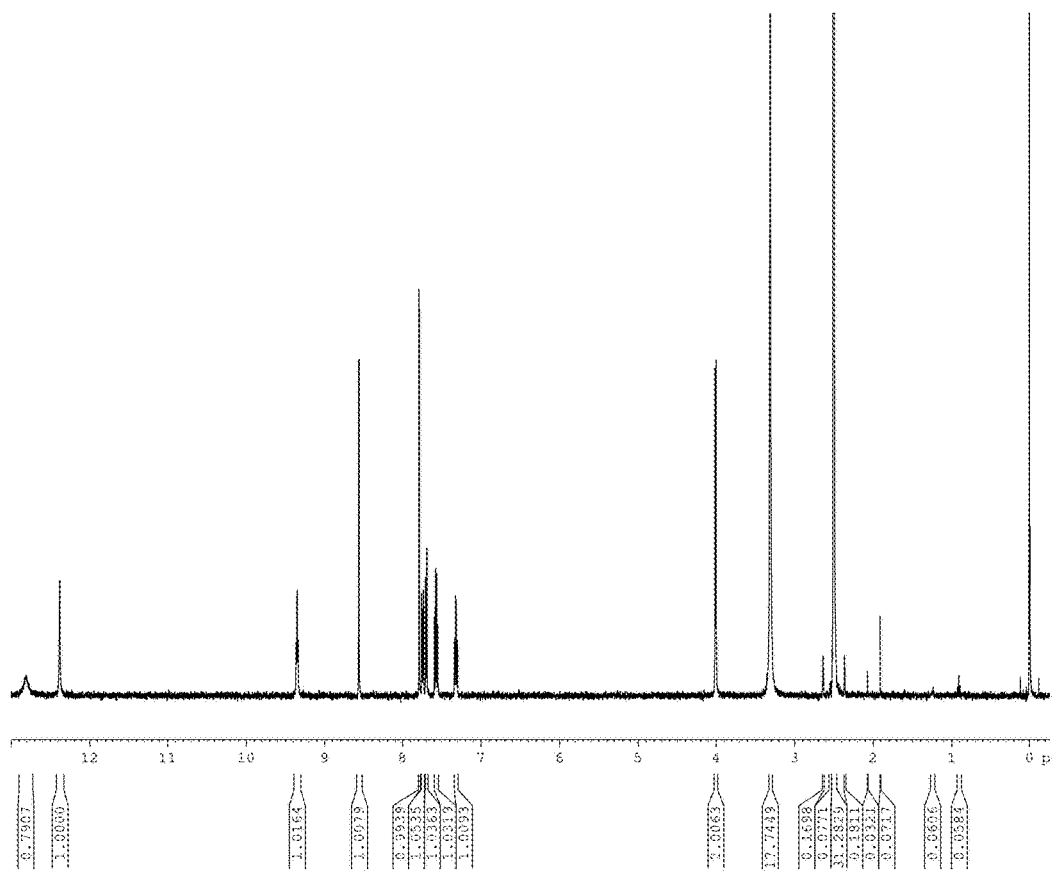
FIG. 15 depicts a $^1$H NMR spectrum of Form B of Compound 1.

Form B was prepared in the binary solvent recrystallization experiment using MEK as primary solvent and water as co-solvent, (Table 3 and Table 4). Form B was also isolated in other single solvent and binary solvents recrystallization experiments in multiple solvent systems (Table 1-Table 4). An estimated 0.48 wt % of MEK and no degradation were observed by $^1$H NMR ($d_6$-DMSO) (FIG. 15). DSC analysis presented two endotherms at 141.5 and 185.2° C., and an exotherm at 146.9° C. (FIG. 16). TGA analysis indicated a weight loss of 0.64%, attributed to loss of MEK, before 155° C. and onset decomposition at 258.0° C. (FIG. 17). In the competitive slurry experiment, Form B converted to Form A (Table 13).

Characterization results of Form B are mostly consistent with a metastable anhydrate polymorph retaining residual solvent. The residual solvents was not released until melt and Form B showed similarity to several other forms (i.e., Forms C, D and E), indicating that Form B might be an inclusion complex in which non-stoichiometry amount of solvent was retained and caused minor changes in crystal lattice.

FIG. 3 provides an XRPD pattern of Form B. A list of X-Ray Diffraction Peaks for Form B is provided below in Table 21.

TABLE 21

X-Ray Diffraction Peaks for Form B

| Two-theta angle (°) | d Space (Å) | Relative Intensity (%) |
|---|---|---|
| 4.34 | 20.37 | 82.64 |
| 7.46 | 11.86 | 17.24 |
| 8.61 | 10.27 | 100 |
| 11.37 | 7.78 | 12.06 |
| 12.90 | 6.86 | 19.52 |
| 14.89 | 5.95 | 34.65 |
| 15.50 | 5.72 | 78.65 |
| 18.76 | 4.73 | 28.42 |
| 19.71 | 4.50 | 10.4 |
| 21.52 | 4.13 | 11.25 |
| 22.15 | 4.01 | 4.18 |
| 22.81 | 3.90 | 13.48 |
| 23.03 | 3.86 | 8.41 |
| 23.77 | 3.74 | 19.1 |
| 24.60 | 3.62 | 6.72 |
| 25.29 | 3.52 | 22.84 |
| 25.73 | 3.46 | 5.58 |
| 26.23 | 3.40 | 7.14 |
| 26.76 | 3.33 | 10.88 |
| 27.49 | 3.24 | 3.85 |
| 28.17 | 3.17 | 18.3 |
| 30.10 | 2.97 | 7.77 |
| 31.76 | 2.82 | 6.67 |
| 32.57 | 2.75 | 5.14 |
| 34.34 | 2.61 | 1.74 |
| 35.94 | 2.50 | 2.24 |
| 37.74 | 2.38 | 1.68 |
| 38.63 | 2.33 | 1.36 |
| 39.27 | 2.29 | 2.07 |
| 41.75 | 2.16 | 1.36 |
| 42.20 | 2.14 | 0.81 |
| 44.45 | 2.04 | 0.87 |

6.2.10 Form C of Compound 1

Figure 18:
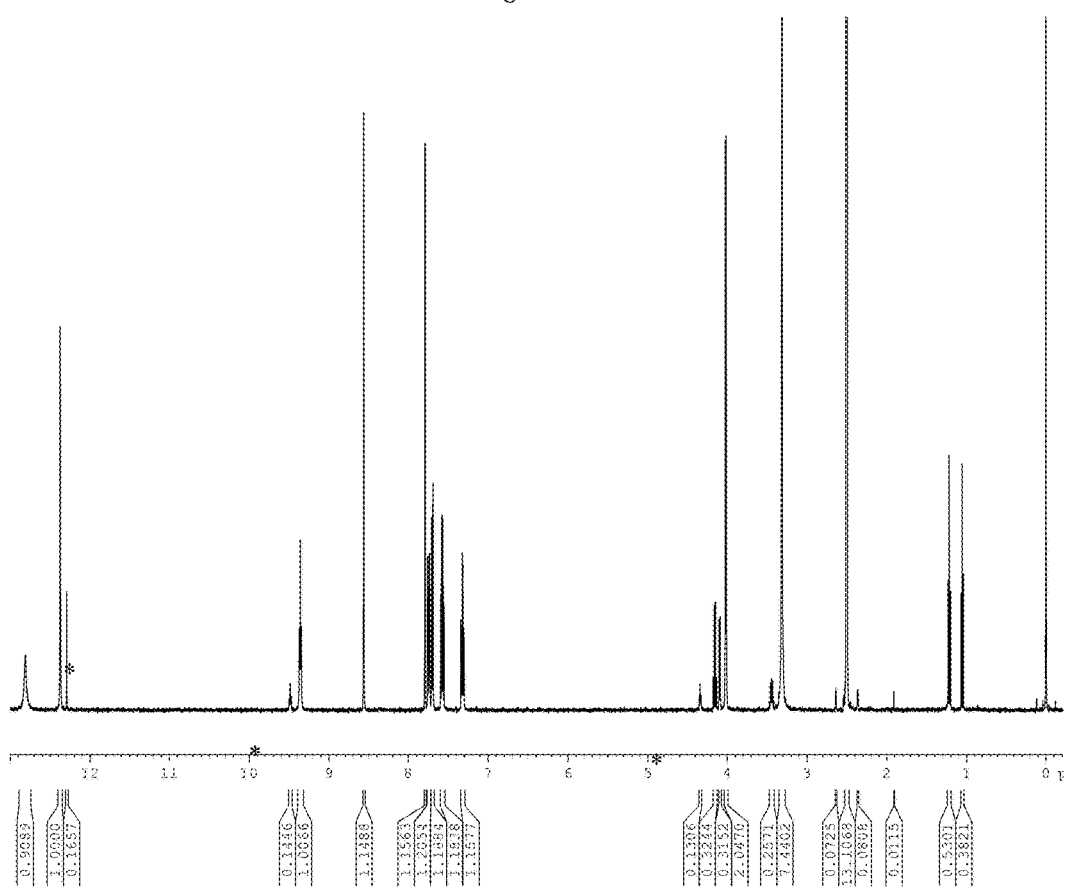
FIG. 18 depicts a $^1$H NMR spectrum of Form C of Compound 1.

Form C was prepared in the binary solvent recrystallization experiment using EtOH as primary solvent and cyclohexane as co-solvent (Table 9 and Table 10). Form C was also isolated in other single solvent and binary solvents recrystallization experiments usually when EtOH and IPAc were used (Table 1-Table 10). An estimated 1.98 wt % of EtOH and additional peaks were observed by $^1$H NMR ($d_6$-DMSO) (FIG. 18). Additional peaks indicated by asterisk in FIG. 18 were noted in the $^1$H NMR. These resonances are likely attributed to a degradation product due to esterification of the carboxylic acid group. Therefore, alcoholic solvents may present the risk of degradation through ester formation. DSC analysis presented four endotherms at 63.5, 77.6, 134.9 and 185.8° C., and an exotherm at 143.0° C. (FIG. 19). TGA analysis indicated a weight loss of 1.08%, attributed to loss of EtOH, before 150.0° C. and onset decomposition at 269.1° C. (FIG. 20). In the competitive slurry experiment, Form C converted to Form A (Table 13).

Characterization results of Form C are mostly consistent with a metastable anhydrate polymorph retaining residual solvent. The residual solvents was not released until melt and Form C showed similarity to several other forms (i.e., Forms B, D and E), indicating that Form C might be an inclusion complex in which non-stoichiometry amount of solvent was retained and caused minor changes in crystal lattice.

FIG. 4 provides an XRPD pattern of Form C. A list of X-Ray Diffraction Peaks for Form C is provided below in Table 22.

TABLE 22

X-Ray Diffraction Peaks for Form C

| Two-theta angle (°) | d Space (Å) | Relative Intensity (%) |
|---|---|---|
| 3.09 | 28.62 | 5.24 |
| 4.35 | 20.32 | 100 |
| 7.46 | 11.85 | 8.25 |
| 8.63 | 10.25 | 76.25 |
| 11.41 | 7.76 | 15.09 |
| 12.93 | 6.85 | 10.8 |
| 14.94 | 5.93 | 23.35 |
| 15.55 | 5.70 | 62.12 |
| 18.80 | 4.72 | 19.03 |
| 19.78 | 4.49 | 8.2 |
| 21.60 | 4.11 | 11.12 |
| 22.51 | 3.95 | 2.83 |
| 22.89 | 3.89 | 8.58 |
| 23.31 | 3.82 | 5.08 |
| 24.10 | 3.69 | 1.43 |
| 24.87 | 3.58 | 6.48 |
| 25.25 | 3.53 | 1.75 |
| 26.34 | 3.38 | 10.28 |
| 27.07 | 3.29 | 4.33 |
| 27.77 | 3.21 | 7.03 |
| 28.10 | 3.18 | 1.59 |
| 28.45 | 3.14 | 5.36 |
| 29.09 | 3.07 | 0.87 |
| 29.43 | 3.04 | 1.09 |
| 29.75 | 3.00 | 3.84 |
| 30.37 | 2.94 | 1.5 |
| 30.73 | 2.91 | 0.36 |
| 31.77 | 2.82 | 2.07 |
| 32.24 | 2.78 | 1.97 |
| 32.86 | 2.73 | 0.55 |
| 34.02 | 2.64 | 1.66 |
| 35.67 | 2.52 | 1.44 |
| 37.86 | 2.38 | 0.98 |
| 38.39 | 2.34 | 0.8 |
| 39.35 | 2.29 | 1.72 |
| 41.85 | 2.16 | 1.01 |
| 42.35 | 2.13 | 0.61 |
| 43.28 | 2.09 | 0.68 |
| 43.74 | 2.07 | 0.55 |
| 44.24 | 2.05 | 0.73 |

6.2.11 Form D of Compound 1

Figure 21:
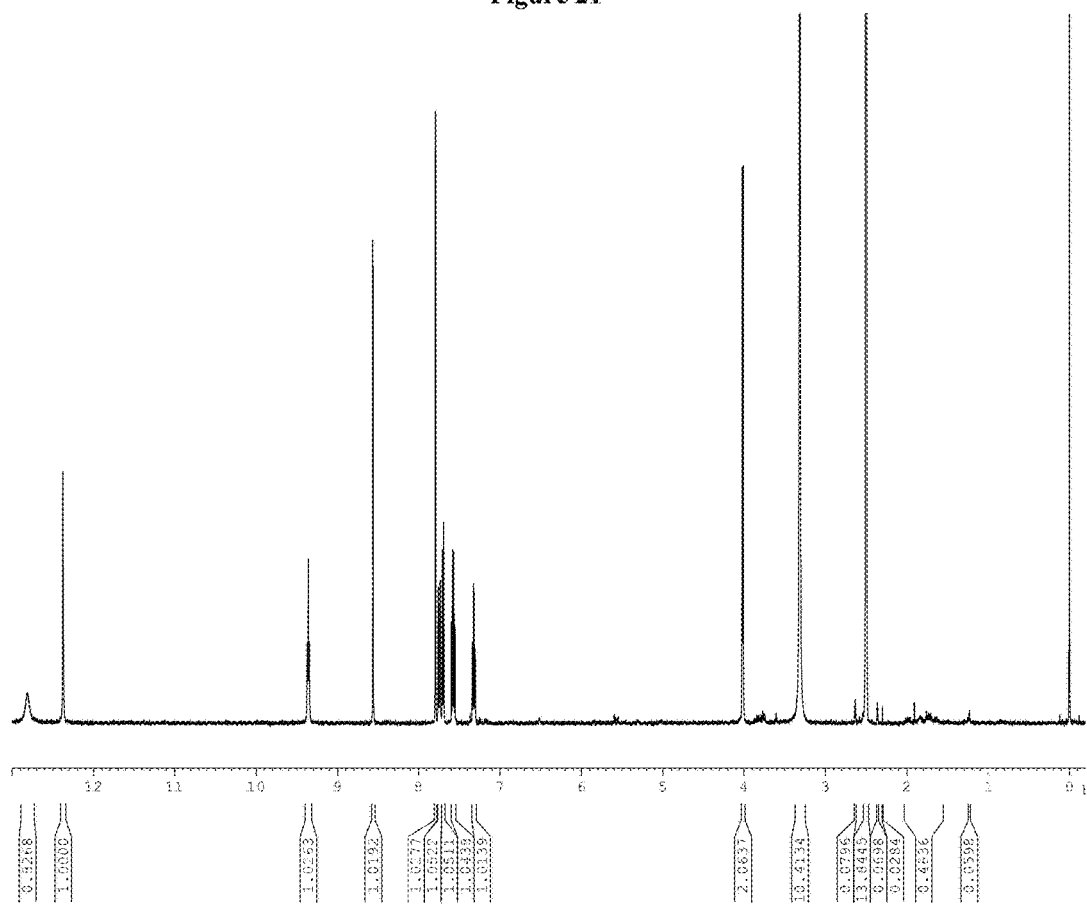
FIG. 21 depicts a $^1$H NMR spectrum of Form D of Compound 1.
Figure 22:
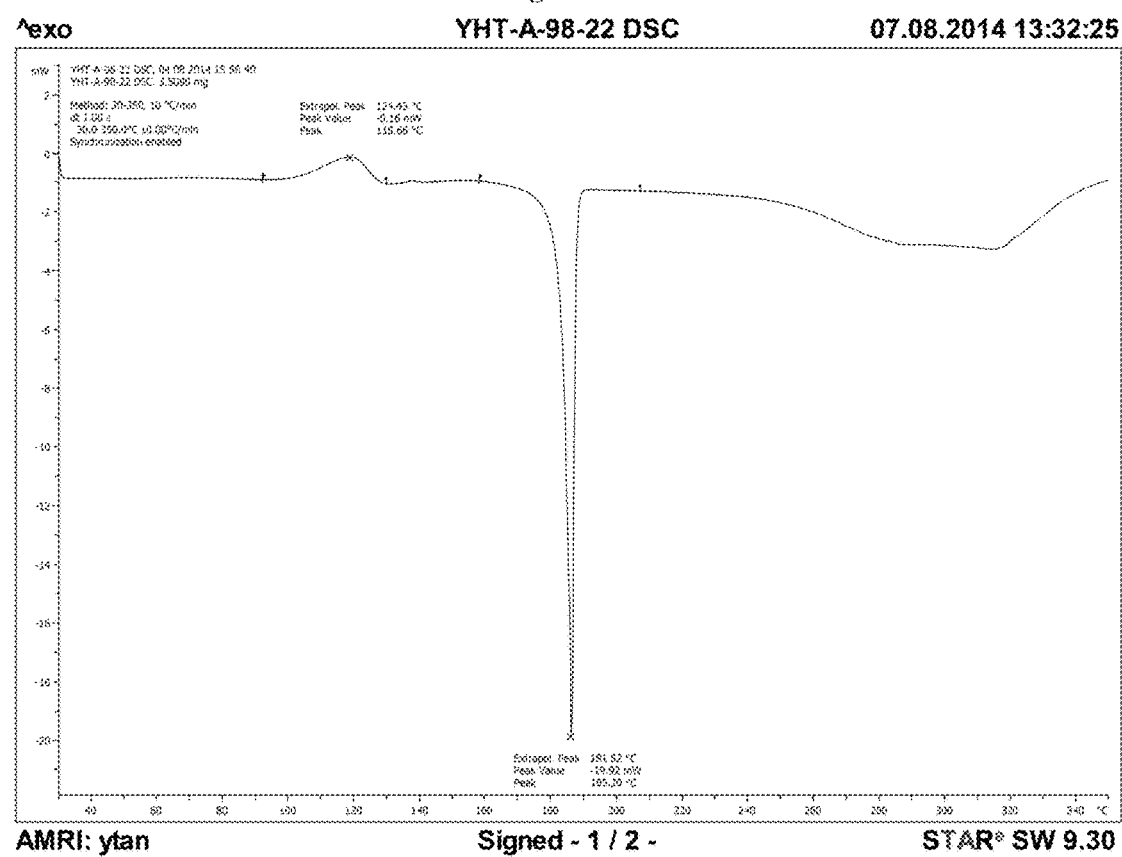
FIG. 22 depicts a DSC thermogram of Form D of Compound 1.
Figure 23:
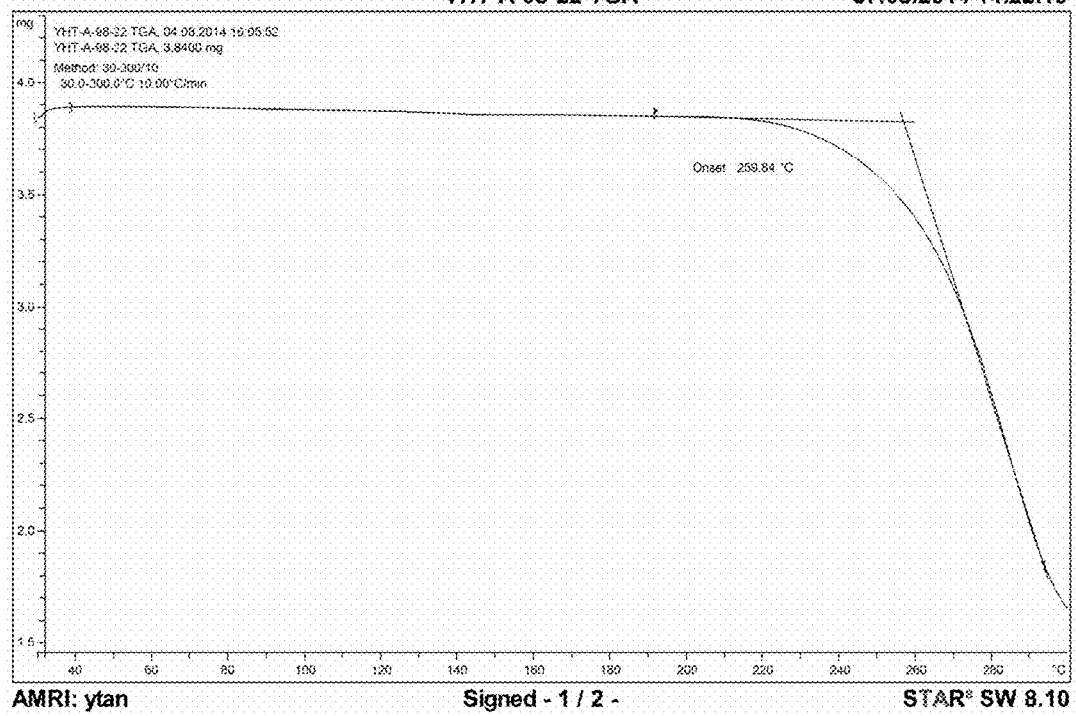
FIG. 23 depicts a TGA thermogram of Form D of Compound 1.
Figure 24:
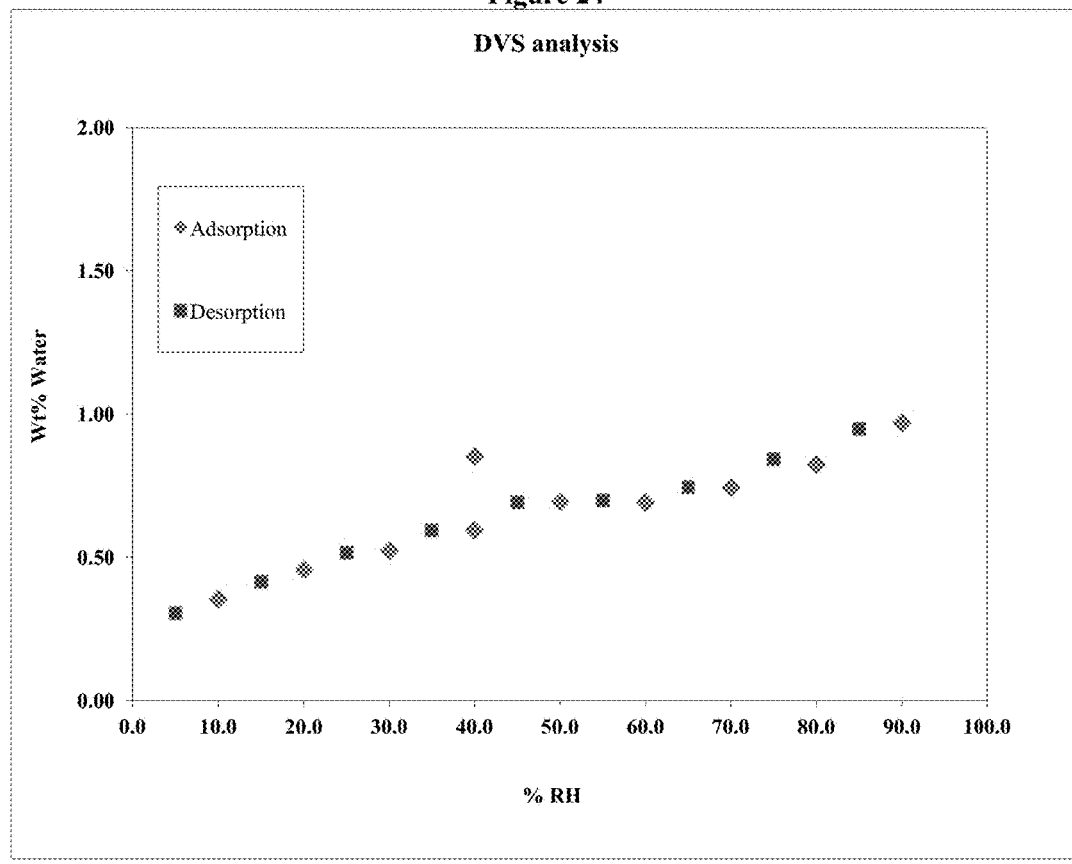
FIG. 24 depicts a DVS analysis of Form D of Compound 1.
Figure 25:
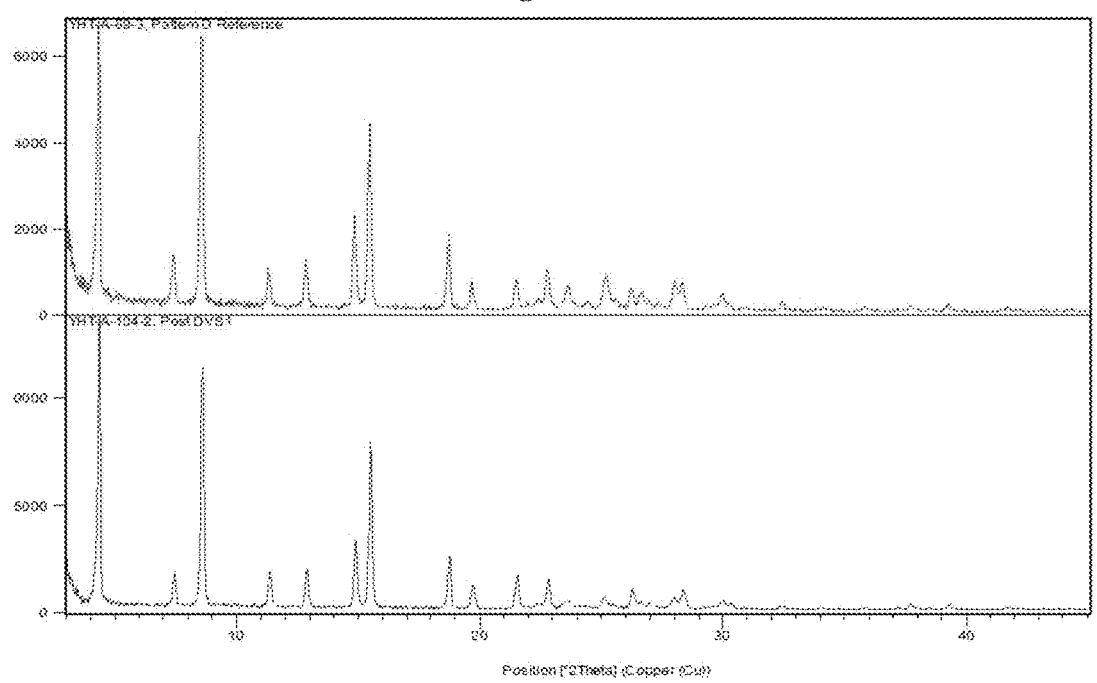
FIG. 25 depicts a XRPD pattern of post-DVS Form D of Compound 1.

Form D was prepared in the binary solvent recrystallization experiment using THF as primary solvent and toluene as co-solvent (Table 5 and Table 6). Form D was also isolated in other single solvent and binary solvents recrystallization experiments in multiple solvent systems (Table 1-Table 10). No detectable solvent or degradation was observed by $^1$H NMR ($d_6$-DMSO) (FIG. 21). DSC analysis presented an endotherm at 185.2° C., and an exotherm at 118.7° C. (FIG. 22). Further analysis by TGA indicated no weight loss before the onset of decomposition at 259.8° C. (FIG. 23). The material adsorbed 0.7 wt % moisture at 60% RH and 1.0 wt % moisture at 90% RH (FIG. 24). This material is considered slightly hygroscopic. The XRPD analysis of the post-DVS material, after drying at 60° C. for 2 hours, recorded an XRPD pattern consistent with the starting material (FIG. 25). Once formed, Form D maintained its chemical and physical form even after storing the material at 60° C. for seven days (Table 15). Aqueous solubility of Form D was not achieved because Form D converted to Form A in aqueous equilibrium (Table 16). The obtained solubility of 0.49 mg/mL represents solubility of Form A. The discrepancy compared to the Form A solubility value described in Table 16 (0.0026 mg/mL) was possibly due to insufficient equilibrium or different residual solvent/ impurity profile. In the single form and competitive slurry experiments, Form D converted to Form A at ambient temperature under all tested conditions.

Characterization results of Form D are mostly consistent with metastable anhydrate polymorph.

FIG. 5 provides an XRPD pattern of Form D. A list of X-Ray Diffraction Peaks for Form D is provided below in Table 23.

TABLE 23

X-Ray Diffraction Peaks for Form D

| Two-theta angle (°) | d Space (Å) | Relative Intensity (%) |
|---|---|---|
| 4.32 | 20.45 | 92.9 |
| 7.44 | 11.88 | 17.03 |
| 8.59 | 10.30 | 100 |
| 11.31 | 7.82 | 13.88 |
| 12.85 | 6.89 | 17.13 |
| 14.85 | 5.96 | 34.18 |
| 15.49 | 5.72 | 68.51 |
| 18.72 | 4.74 | 27.1 |
| 19.71 | 4.50 | 10.18 |
| 21.51 | 4.13 | 10.6 |
| 22.40 | 3.97 | 3.16 |
| 22.75 | 3.91 | 13.28 |
| 23.62 | 3.77 | 7.61 |
| 24.48 | 3.64 | 1.81 |
| 25.17 | 3.54 | 11.43 |
| 26.19 | 3.40 | 6.39 |
| 26.68 | 3.34 | 6.01 |
| 26.96 | 3.31 | 2.19 |
| 27.32 | 3.27 | 1.33 |
| 27.98 | 3.19 | 9.25 |
| 28.35 | 3.15 | 8.91 |
| 29.34 | 3.04 | 1.4 |
| 29.98 | 2.98 | 5.45 |
| 30.30 | 2.95 | 2.44 |
| 32.44 | 2.76 | 3.55 |
| 34.07 | 2.63 | 0.75 |
| 35.81 | 2.51 | 1.34 |
| 37.16 | 2.42 | 1.12 |
| 37.69 | 2.39 | 2.33 |
| 38.44 | 2.34 | 1.07 |
| 39.25 | 2.30 | 2.46 |
| 41.71 | 2.17 | 1.41 |
| 42.19 | 2.14 | 0.91 |
| 44.35 | 2.04 | 0.88 |

6.2.12 Form E of Compound 1

Figure 26:
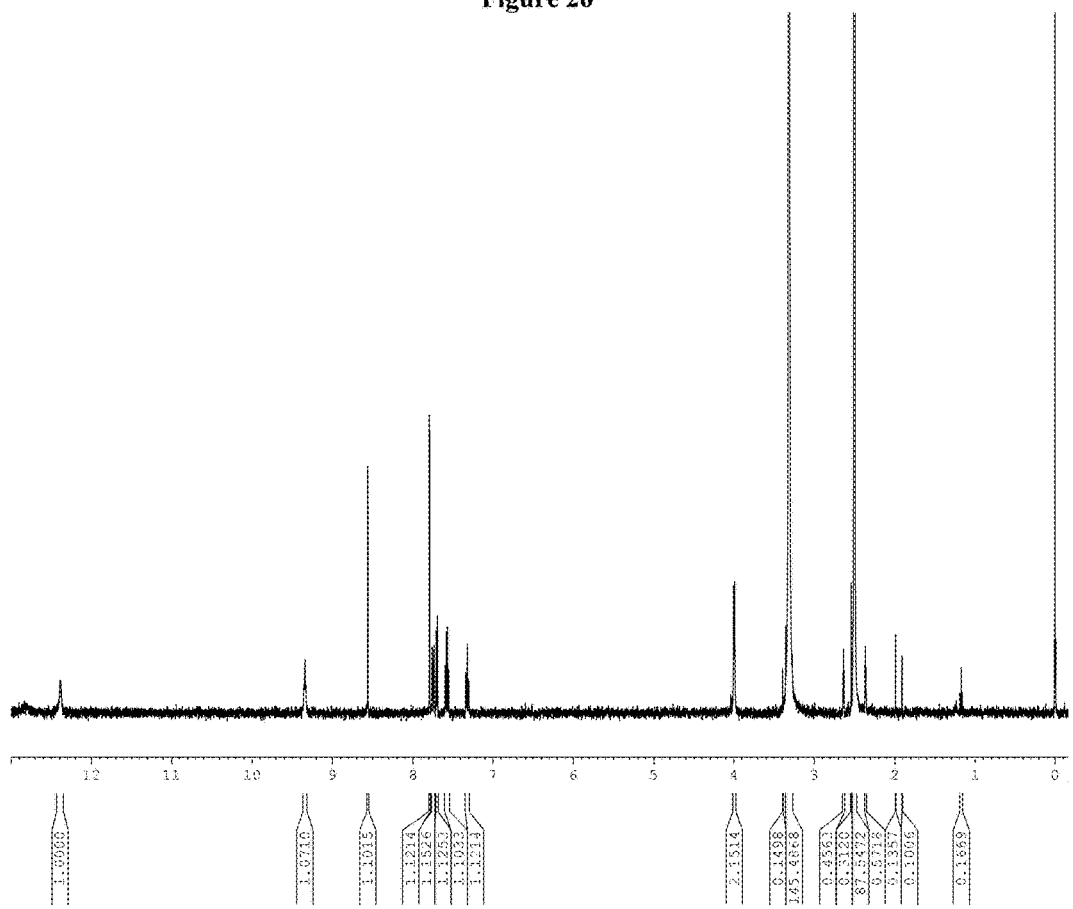
FIG. 26 depicts a $^1$H NMR spectrum of Form E of Compound 1.

Form E was prepared in the binary solvent recrystallization experiment using EtOAc as primary solvent and toluene as co-solvent (Table 5 and Table 6). Form E was also isolated in other single solvent and binary solvents recrystallization experiments in multiple solvent systems (Table 1-Table 10). An estimated 1.66 wt % of EtOAc and no degradation were observed by $^1$H NMR (d$_6$-DMSO) (FIG. 26). DSC analysis presented two endotherms at 154.8 and 185.6° C., and an exotherm at 156.7° C. (FIG. 27). Further analysis by TGA indicated a weight loss of 1.96%, attributed to loss of EtOAc, before 165.0° C. and onset of decomposition at 261.6° C. (FIG. 28). In the competitive slurry experiment, Form E converted to Form A (Table 13).

Characterization results of Form E are mostly consistent with a metastable anhydrate polymorph retaining residual solvent. The residual solvents was not released until melt and Form E showed similarity to several other forms (i.e., Forms B, C and D), indicating that Form E might be an inclusion complex in which non-stoichiometry amount of solvent was retained and caused minor changes in crystal lattice.

FIG. 6 provides an XRPD pattern of Form E. A list of X-Ray Diffraction Peaks for Form E is provided below in Table 24.

TABLE 24

X-Ray Diffraction Peaks for Form E

| Two-theta angle (°) | d Space (Å) | Relative Intensity (%) |
|---|---|---|
| 4.33 | 20.40 | 100 |
| 4.66 | 18.96 | 1.11 |
| 5.42 | 16.31 | 0.89 |
| 5.73 | 15.43 | 0.2 |
| 5.99 | 14.76 | 0.67 |
| 6.16 | 14.36 | 0.78 |
| 6.29 | 14.06 | 0.27 |
| 6.50 | 13.59 | 0.76 |
| 7.46 | 11.85 | 11.12 |
| 8.61 | 10.27 | 90.7 |
| 9.32 | 9.49 | 1.07 |
| 10.07 | 8.78 | 0.37 |
| 10.78 | 8.21 | 0.49 |
| 10.93 | 8.09 | 0.33 |
| 11.37 | 7.78 | 14.51 |
| 12.17 | 7.27 | 0.99 |
| 12.89 | 6.87 | 13.92 |
| 13.45 | 6.58 | 0.54 |
| 14.45 | 6.13 | 0.44 |
| 14.89 | 5.95 | 27.33 |
| 15.50 | 5.72 | 66.57 |
| 16.66 | 5.32 | 0.78 |
| 18.74 | 4.74 | 22.56 |
| 19.73 | 4.50 | 9.11 |
| 20.04 | 4.43 | 0.58 |
| 20.56 | 4.32 | 0.47 |
| 21.53 | 4.13 | 11.42 |
| 21.80 | 4.08 | 3.21 |
| 22.19 | 4.01 | 2.72 |
| 22.57 | 3.94 | 5.03 |
| 22.81 | 3.90 | 13.03 |
| 23.45 | 3.79 | 14.55 |
| 23.87 | 3.73 | 1.37 |
| 24.23 | 3.67 | 4.18 |
| 24.97 | 3.57 | 18.47 |
| 25.35 | 3.51 | 4.98 |
| 26.24 | 3.40 | 8.36 |
| 26.47 | 3.37 | 8.99 |
| 26.96 | 3.31 | 4.6 |
| 27.24 | 3.27 | 2.52 |
| 27.85 | 3.20 | 15.23 |
| 28.36 | 3.15 | 7.68 |
| 29.19 | 3.06 | 2.43 |
| 29.57 | 3.02 | 2.49 |
| 29.85 | 2.99 | 6.95 |
| 30.30 | 2.95 | 2.02 |
| 30.81 | 2.90 | 1.47 |
| 31.25 | 2.86 | 0.42 |
| 32.34 | 2.77 | 4.49 |
| 32.93 | 2.72 | 0.8 |
| 34.10 | 2.63 | 1.64 |
| 34.77 | 2.58 | 0.22 |
| 35.74 | 2.51 | 2.35 |
| 36.36 | 2.47 | 0.37 |
| 37.23 | 2.41 | 0.48 |
| 37.71 | 2.39 | 1.97 |
| 38.36 | 2.35 | 1.17 |
| 39.28 | 2.29 | 2.17 |
| 40.74 | 2.21 | 0.39 |
| 41.66 | 2.17 | 1.45 |
| 42.19 | 2.14 | 0.82 |
| 42.61 | 2.12 | 0.43 |
| 43.29 | 2.09 | 0.4 |
| 43.71 | 2.07 | 0.63 |
| 44.18 | 2.05 | 1.05 |

6.2.13 Form F of Compound 1

Figure 29:
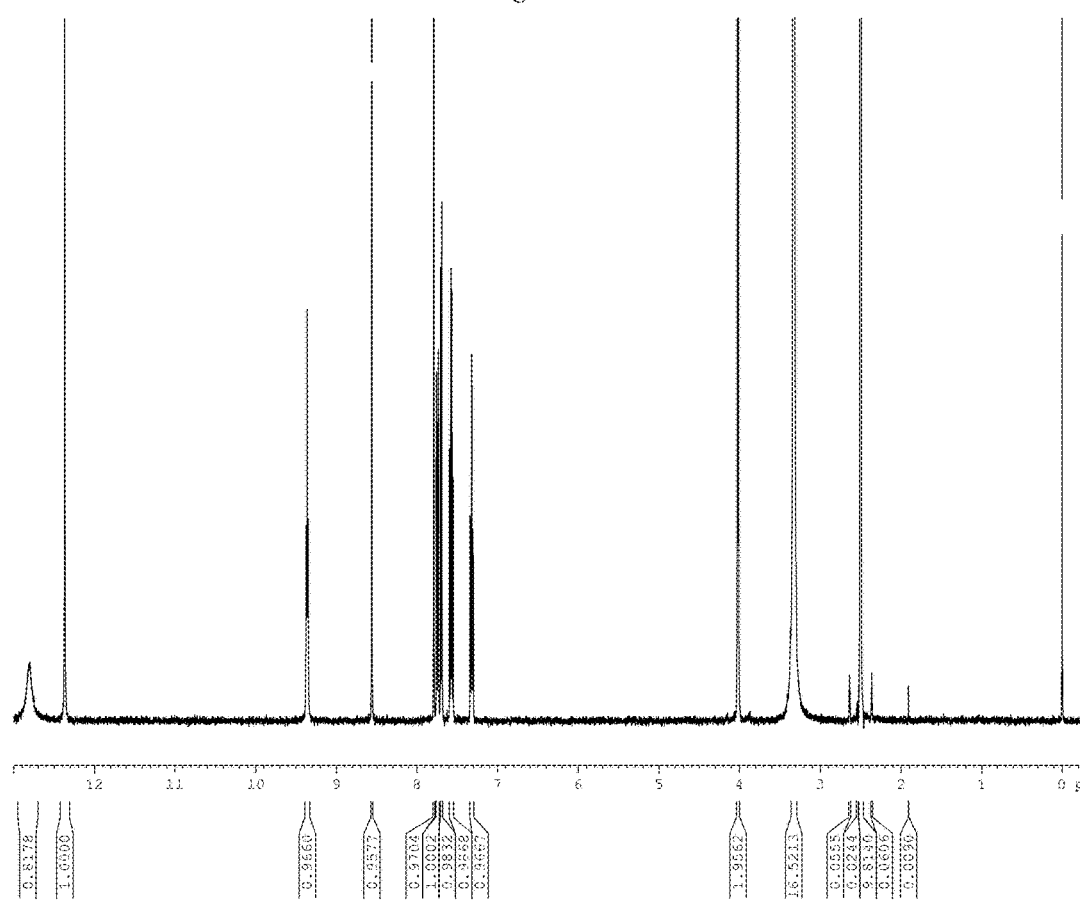
FIG. 29 depicts a $^1$H NMR spectrum of Form F of Compound 1.

Form F was prepared in binary solvent crystallization using water as an anti-solvent (Table 3 and Table 4). Form F was not isolated from single solvent and binary solvent crystallization experiments but a mixture of Forms F and B, or D, or E, or G was encountered in binary solvent crystallization. The $^1$H NMR (DMSO-$d_6$) spectrum was consistent with the structure of Compound 1 with no significant residual solvent (FIG. 29). DSC analysis presented three endotherms at 64.1, 91.3 and 185.9° C. (FIG. 30). Further analysis by TGA indicated a weight loss of 1.86% before 110.0° C. and onset of decomposition at 268.3° C. (FIG. 31). In the competitive slurry experiment, Form F converted to Form A (Table 13).

Characterization results of Form F are mostly consistent with a metastable hydrate polymorph.

FIG. 7 provides an XRPD pattern of Form F. A list of X-Ray Diffraction Peaks for Form F is provided below in Table 25.

TABLE 25

X-Ray Diffraction Peaks for Form F

| Two-theta angle (°) | d Space (Å) | Relative Intensity (%) |
|---|---|---|
| 3.99 | 22.15 | 100 |
| 4.23 | 20.91 | 42.6 |
| 7.89 | 11.20 | 35.92 |
| 8.36 | 10.58 | 30.55 |
| 11.81 | 7.50 | 19.52 |
| 15.21 | 5.82 | 37.6 |
| 15.44 | 5.74 | 33.4 |
| 17.39 | 5.10 | 10.19 |
| 17.79 | 4.99 | 12.96 |
| 19.78 | 4.49 | 13.97 |
| 20.87 | 4.26 | 22.28 |
| 22.98 | 3.87 | 12.77 |
| 23.83 | 3.73 | 11.45 |
| 25.17 | 3.54 | 20.19 |
| 26.10 | 3.41 | 12.71 |
| 27.15 | 3.28 | 8.58 |
| 28.53 | 3.13 | 10.53 |
| 30.30 | 2.95 | 5.79 |
| 31.71 | 2.82 | 12.17 |
| 34.06 | 2.63 | 1.29 |

6.2.14 Form G of Compound 1

Figure 32:
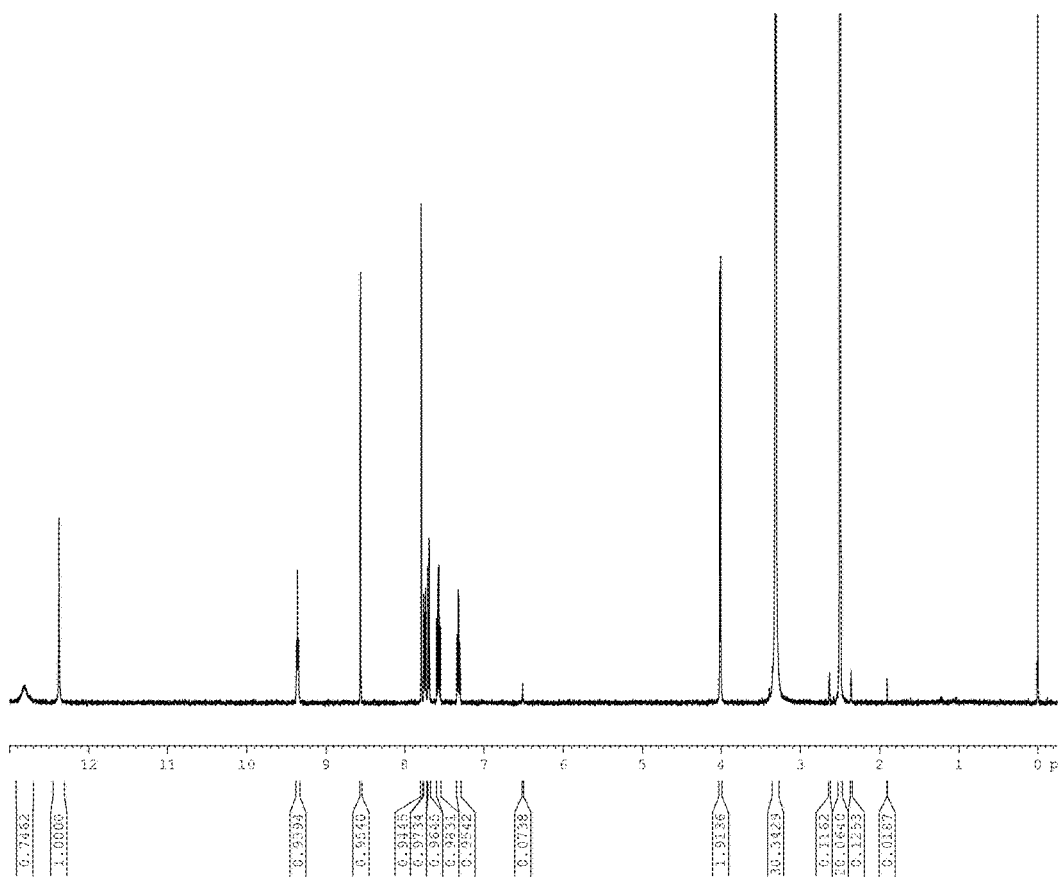
FIG. 32 depicts a $^1$H NMR spectrum of Form G of Compound 1.
Figure 35:
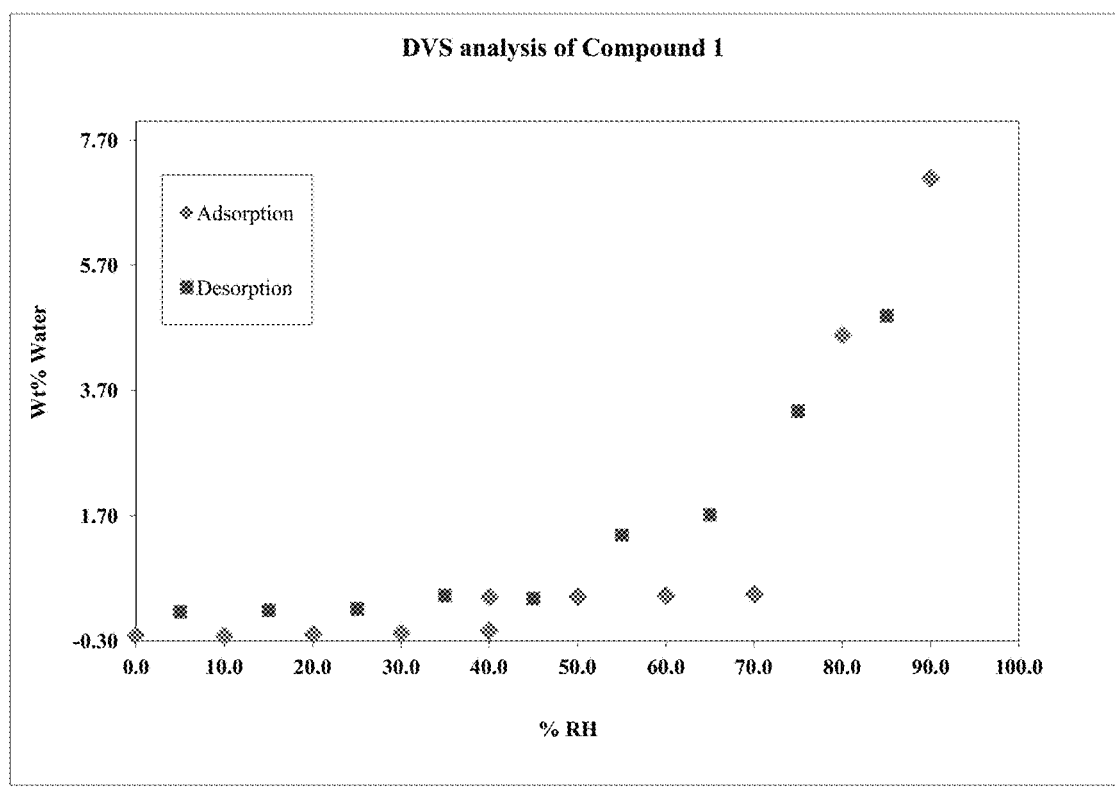
FIG. 35 depicts a DVS analysis of Form G of Compound 1.
Figure 36:
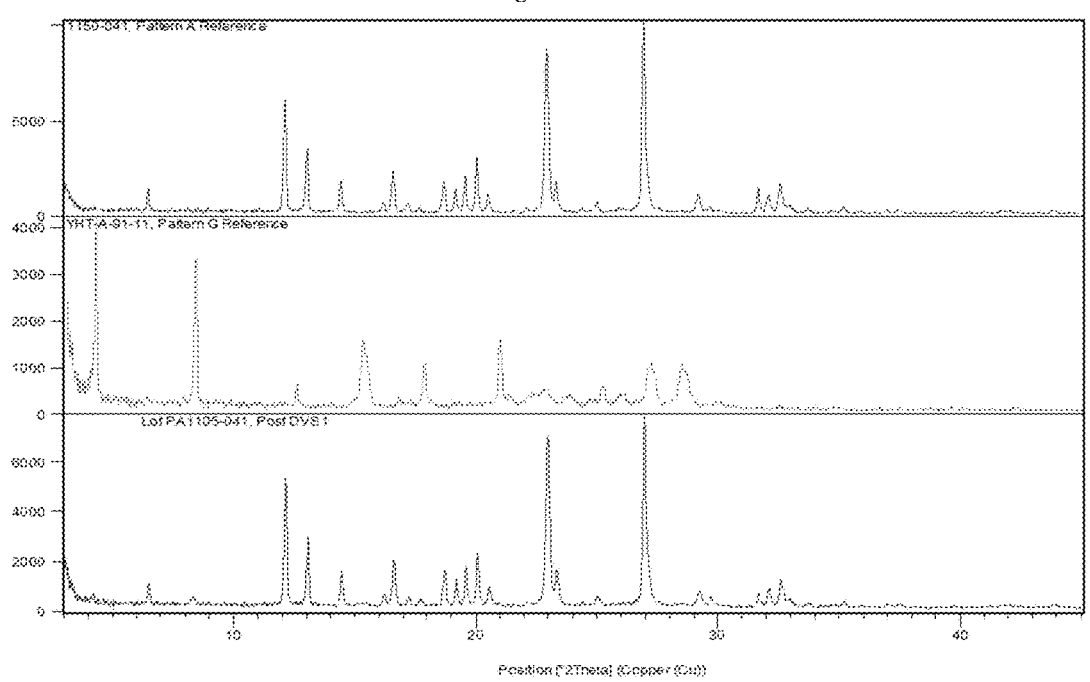
FIG. 36 depicts a XRPD pattern of post-DVS of Form G of Compound 1.

Form G was prepared in the binary solvent recrystallization experiment using IPA as primary solvent and water as co-solvent (Table 3 and Table 4). Form G showed a high degree of similarity to Form F (FIG. 1). No detectable solvent or degradation was observed by $^1$H NMR ($d_6$-DMSO) (FIG. 32). DSC analysis presented two endotherms at 90.5 and 184.9° C. (FIG. 33). Analysis by TGA indicated no weight loss before the onset of decomposition at 263.5° C. (FIG. 34). The material adsorbed 0.4 wt % moisture at 60% RH and 7.1 wt % moisture at 90% RH (FIG. 35). This material is considered as moderately hygroscopic. The XRPD analysis of the post-DVS material after drying at 60° C. for 2 hours, afforded Form A (FIG. 36). Since no apparent hysteresis was observed on DVS, Form G is not a hydrate form. Because it converted to Form A after the DVS experiment and drying, it is likely a metastable anhydrate polymorph. Aqueous slurry experiment also supported that Form G is not a hydrate form because Form G converted to Form A after one day in water (Table 12). When storing Form G at 60° C. for 24 hours a form mixture was observed at day 1, and at day 7 only Form A was obtained (Table 15). Aqueous solubility of Form G was not achieved because Form G converted to Form A in aqueous equilibrium (Table 16). The obtained solubility of 0.061 mg/mL represents solubility of Form A. The discrepancy compared to the Form A solubility value described in Table 16 (0.0026 mg/mL) was possibly due to insufficient equilibrium or different residual solvent/impurity profile. In the single form and competitive slurry experiments, Form G converted to Form A at ambient temperature under all tested conditions.

Characterization results of Form G are mostly consistent with a metastable anhydrate polymorph.

FIG. 8 provides an XRPD pattern of Form G. A list of X-Ray Diffraction Peaks for Form G is provided below in Table 26.

TABLE 26

X-Ray Diffraction Peaks for Form G

| Two-theta angle (°) | d Space (Å) | Relative Intensity (%) |
|---|---|---|
| 4.19 | 21.07 | 100 |
| 8.33 | 10.61 | 80.94 |
| 12.47 | 7.10 | 11.24 |
| 15.19 | 5.83 | 36.87 |
| 15.44 | 5.74 | 22.1 |
| 16.67 | 5.32 | 4.11 |
| 17.81 | 4.98 | 24.01 |
| 19.26 | 4.61 | 1.69 |
| 20.87 | 4.26 | 34.66 |
| 21.33 | 4.17 | 4.01 |
| 22.18 | 4.01 | 5.07 |
| 22.86 | 3.89 | 7.24 |
| 23.71 | 3.75 | 4.57 |
| 24.59 | 3.62 | 3.4 |
| 25.09 | 3.55 | 9.73 |
| 25.89 | 3.44 | 4.8 |
| 27.00 | 3.30 | 19.8 |
| 28.36 | 3.15 | 20.89 |
| 28.63 | 3.12 | 16.14 |
| 29.87 | 2.99 | 2.25 |
| 32.45 | 2.76 | 1.52 |
| 34.70 | 2.59 | 1.57 |
| 39.53 | 2.28 | 1.34 |
| 42.08 | 2.15 | 1.27 |

6.2.15 Form H of Compound 1

Figure 37:
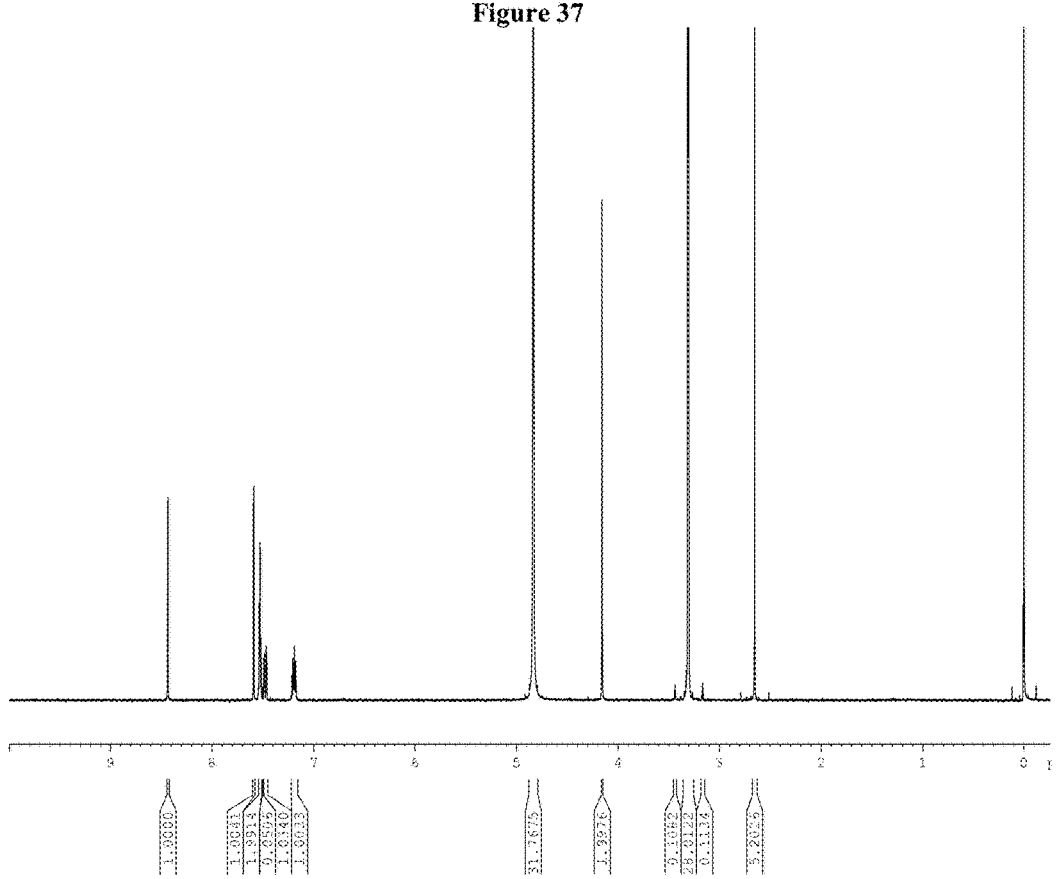
FIG. 37 depicts a $^1$H NMR spectrum of Form H of Compound 1.

Form H was prepared in the binary solvent recrystallization experiment using DMSO as primary solvent and toluene as co-solvent (Table 5 and Table 6). Form H was isolated from conditions where DMSO was used. An estimated 18.9 wt % of DMSO and no degradation were observed by $^1$H NMR (MeOD) (FIG. 37). DSC analysis presented an endotherm at 88.0° C. (FIG. 38). Analysis by TGA indicated two weight losses of 6.4% before 140° C. and 9.8% before 240° C., and the onset of decomposition at 268.1° C. (FIG. 39).

Based on characterization results, Form H is consistent with a mono-DMSO solvate polymorph.

FIG. 9 provides an XRPD pattern of Form H. A list of X-Ray Diffraction Peaks for Form H is provided below in Table 27.

TABLE 27

X-Ray Diffraction Peaks for Form H

| Two-theta angle (°) | d Space (Å) | Relative Intensity (%) |
|---|---|---|
| 3.07 | 28.81 | 20.05 |
| 5.35 | 16.53 | 12.44 |
| 8.56 | 10.33 | 2.24 |
| 10.69 | 8.28 | 18.25 |
| 12.20 | 7.26 | 6.45 |
| 12.62 | 7.01 | 21.51 |
| 13.08 | 6.77 | 5.27 |
| 13.32 | 6.65 | 10.86 |
| 14.08 | 6.29 | 100 |
| 15.46 | 5.73 | 3.68 |
| 16.04 | 5.53 | 2.76 |
| 17.18 | 5.16 | 29.96 |
| 17.69 | 5.01 | 4.89 |
| 17.93 | 4.95 | 15.41 |
| 18.76 | 4.73 | 44.25 |
| 19.69 | 4.51 | 17.85 |
| 20.14 | 4.41 | 2.51 |
| 21.19 | 4.19 | 10.15 |
| 21.40 | 4.15 | 72.29 |
| 22.22 | 4.00 | 3.08 |
| 22.99 | 3.87 | 6.26 |
| 24.02 | 3.70 | 5.81 |
| 24.59 | 3.62 | 31.18 |
| 25.18 | 3.54 | 18.49 |
| 25.75 | 3.46 | 29.33 |
| 26.55 | 3.36 | 7.81 |
| 26.93 | 3.31 | 8.85 |
| 27.53 | 3.24 | 17.48 |
| 28.32 | 3.15 | 2.33 |
| 29.07 | 3.07 | 1.97 |
| 31.19 | 2.87 | 1.53 |
| 31.72 | 2.82 | 6.13 |
| 32.05 | 2.79 | 6.34 |
| 33.70 | 2.66 | 1.26 |
| 35.09 | 2.56 | 3.94 |
| 35.76 | 2.51 | 6.55 |
| 37.23 | 2.42 | 2.48 |
| 37.94 | 2.37 | 1.06 |
| 38.67 | 2.33 | 2.67 |
| 39.26 | 2.29 | 1.16 |
| 39.96 | 2.26 | 0.82 |
| 40.36 | 2.23 | 1.88 |
| 43.14 | 2.10 | 0.79 |
| 44.56 | 2.03 | 3.62 |

6.2.16 Conclusion

During the polymorph study, eight unique polymorphs (Forms A, B, C, D, E, F, G and H) were observed. Form A is characterized as a moderately hygroscopic, anhydrate polymorph and was determined to be the most stable polymorph from slurry experiments, thermal stability and aqueous solubility. Forms B, C, D and E shared many common XRPD diffraction peaks between 15 and 30° 2θ. The small variation in diffraction patterns is probably due to minor changes in crystal lattice due to presence of variable amount of residual solvents. Forms F and G also shared some similarity. Based on NMR and TGA analysis, Forms D and G are likely metastable anhydrate polymorphs. Form H was found to be a DMSO solvate. All the polymorphs converted to Form A in competitive and single form slurry experiments. All four polymorphs showed similar endotherm/exotherm at low temperature, attributed to a melt/recrystallization event, followed by an endothermic event at ~150.0° C. in the DSC analysis. Forms A, D and G were found to be chemically stable over storage as solid at 60° C. for 7 days. However, potential ester degradation product was detected in the solid isolated from EtOH, indicating that alcoholic solvents should be avoided to reduce the potential risk of degradation.

6.3 Polymorph Conversion

The conversion of Form G to Form A was conducted initially on a 2.0 g scale of Compound 1 in seven volumes of 33% acetone in water (2.3 vol of acetone and 4.7 vol of water) with 5.4% w/w of form A seeds of Compound 1. The desired Form A of Compound 1 was recovered in 97% yield. Following this successful trial experiment, a 72.4 g conversion of Form G to Form A was completed in seven volumes of 33% acetone in water and seeding with 2.3% w/w of Form A. The scale up experiment yielded 73.9 g in 97% yield (including added seeds) of Form A.

6.3.1 2.0 g Trial Experiment

To a 25-mL, three-neck, round-bottom flask equipped with an overhead stirrer were charged Form G of Compound 1 (2.0 g, 6.9 mmol), acetone (4.6 mL, 2.3 vol), and $H_2O$ (9.4 mL, 4.7 vol) at 18° C. (room temperature). The slurry was stirred for 10 min at which Form A seeds (0.107 g, 5.4% w/w, lot #1150-041) were added. After 24 h of stirring at 17-18° C., the mixture was filtered in a Buchner funnel and washed with $H_2O$ (4 mL, 2 vol). The wet cake was dried in vacuum oven at 20-25° C. for 16 h to afford 1.90 g of Form A of Compound 1 in 97% yield as a white solid.

6.3.2 74.2 g Scale Up Experiment

To a 1-L, three-neck, round-bottom flask equipped with an overhead stirrer were charged Form G of Compound 1 (74.2 g, 0.26 mol), acetone (171 mL, 2.3 vol), and $H_2O$ (349 mL, 4.7 vol) at 18-20° C. (room temperature). The slurry was stirred for 10 min at which Form A seeds (1.71 g, 2.3% w/w) were added. After 28 h of stirring at 18-20° C., the mixture was filtered in a Buchner funnel and washed with $H_2O$ (140 mL, 2 vol). The wet cake was dried in vacuum oven at 20-25° C. for 42 h to afford 73.9 g of Form A in 97% yield as a white solid.

6.4 Summary of Salt Screen of Compound 1

Following counterions were selected for initial salt formation experiments, based on the pKa of Compound 1 and safety/acceptance in pharmaceutical drug products: Calcium acetate, choline hydroxide, potassium hydroxide, sodium hydroxide, arginine, meglumine, magnesium hydroxide and calcium hydroxide. Solids isolated from the salt formation experiments were characterized. Based on the salt stoichiometry and preliminary stability evaluation by thermal analysis and competitive slurry, five salts (Salt I, Salt II, Salt III, Salt IV and Salt V) were selected for scale up and full characterization. Salt I and Salt II provided poor aqueous solubility at 0.01 mg/mL and 0.03 mg/mL, respectively. All sodium and potassium salts (Salt III, Salt IV and Salt V) showed good solubility (>19 mg/mL). The five salts all had endothermic events at low temperature. Salt II, Salt IV and Salt V exhibited 5-10% weight loss which started below 100° C. DVS of Salt IV showed that it is a stable hydrate throughout humidity range at 25° C. Therefore Salt IV has good solubility and relative stability. Although some endothermic events were observed, Salt III also showed good stability. From thermal holding experiment, Salt VI was discovered. Salt VI was found to be an anhydrate form and only slightly hygroscopic. This form showed more favorable physical property than Salt IV. However, preparation of Salt VI involved thermal holding at 260° C.

6.4.1 Salt Formation on 30 mg Scale

Approximately 30 mg of Compound 1 was weight into 4 mL glass vials equipped with stir bar. Solvent (1.0 or 2.0 mL) was added and the mixture was heated to elevated temperatures 50° C., and then the acetone and MeCN solution was polish filtered through a 0.45 m syringe filter into a clean preheated vial. After hot filtration, basic counterion solution was added drop-wise as summarized in Table 28 and the resulting mixture was cooled to RT at 20° C./h. The vial was inspected for precipitation. If no precipitation or very little precipitation was discovered, the content was evaporated under nitrogen. All precipitates were isolated by filtration.

TABLE 28

| Counterion lists | | | |
|---|---|---|---|
| Name | M.W. | Solvent | Safety Class |
| Calcium acetate hydrate | 176.18 | Water | 1 |
| Choline hydroxide | 121.18 | Water | 1 |

TABLE 28-continued

| Counterion lists | | | |
|---|---|---|---|
| Name | M.W. | Solvent | Safety Class |
| Potassium hydroxide | 56.11 | Water/MeOH | 1 |
| Sodium hydroxide in | 40 | Water/MeOH or Water | 1 |
| l-Arginine | 174.2 | Water | 1 |
| n-methyl-d-glucamine (meglumine) | 195.21 | Water/MeOH | 1 |
| Magnesium nitrate + Sodium hydroxide | 256.41 | Water | 1 |
| Calcium nitrate + Sodium hydroxide | 236.15 | Water | 1 |

The details of 30 mg scale salt formation experiments are summarized in Table 29, Table 30, Table 31, Table 32, Table 33 and Table 34. The reaction was performed at elevated temperature and filtered to ensure complete dissolution of the free acid. If precipitation did not occur instantaneously, crystallization of the potential salts was attempted by cooling or evaporation crystallization. The majority of experiments afforded solids isolable by filtration. The solids from filtration or evaporation were analyzed by XRPD for crystallinity and form. Salt stoichiometry was examined by NMR or IC. The results are summarized in Table 35.

TABLE 29

| Salt formation experiments (1:1 equiv.) part 1 | | | | | | |
|---|---|---|---|---|---|---|
| SM (mg) | CI Solution | CI Actual Conc. (M) | CI Amt (mL) | After CI Addition | After Cooling | Isolation |
| 32.5 | Calcium acetate hydrate in water | 0.25 | 0.41 | ppt | ppt | Filtration, white solid |
| 29.9 | Choline hydroxide in water | 0.5 | 0.21 | Clear | Clear | Evaporation, gel solid |
| 30.1 | Potassium hydroxide in water | 0.5 | 0.21 | ppt | ppt | Filtration, white solid |
| 29.7 | Potassium hydroxide in MeOH | 0.5 | 0.21 | ppt | ppt | Filtration, white solid |
| 29.8 | Sodium hydroxide in water | 0.5 | 0.21 | Clear | ppt | Filtration, white solid |
| 29.7 | Sodium hydroxide in MeOH:water (3/2) | 0.5 | 0.21 | ppt | ppt | Filtration, white solid |
| 29.3 | l-Arginine in water | 0.5 | 0.21 | Clear | Clear | Evaporation, white solid |
| 30 | Meglumine in water | 0.5 | 0.21 | Clear | Clear | Evaporation, gel solid |
| 30.2 | Meglumine in MeOH:water (1/1) | 0.5 | 0.21 | Clear | ppt, small quant. | Evaporation, white solid |
| 30.7 | Magnesium itrate + Sodium hydroxide in water | 0.5 | 0.21/0.21 | ppt | ppt | Filtration, white solid |
| 30.8 | Calcium nitrate + Sodium hydroxide in water | 0.5 | 0.21/0.21 | ppt | ppt | Filtration, white solid |

Solvent = CH$_3$OH;

Solvent Amount = 1 mL;

Temperature = 50° C.;

Equivalent = 1.

TABLE 30

Salt formation experiments (1:1 equiv.) part 2

| SM (mg) | CI Solution | CI Actual Conc. (M) | CI Amt (mL) | After CI Addition | After Cooling | Isolation |
|---|---|---|---|---|---|---|
| 30.5 | Calcium acetate hydrate in water | 0.25 | 0.41 | ppt | ppt | Filtration, white solid |
| 28.8 | Choline hydroxide in water | 0.5 | 0.21 | ppt | ppt, small quant. | Evaporation, gel solid |
| 30.6 | Potassium hydroxide in water | 0.5 | 0.21 | Clear | ppt | Filtration, white solid |
| 31 | Potassium hydroxide in MeOH | 0.5 | 0.21 | ppt | ppt | Filtration, white solid |
| 28.7 | Sodium hydroxide in water | 0.5 | 0.21 | ppt | ppt | Filtration, white solid |
| 30.7 | Sodium hydroxide in MeOH:water (3/2) | 0.5 | 0.21 | ppt | ppt | Filtration, white solid |
| 30.4 | l-Arginine in water | 0.5 | 0.21 | ppt | ppt, small quant. | Filtration, not enough solid |
| 31.3 | Meglumine in water | 0.5 | 0.21 | Clear | Clear | Evaporation, gel solid |
| 29.9 | Meglumine in MeOH:water (1/1) | 0.5 | 0.21 | Clear | ppt | Filtration, white solid |
| 31.7 | Magnesium nitrate + Sodium hydroxide in water | 0.5 | 0.21/0.21 | ppt | ppt | Filtration, white solid |
| 29.6 | Calcium nitrate + Sodium hydroxide in water | 0.5 | 0.21/0.21 | ppt | ppt | Filtration, white solid |

Solvent = Acetone;
Solvent Amount = 1 mL;
Temperature = 50° C.;
Equivalent = 1.

TABLE 31

Salt formation experiments (1:1 equiv.) part 3

| SM (mg) | CI Solution | CI Actual Conc. (M) | CI Amt (mL) | After CI Addition | After Cooling | Isolation |
|---|---|---|---|---|---|---|
| 31.1 | Calcium acetate hydrate in water | 0.25 | 0.41 | ppt | ppt | Filtration, white solid |
| 31 | Choline hydroxide in water | 0.5 | 0.21 | ppt | ppt, small quant. | Evaporation, gel solid |
| 29.6 | Potassium hydroxide in water | 0.5 | 0.21 | ppt | ppt | Filtration, white solid |
| 31.3 | Potassium hydroxide in MeOH | 0.5 | 0.21 | ppt | ppt | Filtration, white solid |
| 30.7 | Sodium hydroxide in water | 0.5 | 0.21 | ppt | ppt | Filtration, white solid |
| 29.8 | Sodium hydroxide in MeOH:water (3/2) | 0.5 | 0.21 | ppt | ppt | Filtration, white solid |
| 30.8 | l-Arginine in water | 0.5 | 0.21 | ppt | ppt, gel solid | Evaporation, white solid |
| 30.6 | Meglumine in water | 0.5 | 0.21 | ppt | ppt, gel solid | Evp, gel solid |
| 31.4 | Meglumine in MeOH:water (1/1) | 0.5 | 0.21 | ppt | ppt | Filtration, white solid |
| 30.4 | Magnesium nitrate + Sodium hydroxide in water | 0.5 | 0.21/0.21 | ppt | ppt | Filtration, white solid |

TABLE 31-continued

Salt formation experiments (1:1 equiv.) part 3

| SM (mg) | CI Solution | CI Actual Conc. (M) | CI Amt (mL) | After CI Addition | After Cooling | Isolation |
|---|---|---|---|---|---|---|
| 30.1 | Calcium nitrate + Sodium hydroxide in water | 0.5 | 0.21/0.21 | ppt | ppt | Filtration, white solid |

Solvent = $CH_3CN$;
Solvent Amount = 2 mL;
Temperature = 50° C.;
Equivalent = 1.

TABLE 32

Salt formation experiments (2:1 or 1:2 equiv.) part 1

| SM (mg) | CI Solution | CI Actual Conc. (M) | Equiv. | CI Amt (mL) | After CI addition | After cooling | Isolation |
|---|---|---|---|---|---|---|---|
| 29.2 | Calcium acetate hydrate in water | 0.25 | 2.1 | 0.87 | ppt | ppt | Filtration, white solid |
| 32.3 | Choline hydroxide in water | 0.5 | | 0.43 | Clear | Clear | Evaporation, gel solid |
| 31.3 | Potassium hydroxide in water | 0.5 | | 0.43 | Clear | Clear | Evaporation, yellow solid |
| 33.0 | Potassium hydroxide in MeOH | 0.5 | | 0.43 | ppt | ppt | Filtration, white solid |
| 29.9 | Sodium hydroxide in water | 0.5 | | 0.43 | ppt | ppt | Filtration, white solid |
| 32.9 | Sodium hydroxide in MeOH:water (3/2) | 0.5 | | 0.43 | ppt | ppt | Filtration, white solid |
| 30.6 | l-Arginine in water | 0.5 | | 0.43 | Clear | Clear | Evaporation, white solid |
| 30.2 | Meglumine in water | 0.5 | | 0.43 | Clear | Clear | Evaporation, gel solid |
| 32.2 | Meglumine in MeOH:water (1/1) | 0.5 | | 0.43 | Clear | Clear | Evaporation, gel solid |
| 30.8 | Magnesium nitrate + Sodium hydroxide in water | 0.5 | | 0.43/0.87 | ppt | ppt | Filtration, white solid |
| 31.5 | Calcium nitrate + Sodium hydroxide in water | 0.5 | | 0.43/0.87 | ppt | ppt | Filtration, white solid |
| 32.4 | Calcium acetate hydrate in water | 0.25 | 0.51 | 0.21 | ppt | ppt | Filtration, white solid |
| 30.7 | Calcium nitrate + Sodium hydroxide in water | 0.5 | | 0.11/0.21 | ppt | ppt | Filtration, white solid |

Solvent = $CH_3OH$;
Solvent Amount = 1 mL;
Temperature = 50° C.

TABLE 33

Salt formation experiments (2:1 or 1:2 equiv.) part 2

| SM (mg) | CI Solution | CI Actual Conc. (M) | Equiv. | CI Amt (mL) | After CI addition | After cooling | Isolation |
|---|---|---|---|---|---|---|---|
| 30.3 | Calcium acetate hydrate in water | 0.25 | 2.1 | 0.87 | ppt | ppt | Filtration, white solid |
| 29.7 | Choline hydroxide in water | 0.5 | | 0.43 | Clear | Clear | Evaporation, gel solid |
| 28.8 | Potassium hydroxide in water | 0.5 | | 0.43 | Clear | Clear | Evaporation, yellow solid |

TABLE 33-continued

Salt formation experiments (2:1 or 1:2 equiv.) part 2

| SM (mg) | CI Solution | CI Actual Conc. (M) | Equiv. | CI Amt (mL) | After CI addition | After cooling | Isolation |
|---|---|---|---|---|---|---|---|
| 30.7 | Potassium hydroxide in MeOH | 0.5 | | 0.43 | ppt | ppt | Filtration, white solid |
| 29.3 | Sodium hydroxide in water | 0.5 | | 0.43 | ppt | ppt | Filtration, white solid |
| 31.4 | Sodium hydroxide in MeOH:water (3/2) | 0.5 | | 0.43 | ppt | ppt | Filtration, white solid |
| 31.5 | 1-Arginine in water | 0.5 | | 0.43 | Clear | Clear | Evaporation, white solid |
| 28.8 | Meglumine in water | 0.5 | | 0.43 | Clear | Clear | Evaporation, gel solid |
| 29.3 | Meglumine in MeOH:water (1/1) | 0.5 | | 0.43 | Clear | Clear | Evaporation, gel solid |
| 29.3 | Magnesium nitrate + Sodium hydroxide in water | 0.5 | | 0.43/0.87 | ppt | ppt | Filtration, white solid |
| 28.8 | Calcium nitrate + Sodium hydroxide in water | 0.5 | | 0.43/0.87 | ppt | ppt | Filtration, white solid |
| 31.3 | Calcium acetate hydrate in water | 0.25 | 0.51 | 0.21 | ppt | ppt | Filtration, white solid |
| 29.7 | Calcium nitrate + Sodium hydroxide in water | 0.5 | | 0.11/0.21 | ppt | ppt | Filtration, white solid |

Solvent = Acetone;
Solvent Amount = 1 mL;
Temperature = 50° C.

TABLE 34

Salt formation experiments (2:1 or 1:2 equiv.) part 3

| SM (mg) | CI Solution | CI Actual Conc. (M) | Equiv. | CI Amt (mL) | After CI addition | After cooling | Isolation |
|---|---|---|---|---|---|---|---|
| 33.9 | Calcium acetate hydrate in water | 0.25 | 2.1 | 0.87 | ppt | ppt | Filtration, white solid |
| 32.5 | Choline hydroxide in water | 0.5 | | 0.43 | Clear | Clear | Evaporation, gel solid |
| 30.1 | Potassium hydroxide in water | 0.5 | | 0.43 | Clear | Clear | Evaporation, yellow solid |
| 31.1 | Potassium hydroxide in MeOH | 0.5 | | 0.43 | ppt | ppt | Filtration, white solid |
| 30.4 | Sodium hydroxide in water | 0.5 | | 0.43 | ppt | ppt | Filtration, white solid |
| 30.7 | Sodium hydroxide in MeOH:water (3/2) | 0.5 | | 0.43 | ppt | ppt | Filtration, white solid |
| 30.5 | 1-Arginine in water | 0.5 | | 0.43 | ppt | ppt | Evaporation, white solid |
| 33.2 | Meglumine in water | 0.5 | | 0.43 | Clear | Clear | Evaporation, gel solid |
| 29.7 | Meglumine in MeOH:water (1/1) | 0.5 | | 0.43 | ppt | ppt | Evaporation, white solid |
| 32.4 | Magnesium nitrate + Sodium hydroxide in water | 0.5 | | 0.43/0.87 | ppt | ppt | Filtration, white solid |
| 29.7 | Calcium nitrate + Sodium hydroxide in water | 0.5 | | 0.43/0.87 | ppt | ppt | Filtration, white solid |
| 29.5 | Calcium acetate hydrate in water | 0.25 | 0.51 | 0.21 | ppt | ppt | Filtration, white solid |

TABLE 34-continued

Salt formation experiments (2:1 or 1:2 equiv.) part 3

| SM (mg) | CI Solution | CI Actual Conc. (M) | Equiv. | CI Amt (mL) | After CI addition | After cooling | Isolation |
|---|---|---|---|---|---|---|---|
| 30.0 | Calcium nitrate + Sodium hydroxide in water | 0.5 | | 0.11/0.21 | ppt | ppt | Filtration, white solid |

Solvent = CH$_3$CN;
Solvent Amount = 2 mL;
Temperature = 50° C.

TABLE 35

Salt formation experiments - characterization summary (1:1 equiv.)

| Solvent | CI Solution (0.5M unless specified) | XRPD | NMR | API:CI Ratio by IC |
|---|---|---|---|---|
| MeOH | calcium acetate in water | Salt I | No degradation | 1:0.56 |
| | calcium nitrate + sodium hydroxide in water | | No degradation | 1:0.52 |
| | calcium acetate hydrate in water | — | — | |
| acetone | calcium acetate in water | Salt II | No degradation | 1:0.50 |
| | calcium nitrate + Sodium hydroxide in water | | No degradation | 1:0.51 |
| | Calcium acetate in water | — | — | |
| | Calcium acetate in water | — | — | |
| | Calcium nitrate + Sodium hydroxide in water | Salt II + impurity | — | — |
| MeOH | Calcium acetate in water | Salt II | — | — |
| MeCN | calcium acetate in water | — | — | |
| | calcium nitrate + sodium hydroxide in water | — | — | |
| | Calcium acetate hydrate in water | — | — | |
| | Calcium acetate hydrate in water | — | — | |
| MeCN | Calcium nitrate + Sodium hydroxide in water | Salt II + impurity | — | — |
| MeOH | potassium hydroxide in MeOH | Salt III | — | — |
| MeCN | potassium hydroxide in water | Salt III | No degradation | 1:0.65 |
| | potassium hydroxide in MeOH | — | — | |
| acetone | Sodium hydroxide in water | Salt IV | No degradation | 1:1 |
| | Sodium hydroxide in MeOH | Salt IV | — | — |
| MeCN | Sodium hydroxide in water | Salt IV | — | — |
| | Sodium hydroxide in MeOH | Salt IV + impurity | No degradation | 1:0.84 |
| MeOH | Sodium hydroxide in water | Salt V | No degradation | 1:1.48 |
| | Sodium hydroxide in MeOH | — | — | |
| acetone | Sodium hydroxide in water | — | — | |
| | Sodium hydroxide in MeOH | — | — | |
| MeCN | Sodium hydroxide in water | — | — | |
| | Sodium hydroxide in MeOH | — | — | |

Overall salt formation was confirmed with counterion ratio of approximately 0.5 to 1.5 equivalents. Most salts exhibited polymorphism with observation of multiple unique XRPD patterns: four for calcium salts, two for choline salts, seven for potassium salts, and eight for sodium salts. A crystalline salt was obtained using meglumine but only 0.38 equivalents of meglumine were detected. Magnesium also afforded a crystalline mono-salt.

6.4.2 Slurry Experiments

Calcium, sodium, and potassium salts were used to setup different competitive slurry experiments. For competitive slurry of calcium salts (~5-6 mg of Salt I and Salt II) were weighed into a 5.0 mL clear vial equipped with magnetic stir bars. These steps were repeated for potassium salt material (~5-6.5 mg of Salt III) and sodium salt materials (~2.6-6.4 mg of Salt IV and Salt V). Acetone, 1.0 mL, was added to each vial to achieve free-flowing slurry and allowed to equilibrate at room temperature. 50 μL of water was added to the potassium and sodium salt mixtures to increase solubility. All slurries, 400 μL, were filtered through 0.45 micron centrifuge filters after one and seven days of equilibration. The solids were analyzed by XRPD to check for salt conversion (Table 36).

It was found that Salt I, Salt III and Salt V were the most stable polymorphs in these solvent systems. These three salts were selected for scale up and full characterization.

TABLE 36

Competitive Slurry

| Salt | Parent Materials | Weight (mg) | Solvent | Vol. (mL) | Temp. (° C.) | Aliquot time point Day | Aliquot time point XRPD | Aliquot time point Day | Aliquot time point XRPD |
|---|---|---|---|---|---|---|---|---|---|
| Ca²⁺ | Salt I, (filtration) | 5.36 | Acetone | 1.0 | RT | 1 | Salt I | 7 | Salt I |
|  | Salt II, (filtration) | 6.53 |  |  |  |  |  |  |  |
| K⁺ | Salt III, (filtration) | 6.57 | Acetone Water | 1.5 0.05 | RT | 1 | Salt III | 7 | Salt III |
| Na⁺ | Salt IV, (filtration) | 6.36 | Acetone Water | 1.0 0.05 | RT | 1 | Salt V + impurity | 7 | Salt V |
|  | Salt V, (filtration) | 6.31 |  |  |  |  |  |  |  |

6.4.3 Characterization Summary of Salts I, II, III, IV, V, VI, VII, VIII, IX and X Salt I, Salt II, Salt III, Salt IV, Salt V, Salt VI, Salt VII, Salt VIII, Salt IX and Salt X were characterized to evaluate its physical form and stability. Since all these salt forms showed low temperature endothermic events, except Salt VIII, thermal holding experiments were performed in an attempt to isolate high melting salt form. Salt VI was obtained from the thermal holding experiments (Table 50) and characterized. Table 37 summarizes the characterization results for each salt.

TABLE 37

Characterization summary of Salts I, II, III, IV, V, VI, VII, VIII, IX and X

|  | Salt I | Salt II | Salt III |
|---|---|---|---|
| DSC (° C.) | Endotherm at 104.0, 170.6, 179.1 and 210.6 | Endotherm at 115.5, 127.0, 220.8, 311.3 Exotherm at 200.5 | Endotherm at 54.3, 109.3, 314.4 |
| TGA (Weight loss) | 0.34% @ 65-105° C. 1.41% @ 140-190° C. onset of decomposition at 213.8° C. | 10.98% @ 65-140° C., 0.33% @ 150-180° C. onset decomposition at 298.0° C. | 0.91% @ 40-70° C., 0.25% @ 100-120° C., onset decomposition at 297.2° C. |
| NMR | 0.24 wt % MeOH | 0.32 wt % Acetone | 0.24 wt % MeCN |
| Cmpd 1:Cl ratio by IC | 1:0.37 | 1:0.69 | 1:0.94 |
| Moisture Sorption | 60% RH: 1.0 wt % 90% RH: 4.1 wt % (moderately hygroscopic) | 60% RH: 11.9 wt % 90% RH: 12.0 wt % (moderately hygroscopic) | 60% RH: 2.1 wt % 90% RH: 4.5 wt % (moderately hygroscopic) |
| Aqueous Solubility (mg/mL) | 0.01 | 0.03 | 35.8 |
|  | Standard curve linear range 0.008 to 0.2 mg/mL. | | |
| XRPD (1 day) | Salt I + Extra peaks | Salt II | Salt IX |
| hydration property | anhydrate (60% RH) to monohydrate (90% RH) | di-hydrate | hemi-(60% RH) to mono-hydrate (90% RH) |
| Comment | Hemi-calcium Salt | Hemi-calcium Salt | Mono-potassium Salt |

|  | Salt IV | Salt V | Salt VI |
|---|---|---|---|
| DSC (° C.) | Endotherm at 107.9, 307.4 Exotherm at 217.2 | Endotherm at 93.3 (no melting was observed between 70-320° C.) | Endotherm at 282.4 and 308.4, Exotherm at 283.9 |
| TGA (Weight loss) | 5.43% @ 60-120° C. onset of decomposition at 302.5° C. | 5.85% @ 40-130° C., onset decomposition at 344.77° C. | onset decomposition at 305.7° C. |
| NMR | 0.29 wt % Acetone | 2.26 wt % Acetone | No degradation |

TABLE 37-continued

Characterization summary of Salts I, II, III, IV, V, VI, VII, VIII, IX and X

| | Salt IV | Salt V | Salt VI |
|---|---|---|---|
| Cmpd 1:Cl ratio by IC | 1:1.12 | 1:1.86 | N/A |
| Moisture Sorption | 60% RH: 6.1 wt % 90% RH: 6.5 wt % (moderately hygroscopic) | 60% RH: 6.0 wt % 90% RH: 6.4 wt % (moderately hygroscopic) | 60% RH: 0.3 wt % 90% RH: 0.7 wt % |
| Aqueous Solubility (mg/mL) | 19 | 79.8 | N/A |
| | Standard curve linear range 0.008 to 0.2 mg/mL. | | |
| XRPD (1 day) | Salt IV + Extra peaks | Salt V + Extra peaks | N/A |
| hydration property | monohydrate | monohydrate | anhydrate |
| Comment | Mono-sodium Salt | Bis-sodium Salt | Mono-sodium Salt |

| | Salt VII | Salt VIII | Salt IX |
|---|---|---|---|
| DSC (° C.) | Broad transition before 90 (might be water loss), Possible glass transition at 160, onset decomposition at 294.9 | No thermic change before onset decomposition at 294.1 | Endothermic at 82.8; Exotherm at 229.5; Onset decomposition at 293.9 |
| TGA (Weight loss) | onset decomposition at 290.6 | onset decomposition at 291.2 | onset decomposition at 301.8 |
| NMR | No detectable solvent, no degradation | No detectable solvent, no degradation | 0.01 wt % Acetone |
| Cmpd 1:Cl ratio by IC | 1:1.15 | 1:1.09 | 1:1.09 |
| Moisture Sorption | 60% RH: 0.9 wt % 90% RH: 2.9 wt % | 60% RH: 1.0 wt % 90% RH: 2.7 wt % | 60% RH: 0.3 wt % 90% RH: 0.3 wt % |
| Aqueous Solubility (mg/mL) | | | |
| XRPD (1 day) | | | |
| hydration property | | | |
| Comment | Mono-sodium Salt | Mono-sodium Salt | Mono-sodium Salt |

| | Salt X |
|---|---|
| DSC (° C.) | Endothermic at 91.3 and 149.3; Exotherm at 230.6; Onset decomposition at 294.7 |
| TGA (Weight loss) | onset 1.3 wt % loss at 79.2; onset 2.3 wt % loss at 135.1; onset decomposition at 296.7 |
| NMR | 3.5 wt % of 4-hydroxybutanoic acid |
| Cmpd 1:Cl ratio by IC | 1:1.00 |
| Moisture Sorption | |
| Aqueous Solubility (mg/mL) | |
| XRPD (1 day) | |
| hydration property | |
| Comment | Mono-sodium Salt |

6.4.4 Salt I of Compound 1

Figure 47:
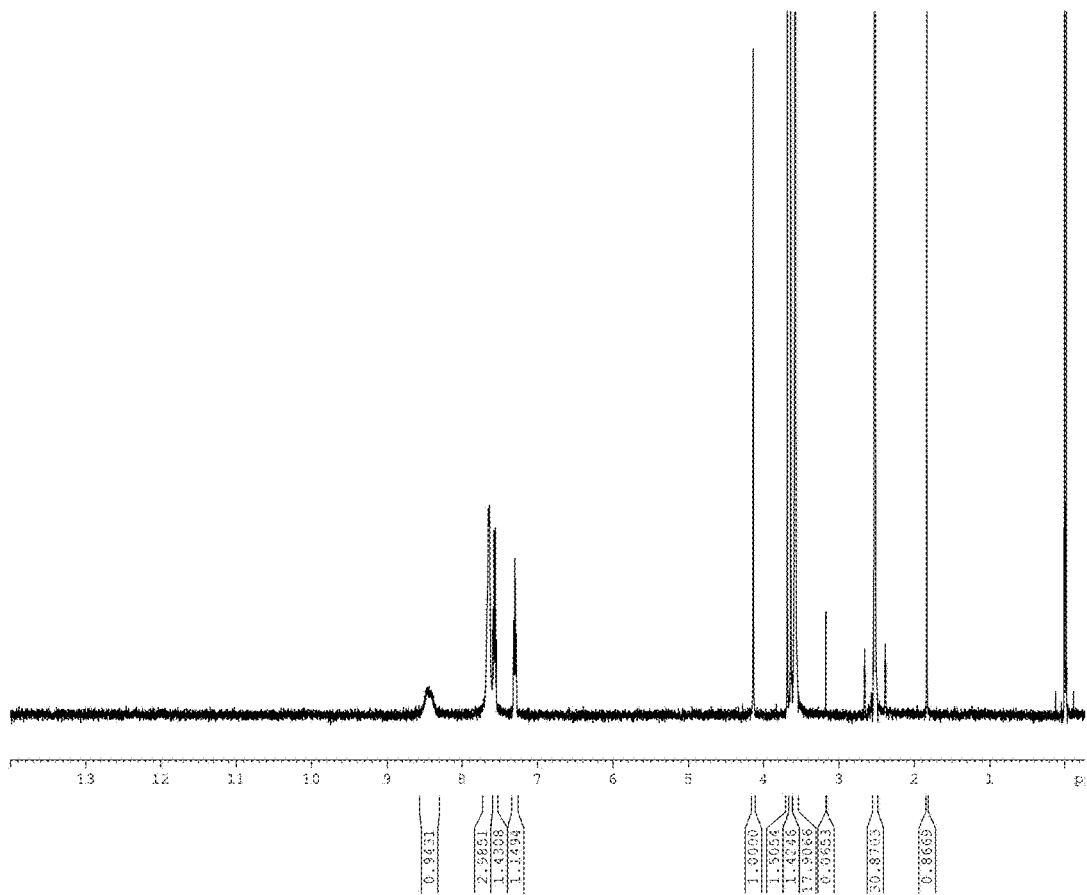
FIG. 47 depicts a $^1$H NMR spectrum of Salt I of Compound 1.

Salt I of Compound 1 is a hemi-calcium salt. Salt I was obtained in filtration from the salt formation experiment using methanol as primary solvent (Table 48, FIG. 40). An estimated 0.24 wt % of MeOH was observed by $^1$H NMR (d$_6$-DMSO) (Table 37, FIG. 47). From IC analysis, Compound 1 free acid:calcium ratio was determined to be 1.0:0.4, consistent with a hemi-calcium salt. DSC analysis presented four endotherms at 104.0, 170.6, 179.1 and 210.6°

Figure 46:
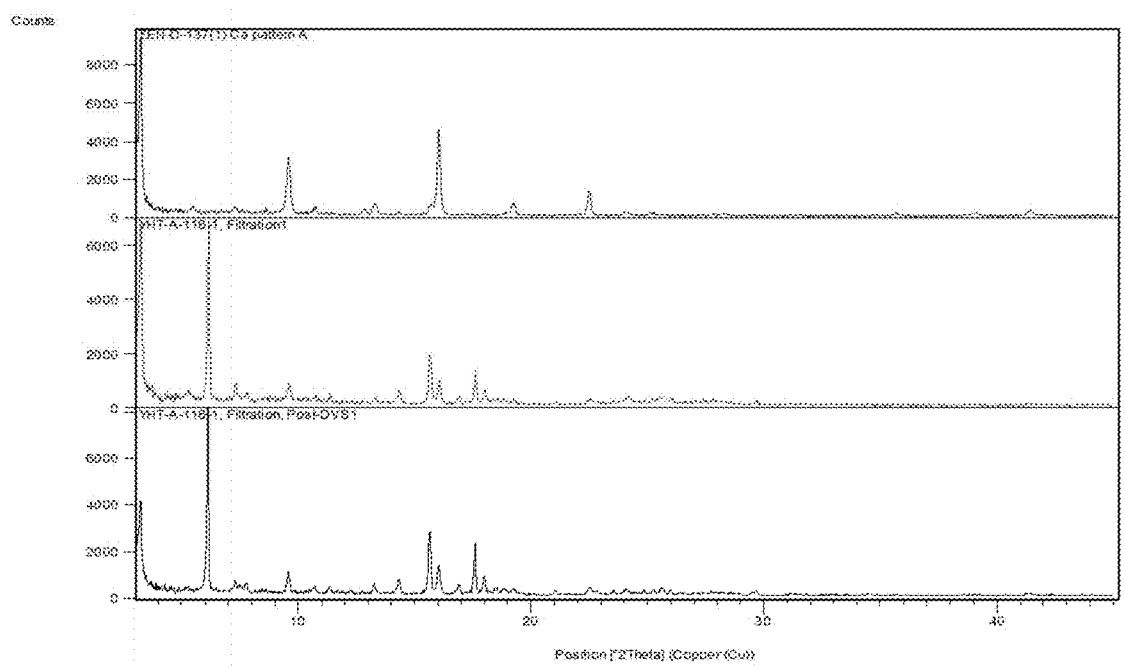
FIG. 46 depicts a XRPD stackplot of Salt I of Compound 1 before (middle) and after DVS (bottom) analysis.
Figure 50:
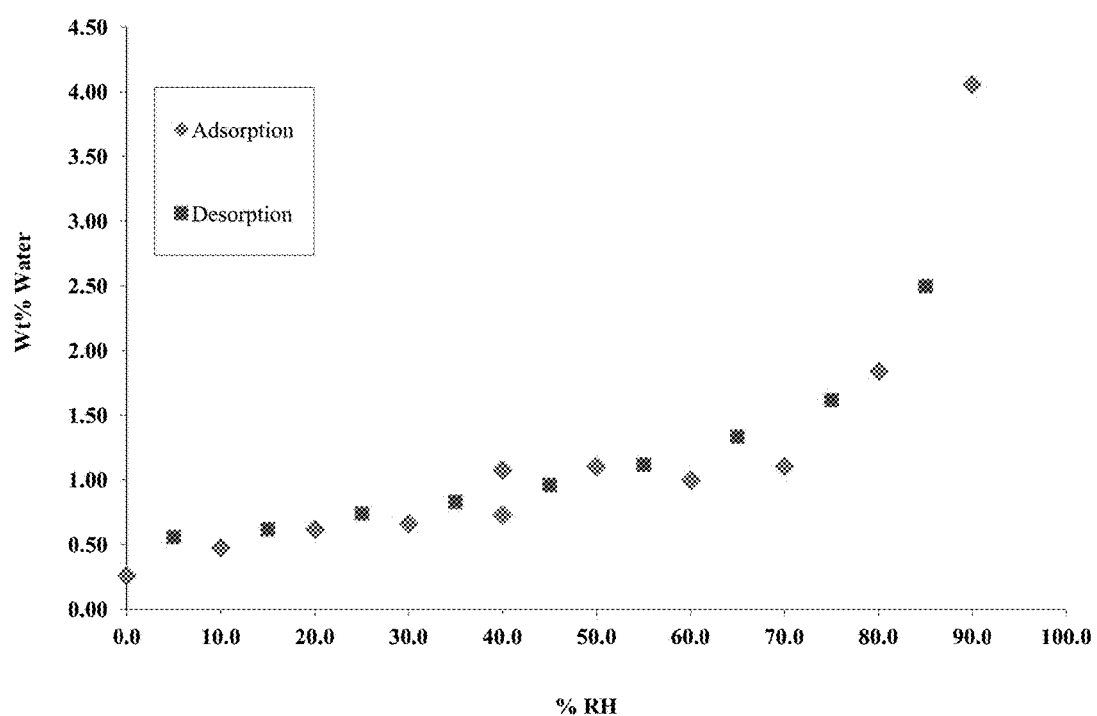
FIG. 50 depicts a DVS thermogram of Salt I of Compound 1.

C. (FIG. 48). TGA analysis indicated a two weight losses: 0.34% at 65-105° C. (attributed to loss of residual MeOH), and 1.41% at 140-190° C. and onset decomposition at 213.8° C. (FIG. 49). To further investigate the material's moisture sorption behavior, DVS analysis was carried out. The material adsorbed 1.0 wt % moisture at 60% RH, and 4.1 wt % moisture at 90% RH, indicating that it is moderately hygroscopic (FIG. 50). The XRPD analysis of the post-DVS material after drying at 60.0° C. for two hours, recorded a consistent XRPD pattern as the starting material (FIG. 46).

Salt I exhibited no change in physical form upon exposure to 60° C. for a period of seven days (Table 49). It was also chemically stable based on HPLC analysis. It was found that Salt I is sparingly soluble in the aqueous solubility study, where a solubility of 0.01 mg/mL was obtained.

FIG. 40 provides an XRPD pattern of Salt I. A list of XRPD Peaks for Salt I is provided below in Table 38.

TABLE 38

X-Ray Diffraction Peaks for Salt I

| Two-theta angle (°) | d Space (Å) | Relative Intensity (%) |
|---|---|---|
| 3.20 | 27.61 | 90.18 |
| 4.09 | 21.60 | 1.21 |
| 4.51 | 19.58 | 7.6 |
| 4.85 | 18.23 | 4.2 |
| 4.99 | 17.70 | 4.19 |
| 5.19 | 17.04 | 8 |
| 5.43 | 16.27 | 9.32 |
| 5.69 | 15.54 | 6.49 |
| 6.01 | 14.71 | 5.98 |
| 6.49 | 13.61 | 5.32 |
| 6.92 | 12.77 | 2.72 |
| 7.21 | 12.27 | 3.38 |
| 8.29 | 10.67 | 5.25 |
| 8.47 | 10.44 | 3.08 |
| 9.17 | 9.64 | 2.21 |
| 9.53 | 9.28 | 32.9 |
| 10.39 | 8.51 | 4.58 |
| 10.58 | 8.37 | 5.32 |
| 11.30 | 7.83 | 2.4 |
| 11.87 | 7.45 | 3.31 |
| 12.10 | 7.31 | 4.51 |
| 12.23 | 7.23 | 4.1 |
| 12.73 | 6.95 | 5.94 |
| 13.23 | 6.69 | 17.06 |
| 14.23 | 6.22 | 5.17 |
| 15.60 | 5.68 | 23.52 |
| 15.97 | 5.55 | 100 |
| 17.21 | 5.15 | 2.21 |
| 17.49 | 5.07 | 3.54 |
| 18.08 | 4.91 | 3.02 |
| 18.88 | 4.70 | 4.87 |
| 19.15 | 4.63 | 18.36 |
| 22.00 | 4.04 | 3.38 |
| 22.41 | 3.97 | 31.57 |
| 23.92 | 3.72 | 7.89 |
| 25.25 | 3.53 | 5.93 |
| 25.60 | 3.48 | 6.38 |
| 26.35 | 3.38 | 3.02 |
| 26.67 | 3.34 | 2.1 |
| 27.76 | 3.21 | 4.32 |
| 28.21 | 3.16 | 5.53 |
| 29.29 | 3.05 | 9.13 |
| 31.08 | 2.88 | 2.7 |
| 31.46 | 2.84 | 2.95 |
| 31.82 | 2.81 | 3.11 |
| 33.44 | 2.68 | 2.71 |
| 34.63 | 2.59 | 1.81 |
| 35.58 | 2.52 | 3.51 |
| 37.97 | 2.37 | 1.24 |
| 38.65 | 2.33 | 3.26 |
| 38.96 | 2.31 | 5.02 |

TABLE 38-continued

X-Ray Diffraction Peaks for Salt I

| Two-theta angle (°) | d Space (Å) | Relative Intensity (%) |
|---|---|---|
| 41.35 | 2.18 | 6.64 |
| 42.29 | 2.14 | 4.11 |
| 43.31 | 2.09 | 0.84 |

6.4.5 Salt II of Compound 1

Salt II of Compound 1 is a dihydrated hemi-calcium salt. Salt II was obtained in filtration from the salt formation experiment using acetone as primary solvent (Table 48, FIG. 51). An estimated 0.32 wt % of acetone was observed by $^1$H NMR ($d_6$-DMSO) (Table 37, FIG. 52). The ratio of Compound 1 free acid to calcium counterion was 1.0:0.69, indicating it is a hemi-calcium salt.

Figure 51:
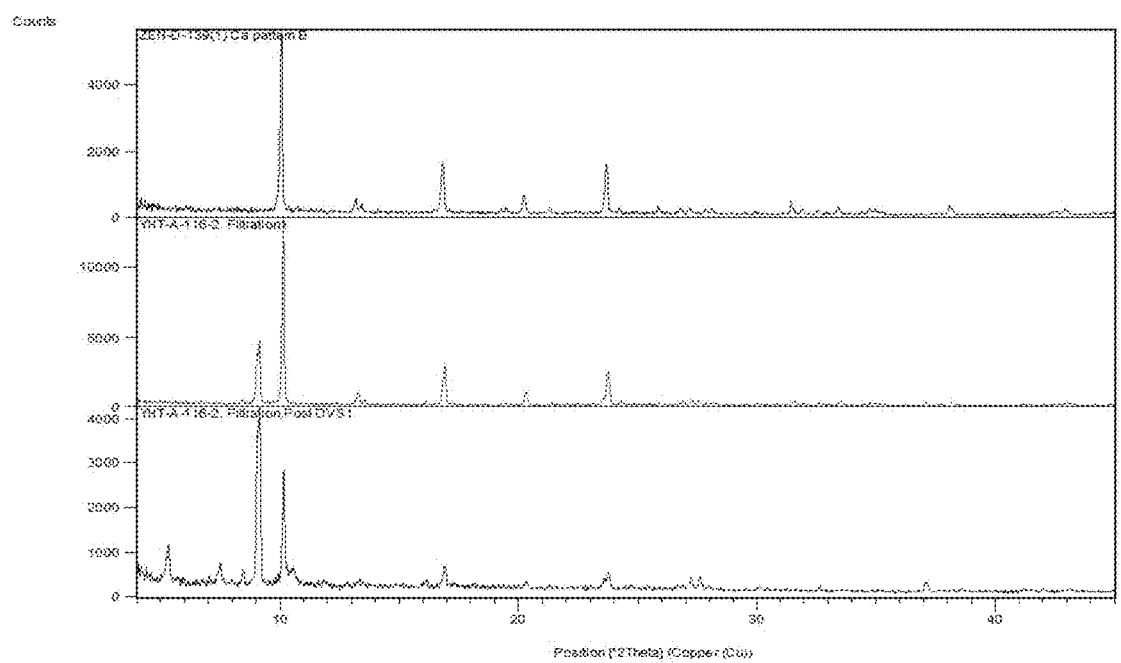
FIG. 51 depicts a XRPD stackplot of Salt II of Compound 1 before (middle) and after DVS (bottom) analysis.
Figure 52:
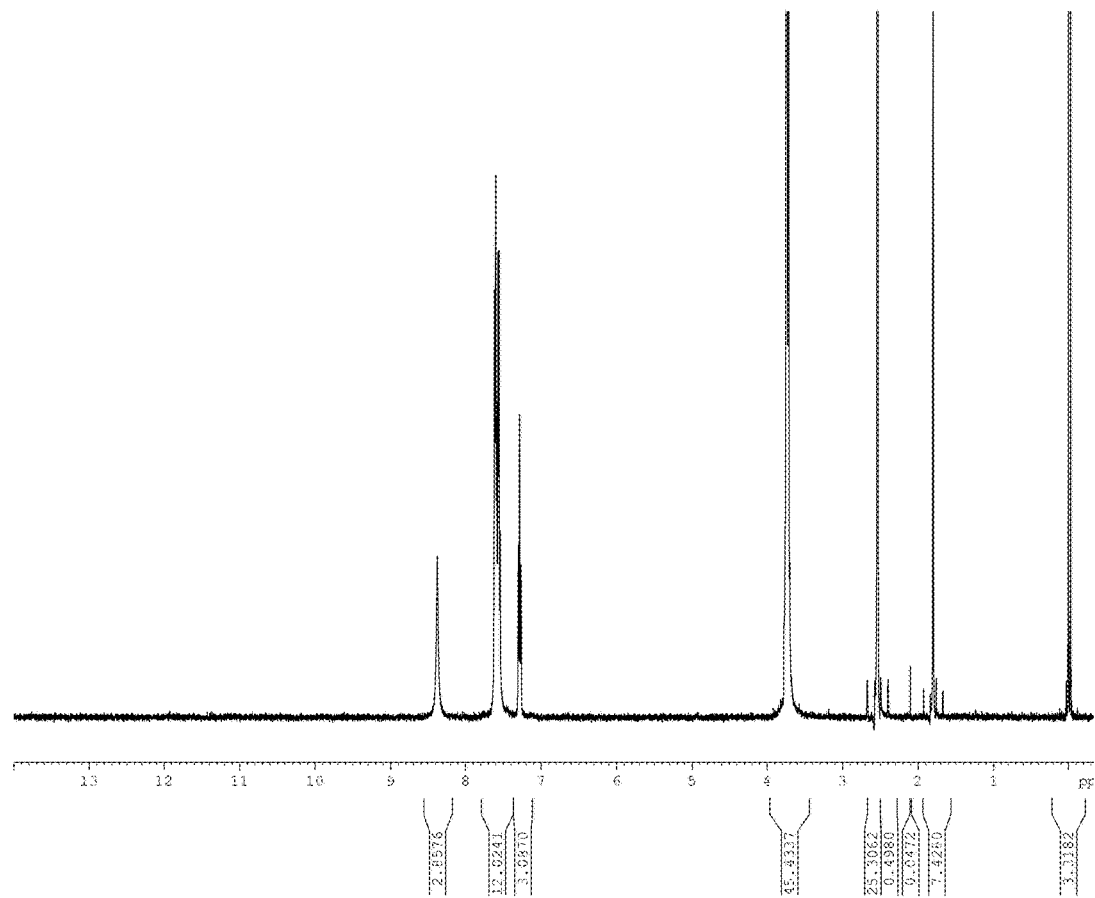
FIG. 52 depicts a $^1$H NMR spectrum of Salt II of Compound 1.
Figure 55:
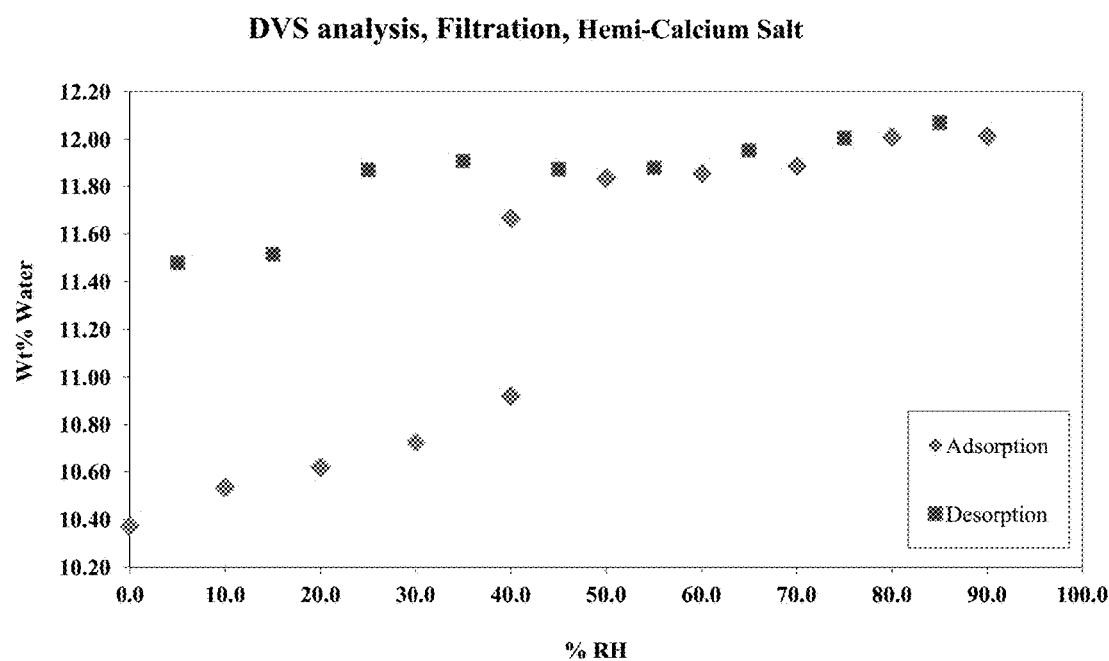
FIG. 55 depicts a DVS thermogram of Salt II of Compound 1.

DSC analysis presented four endotherms at 115.5, 127.0, 220.8, 311.3° C. and an exotherm at 220.5° C. (FIG. 53). TGA analysis indicated a two weight losses: 10.98% at 65-140° C. (attributed to water loss), 0.33% at 150-180° C. and onset decomposition at 298.0° C. (FIG. 54). The material adsorbed 11.9 wt % moisture at 60% RH, and 12.0 wt % moisture at 90% RH, indicating that it is moderately hygroscopic (FIG. 55). Slight hysteresis was observed at 0-40% RH. The XRPD analysis of the post-DVS material after drying at 60.0° C. for two hours, recorded a new XRPD pattern (bottom) (FIG. 51). TGA and DVS results indicated that Salt II is a dihydrate, which is stable above 40% RH.

Salt II exhibited no change in physical form upon exposure to 60° C. for a period of seven days (Table 49). Chemical purity of the thermally stressed solid was assessed by HPLC and no significant reduction in purity was observed. It was found that Salt II remained sparingly soluble in the aqueous solubility study, where a solubility of 0.03 mg/mL was obtained.

FIG. 41 provides an XRPD pattern of Salt II. A list of XRPD Peaks for Salt II is provided below in Table 39.

TABLE 39

X-Ray Diffraction Peaks for Salt II

| Two-theta angle (°) | d Space (Å) | Relative Intensity (%) |
|---|---|---|
| 3.37 | 26.19 | 23.10 |
| 3.81 | 23.16 | 0.13 |
| 3.94 | 22.45 | 2.32 |
| 4.15 | 21.28 | 4.74 |
| 4.33 | 20.43 | 4.51 |
| 4.59 | 19.25 | 1.91 |
| 4.77 | 18.54 | 2.30 |
| 5.12 | 17.28 | 1.77 |
| 5.51 | 16.03 | 1.14 |
| 6.07 | 14.55 | 2.22 |
| 6.25 | 14.15 | 1.09 |
| 7.27 | 12.16 | 1.77 |
| 7.45 | 11.86 | 1.82 |
| 7.82 | 11.31 | 1.77 |
| 8.03 | 11.01 | 1.75 |
| 8.56 | 10.32 | 0.22 |
| 8.83 | 10.02 | 2.15 |
| 10.07 | 8.78 | 100.00 |
| 10.39 | 8.52 | 3.22 |
| 10.71 | 8.26 | 1.84 |
| 11.32 | 7.82 | 1.04 |
| 11.56 | 7.66 | 0.73 |
| 11.70 | 7.56 | 1.49 |

TABLE 39-continued

X-Ray Diffraction Peaks for Salt II

| Two-theta angle (°) | d Space (Å) | Relative Intensity (%) |
| --- | --- | --- |
| 13.21 | 6.70 | 7.45 |
| 13.46 | 6.58 | 3.58 |
| 14.10 | 6.28 | 1.43 |
| 14.36 | 6.17 | 0.80 |
| 15.32 | 5.78 | 0.93 |
| 15.58 | 5.69 | 0.44 |
| 16.86 | 5.26 | 27.14 |
| 19.28 | 4.60 | 2.06 |
| 19.51 | 4.55 | 3.28 |
| 20.23 | 4.39 | 9.96 |
| 20.68 | 4.29 | 0.15 |
| 21.32 | 4.17 | 2.82 |
| 22.41 | 3.97 | 1.76 |
| 22.95 | 3.88 | 1.05 |
| 23.71 | 3.75 | 26.87 |
| 24.27 | 3.67 | 2.66 |
| 24.90 | 3.58 | 1.19 |
| 25.87 | 3.44 | 3.47 |
| 26.21 | 3.40 | 0.61 |
| 26.83 | 3.32 | 2.54 |
| 27.15 | 3.28 | 3.24 |
| 27.57 | 3.24 | 0.57 |
| 27.85 | 3.20 | 2.38 |
| 28.12 | 3.17 | 2.44 |
| 28.95 | 3.08 | 0.53 |
| 29.24 | 3.05 | 0.64 |
| 29.53 | 3.02 | 0.48 |
| 29.95 | 2.98 | 1.62 |
| 31.08 | 2.88 | 0.60 |
| 31.47 | 2.84 | 6.68 |
| 31.90 | 2.81 | 2.70 |
| 32.59 | 2.75 | 1.65 |
| 32.97 | 2.72 | 0.47 |
| 33.42 | 2.68 | 3.66 |
| 34.73 | 2.58 | 2.95 |
| 34.97 | 2.57 | 2.37 |
| 35.25 | 2.55 | 1.08 |
| 36.09 | 2.49 | 0.62 |
| 38.09 | 2.36 | 4.79 |
| 39.69 | 2.27 | 0.70 |
| 41.35 | 2.18 | 0.91 |
| 42.56 | 2.12 | 1.54 |
| 42.94 | 2.11 | 2.32 |
| 44.06 | 2.05 | 0.86 |

6.4.6 Salt III of Compound 1

Figure 56:
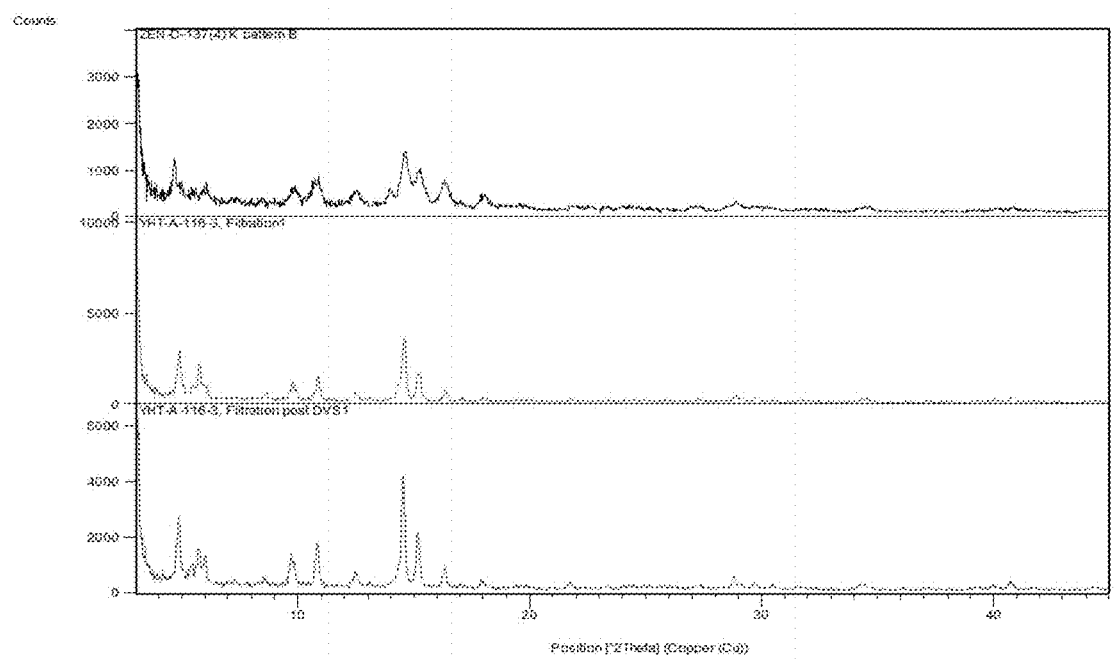
FIG. 56 depicts a XRPD stackplot of Salt III of Compound 1 before (middle) and after DVS (bottom) analysis.
Figure 57:
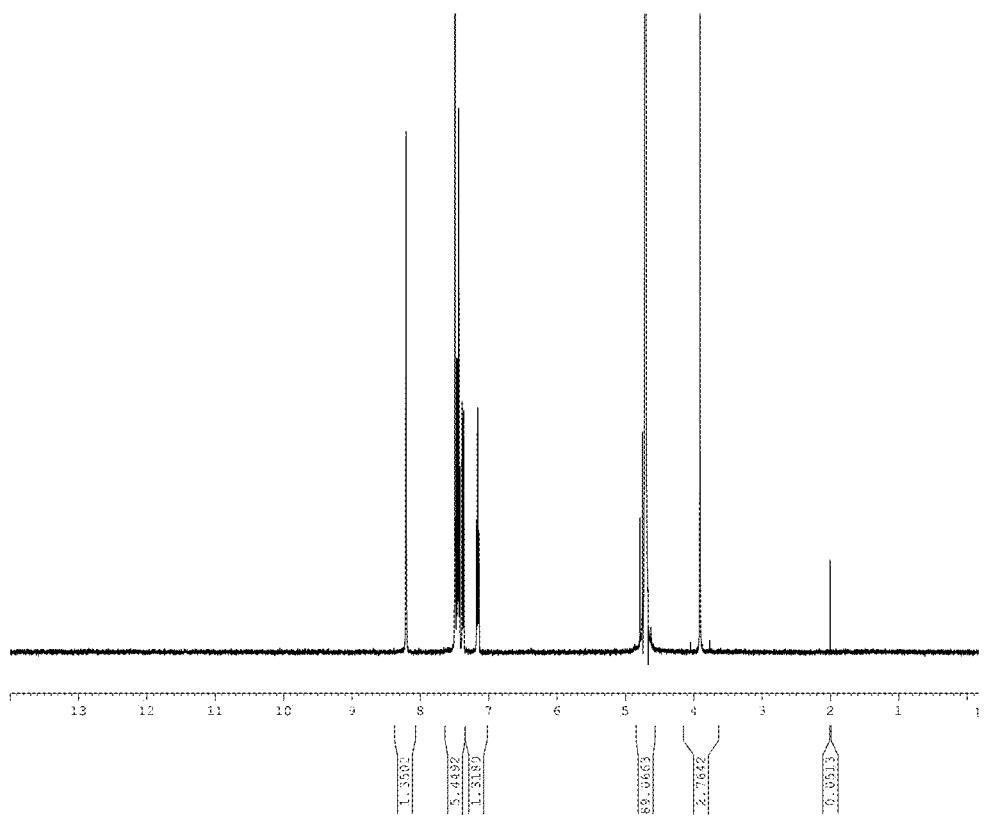
FIG. 57 depicts a ¹H NMR spectrum of Salt III of Compound 1.
Figure 60:
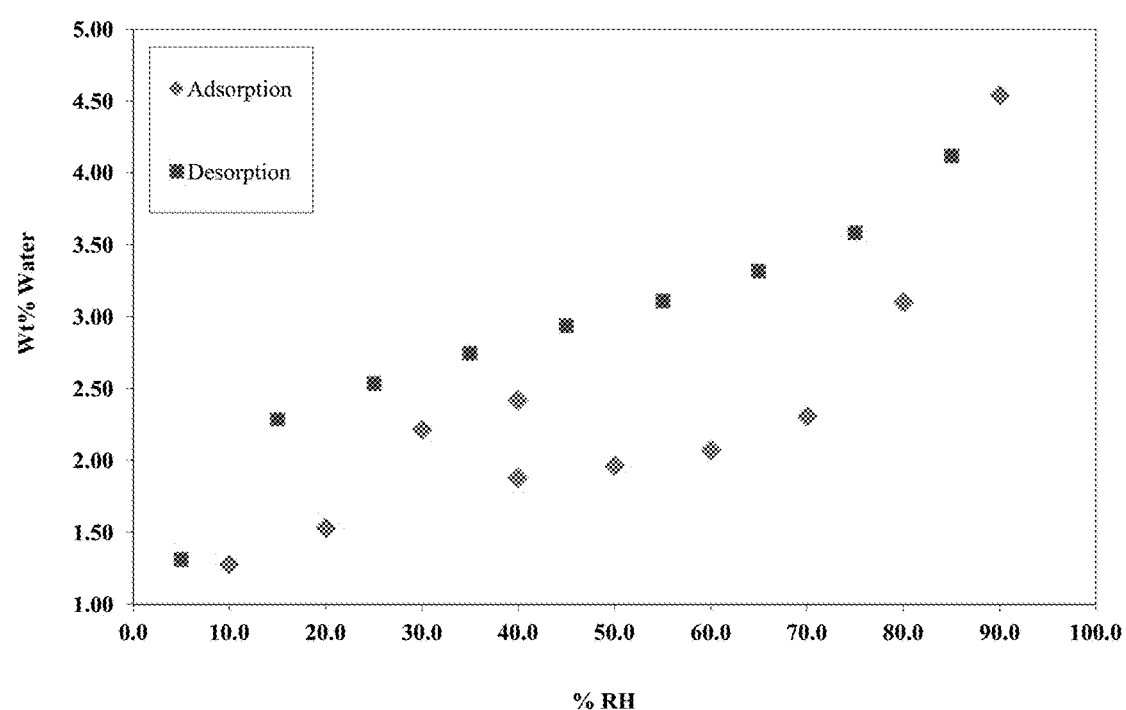
FIG. 60 depicts a DVS thermogram of Salt III of Compound 1.

Salt III of Compound 1 is a mono-potassium salt. Salt III was obtained in filtration from the salt experiment using acetonitrile as primary solvent (Table 36, FIG. 56). An estimated 0.24 wt % of CH$_3$CN was observed by $^1$H NMR (Table 50, FIG. 52). The ratio of Compound 1 free acid: potassium was determined by IC analysis to be 1.0:0.9 indicating it is a mono-potassium salt. DSC analysis presented three endotherms at 54.3, 109.3 and 314.4° C. (FIG. 58). TGA analysis indicated two weight losses: 0.91% at 40-70° C., and 0.25% at 100-120° C. and onset decomposition at 297.2° C. (FIG. 59). The material adsorbed 2.1 wt % moisture at 60% RH, and 4.5 wt % moisture at 90% RH, indicating it is moderately hygroscopic (FIG. 60). Mild hysteresis was observed indicating presence of potential hydrate form. The XRPD analysis of the post-DVS material after drying at 60.0° C. for two hours, recorded a similar XRPD pattern as the starting material (FIG. 56).

Salt III exhibited no change in physical form upon exposure to 60° C. for a period of seven days (Table 48). Chemical purity of the thermally stressed solid was assessed by HPLC and no reduction in purity was observed. Aqueous solubility measurement of potassium salt in deionized water was carried out in room temperature. The materials after 24 hour equilibrium converted from Salt III to Salt IX, and remained as Salt IX on day seven. Collected filtrate was subjected to HPLC analysis and a solubility of 35.8 mg/mL was attained.

Multiple thermal transitions (endothermic) were observed on DSC analysis with some occur at low temperature. In an effort to isolate a high melt crystal form, the material was held at 130° C. for 2 minutes followed by cooling to ambient temperature. XRPD analysis of the resulting solid was consistent with Salt III.

Based on the characterization results, Salt III showed a tendency to form hydrate form. Although several low temperature thermal events were observed, the material appeared to be stable under thermal stress.

FIG. 42 provides an XRPD pattern of Salt III. A list of XRPD Peaks for Salt III is provided below in Table 40.

TABLE 40

X-Ray Diffraction Peaks for Salt III

| Two-theta angle (°) | d Space (Å) | Relative Intensity (%) |
| --- | --- | --- |
| 4.18 | 21.14 | 2.11 |
| 4.71 | 18.77 | 65.00 |
| 4.98 | 17.76 | 18.65 |
| 5.61 | 15.75 | 17.46 |
| 6.06 | 14.60 | 34.64 |
| 6.41 | 13.80 | 11.03 |
| 6.73 | 13.14 | 7.69 |
| 7.14 | 12.39 | 7.87 |
| 7.39 | 11.96 | 12.77 |
| 8.01 | 11.04 | 11.19 |
| 8.55 | 10.34 | 4.72 |
| 8.78 | 10.07 | 5.16 |
| 9.03 | 9.80 | 9.46 |
| 9.73 | 9.09 | 20.42 |
| 9.88 | 8.95 | 34.85 |
| 10.72 | 8.26 | 39.75 |
| 10.89 | 8.12 | 50.42 |
| 11.76 | 7.53 | 8.26 |
| 11.89 | 7.44 | 9.01 |
| 12.48 | 7.09 | 25.58 |
| 12.97 | 6.83 | 8.88 |
| 13.29 | 6.66 | 4.99 |
| 13.97 | 6.34 | 27.99 |
| 14.54 | 6.09 | 90.90 |
| 14.65 | 6.05 | 100.00 |
| 15.18 | 5.84 | 62.41 |
| 15.29 | 5.79 | 66.49 |
| 16.35 | 5.42 | 49.40 |
| 16.49 | 5.37 | 37.96 |
| 17.01 | 5.21 | 2.87 |
| 17.17 | 5.16 | 6.63 |
| 18.09 | 4.90 | 22.64 |
| 19.70 | 4.51 | 4.56 |
| 21.78 | 4.08 | 6.45 |
| 22.62 | 3.93 | 6.14 |
| 23.13 | 3.85 | 3.58 |
| 23.99 | 3.71 | 6.61 |
| 24.44 | 3.64 | 7.47 |
| 25.16 | 3.54 | 2.65 |
| 25.44 | 3.50 | 4.44 |
| 25.88 | 3.44 | 2.22 |
| 27.37 | 3.26 | 6.45 |
| 28.88 | 3.09 | 16.07 |
| 29.93 | 2.99 | 3.52 |
| 32.09 | 2.79 | 2.50 |
| 34.55 | 2.60 | 7.41 |
| 37.21 | 2.42 | 1.67 |
| 40.15 | 2.25 | 3.75 |
| 40.86 | 2.21 | 4.58 |
| 41.95 | 2.16 | 1.21 |

6.4.7 Salt IV of Compound 1

Figure 61:
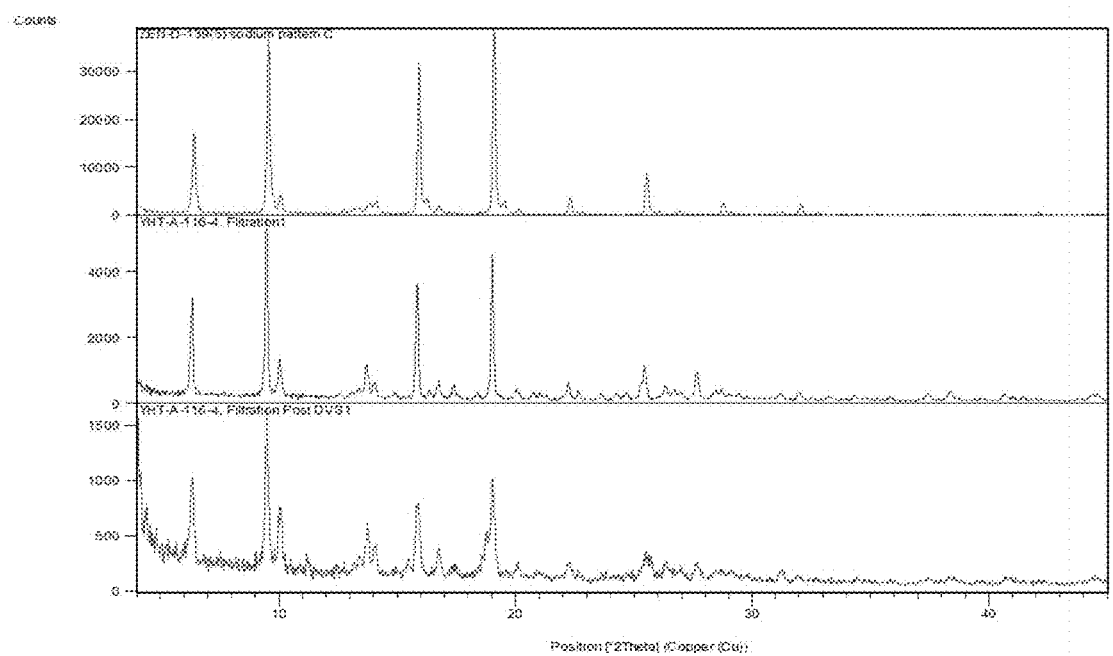
FIG. 61 depicts a XRPD stackplot of Salt IV of Compound 1 before (middle) and after DVS (bottom) analysis.
Figure 62:
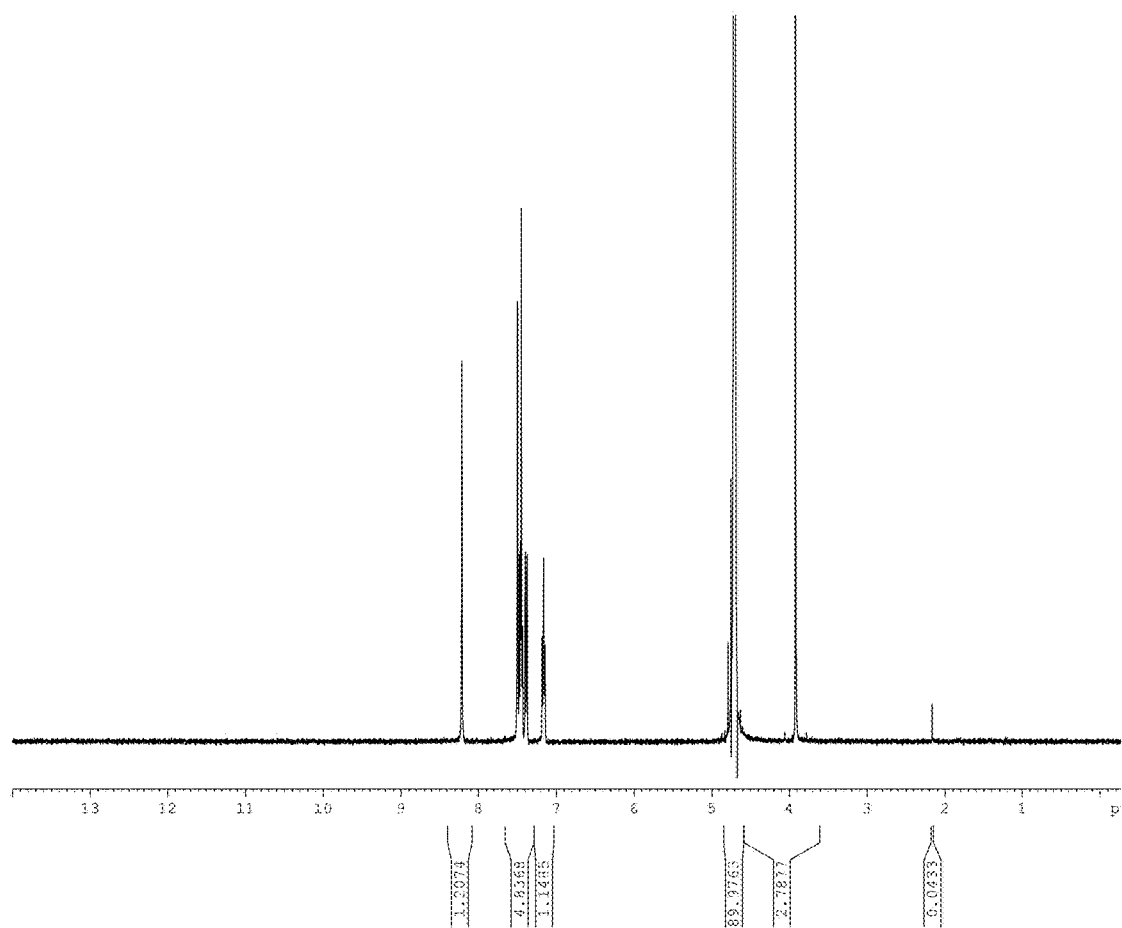
FIG. 62 depicts a ¹H NMR spectrum of Salt IV of Compound 1.
Figure 65:
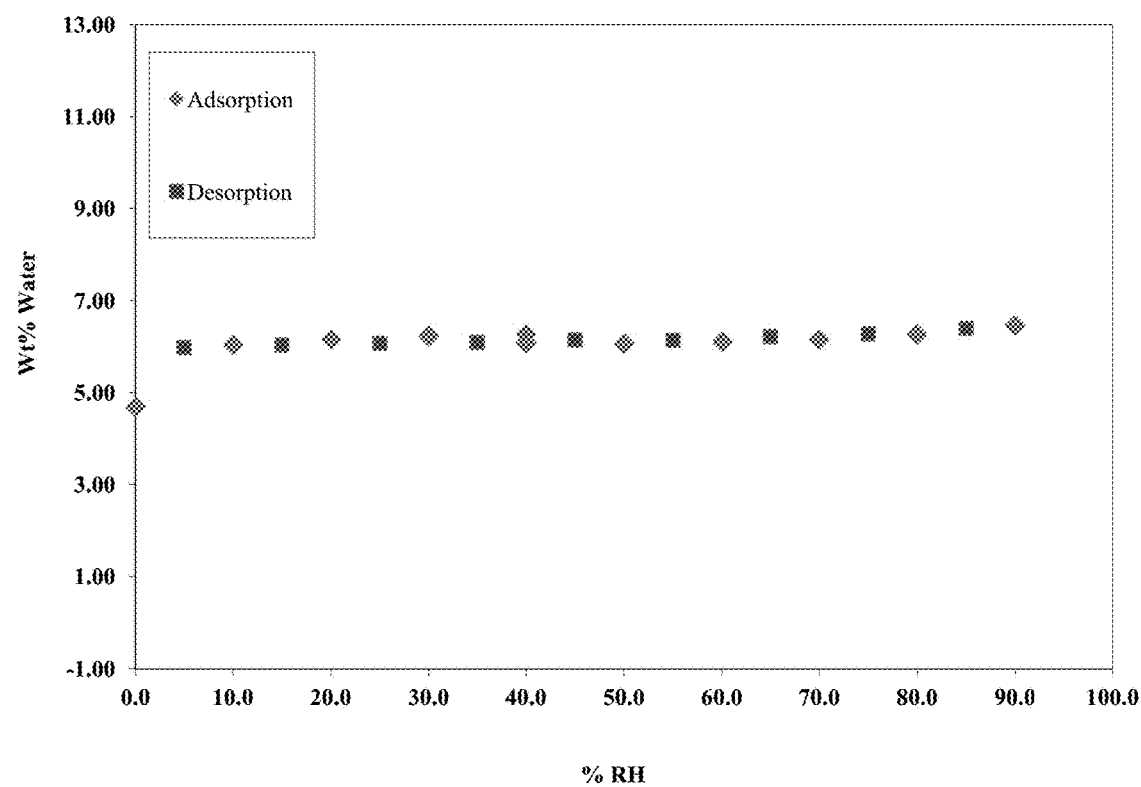
FIG. 65 depicts a DVS thermogram of Salt IV of Compound 1.

Salt IV of Compound 1 is a monohydrated mono-sodium salt. Salt IV was obtained in filtration from the recrystallization experiment using acetone as primary solvent (Table 36, FIG. 61). IC analysis of this material indicated the material had a Compound 1 free acid:sodium ratio of 1.0:1.1, consistent with a mono-sodium salt. An estimated 0.29 wt % of acetone was observed by $^1$H NMR (Table 50, FIG. 62). DSC analysis presented two endotherms at 107.9, 307.4° C. and an exotherm at 217.2° C. (FIG. 63). TGA analysis indicated a weight loss of 5.43% at 60-120° C. attributed to water loss followed by an onset decomposition at 302.5° C. (FIG. 64). The material adsorbed 6.1 wt % moisture at 60% RH, and 6.5 wt % moisture at 90% RH, indicating it is moderately hygroscopic (FIG. 65). The XRPD analysis of the post-DVS material after drying at 60.0° C. for two hours, recorded a consistent XRPD pattern as the starting material (FIG. 61). DVS analysis showed that Salt IV is a stable hydrate.

In an effort to isolate a high melt crystal form through a dehydration/recrystallization process, Salt IV was held at 130° C. for 2 minutes followed by cooling to ambient temperature. XRPD analysis of the resulting solid was consistent with Salt IV. The holding experiment was repeated by holding the material at 260° C., a temperature higher than the exothermic event at 217.2° C. A conversion to a new salt (Salt VI) was observed.

In the aqueous solubility study, no form change was observed after slurring Salt IV in water for 13 days (Table 49). A solubility of 19.0 mg/mL was attained. When storing Salt IV at 60° C., no polymorph conversion or degradation of the material was observed at day 1, and 7 (Table 48).

FIG. 43 provides an XRPD pattern of Salt IV. A list of XRPD Peaks for Salt IV is provided below in Table 41.

TABLE 41

X-Ray Diffraction Peaks for Salt IV

| Two-theta angle (°) | d Space (Å) | Relative Intensity (%) |
|---|---|---|
| 3.18 | 27.83 | 100.00 |
| 4.17 | 21.18 | 0.82 |
| 4.78 | 18.50 | 0.36 |
| 5.23 | 16.91 | 0.58 |
| 5.62 | 15.74 | 0.54 |
| 5.86 | 15.08 | 0.21 |
| 5.93 | 14.91 | 0.36 |
| 6.29 | 14.04 | 9.51 |
| 6.44 | 13.73 | 5.33 |
| 6.74 | 13.11 | 0.33 |
| 7.43 | 11.90 | 0.15 |
| 9.45 | 9.36 | 30.33 |
| 9.66 | 9.16 | 5.46 |
| 9.94 | 8.90 | 1.64 |
| 10.63 | 8.33 | 0.56 |
| 11.83 | 7.48 | 0.30 |
| 12.03 | 7.36 | 0.07 |
| 12.62 | 7.01 | 1.03 |
| 13.24 | 6.68 | 0.45 |
| 13.61 | 6.50 | 0.86 |
| 14.57 | 6.08 | 0.13 |
| 14.85 | 5.97 | 0.32 |
| 15.05 | 5.89 | 0.07 |
| 15.80 | 5.61 | 26.27 |
| 16.17 | 5.48 | 6.01 |
| 16.68 | 5.32 | 0.55 |
| 16.98 | 5.22 | 0.03 |
| 17.37 | 5.11 | 0.69 |
| 18.31 | 4.85 | 0.85 |
| 19.00 | 4.67 | 30.80 |
| 19.43 | 4.57 | 7.57 |
| 19.94 | 4.45 | 0.92 |
| 20.72 | 4.29 | 0.55 |
| 22.20 | 4.00 | 2.92 |
| 22.69 | 3.92 | 1.22 |
| 23.63 | 3.77 | 0.28 |
| 24.22 | 3.68 | 0.26 |
| 25.42 | 3.50 | 6.32 |
| 26.01 | 3.43 | 1.49 |
| 26.70 | 3.34 | 0.73 |
| 27.54 | 3.24 | 1.09 |
| 28.35 | 3.15 | 0.53 |
| 28.67 | 3.11 | 2.01 |
| 29.39 | 3.04 | 1.15 |
| 31.24 | 2.86 | 0.43 |
| 31.97 | 2.80 | 1.32 |
| 32.69 | 2.74 | 0.75 |
| 33.18 | 2.70 | 0.20 |
| 34.29 | 2.61 | 0.79 |
| 34.73 | 2.58 | 0.32 |
| 35.82 | 2.51 | 0.33 |
| 37.41 | 2.40 | 1.04 |
| 37.84 | 2.38 | 0.12 |
| 38.27 | 2.35 | 1.51 |
| 38.67 | 2.33 | 0.46 |
| 39.65 | 2.27 | 0.13 |
| 40.64 | 2.22 | 1.05 |
| 41.02 | 2.20 | 0.41 |
| 41.48 | 2.18 | 0.47 |
| 41.90 | 2.16 | 0.40 |
| 42.80 | 2.11 | 0.10 |
| 43.80 | 2.07 | 0.23 |
| 44.32 | 2.04 | 0.65 |
| 44.59 | 2.04 | 0.92 |

6.4.8 Salt V of Compound 1

Figure 66:
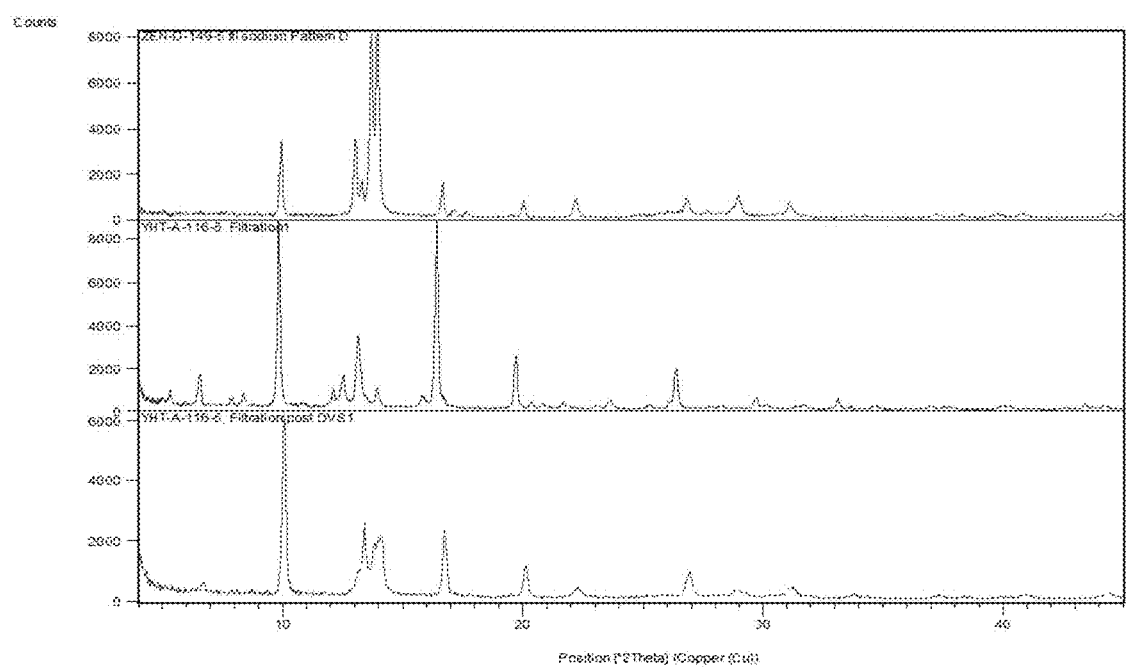
FIG. 66 depicts a XRPD stackplot of Salt V of Compound 1 before (middle) and after DVS (bottom) analysis.
Figure 67:
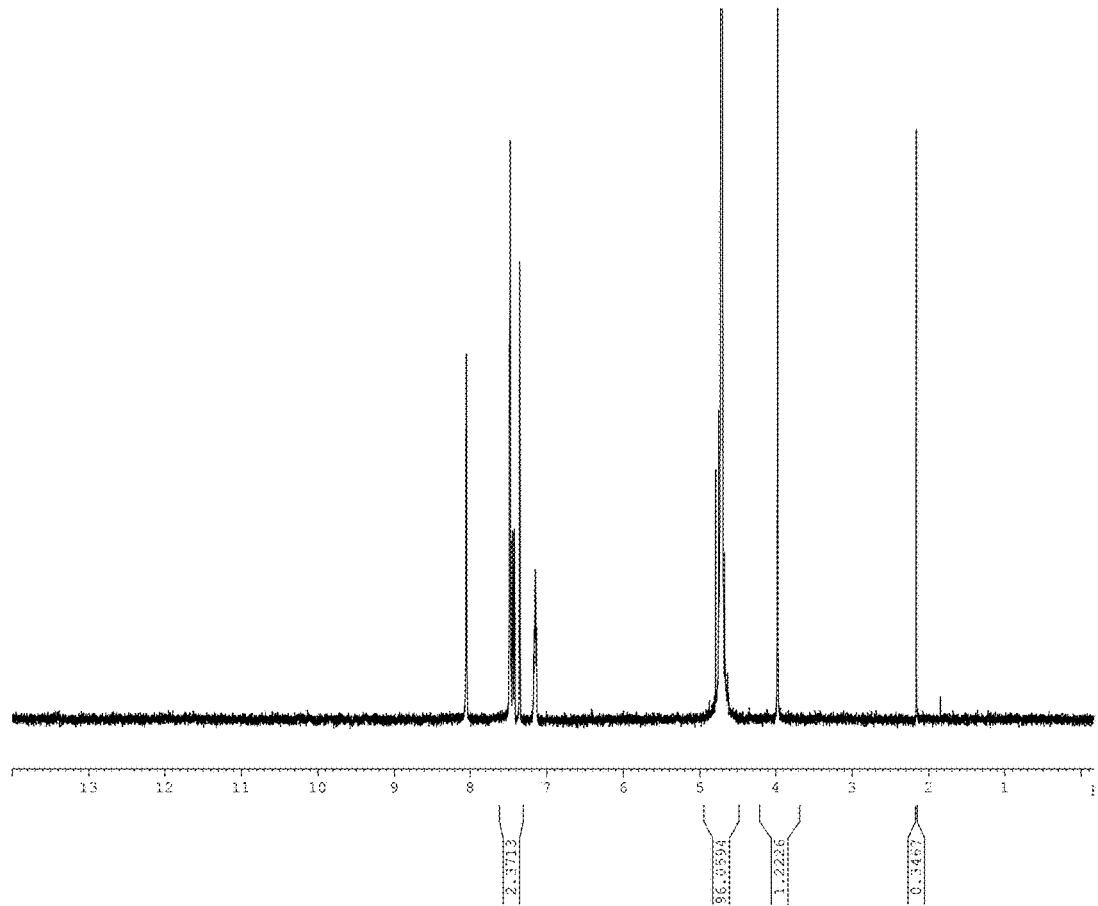
FIG. 67 depicts a ¹H NMR spectrum of Salt V of Compound 1.
Figure 70:
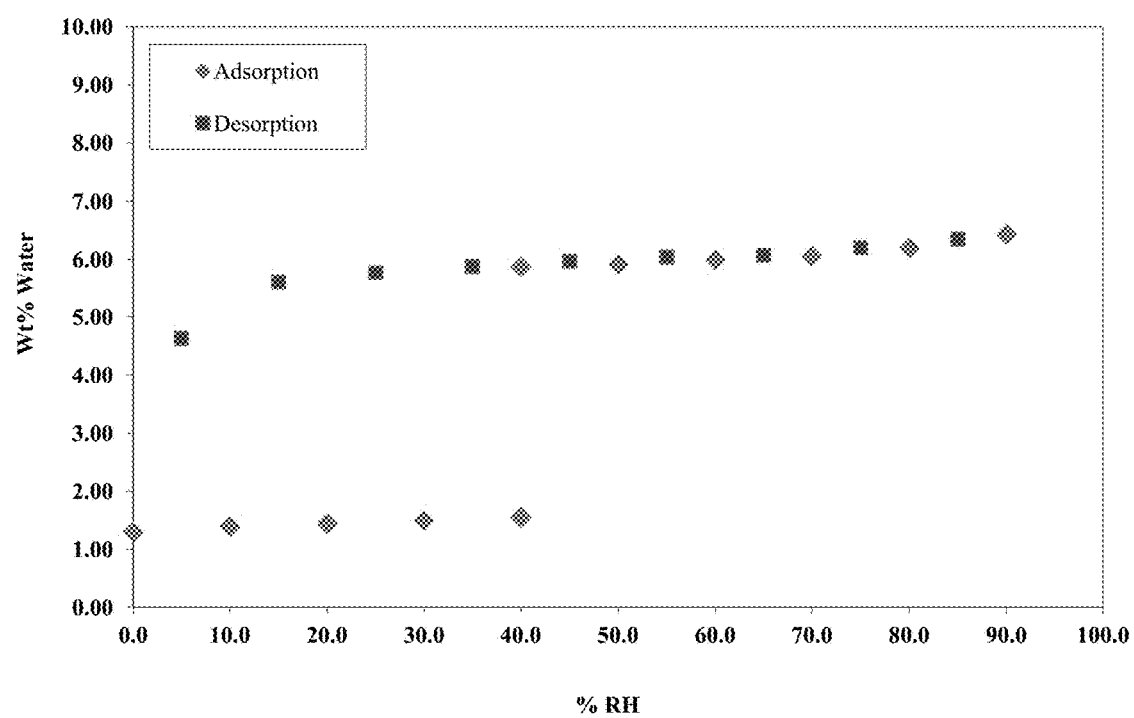
FIG. 70 depicts a DVS thermogram of Salt V of Compound 1.

Salt V of Compound 1 is a monohydrated bis-sodium salt. Salt V was obtained in filtration from the recrystallization experiment using acetone as primary solvent (Table 36, FIG. 66). IC analysis of this material indicated the material had a Compound 1 free acid:sodium ratio of 1.0:1.9, consistent with a bis-sodium salt. An estimated 2.26 wt % of acetone was observed by $^1$H NMR (Table 50, FIG. 67). DSC analysis presented an endotherm at 93.3° C. (FIG. 68). TGA analysis indicated a weight loss of 5.85% at 40-130° C. attributed to water loss, followed by an onset of decomposition at 344.8° C. (FIG. 69). The material adsorbed 6.0 wt % moisture at 60% RH, and 6.4 wt % moisture at 90% RH, indicating it is moderately hygroscopic (FIG. 70). Significant hysteresis was observed at 0-40% RH, indicating it is not a stable hydrate that may lose water at low humidity. The XRPD analysis of the post-DVS material after drying at 60.0° C. for two hours, recorded a XRPD pattern mostly consistent with Salt V with a few missing peaks (FIG. 66).

No melting event was observed for this bis-sodium salt when subject to heating between 70-410° C. at the rate of 1° C./min on melting apparatus. The white crystalline Salt V remained unchanged until it reached the decomposition temperature (>320° C.) as shown in Table 51. The material showed a high solubility at 80.0 mg/mL.

FIG. 44 provides an XRPD pattern of Salt V. A list of XRPD Peaks for Salt V is provided below in Table 42.

TABLE 42

X-Ray Diffraction Peaks for Salt V

| Two-theta angle (°) | d Space (Å) | Relative Intensity (%) |
|---|---|---|
| 3.15 | 28.01 | 33.88 |
| 3.33 | 26.55 | 20.18 |
| 3.51 | 25.19 | 3.70 |
| 3.65 | 24.18 | 1.01 |
| 4.19 | 21.10 | 1.34 |
| 4.45 | 19.86 | 0.31 |
| 4.74 | 18.66 | 1.46 |
| 5.09 | 17.35 | 2.23 |
| 5.24 | 16.87 | 1.10 |
| 5.40 | 16.37 | 2.15 |
| 5.75 | 15.38 | 2.50 |
| 6.00 | 14.73 | 1.57 |
| 6.24 | 14.18 | 1.74 |
| 6.43 | 13.75 | 1.73 |
| 6.64 | 13.32 | 2.14 |
| 7.29 | 12.13 | 1.51 |
| 7.45 | 11.87 | 1.27 |
| 7.58 | 11.66 | 1.44 |
| 7.92 | 11.16 | 1.53 |
| 8.57 | 10.32 | 1.38 |
| 9.21 | 9.61 | 1.32 |
| 9.39 | 9.42 | 0.71 |
| 9.97 | 8.87 | 100.00 |
| 13.02 | 6.80 | 12.96 |
| 13.31 | 6.65 | 33.72 |
| 13.64 | 6.49 | 39.41 |
| 13.97 | 6.34 | 37.17 |
| 16.69 | 5.31 | 63.51 |
| 17.13 | 5.18 | 3.63 |
| 17.65 | 5.03 | 1.29 |
| 18.09 | 4.90 | 0.97 |
| 18.65 | 4.76 | 0.53 |
| 19.51 | 4.55 | 2.67 |
| 20.06 | 4.43 | 28.05 |
| 22.15 | 4.01 | 16.77 |
| 22.50 | 3.95 | 0.78 |
| 22.87 | 3.89 | 0.48 |
| 23.41 | 3.80 | 0.40 |
| 24.54 | 3.63 | 1.23 |
| 25.01 | 3.56 | 1.99 |
| 25.70 | 3.47 | 0.20 |
| 26.29 | 3.39 | 10.34 |
| 26.87 | 3.32 | 23.31 |
| 27.81 | 3.21 | 3.07 |
| 28.89 | 3.09 | 8.62 |
| 29.06 | 3.07 | 9.74 |
| 29.90 | 2.99 | 0.54 |
| 30.29 | 2.95 | 2.38 |
| 30.60 | 2.92 | 2.03 |
| 31.08 | 2.88 | 21.52 |
| 31.97 | 2.80 | 0.89 |
| 32.21 | 2.78 | 0.56 |
| 33.85 | 2.65 | 4.03 |
| 34.24 | 2.62 | 3.76 |
| 35.73 | 2.51 | 0.64 |
| 37.31 | 2.41 | 2.39 |
| 38.39 | 2.34 | 1.09 |
| 39.71 | 2.27 | 1.60 |
| 40.87 | 2.21 | 6.46 |
| 42.01 | 2.15 | 0.67 |
| 44.30 | 2.04 | 8.24 |

6.4.9 Salt VI of Compound 1

Figure 71:
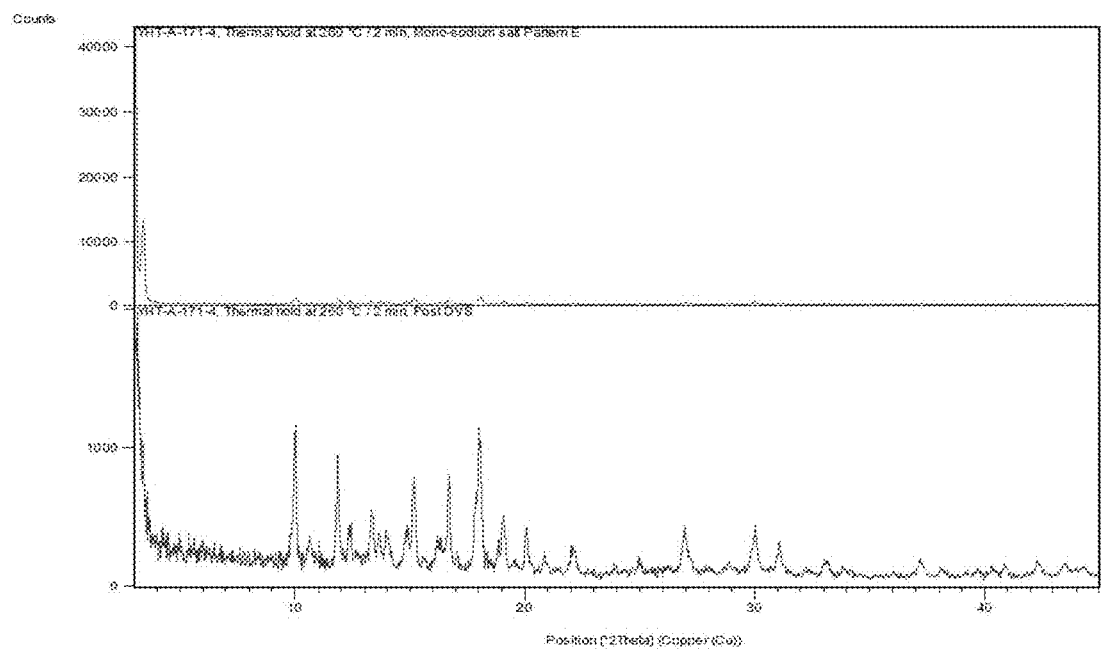
FIG. 71 depicts a XRPD stackplot of Salt VI of Compound 1 before (top) and after DVS (bottom) analysis.
Figure 73:
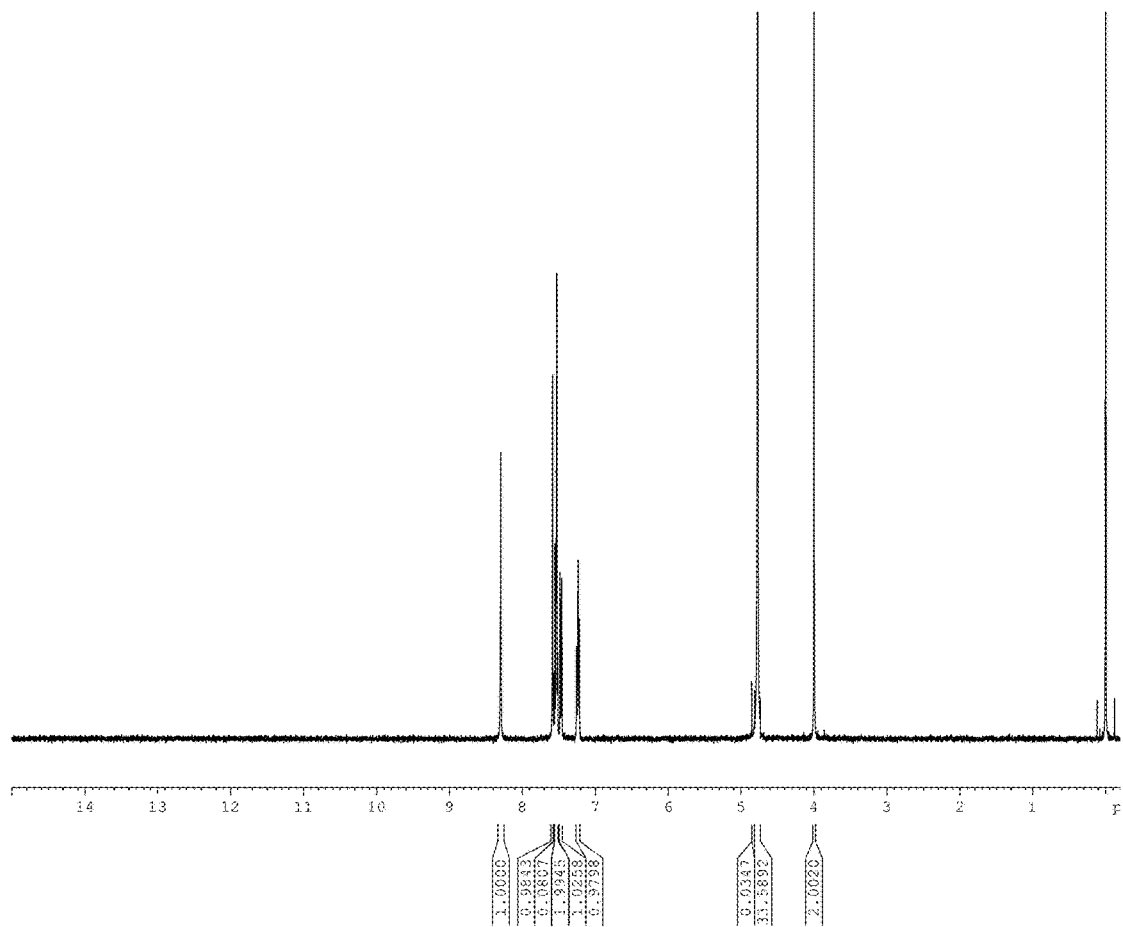
FIG. 73 depicts a ¹H NMR spectrum of Salt VI of Compound 1.
Figure 76:
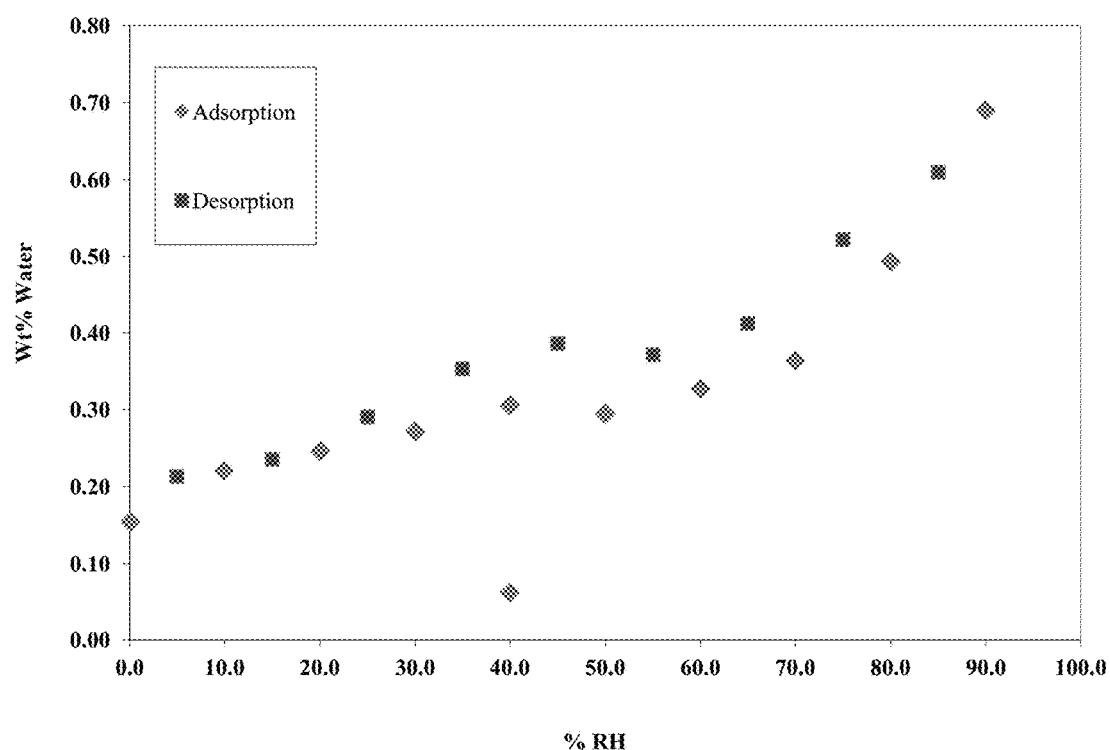
FIG. 76 depicts a DVS thermogram of Salt VI of Compound 1.

Salt VI of Compound 1 is an anhydrous mono-sodium salt. Salt VI was isolated from the thermal holding experiment (Table 50, FIG. 71). No degradation was observed by $^1$H NMR (Table 50, FIG. 73). DSC analysis presented two endothermic peaks at 282.4 and 308.4° C. and an exothermic peak at 283.9° C. (FIG. 74). No weight loss was observed by TGA, and the onset decomposition temperature is 305.7° C. (FIG. 75). The material adsorbed 0.3 wt % moisture at 60% RH, and 0.7 wt % moisture at 90% RH, indicating it is slightly hygroscopic material (FIG. 76).

Figure 72:
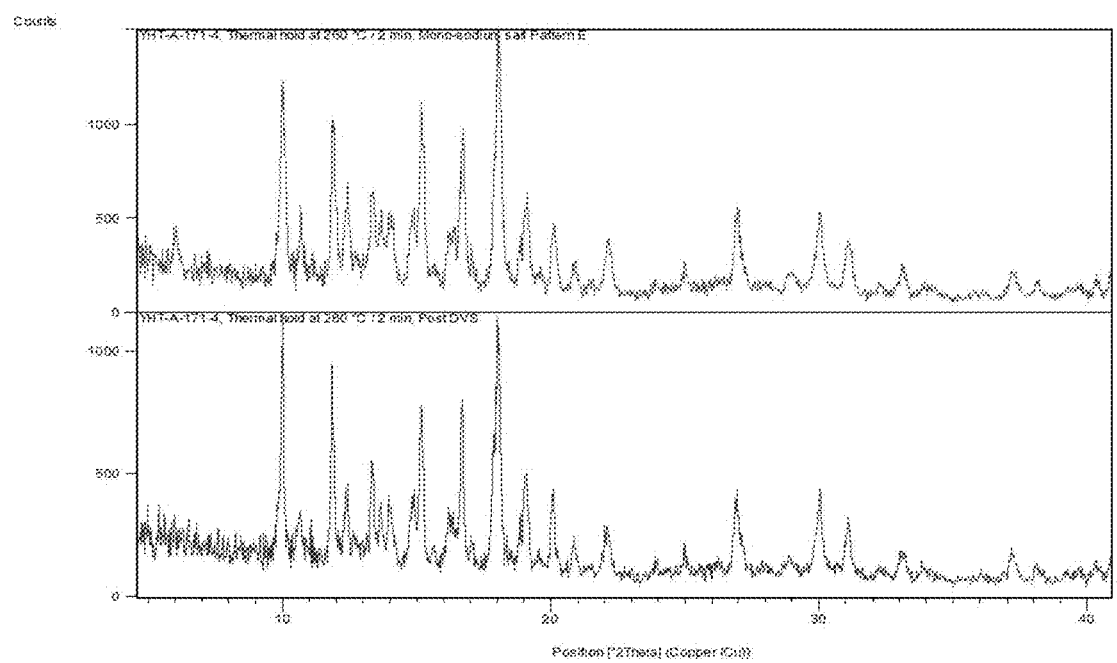
FIG. 72 depicts a XRPD stackplot (zoom in) of Salt VI of Compound 1 before (top) and after DVS (bottom) analysis.

The XRPD analysis of the post-DVS material after drying at 60.0° C. for two hours, recorded a consistent XRPD diffractogram (FIG. 72). These results indicated that Salt VI is a stable anhydrate form of mono-sodium salt.

FIG. 45 provides an XRPD pattern of Salt VI. A list of XRPD Peaks for Salt VI is provided below in Table 43.

TABLE 43

X-Ray Diffraction Peaks for Salt VI

| Two-theta angle (°) | d Space (Å) | Relative Intensity (%) |
|---|---|---|
| 3.03 | 29.12 | 100.00 |
| 3.39 | 26.05 | 41.75 |
| 4.42 | 19.99 | 1.12 |
| 4.63 | 19.08 | 1.77 |
| 5.01 | 17.62 | 2.09 |
| 5.40 | 16.37 | 2.37 |
| 5.81 | 15.21 | 1.21 |
| 6.23 | 14.19 | 0.78 |
| 6.42 | 13.77 | 0.58 |
| 7.06 | 12.52 | 0.74 |
| 7.66 | 11.55 | 0.95 |
| 8.96 | 9.87 | 0.82 |
| 10.06 | 8.79 | 9.02 |
| 10.68 | 8.28 | 1.75 |
| 11.53 | 7.67 | 0.14 |
| 11.89 | 7.45 | 8.37 |
| 12.42 | 7.13 | 2.13 |
| 13.40 | 6.61 | 3.37 |
| 13.73 | 6.45 | 1.19 |
| 14.04 | 6.31 | 2.74 |
| 14.91 | 5.94 | 2.99 |
| 15.22 | 5.82 | 4.62 |
| 15.67 | 5.65 | 0.68 |
| 16.33 | 5.43 | 2.07 |
| 16.74 | 5.30 | 6.01 |
| 17.10 | 5.19 | 0.92 |
| 17.82 | 4.98 | 2.82 |
| 18.11 | 4.90 | 7.43 |
| 18.48 | 4.80 | 0.20 |
| 19.07 | 4.65 | 3.04 |
| 20.15 | 4.41 | 2.67 |
| 20.94 | 4.24 | 1.42 |
| 21.47 | 4.14 | 0.36 |
| 22.05 | 4.03 | 1.14 |
| 23.37 | 3.81 | 0.40 |
| 24.03 | 3.70 | 0.27 |
| 24.96 | 3.57 | 0.53 |
| 26.38 | 3.38 | 0.03 |
| 26.96 | 3.31 | 2.44 |
| 28.88 | 3.09 | 0.42 |
| 30.07 | 2.97 | 2.24 |
| 31.04 | 2.88 | 1.20 |
| 31.61 | 2.83 | 0.78 |
| 33.20 | 2.70 | 0.73 |
| 33.94 | 2.64 | 0.24 |
| 34.87 | 2.57 | 0.41 |
| 37.20 | 2.42 | 0.75 |
| 38.13 | 2.36 | 0.29 |
| 39.72 | 2.27 | 0.18 |
| 40.29 | 2.24 | 0.31 |
| 40.97 | 2.20 | 0.51 |
| 42.35 | 2.13 | 0.63 |
| 43.41 | 2.08 | 0.31 |
| 44.38 | 2.04 | 0.40 |

6.4.10 Salt VII of Compound 1

Figure 85:
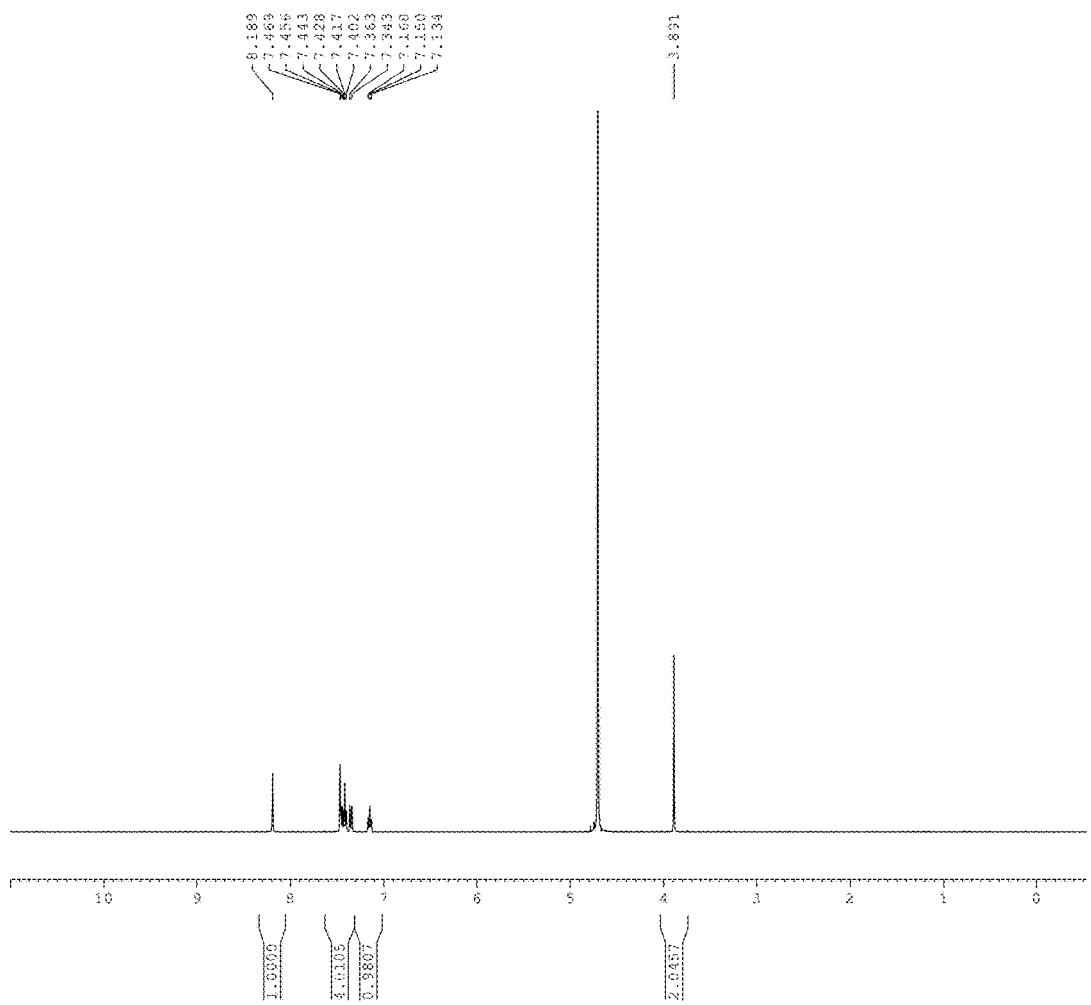
FIG. 85 depicts a ¹H NMR spectrum of Salt VII of Compound 1.
Figure 88:
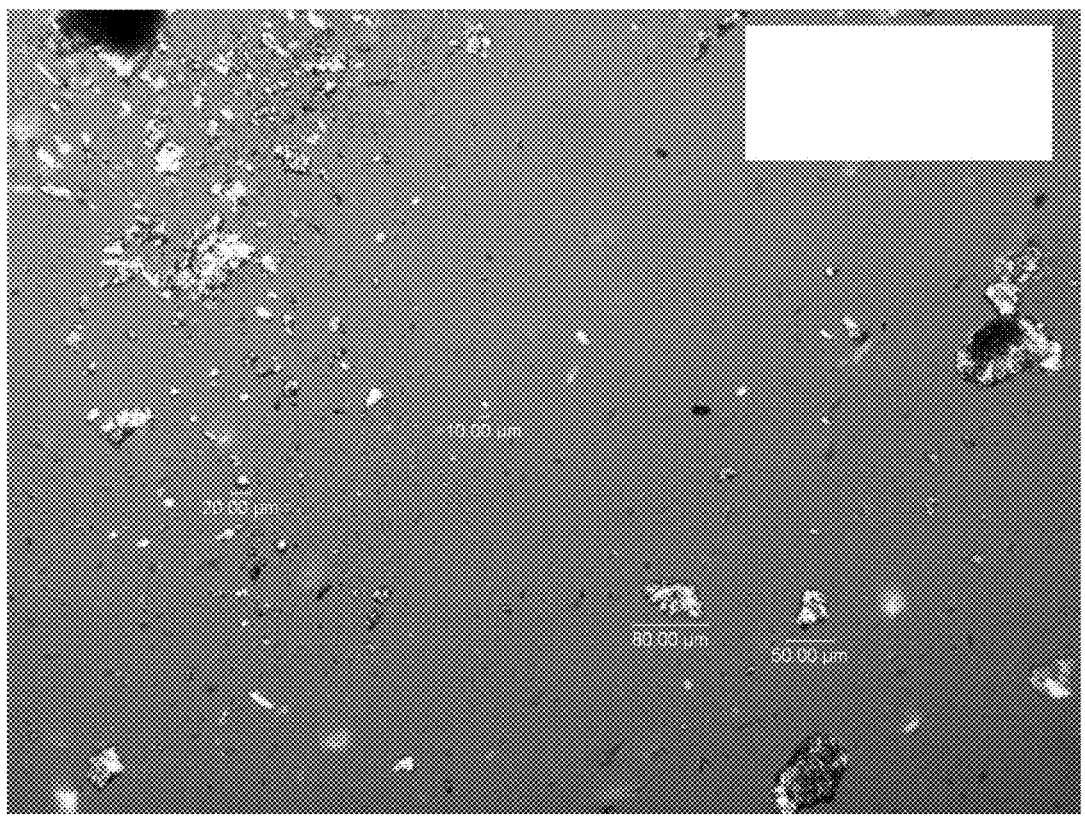
FIG. 88 depicts a microscopy analysis of Salt VII of Compound 1.

Salt VII of Compound 1 is a mono-sodium salt and a possible hydrate form. It was obtained from the salt formation experiment in MeOH. IC analysis of this material indicated the material had a free acid:sodium ratio of 1.0:1.2, consistent with a mono-sodium salt. $^1$H NMR (D$_2$O) analysis was consistent with the chemical structure and no solvent was detected (FIG. 85). DSC analysis showed a broad transition before 90° C., which might be from water loss and a possible glass transition at 160° C. (FIG. 86). TGA analysis indicated no weight loss and onset decomposition at 290.6° C. (FIG. 87). Polarized microscopy analysis revealed birefringent particles, ~10.0 μm to 80.0 μm (FIG. 88).

Figure 89:
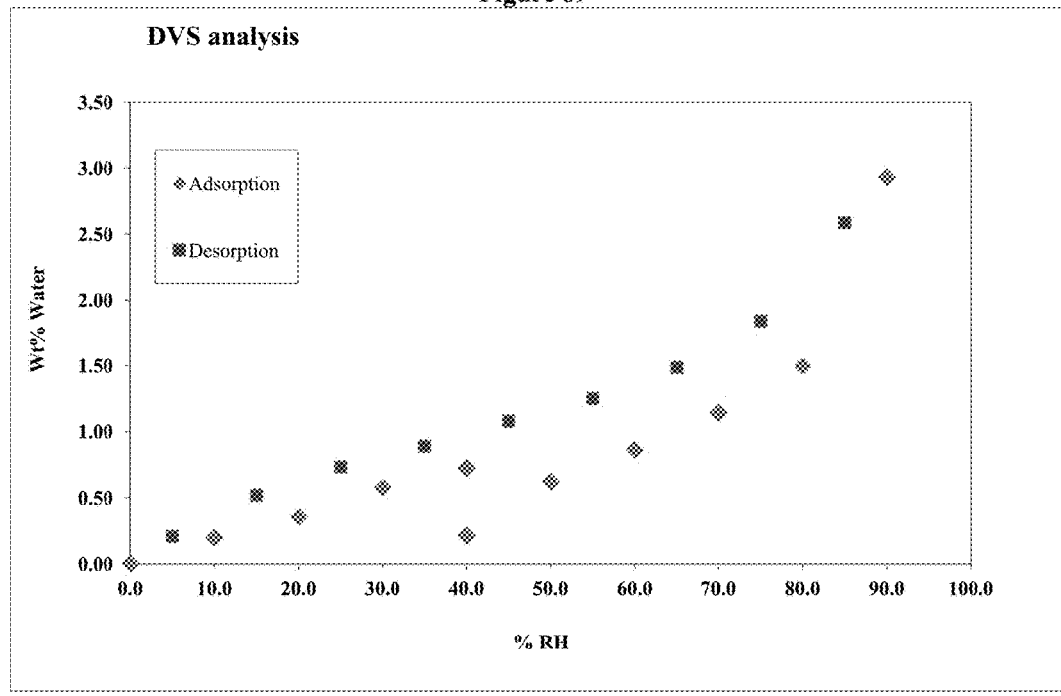
FIG. 89 depicts a DVS thermogram of Salt VII of Compound 1.
Figure 90:
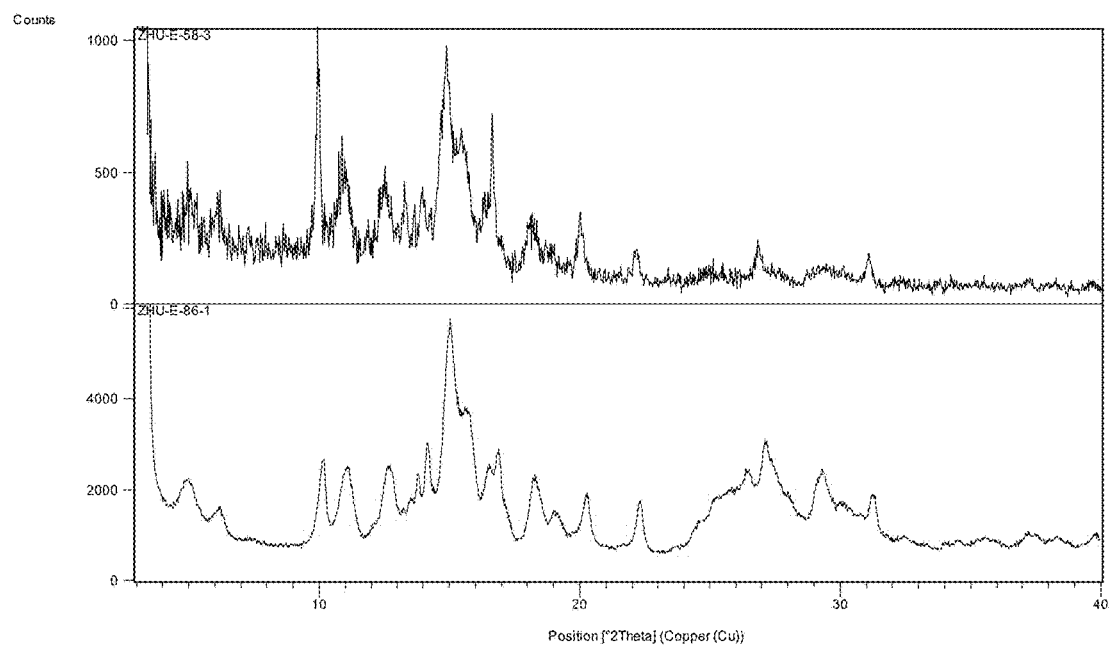
FIG. 90 depicts a XRPD stackplot of Salt VII of Compound 1 before (top) and after DVS (bottom) analysis.

In the moisture sorption analysis, the material adsorbed 0.9 wt % moisture at 60% RH, and 2.9 wt % moisture at 90% RH (FIG. 89). The XRPD analysis of the post-DVS material after drying at 60.0° C. for two hours, recorded a XRPD pattern consistent with the starting material (FIG. 90). DVS analysis showed minor hysteresis indicating that Salt VII of Compound 1 is a possible hydrate with variable water content depending on the environment humidity.

The polymorph form was stable after seven days of stirring in acetone and no change in XRPD pattern was observed. After seven days of storage at 60° C., no change in XRPD pattern and no degradation were observed by HPLC.

Approximately 160 mg of Compound 1 was weighed in a 20.0 mL clear vial equipped with magnetic stir bars and dissolved with minimum amount of methanol at 50° C. Prior to CI addition, each solution was polish filtered through a 0.45 μm syringe filter into clean preheated vials. After hot filtration, 1.2 mL of 0.5 M aqueous sodium hydroxide was added drop-wise. The vials were cooled to ambient temperature at a rate of 20° C./hour and allowed to equilibrate with stirring at ambient temperature overnight with slow cooling. The resulting solids were transferred into a Bichner funnel (with grade 1 Whatman paper) and isolated by filtration. All obtained solids were dried under vacuum (~30 inches Hg) and analyzed by XRPD to determine the solid pattern, $^1$H NMR to confirm structure and IC for salt stoichiometry (Table 37).

Figure 84:
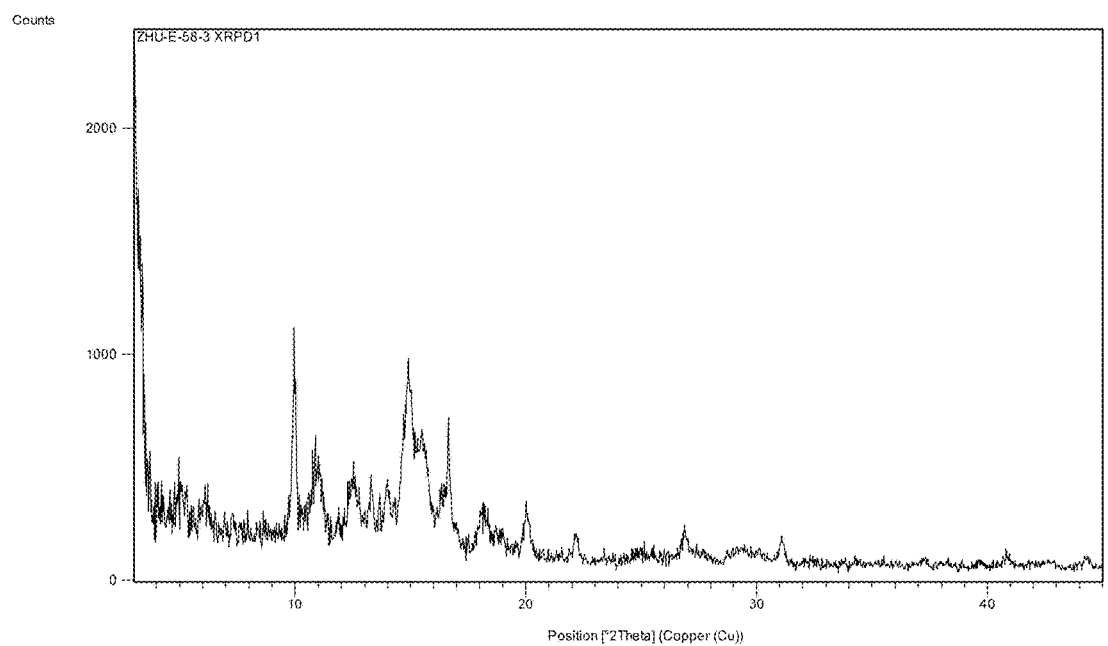
FIG. 84 depicts a XRPD Diffractogram of Salt VII of Compound 1.

FIG. 84 provides an XRPD pattern of Salt VII. A list of XRPD Peaks for Salt VII is provided below in Table 44.

TABLE 44

X-Ray Diffraction Peaks for Salt VII

| Two-theta angle (°) | d Space (Å) | Relative Intensity (%) |
|---|---|---|
| 3.40 | 25.96 | 100.00 |
| 3.71 | 23.80 | 48.20 |
| 4.08 | 21.67 | 27.72 |
| 4.31 | 20.50 | 29.20 |
| 4.95 | 17.86 | 29.21 |
| 5.07 | 17.43 | 35.50 |
| 5.33 | 16.58 | 33.39 |
| 5.59 | 15.82 | 25.36 |
| 6.11 | 14.46 | 33.91 |
| 6.55 | 13.49 | 22.93 |
| 6.95 | 12.72 | 18.29 |
| 7.27 | 12.15 | 21.19 |
| 7.60 | 11.64 | 17.55 |
| 7.79 | 11.35 | 16.23 |
| 8.49 | 10.42 | 18.29 |
| 8.62 | 10.26 | 18.46 |
| 9.54 | 9.27 | 21.65 |
| 9.96 | 8.88 | 94.70 |
| 10.87 | 8.14 | 48.51 |
| 11.53 | 7.67 | 20.75 |
| 11.88 | 7.45 | 23.67 |
| 12.53 | 7.06 | 36.50 |
| 12.78 | 6.92 | 27.31 |
| 13.28 | 6.67 | 34.98 |
| 13.64 | 6.49 | 28.43 |
| 13.97 | 6.34 | 32.67 |
| 14.31 | 6.19 | 28.60 |

TABLE 44-continued

X-Ray Diffraction Peaks for Salt VII

| Two-theta angle (°) | d Space (Å) | Relative Intensity (%) |
|---|---|---|
| 14.90 | 5.94 | 86.48 |
| 15.48 | 5.72 | 54.80 |
| 15.73 | 5.63 | 39.86 |
| 16.37 | 5.41 | 33.98 |
| 16.66 | 5.32 | 60.39 |
| 18.02 | 4.92 | 20.75 |
| 18.68 | 4.75 | 15.27 |
| 20.03 | 4.43 | 27.28 |
| 20.76 | 4.28 | 7.31 |
| 20.96 | 4.24 | 7.06 |
| 21.58 | 4.12 | 6.69 |
| 22.15 | 4.01 | 13.35 |
| 24.89 | 3.58 | 5.75 |
| 25.46 | 3.50 | 6.34 |
| 25.82 | 3.45 | 5.02 |
| 26.83 | 3.32 | 11.50 |
| 28.73 | 3.11 | 6.55 |
| 29.35 | 3.04 | 7.21 |
| 31.10 | 2.88 | 12.92 |
| 32.28 | 2.77 | 2.27 |
| 32.84 | 2.73 | 3.85 |
| 33.75 | 2.66 | 2.21 |
| 34.30 | 2.61 | 2.49 |
| 37.27 | 2.41 | 3.03 |
| 38.29 | 2.35 | 2.09 |
| 38.86 | 2.32 | 0.56 |
| 39.67 | 2.27 | 1.86 |
| 40.80 | 2.21 | 7.08 |
| 44.33 | 2.04 | 3.68 |

6.4.11 Salt VIII of Compound 1

Figure 92:
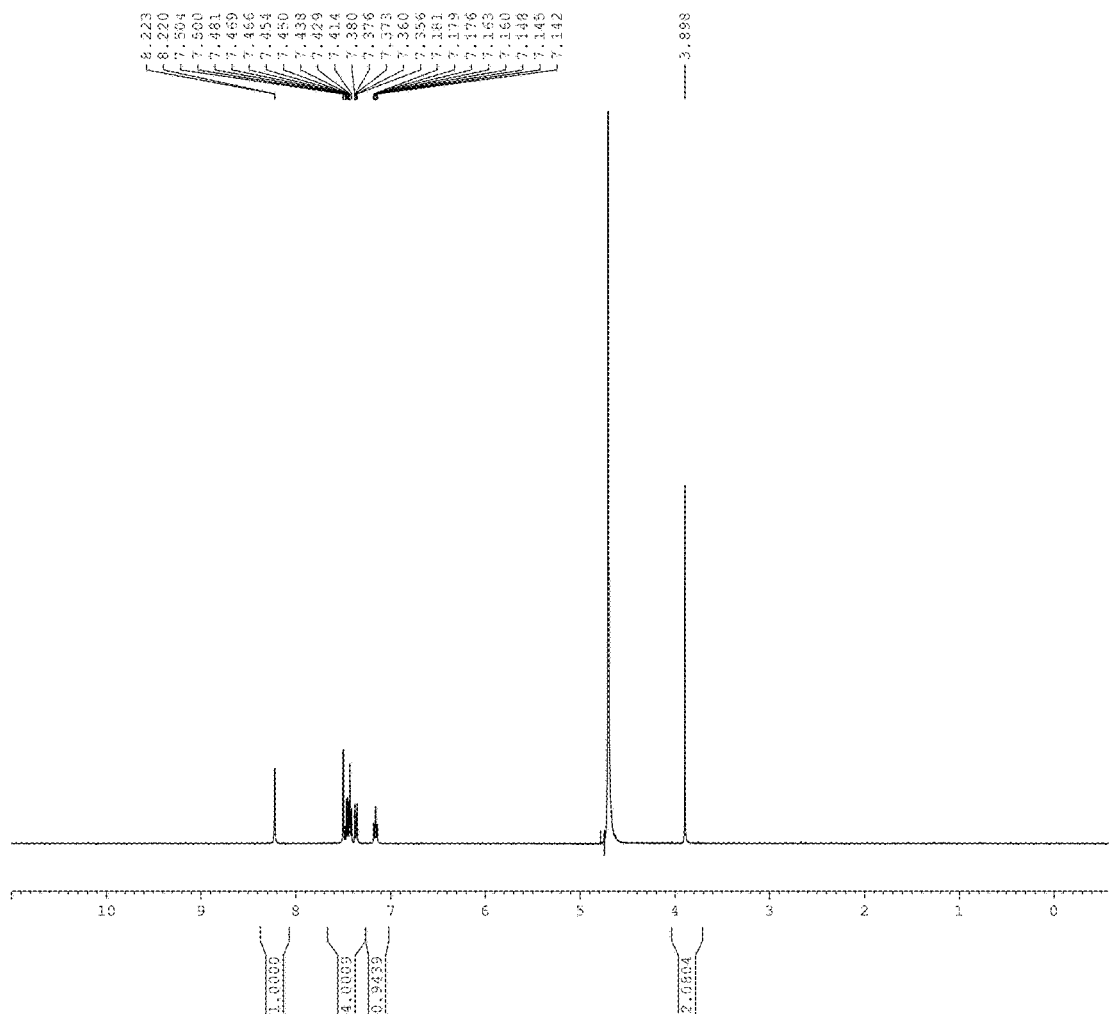
FIG. 92 depicts a ¹H NMR spectrum of Salt VIII of Compound 1.
Figure 95:
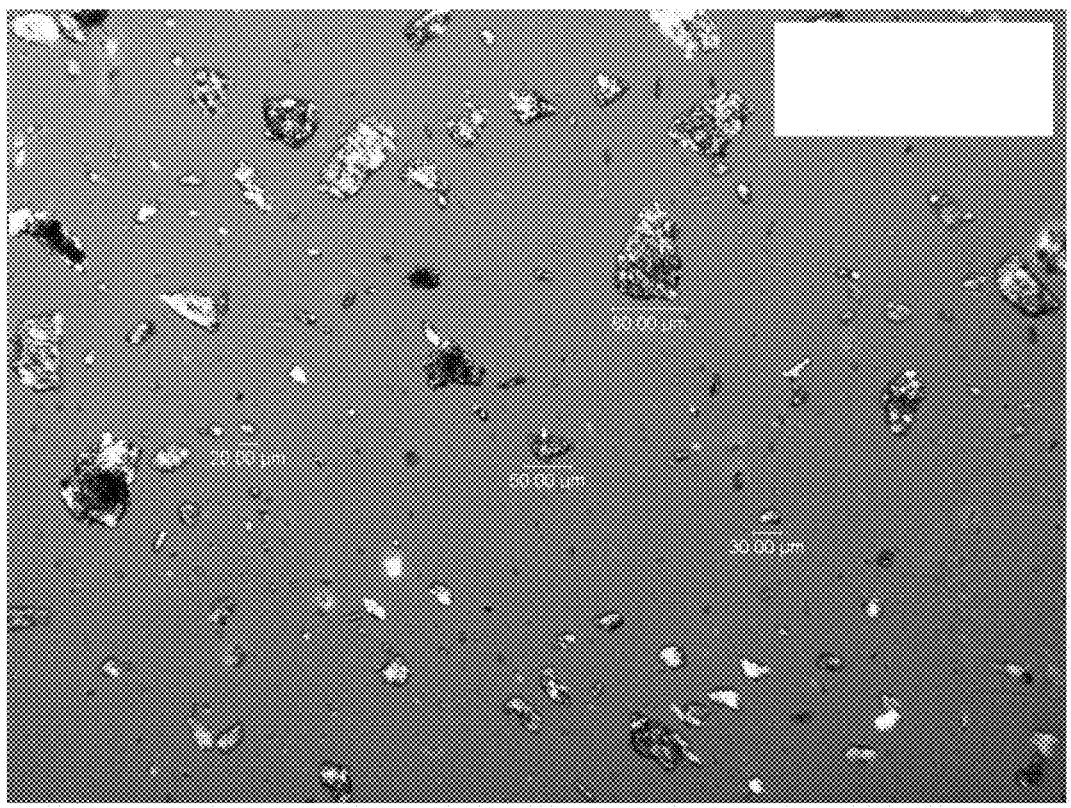
FIG. 95 depicts a microscopy analysis of Salt VIII of Compound 1.

Salt VIII of Compound 1 is a mono-sodium salt and a stable anhydrate polymorph. It was obtained from the slurry experiment using MeOH as solvent (FIG. 91). IC analysis of this material indicated the material had a free acid:sodium ratio of 1.0:1.1, consistent with a mono-sodium salt. No degradation was observed by $^1$H NMR (D$_2$O) (FIG. 92). DSC analysis showed no thermic change before onset decomposition at 294.0° C. (FIG. 93). TGA analysis showed no weight loss and an onset decomposition at 291.2° C. (FIG. 94). Polarized microscopy analysis revealed birefringent particles, ~20.0 μm to 80.0 μm (FIG. 95).

Figure 96:
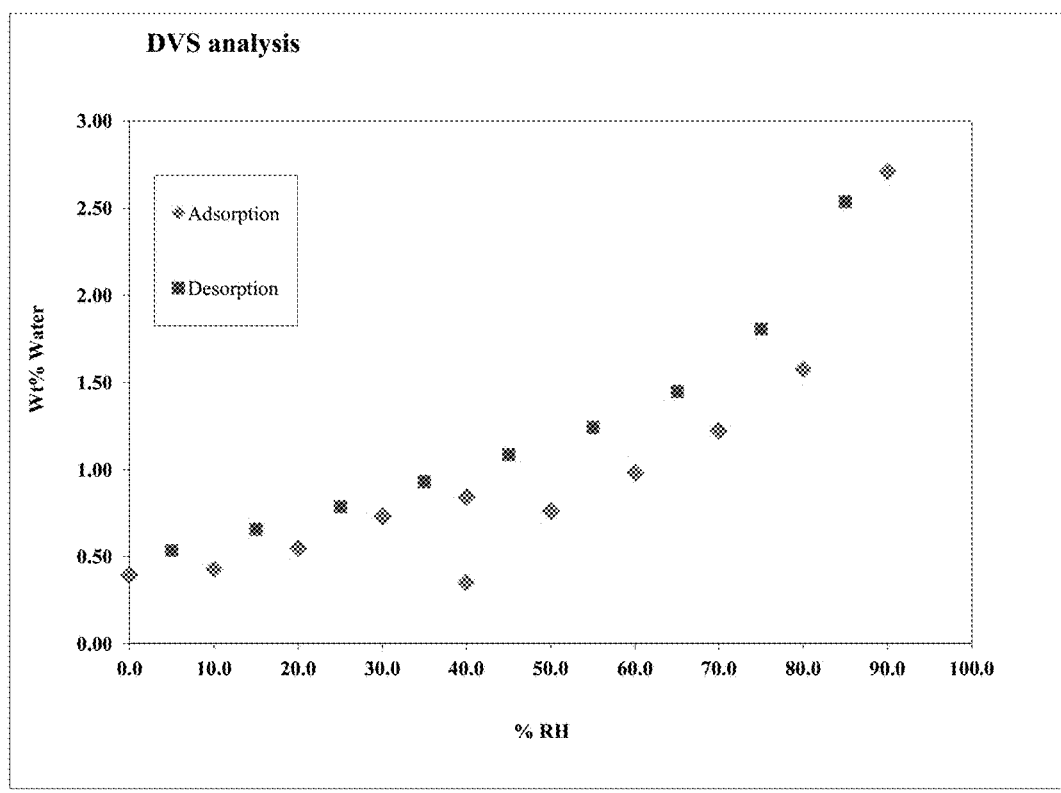
FIG. 96 depicts a DVS thermogram of Salt VIII of Compound 1.
Figure 97:
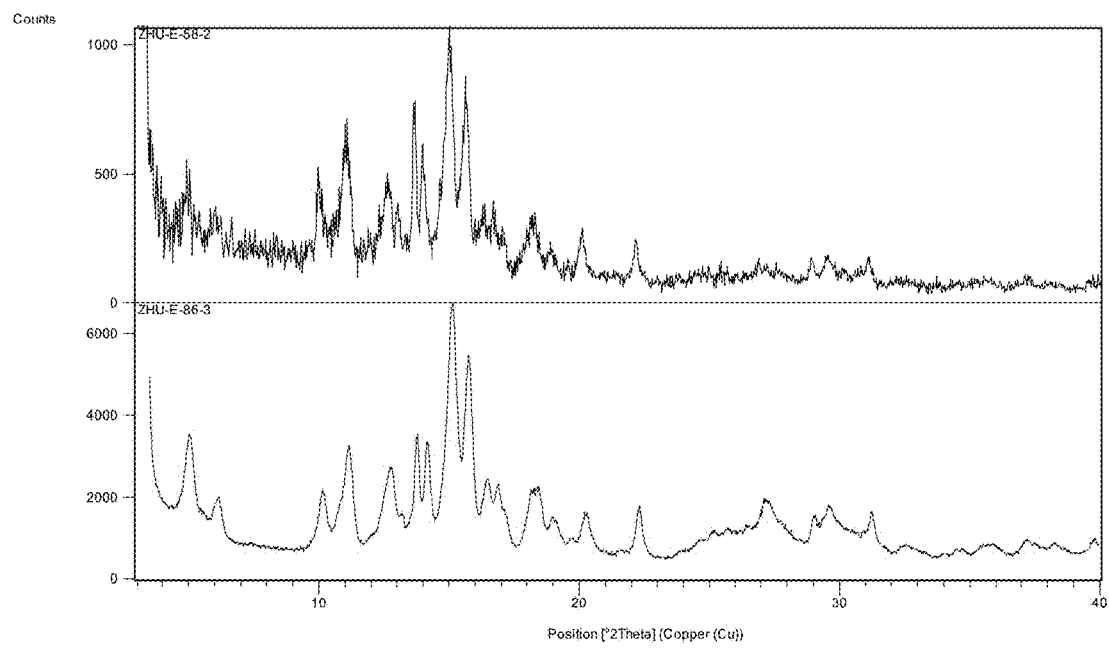
FIG. 97 depicts a XRPD stackplot of Salt VIII of Compound 1 before (top) and after DVS (bottom) analysis.

Salt VIII of Compound 1 adsorbed 1.0 wt % moisture at 60% RH, and 2.7 wt % moisture at 90% RH (FIG. 96). The XRPD analysis of the post-DVS material after drying at 60.0° C. for two hours, showed an XRPD pattern consistent with the starting material (FIG. 97).

Salt VIII of Compound 1 was stable after seven days of stirring in acetone and no change in XRPD pattern was observed. In competitive slurry experiments, Salt VIII of Compound 1 was stable in an acetone slurry after seven days of equilibration. After seven days of storage at 60° C., no change in XRPD pattern and no degradation were observed by HPLC.

Approximately 150 mg of Salt IV of Compound 1 was placed into a 20.0 mL clear vial equipped with magnetic stir bars. Methanol (10.0 mL) was added to achieve free-flowing slurry and allowed to equilibrate at room temperature. The slurry was transferred into a Büchner funnel (with grade 1 Whatman paper) after one day of equilibration. The resulting solid was dried under vacuum (~30 inches Hg) and analyzed by XRPD to determine the solid pattern, $^1$H NMR to confirm structure and IC for salt stoichiometry (Table 37).

FIG. 91 provides an XRPD pattern of Salt VIII. A list of XRPD Peaks for Salt VIII is provided below in Table 45.

TABLE 45

X-Ray Diffraction Peaks for Salt VIII

| Two-theta angle (°) | d Space (Å) | Relative Intensity (%) |
|---|---|---|
| 3.06 | 28.86 | 100.00 |
| 3.39 | 26.07 | 73.24 |
| 3.64 | 24.29 | 31.30 |
| 3.79 | 23.31 | 27.13 |
| 3.95 | 22.36 | 24.85 |
| 4.54 | 19.47 | 16.91 |
| 4.94 | 17.89 | 27.50 |
| 5.07 | 17.44 | 23.21 |
| 5.21 | 16.95 | 18.18 |
| 5.40 | 16.37 | 16.87 |
| 6.02 | 14.69 | 17.08 |
| 6.27 | 14.11 | 14.06 |
| 6.65 | 13.28 | 15.61 |
| 7.18 | 12.31 | 12.13 |
| 8.00 | 11.06 | 6.23 |
| 8.37 | 10.56 | 10.79 |
| 9.32 | 9.49 | 9.06 |
| 10.00 | 8.85 | 22.09 |
| 10.43 | 8.48 | 13.83 |
| 11.04 | 8.01 | 30.28 |
| 11.94 | 7.41 | 9.98 |
| 12.72 | 6.96 | 21.11 |
| 13.01 | 6.80 | 18.85 |
| 13.71 | 6.46 | 35.02 |
| 13.97 | 6.34 | 31.38 |
| 14.66 | 6.04 | 24.16 |
| 15.01 | 5.90 | 54.69 |
| 15.65 | 5.66 | 43.71 |
| 15.73 | 5.63 | 34.23 |
| 16.34 | 5.42 | 15.36 |
| 16.69 | 5.31 | 16.66 |
| 17.14 | 5.17 | 10.36 |
| 17.37 | 5.11 | 6.32 |
| 18.31 | 4.84 | 16.85 |
| 18.91 | 4.69 | 8.79 |
| 19.57 | 4.54 | 5.57 |
| 20.13 | 4.41 | 13.39 |
| 22.17 | 4.01 | 10.89 |
| 24.68 | 3.61 | 3.20 |
| 25.02 | 3.56 | 3.44 |
| 26.92 | 3.31 | 5.68 |
| 28.96 | 3.08 | 6.20 |
| 29.53 | 3.02 | 6.68 |
| 31.12 | 2.87 | 6.69 |
| 32.42 | 2.76 | 1.62 |
| 33.47 | 2.68 | 1.24 |
| 33.76 | 2.66 | 0.81 |
| 34.58 | 2.59 | 1.21 |
| 35.75 | 2.51 | 1.74 |
| 37.25 | 2.41 | 2.01 |
| 39.65 | 2.27 | 1.30 |
| 40.87 | 2.21 | 1.65 |
| 42.36 | 2.13 | 1.62 |
| 43.42 | 2.08 | 1.57 |
| 44.34 | 2.04 | 1.72 |

6.4.12 Salt IX of Compound 1

Figure 99:
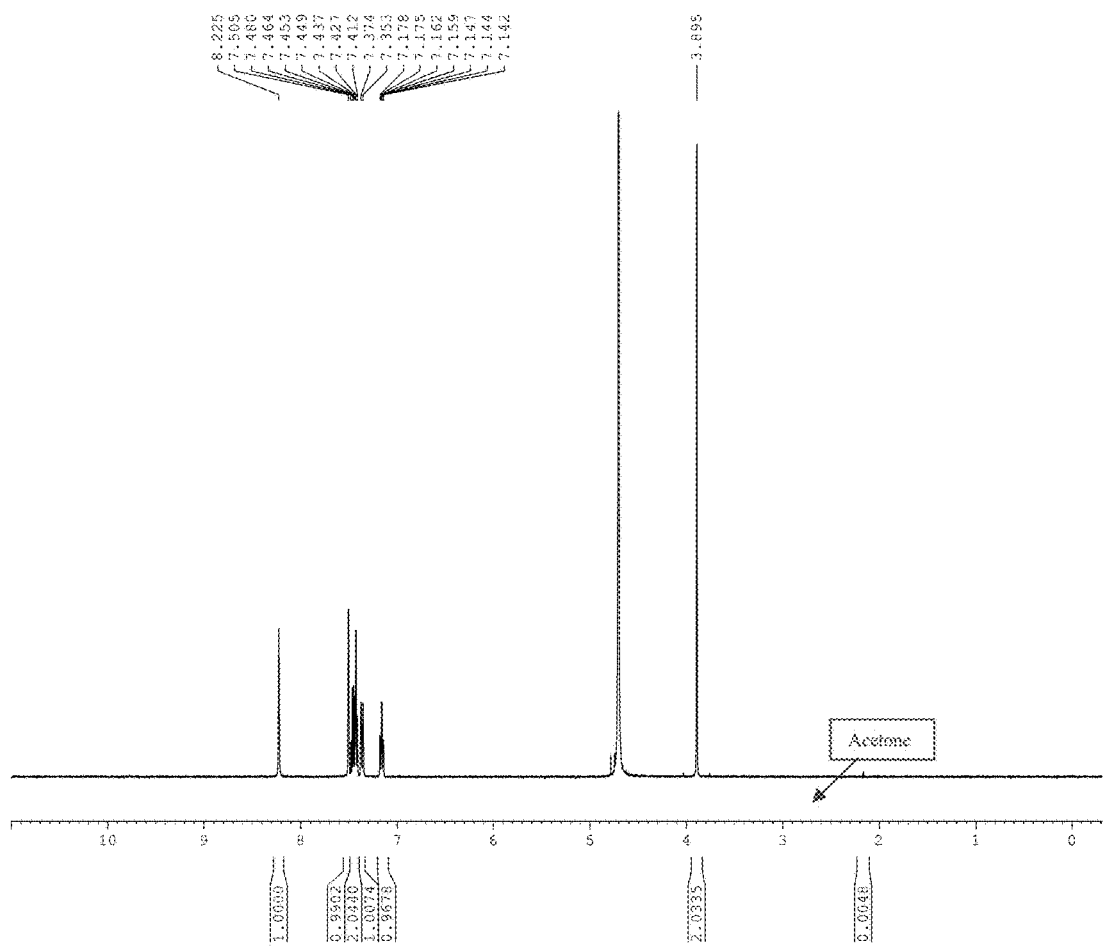
FIG. 99 depicts a ¹H NMR spectrum of Salt IX of Compound 1.
Figure 102:
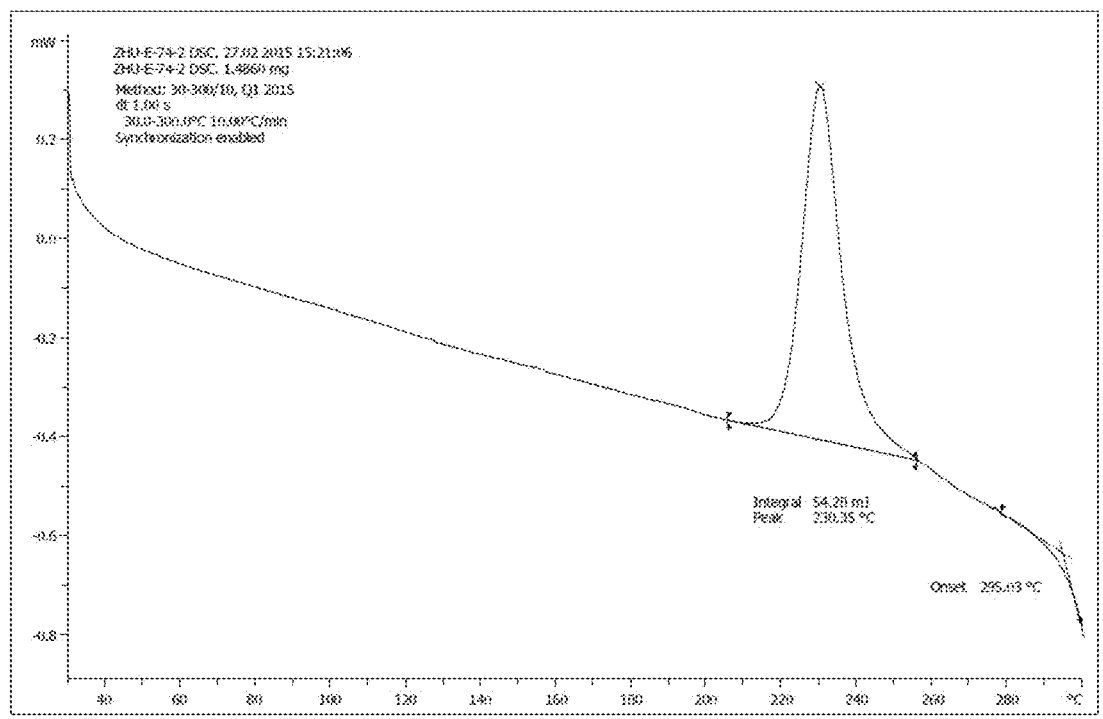
FIG. 102 depicts a DSC thermogram of Salt IX of Compound 1.
Figure 103:
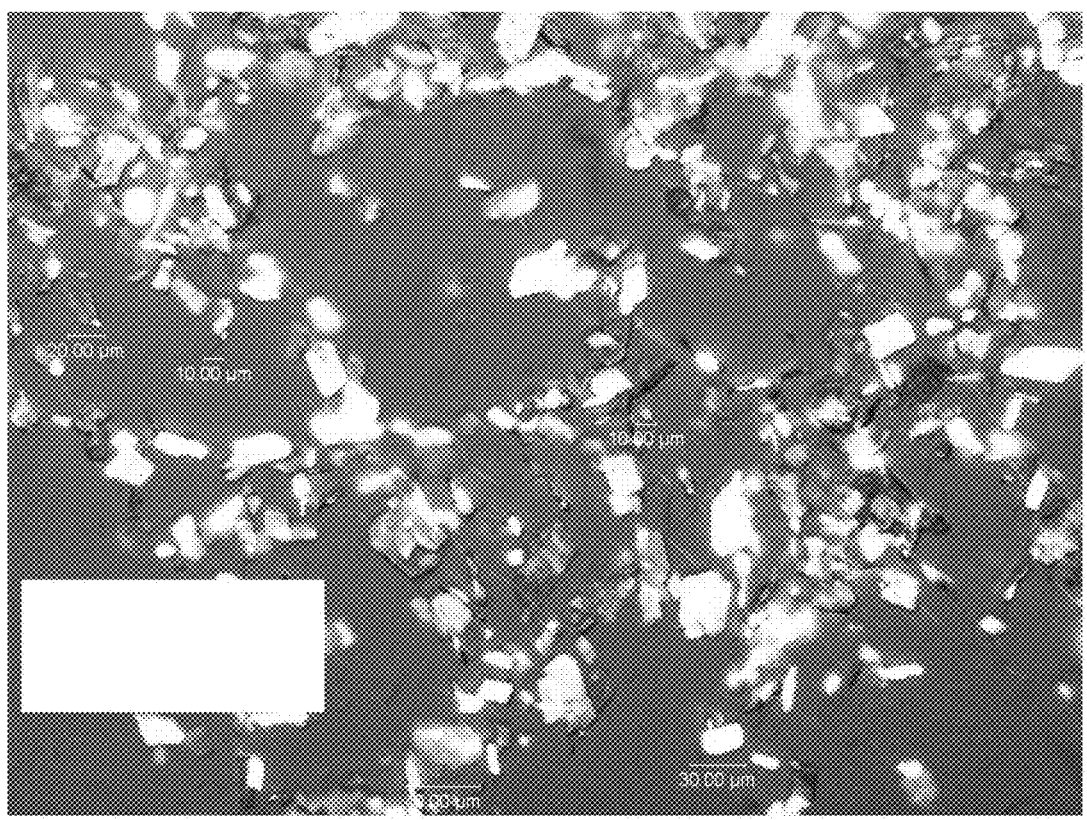
FIG. 103 depicts a microscopy analysis of Salt IX of Compound 1.

Salt IX of Compound 1 is a mono-sodium salt and an anhydrate polymorph. It was obtained from salt formation experiments in acetone (FIG. 98). IC analysis of this material indicated the material had a free acid:sodium ratio of 1.0:1.1, consistent with a mono-sodium salt. An estimated 0.01 wt % of acetone was observed by $^1$H NMR (D$_2$O) (FIG. 99). DSC analysis showed an endotherm at 82.8° C. and exotherm at 229.5° C. (FIG. 100). However, DSC analysis of the post thermal holding experiment at 150° C. showed no endothermic change before 180° C. (FIG. 102). XRPD analysis of the post thermal holding experiment gave material consistent with the starting material, which indicated the endothermic change was not related to a form change. TGA analysis indicated no weight loss and an onset decomposition of 301.8° C. (FIG. 101). Polarized microscopy analysis revealed birefringent particles, ~10.0 µm to 40.0 µm (FIG. 103).

Figure 104:
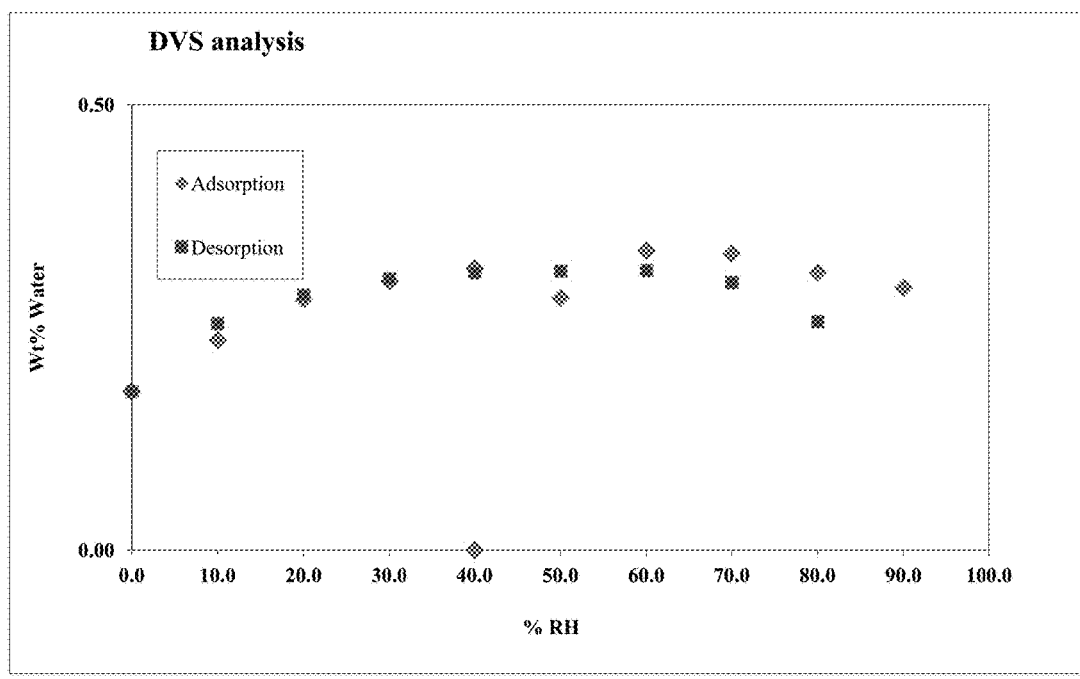
FIG. 104 depicts a XRPD stackplot of Salt IX of Compound 1 before (top) and after DVS (bottom) analysis.

The material adsorbed 0.3 wt % moisture at 60% RH, and 0.3 wt % moisture at 90% RH (FIG. 104). The XRPD analysis of the post-DVS material after drying at 60.0° C. for two hours, showed an XRPD pattern consistent with Salt IV of Compound 1.

After seven days of stirring in water and acetone, all Salt IX of Compound 1 had converted to Salt VIII or Salt IV. After seven days of storage at 60° C., no change in XRPD pattern and no degradation were observed by HPLC.

Approximately 1.6 g of Compound 1 was placed into a 250 mL round bottom flask equipped with stir bar and dissolved with 123.0 mL of acetone at 50° C. The solution was polish filtered through a 0.45 M syringe filter into clean preheated flask. After hot filtration, 12.7 mL of 0.5 M sodium hydroxide was added drop-wise to generate a white color suspension. After stirred at 50° C. for 10 minutes, the flask was cooled to ambient temperature at a rate of 20° C./hour and allowed to equilibrate with stirring at ambient temperature overnight with slow cooling. The resulting solids were transferred into a Büchner funnel (with grade 1 Whatman paper) and isolated by filtration. The clear solutions were kept at ambient temperature. The obtained solid was dried under vacuum (~30 inches Hg) and analyzed by XRPD to determine the solid pattern, $^1$H NMR to confirm structure and IC for salt stoichiometry.

FIG. 98 provides an XRPD pattern of Salt IX. A list of XRPD Peaks for Salt IX is provided below in Table 46.

TABLE 46

X-Ray Diffraction Peaks for Salt IX

| Two-theta angle (°) | d Space (Å) | Relative Intensity (%) |
|---|---|---|
| 3.05 | 28.95 | 78.75 |
| 3.19 | 27.68 | 100.00 |
| 4.33 | 20.41 | 6.91 |
| 4.57 | 19.34 | 6.24 |
| 5.11 | 17.30 | 4.92 |
| 5.25 | 16.82 | 4.17 |
| 5.71 | 15.47 | 5.57 |
| 6.32 | 13.98 | 35.72 |
| 7.68 | 11.51 | 4.25 |
| 7.88 | 11.22 | 4.40 |
| 9.47 | 9.34 | 99.14 |
| 9.93 | 8.91 | 7.57 |
| 10.04 | 8.81 | 9.36 |
| 12.63 | 7.01 | 4.96 |
| 13.06 | 6.78 | 6.44 |
| 13.69 | 6.47 | 21.62 |
| 14.01 | 6.32 | 13.40 |
| 14.89 | 5.95 | 3.86 |
| 15.83 | 5.60 | 65.85 |
| 16.31 | 5.44 | 4.42 |
| 16.68 | 5.32 | 4.05 |
| 17.39 | 5.10 | 5.60 |
| 18.33 | 4.84 | 2.89 |
| 19.01 | 4.67 | 79.21 |
| 19.94 | 4.45 | 4.88 |
| 20.72 | 4.29 | 4.76 |
| 20.88 | 4.25 | 2.57 |
| 22.12 | 4.02 | 7.77 |
| 22.27 | 3.99 | 6.70 |
| 22.60 | 3.93 | 5.31 |
| 23.58 | 3.77 | 2.40 |

TABLE 46-continued

X-Ray Diffraction Peaks for Salt IX

| Two-theta angle (°) | d Space (Å) | Relative Intensity (%) |
|---|---|---|
| 24.21 | 3.68 | 2.54 |
| 24.69 | 3.61 | 2.16 |
| 25.47 | 3.50 | 17.07 |
| 26.26 | 3.39 | 2.92 |
| 26.62 | 3.35 | 4.83 |
| 27.63 | 3.23 | 10.05 |
| 28.42 | 3.14 | 4.76 |
| 28.73 | 3.11 | 5.48 |
| 29.44 | 3.03 | 5.15 |
| 31.25 | 2.86 | 2.74 |
| 31.90 | 2.81 | 3.89 |
| 32.51 | 2.75 | 1.25 |
| 33.23 | 2.70 | 1.41 |
| 34.35 | 2.61 | 3.94 |
| 35.85 | 2.50 | 1.23 |
| 37.39 | 2.41 | 4.41 |
| 38.30 | 2.35 | 6.23 |
| 39.79 | 2.27 | 0.81 |
| 40.61 | 2.22 | 4.40 |
| 41.44 | 2.18 | 2.34 |
| 41.96 | 2.15 | 1.04 |
| 44.56 | 2.03 | 3.89 |

6.4.13 Salt X of Compound 1

Figure 106:
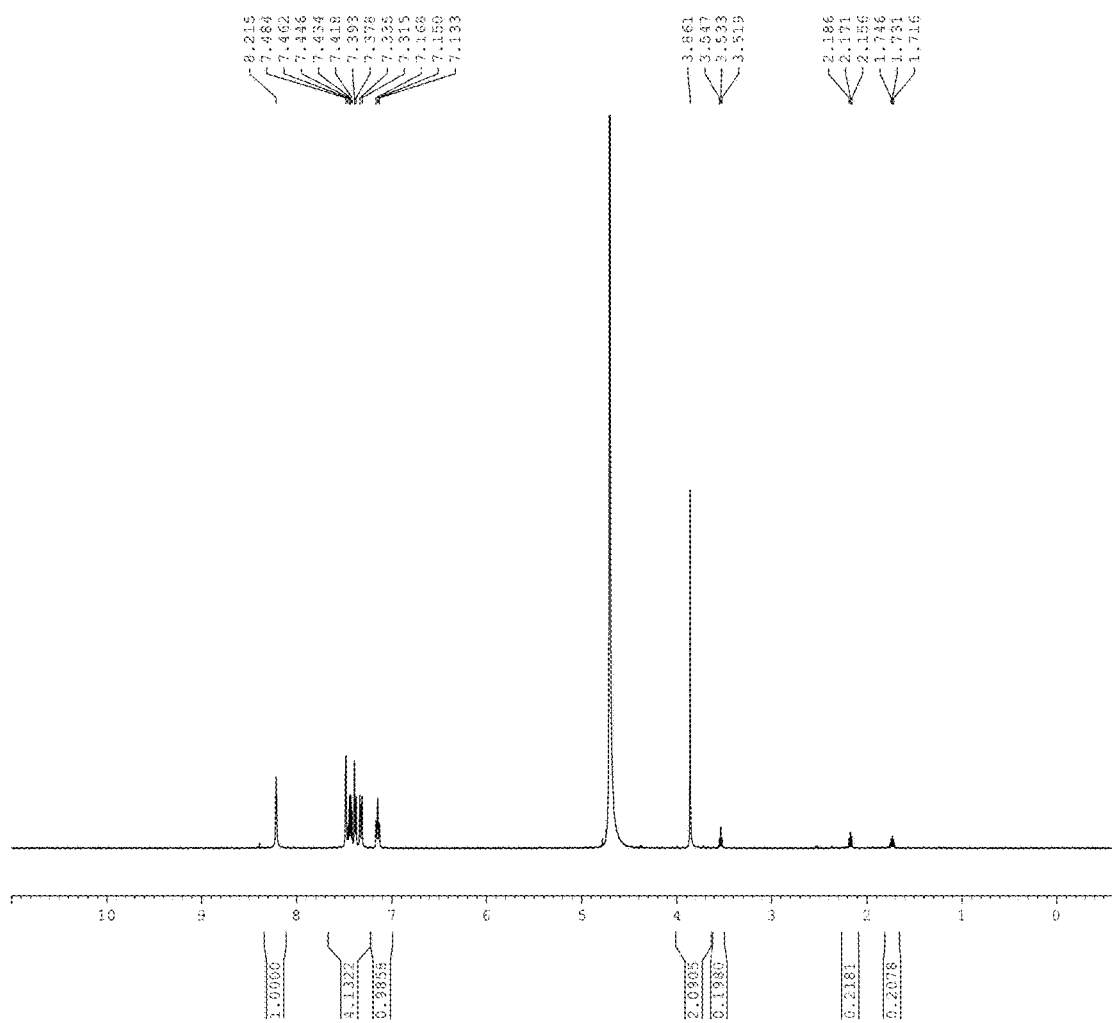
FIG. 106 depicts a ¹H NMR spectrum of Salt X of Compound 1.
Figure 109:
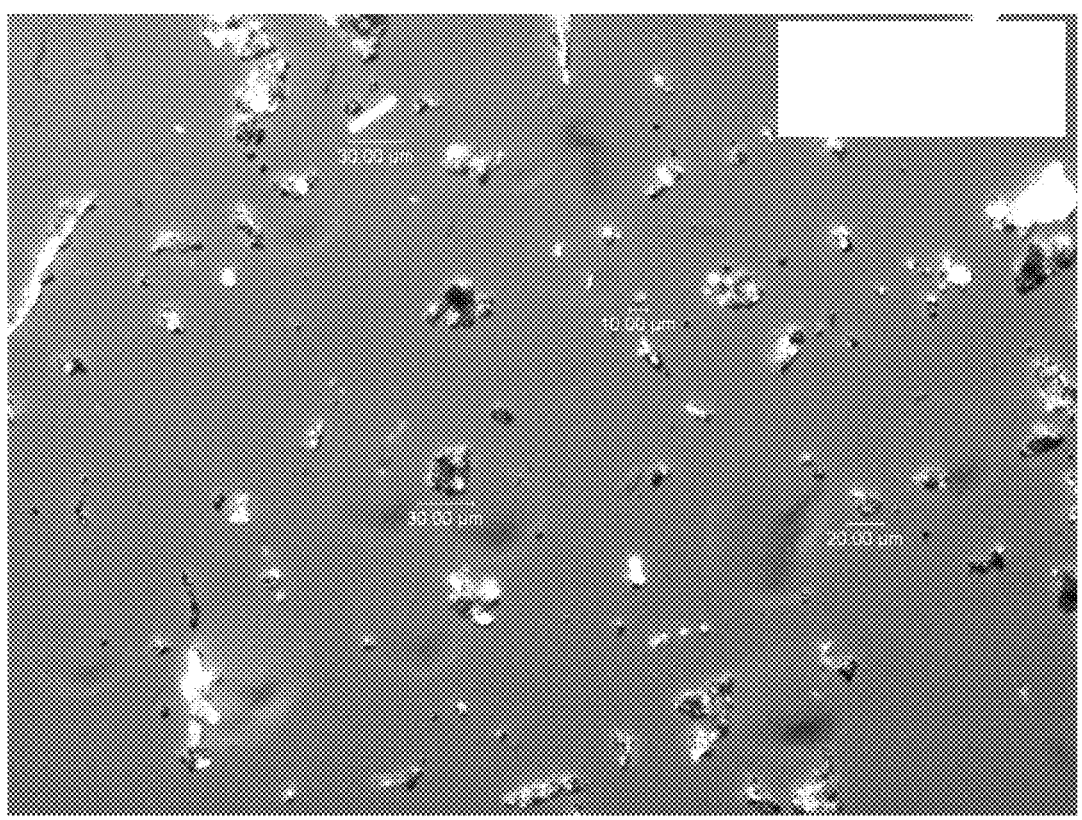
FIG. 109 depicts a microscopy analysis of Salt X of Compound 1.

Salt X of Compound 1 is a mono-sodium salt and an unstable hydrate polymorph. It was obtained from the binary solvent crystallization experiment, using water as primary solvent and THF as anti-solvent (FIG. 105). IC analysis of this material indicated the material had a free acid:sodium ratio of 1.0:1.0, consistent with a mono-sodium salt. $^1$H NMR (D$_2$O) analysis indicated this material contained an estimated 3.5 wt % of 4-hydroxybutanoic acid, which was the contamination of tetrahydrofuran peroxides (FIG. 106). DSC analysis showed two endotherms at 91.3° C. and 149.3° C., respectively and an exotherm at 230.6° C. (FIG. 107). TGA analysis indicated a 1.3% weight loss at 60-120° C. and a 2.3% weight loss at 120-180° C., followed by an onset decomposition at 296.7° C. (FIG. 108). Polarized microscopy analysis revealed birefringent particles, ~10.0 μm to 40.0 μm (FIG. 109).

After seven days of stirring in water and acetone, all Salt X converted to Salt VII or Salt IV. After seven days of storage at 60° C., no change in XRPD pattern and no degradation were observed by HPLC.

Approximately 168 mg of Salt IV of Compound 1 was placed into a 50.0 mL clear glass vial equipped with stir bar and dissolved in 4.3 mL of water at 60° C. Tetrahydrofuran, 12.8 mL, was added drop-wise at the same temperature. The vial was cooled to ambient temperature at a rate of 20° C./hour and allowed to equilibrate with stirring at ambient temperature over 24 hours. The solvent was evaporated to dryness under a gentle stream of nitrogen gas. The obtained solid was dried under vacuum (~30 inches Hg) and analyzed by XRPD to determine the solid form, $^1$H NMR to confirm structure and IC for salt stoichiometry.

FIG. 105 provides an XRPD pattern of Salt X. A list of XRPD Peaks for Salt X is provided below in Table 47.

TABLE 47

X-Ray Diffraction Peaks for Salt X

| Two-theta angle (°) | d Space (Å) | Relative Intensity (%) |
|---|---|---|
| 3.20 | 27.65 | 60.05 |
| 3.74 | 23.61 | 100.00 |
| 4.11 | 21.51 | 11.05 |
| 4.23 | 20.90 | 8.87 |
| 4.36 | 20.28 | 6.93 |
| 4.59 | 19.26 | 5.18 |
| 4.78 | 18.48 | 7.24 |
| 5.03 | 17.59 | 6.96 |
| 5.22 | 16.92 | 5.19 |
| 5.43 | 16.27 | 5.79 |
| 5.62 | 15.72 | 5.24 |
| 5.88 | 15.04 | 8.05 |
| 6.06 | 14.58 | 7.87 |
| 6.28 | 14.08 | 10.30 |
| 6.76 | 13.08 | 5.00 |
| 7.24 | 12.20 | 5.19 |
| 7.41 | 11.92 | 4.33 |
| 7.83 | 11.30 | 4.33 |
| 8.01 | 11.03 | 4.13 |
| 9.50 | 9.31 | 14.32 |
| 10.37 | 8.53 | 3.76 |
| 11.01 | 8.04 | 3.65 |
| 11.15 | 7.93 | 7.58 |
| 11.38 | 7.78 | 3.38 |
| 12.12 | 7.30 | 2.94 |
| 12.75 | 6.94 | 3.38 |
| 13.58 | 6.52 | 7.26 |
| 14.37 | 6.16 | 7.76 |
| 14.87 | 5.96 | 5.54 |
| 15.06 | 5.88 | 7.16 |
| 15.41 | 5.75 | 44.42 |
| 15.78 | 5.62 | 11.20 |
| 16.65 | 5.32 | 4.31 |
| 18.71 | 4.74 | 31.15 |
| 19.70 | 4.51 | 15.61 |
| 20.35 | 4.36 | 11.27 |
| 20.88 | 4.26 | 13.46 |
| 22.16 | 4.01 | 14.64 |
| 22.49 | 3.95 | 10.09 |
| 23.83 | 3.73 | 20.69 |
| 24.73 | 3.60 | 9.74 |
| 25.62 | 3.48 | 60.92 |
| 26.38 | 3.38 | 8.68 |
| 27.11 | 3.29 | 11.10 |
| 28.71 | 3.11 | 10.22 |
| 29.79 | 3.00 | 8.15 |
| 30.65 | 2.92 | 4.71 |
| 31.15 | 2.87 | 6.76 |
| 32.80 | 2.73 | 4.49 |
| 34.52 | 2.60 | 2.50 |
| 35.81 | 2.51 | 0.77 |
| 37.64 | 2.39 | 0.99 |
| 38.77 | 2.32 | 1.44 |
| 41.35 | 2.18 | 1.24 |
| 42.26 | 2.14 | 2.24 |
| 43.70 | 2.07 | 3.25 |
| 44.25 | 2.05 | 2.30 |

6.4.14 400 mg Scale Preparation of Salt I, Salt II, Salt III, Salt IV and Salt V Approximately 400 mg of Compound 1 was placed into 20 mL clear glass vials equipped with stir bars and dissolved with a minimum amount of solvents at 50° C. Methanol was used as the primary solvent to dissolve Compound 1 before addition of counter ion (CI) (0.25 M calcium acetate hydrate/H$_2$O) to generate Salt I. Acetone was used as primary solvent for dissolving Compound 1 before addition of CI to generate Salt II. Prior to CI addition, each solution was polish filtered through a 0.45 μm syringe filter into clean preheated vials. After hot filtration, 5.8 mL of 0.25 M calcium acetate hydrate was added drop-wise. The vials were cooled to ambient temperature at a rate of 20° C./hr and allowed to equilibrate with stirring at ambient temperature overnight with slow cooling. The resulting solids were transferred into a Büchner funnel (with grade 1 Whitman paper) and isolated by filtration. The clear solutions were kept in RT. All obtained solids were analyzed by XRPD to characterize the solid (Table 48)

Approximately 400 mg of Compound 1 was placed into 20 mL clear glass vial equipped with stir bar and dissolved with a minimum amount of solvent at 50° C. Acetonitrile was used as the primary solvent to dissolve Compound 1 before addition of counter ion (CI) (0.5 M potassium hydroxide/$H_2O$) to generate Salt III. Prior to CI addition, the solution was polish filtered through a 0.45 μm syringe filter into a clean preheated vial. After hot filtration, 1.9 mL of 0.5 M potassium hydroxide was added drop-wise. The vial was cooled to ambient temperature at a rate of 20° C./hr and allowed to equilibrate with stirring at ambient temperature overnight with slow cooling. The resulting solid was transferred into a Buchner funnel (with grade 1 Whitman paper) and isolated by filtration. The clear solution was kept in RT. Obtained solid was analyzed by XRPD to characterize the solid (Table 48)

Approximately ~250 to 400 mg of Compound 1 was placed into 20 mL clear glass vials equipped with stir bars and dissolved with a minimum amount of solvents at 50° C. Acetone was used as the primary solvent to dissolve Compound 1 before addition of CI (0.5 M sodium hydroxide/$H_2O$) to generate Salt IV and Salt V. Prior to CI addition, each solution was polish filtered through a 0.45 μm syringe filter into clean preheated vials. After hot filtration, 1.8 mL of 0.5 M sodium hydroxide was added drop-wise to generate Salt IV, and 5.8 mL of 0.5 M sodium hydroxide was added drop-wise to generate Salt V. The vials were cooled to ambient temperature at a rate of 20° C./hr and allowed to equilibrate with stirring at ambient temperature overnight with slow cooling. The resulting solids were transferred into a Buchner funnel (with grade 1 Whitman paper) and isolated by filtration. The clear solutions were kept in RT. All obtained solids were analyzed by XRPD to characterize the solid (Table 48)

Details of the experiments are summarized in Table 48.

TABLE 48

Scale up of Salts I, II, III, IV and V

| Salt | API amnt. (mg) | Primary Solvent | Temp. (° C.) | Primary solvent Vol. (mL) | CI Vol. (mL) | Precipitation/ Isolation | pH of Filtrate | Recovery (mg) | Yield (%, filtration) | XRPD |
|---|---|---|---|---|---|---|---|---|---|---|
| $Ca^{2+}$ | 398.9 | MeOH | 50.0 | 13.3 | 4.8 | PPT formed, Filtration | 6.07 | 407.1 | 91.9 | Salt I |
| $Ca^{2+}$ | 402.3 | Acetone | 50.0 | 23.4 | 5.8 | PPT formed, Filtration | 6.56 | 561.8 | 116.4 | Salt II |
| $K^+$ | 396.7 | MeCN | 50.0 | 27.7 | 1.9 | PPT formed, Filtration | 9.74 | 149 | 32.9 | Salt III |
| $K^+$ | 320.4 | MeCN | 50.0 | 22.7 | 2.3 | PPT formed, Filtration | 7.50 | 273.4 | 74.8 | Salt III + H |
| $Na^+$ | 251.2 | Acetone | 50.0 | 18.4 | 1.8 | PPT formed, Filtration | 8.54 | 241.4 | 80.1 | Salt IV |
| $Na^+$ | 405.3 | Acetone | 50.0 | 23.5 | 5.8 | PPT formed, Filtration | 9.24 | 400.5 | 82.3 | Salt V |

*Cooling method - Slow Cooling (20° C./hr)

Table 49 provides thermal stability data. Table 50 provides TGA thermal data. Table 51 provides stability of crystalline materials from selected salts in different humidity.

TABLE 49

Thermal Stability Experiments

| Parent Material | Weight (mg) | Temp (° C.) | Aliquot time point Day | XRPD | Aliquot time point Day | XRPD | Parent Material HPLC (% AUC) | HPLC (% AUC) |
|---|---|---|---|---|---|---|---|---|
| Filtration, Salt I | 42.4 | 60.0 | 1 | Salt I | 7 | Salt I | N/A* | N/A* |
| Filtration, Salt II | 47.2 | 60.0 | 1 | Salt II | 7 | Salt II | 99.9 | 99.9 |
| Filtration, Salt III | 35.6 | 60.0 | 1 | Salt III | 7 | Salt III | 99.9 | 99.9 |

TABLE 49-continued

Thermal Stability Experiments

| Parent Material | Weight (mg) | Temp (° C.) | Aliquot time point Day | XRPD | Aliquot time point Day | XRPD | Parent Material HPLC (% AUC) | HPLC (% AUC) |
|---|---|---|---|---|---|---|---|---|
| Filtration, Salt IV | 37.8 | 60.0 | 1 | Salt IV | 7 | Salt IV | 99.9 | 99.9 |
| Filtration, Salt V | 3.6.4 | 60.0 | 1 | Salt V | 7 | Salt V | 99.9 | 99.9 |

*Materials poorly dissolved in $D_2O$, DMSO, or diluent for HPLC analysis. No degradation of the materials (before and after thermal stress analysis) based on $^1H$ NMR.

TABLE 50

TGA thermal hold experiments of crystalline materials from selected salts

| Parent Material | Weight (mg) | Thermal Hold Temperature range, ° C. | Holding Temp./time | XRPD Pre-thermal hold | Post thermal hold | Post thermal hold, sample left on bench top, 24 hrs* |
|---|---|---|---|---|---|---|
| Filtration, Salt IV | 6.184 | 30-130, at 10° C./min | 130° C./ 2 min | Salt IV | Salt IV | Salt IV |
| Filtration, Salt IV | 4.957 | 180-260, at 10° C./min | 260° C./ 2 min | Salt IV | Salt VI | Salt VI |
| Filtration, Salt V | 8.84 | 30-160, at 10° C./min | 160° C./ 2 min | Salt V | Salt V + missing peaks | Salt V + missing peaks |
| Filtration, Salt III | 8.208 | 30-130, at 10° C./min | 130° C./ 2 min | Salt III + Salt IX | Salt III | Salt III |

TABLE 51

Stability of Crystalline materials from selected salts in different humidity.

| Parent Material | Weight (mg) | Humidity condition | XRPD Initial | Post humidity exposure |
|---|---|---|---|---|
| Filtration, Salt V | 4.35 | 0% RH, RT | Salt V | Salt V + missing peaks |
| Filtration, Salt V | 7.12 | 65% RH, RT | Salt V | Salt V |
| Filtration, Salt IV | 11.5 | 65% RH, RT | Salt IV | Salt IV + missing peaks |
| Filtration, Salt III | 19.23 | 65% RH, RT | Salt III + Salt IX | Salt III + Salt IX |

6.5 Synthesis of Compound 1

6.5.1 Preparation of 5-(3-fluorophenyl)-3-chloro-2-cyanopyridine (4)

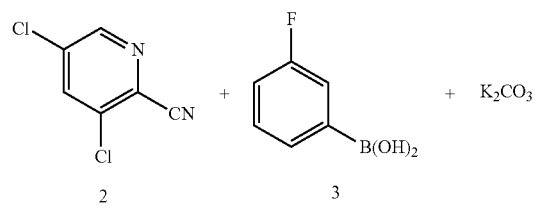

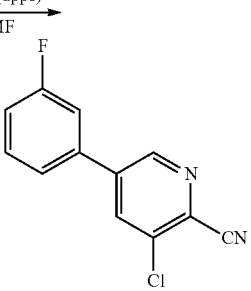

Potassium carbonate (1785 g, 1.49 eq), 3,5-dichloro-2-cyanopyridine (1500 g, 1.0 eq), (3-fluorophenyl)boronic acid (1069.5 g, 1.0 eq), dichloro[1,1'-bis(diphenylphosphino) ferrocene]palladium (II) (DCM adduct $PdCl_2$(dppf)) (30 g, 0.004 eq) and dimethylformamide (10.6 kg) were charged to a 30 L reactor equipped with an over-head agitator, condenser, thermocouple and nitrogen sparger. The mixture was agitated and sparged with nitrogen gas through the dip-tube for ca. 30 minutes. Degassed water (969 g) was slowly charged to the mixture while maintaining a temperature of less than 45° C.

The reaction mixture was agitated at 20 to 45° C. and sparged with nitrogen gas through the dip-tube for 30 minutes, followed by agitation at 50° C. (between 47 to 53° C.) for 12 to 24 hours until the reaction was determined to be complete due to the disappearance of compound 2 as measured by HPLC.

The reaction mixture was cooled to 22° C. (between 19 to 25° C.). n-Heptane (2.2 kg) and water (12.9 kg) were charged to the reaction mixture while keeping the temperature at no more than 45° C. After the mixture was agitated at 22° C. (between 19 to 25° C.) for 1 to 2 hours, crude 5-(3-fluorophenyl)-3-chloro-2-cyanopyridine (4) was isolated as a solid by filtration.

The crude 5-(3-fluorophenyl)-3-chloro-2-cyanopyridine (4) was transferred into an empty reactor with water (12.9 kg). The mixture was agitated at 22° C. (between 19 to 25° C.) for 2 hours. Crude 5-(3-fluorophenyl)-3-chloro-2-cyanopyridine (4) was isolated as a solid by filtration and washed with water (3 kg).

The crude 5-(3-fluorophenyl)-3-chloro-2-cyanopyridine (4) was transferred into an empty reactor with 2-propanol (14.25 kg). The mixture was agitated at reflux at 82° C. for 1 to 2 hours. After cooling to 22° C. (19 to 25° C.), the mixture was agitated at 22° C. (19 to 25° C.) for 2 to 3 hours. 5-(3-fluorophenyl)-3-chloro-2-cyanopyridine (4) was isolated as a solid by filtration and rinsed with 2-propanol (2.36 kg).

Figure 77:
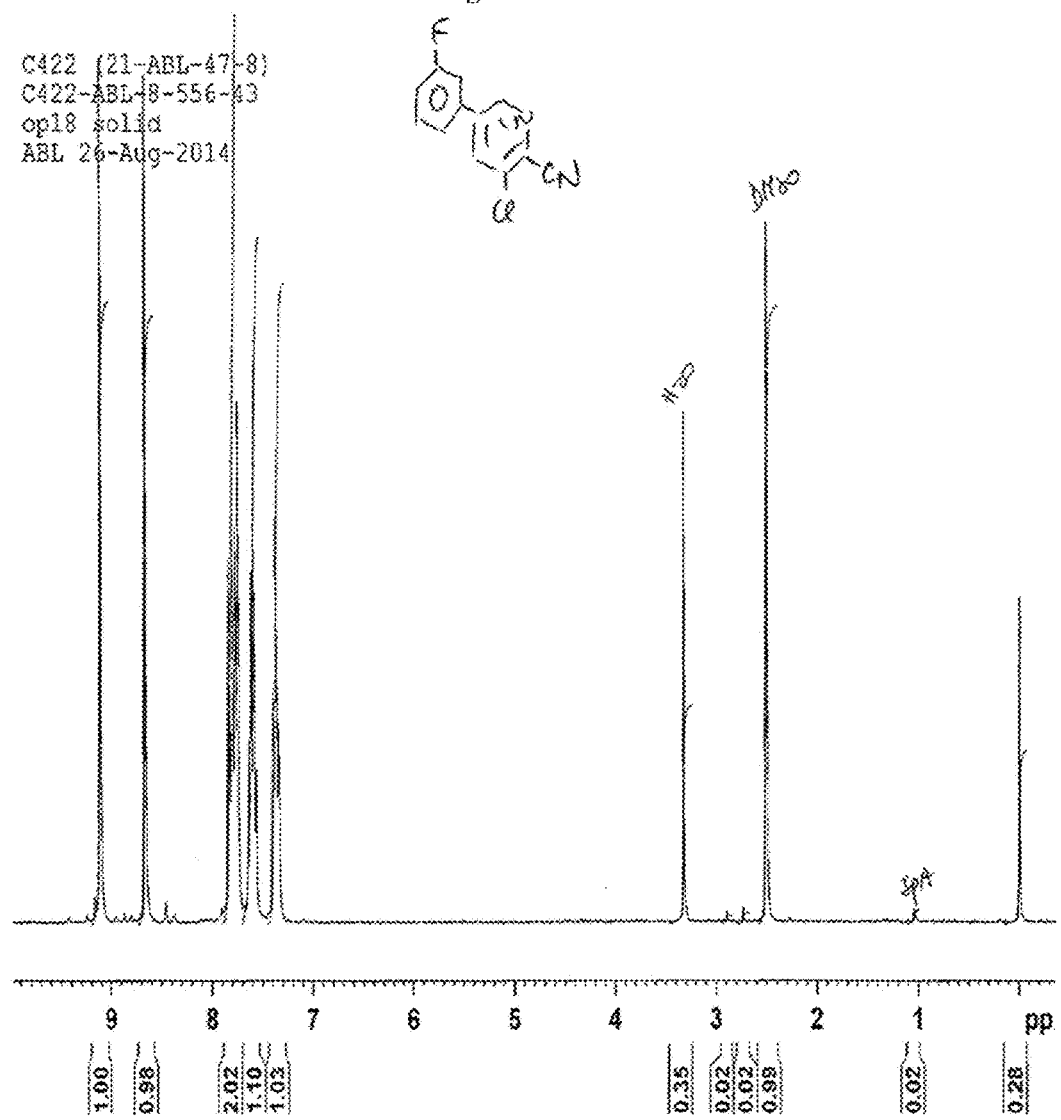
FIG. 77 depicts a ¹H NMR spectrum of 5-(3-fluorophenyl)-3-chloro-2-cyanopyridine.

After being dried under vacuum at 50° C. until the water content was less than 1.5% (~16 hours), 1736.9 g 5-(3-fluorophenyl)-3-chloro-2-cyanopyridine (4) was obtained as a brown solid (yield 86%). FIG. 77 depicts the $^1$H NMR spectrum of 5-(3-fluorophenyl)-3-chloro-2-cyanopyridine (4).

6.5.2 Preparation of 5-(3-fluorophenyl)-3-methoxy-2-cyanopyridine (5)

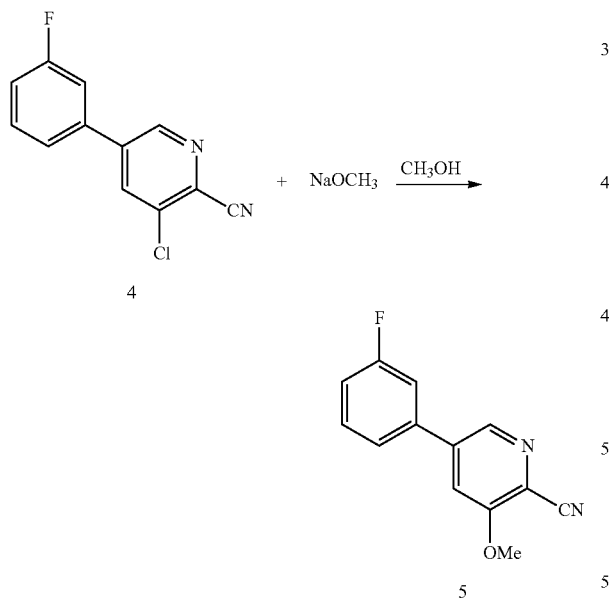

5-(3-fluorophenyl)-3-chloro-2-cyanopyridine (1.2 kg, 1.0 eq) and methanol (17.8 kg) were charged to a 30 L reactor equipped with an over-head agitator, condenser, thermocouple and nitrogen bubbler. 25% sodium methoxide in methanol (2.01 kg, 1.8 eq) was charged to the reactor and rinsed with methanol (1.2 kg). The reaction mixture was agitated at reflux (ca. 68° C.) for 12 to 24 hours until the reaction was determined to be complete.

The reaction mixture was distilled under vacuum to a volume of ca. 12 L with a maximum bath/jacket temperature of 50° C. After the mixture was cooled to 22° C. (19 to 25° C.), water (12 kg) was charged. After the mixture was agitated at 22° C. (19 to 25° C.) for 1 to 2 hours, crude 5-(3-fluorophenyl)-3-methoxy-2-cyanopyridine (5) was isolated as a solid by filtration. The filter cake was washed with methanol (0.95 kg) and pulled dry until no filtrate was observed.

The crude 5-(3-fluorophenyl)-3-methoxy-2-cyanopyridine (5) was transferred into an empty reactor with acetone (19.2 kg) and agitated at 22° C. (between 19 to 25° C.) until all solids dissolved (~1 hour).

A celite pad (ca. 1") was packed in a 3 L glass Buchner funnel and wetted with acetone. Activated carbon Darco G-60 (0.24 kg) was packed on the top of the celite pad. A second celite pad (ca 1") was packed on the top of the carbon and wetted with acetone. The acetone solution was filtered through the carbon/celite pad and rinsed with acetone (4.8 kg).

The acetone solution was distilled under vacuum (bath temperature of 50° C.) to a volume of 4.8 L. Methanol (3.6 kg) was charged and the suspension and concentrated to 4.8 L. The acetone chasing was repeated twice. The slurry was agitated at 22° C. (19 to 25° C.) for 2 to 3 hours, 5-(3-fluorophenyl)-3-methoxy-2-cyanopyridine (5), filtered and washed with methanol (2.4 kg).

Figure 78:
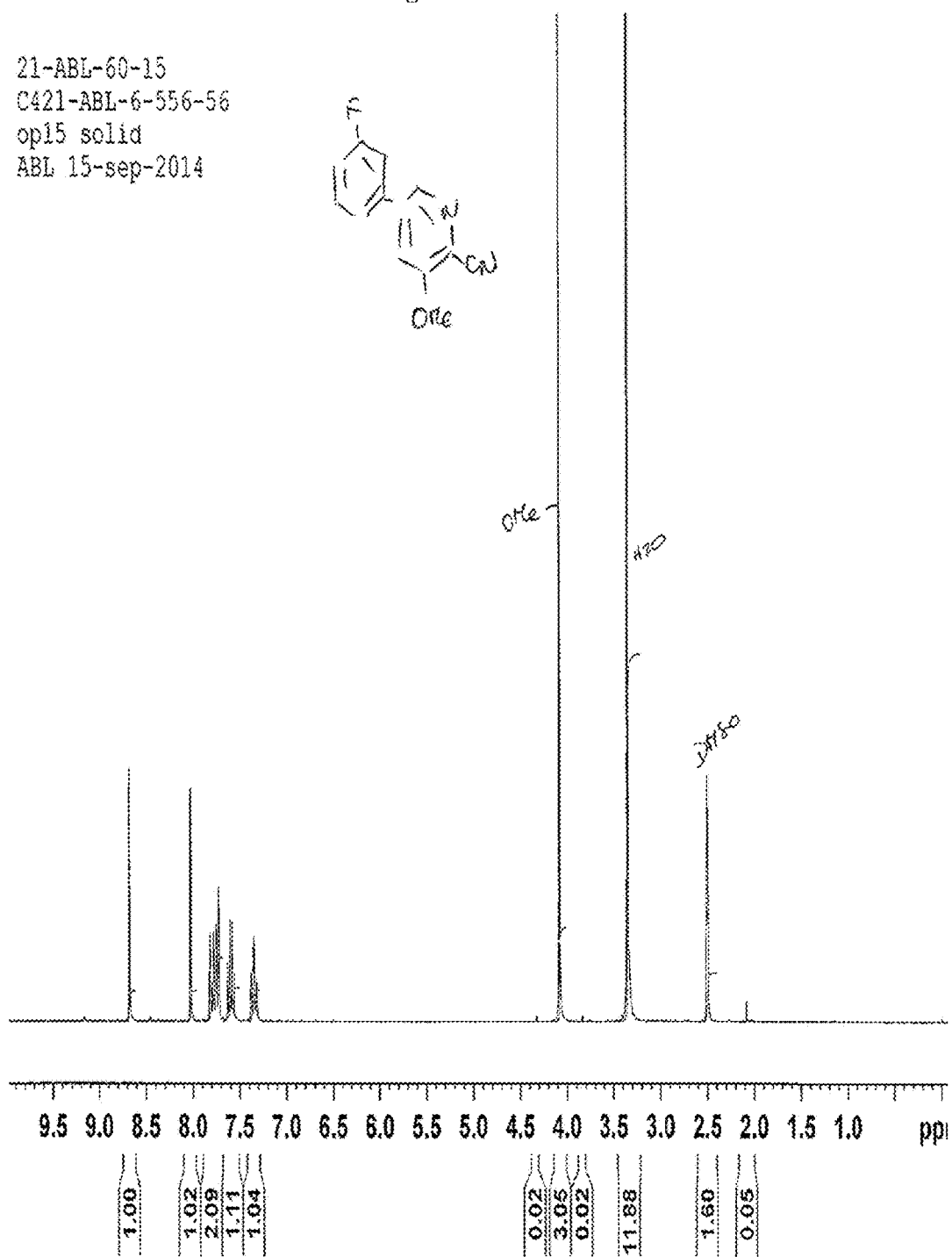
FIG. 78 depicts a ¹H NMR spectrum of 5-(3-fluorophenyl)-3-methoxy-2-cyanopyridine.

The isolated 5-(3-fluorophenyl)-3-methoxy-2-cyanopyridine (5) was dried under vacuum at 45° C. to give 992.3 g 5-(3-fluorophenyl)-3-methoxy-2-cyanopyridine (5) in 84% yield. FIG. 78 depicts the $^1$H NMR spectrum of 5-(3-fluorophenyl)-3-methoxy-2-cyanopyridine (5).

6.5.3 Preparation of 5-(3-fluorophenyl)-3-hydroxypyridine-2-carboxylic acid (6)

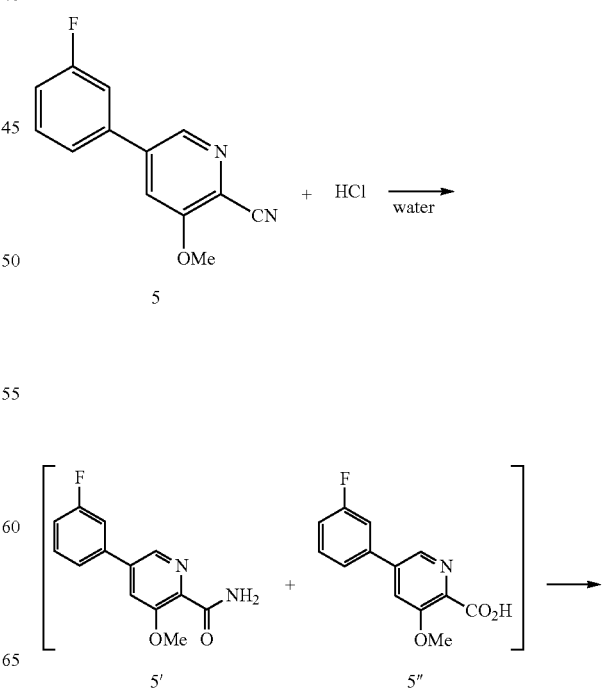

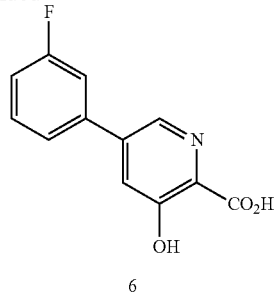

6

5-(3-fluorophenyl)-3-methoxy-2-cyanopyridine (1.35 kg, 1.0 eq) and 37% aqueous HCl (9.72 kg) were charged to a 30 L reactor with condenser, agitator, nitrogen line and scrubber containing ca. 20% aqueous sodium hydroxide. The reaction mixture was heated gradually to 70° C. (67 to 73° C.) over 2 hours.

Figure 81:
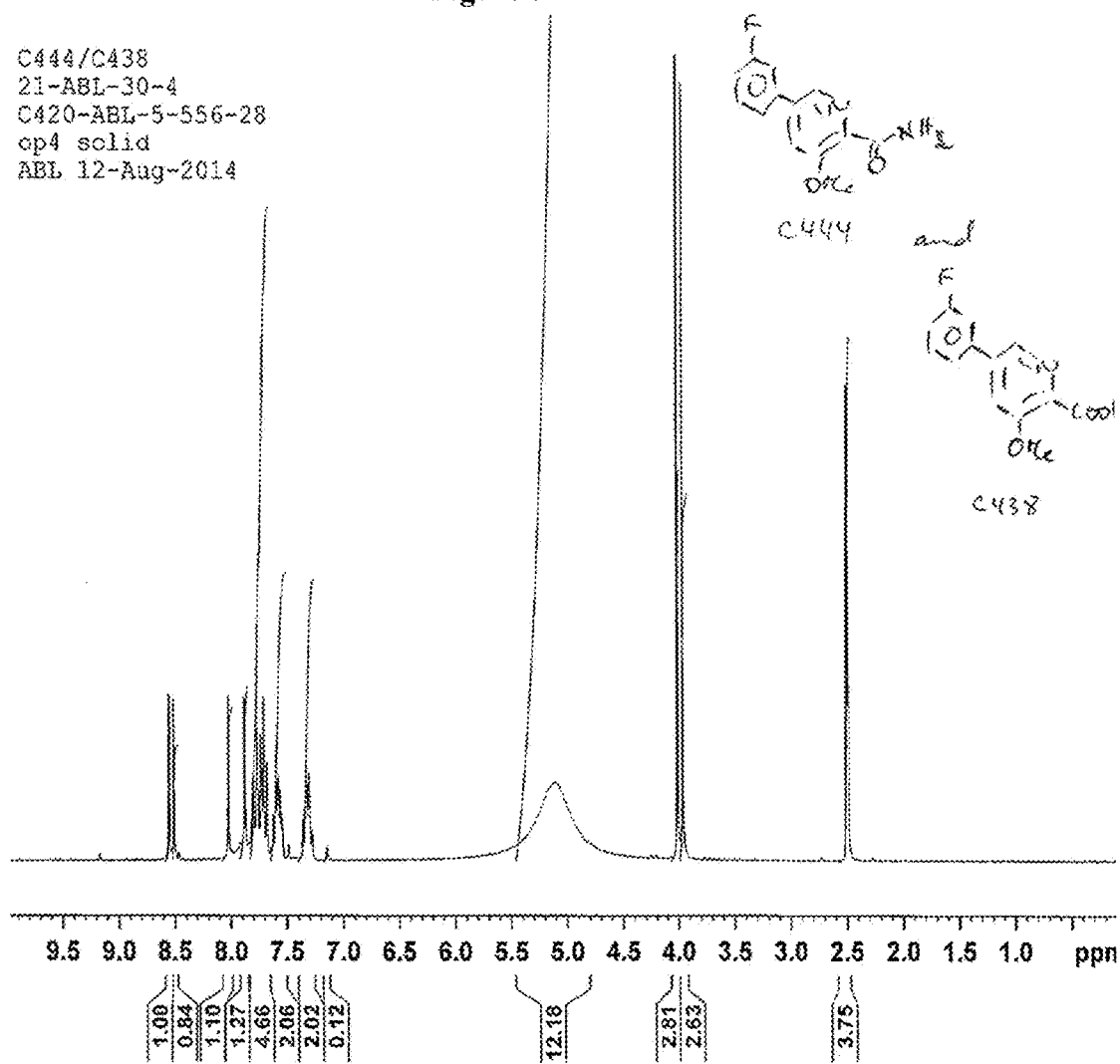
FIG. 81 depicts a ¹H NMR spectrum of a mixture of 5-(3-fluorophenyl)-3-methoxypicolinamide and 5-(3-fluorophenyl)-3-methoxypicolinic acid.

After the mixture was agitated at 70° C. (67 to 73° C.) for 3 hours, water (8.1 kg) was charged. The reaction mixture was heated to reflux (108 to 110° C.) and agitated until the reaction was determined to be complete when the total AUC of 5-(3-fluorophenyl)-3-methoxy-2-cyanopyridine 5, 5-(3-fluorophenyl)-3-methoxypicolinamide (5') (See $^1$H NMR in FIG. 81) and 5-(3-fluorophenyl)-3-methoxypicolinic acid (5") (See $^1$H NMR in FIG. 81) was less than 1% as measured by HPLC (16 to 48 hr expected).

An alternative procedure after the water is charged comprises of: a) refluxing for ca. 16 hours; b) charging additional concentrated HCl (1.62 kg) to the reaction mixture; c) refluxing for 6 hours; d) charging another portion of concentrated HCl (1.62 kg) to the reaction mixture; and e) refluxing for 12 hours; and f) proceeding to HPLC analysis.

After the reaction mixture was cooled to 22° C. (19° C. to 25° C., water (4.05 kg), was charged and the reaction mixture agitated at 22° C. (19° C. to 25° C.) for ca. 3 to 4 hours. The solids were isolated by filtration, rinsed with water (6.75 kg) and dried.

The solid was transferred into a reactor with acetone (11.75 kg) and agitated at reflux (ca 58° C.) for 2 hours. The mixture was cooled to 22° C. (19° C. to 25° C.) and agitated at 22° C. for 2 hours. The solid was isolated by filtration and rinsed with water (2.13 kg).

Figure 79:
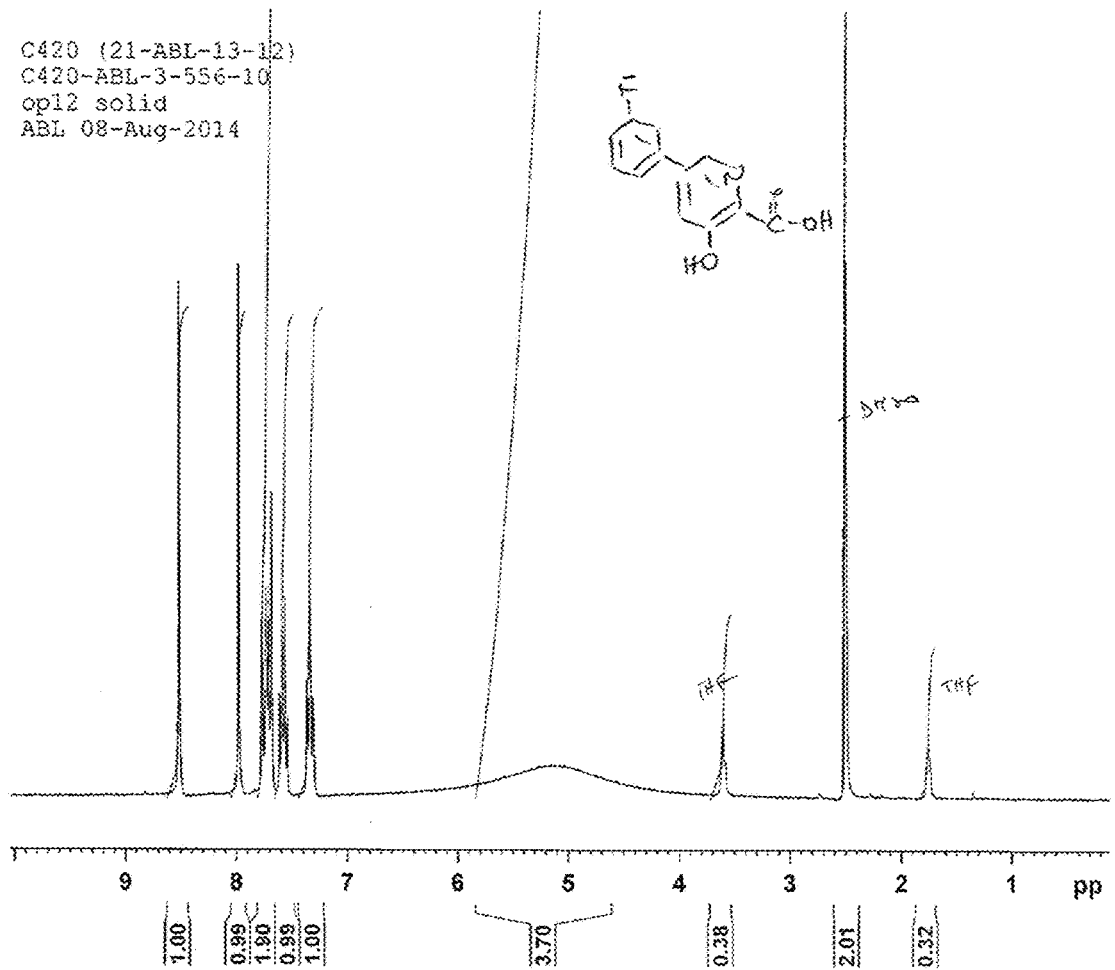
FIG. 79 depicts a ¹H NMR spectrum of 5-(3-fluorophenyl)-3-hydroxypyridine-2-carboxylic acid.

The solid was dried under vacuum at 45 to 50° C. until the water content was less than 0.5% wt. 1200.3 g of 5-(3-fluorophenyl)-3-hydroxypyridine-2-carboxylic acid (6) was obtained as an off-white solid in 84% yield. FIG. 79 depicts the $^1$H NMR spectrum of 5-(3-fluorophenyl)-3-hydroxypyridine-2-carboxylic acid (6).

6.5.4 Preparation of N-carboxymethyl-5-(3-fluorophenyl)-3-hydroxypyridine-2-carboxamide (1)

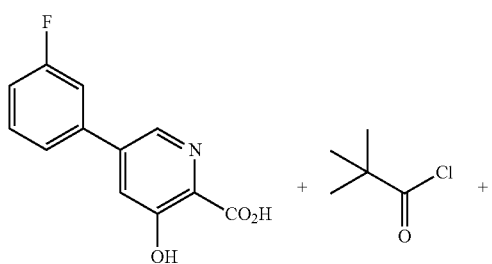

6

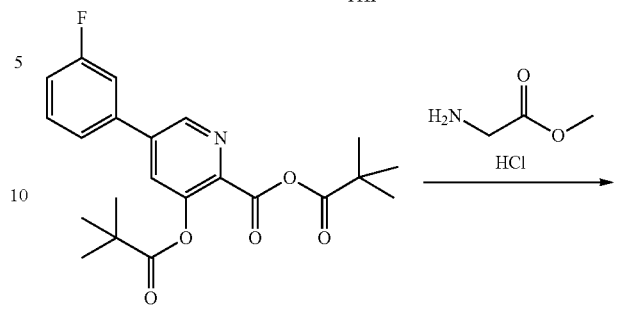

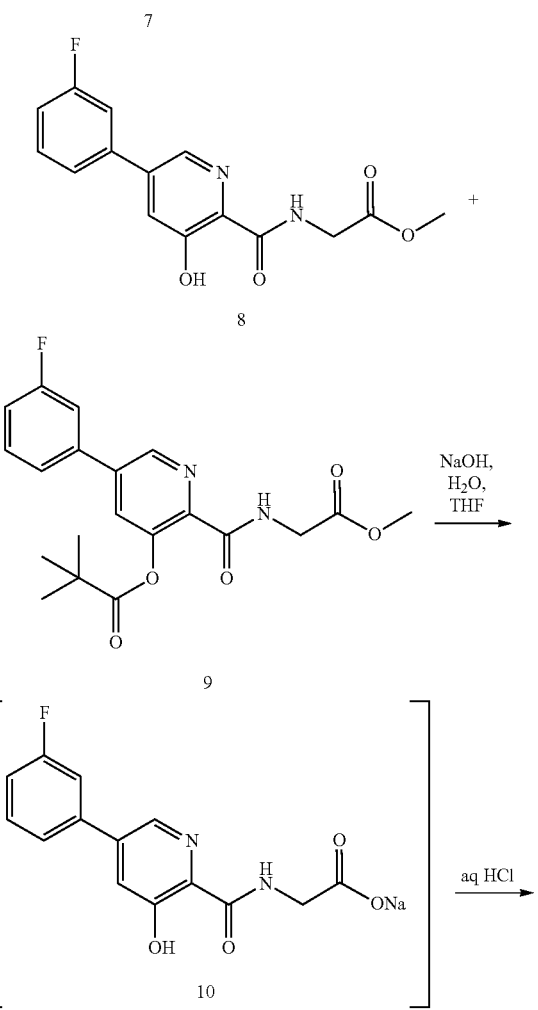

5-(3-fluorophenyl)-3-hydroxypyridine-2-carboxylic acid (1.8 kg), THF (7.2 kg) and N,N-diisopropylethylamine (2.2 kg) were charged to a 30 L reactor with stirrer, addition funnel, condenser, and nitrogen bubbler. The mixture was cooled to 3° C. (0 to 6° C.).

Trimethylacetyl chloride (2.05 kg, 2.2 eq) was added via an addition funnel to the reaction mixture while keeping the temperature around 3° C. (0 to 6° C.). The reaction mixture was agitated at 3° C. (0 to 6° C.) until the reaction was determined to be complete by HPLC (1 to 3 hours).

Glycine methyl ester HCl salt (1.21 kg, 1.25 eq.) was added to the reaction mixture followed by N,N-diisopropylethylamine (1.31 kg, 1.30 eq.) while keeping the temperature below 22° C.

The reaction mixture was agitated at 22° C. (19 to 25° C.) until deemed complete by HPLC (4 to 12 hours expected).

Figure 82:
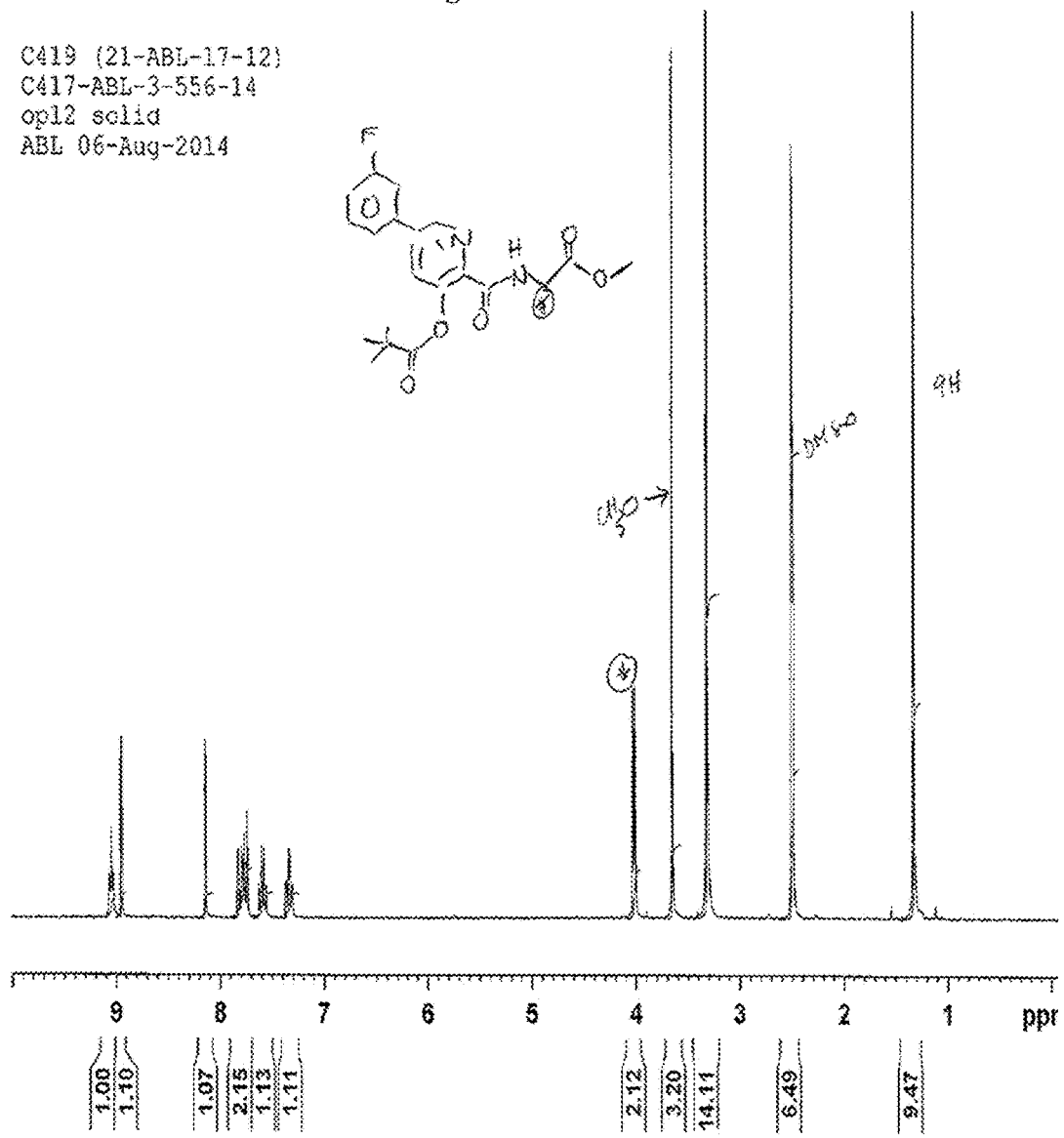
FIG. 82 depicts a ¹H NMR spectrum of 5-(3-fluorophenyl)-2-(2-methoxy-2-oxoethylcarbamoyl)pyridin-3-yl pivalate.
Figure 83:
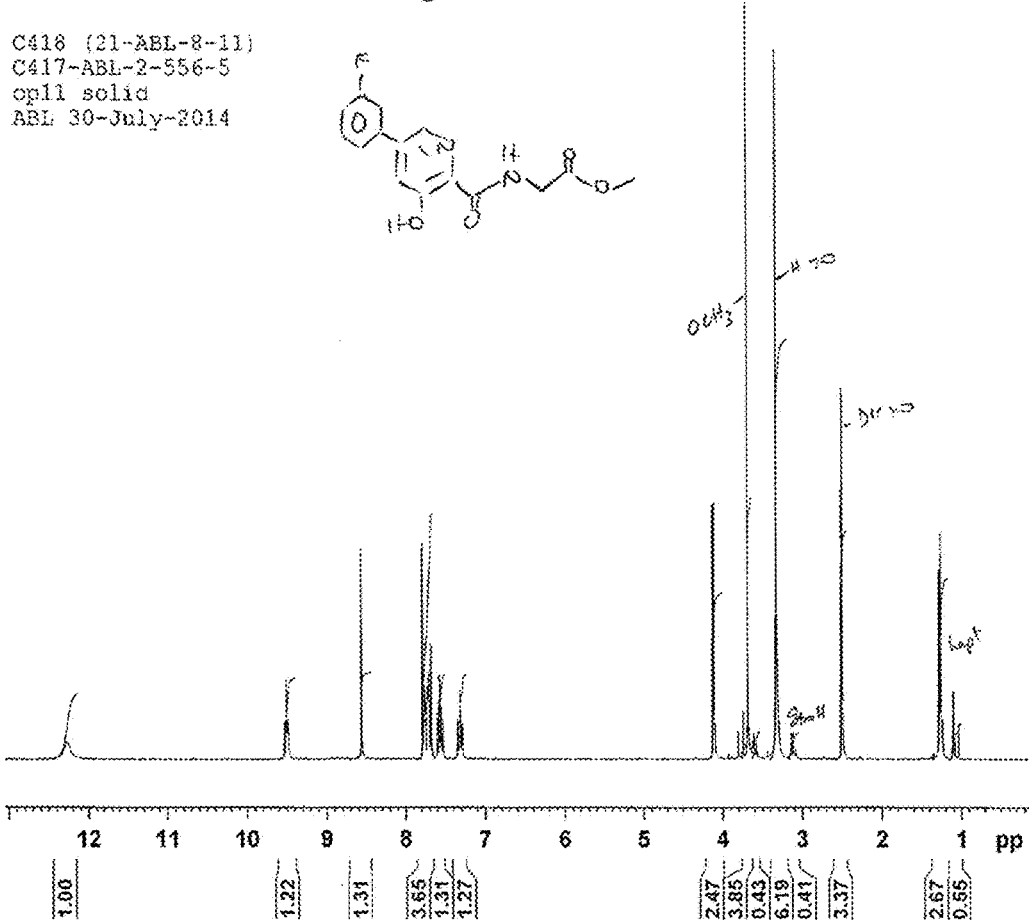
FIG. 83 depicts a ¹H NMR spectrum of 2-(5-(3-fluorophenyl)-3-hydroxypicolinamido)acetate.

Ethanol (4.32 kg) was added and the reaction mixture and agitated for 15 to 30 minutes. The reaction mixture was distilled under reduce pressure at a maximum temperature of 45° C. to ca. 5 volumes. The solvent switch was repeated twice Ethanol (4.32 kg) and water (9.0 kg) were added to the reaction mixture and agitated at 22° C. (19 to 25° C.) for 3 hours. The solid was isolated by filtration, rinsed with a mixture of water (1.8 kg) and ethanol (1.42 kg), followed by rinsing with water (1.8 kg). The solid was dried on the filter for ca. 2 hours. The resulting solid was white to off-white and contained 3 to 5% of methyl 2-(5-(3-fluorophenyl)-3-hydroxypicolinamido)acetate (8) (See $^1$H NMR in FIG. 83) and 94 to 97% 5-(3-fluorophenyl)-2-(2-methoxy-2-oxoethylcarbamoyl)pyridin-3-yl pivalate (9) (See $^1$H NMR in FIG. 82).

The methyl 2-(5-(3-fluorophenyl)-3-hydroxypicolinamido)acetate (8) and 5-(3-fluorophenyl)-2-(2-methoxy-2-oxoethylcarbamoyl)pyridin-3-yl pivalate (9) mixture, and THF (11.16 kg) were charged to a 30 L reactor with stirrer, addition funnel, thermocouple and nitrogen line. The mixture was agitated at 22° C. (19 to 25° C.) until all solids dissolved, followed by the addition of water (9.0 kg). A solution of 50% NaOH (1.85 kg) in water (1.8 kg) was added to the reaction mixture while keeping the temperature around 3° C. (0 to 5° C.). The reaction mixture was warmed to 22° C. (19 to 25° C.) and agitated until the reaction was deemed to be complete.

The reaction mixture was adjusted to ~pH 2, by adding concentrated HCl (ca. 2.36 kg, 3.1 eq.) while keeping the temperature below 25° C. The reaction mixture was agitated at 22° C. (19 to 25° C.) for ca. 30 minutes to 1 hour. The organic phase was separated and filtered through a one μm filter.

The solution was distilled under reduced pressure at not more than 45° C. to ca. 3 volumes. Acetone (5.65 kg) was charged, followed by distillation under vacuum to ca. 3 volumes. After the solvent chase was twice repeated, water (10.8 kg) was charged to the slurry, followed by agitation at 22° C. (19 to 25° C.) for at least 2 hours. The solid was isolated by filtration, washed with a mixture of acetone (1.42 kg) and water (1.8 kg).

Figure 80:
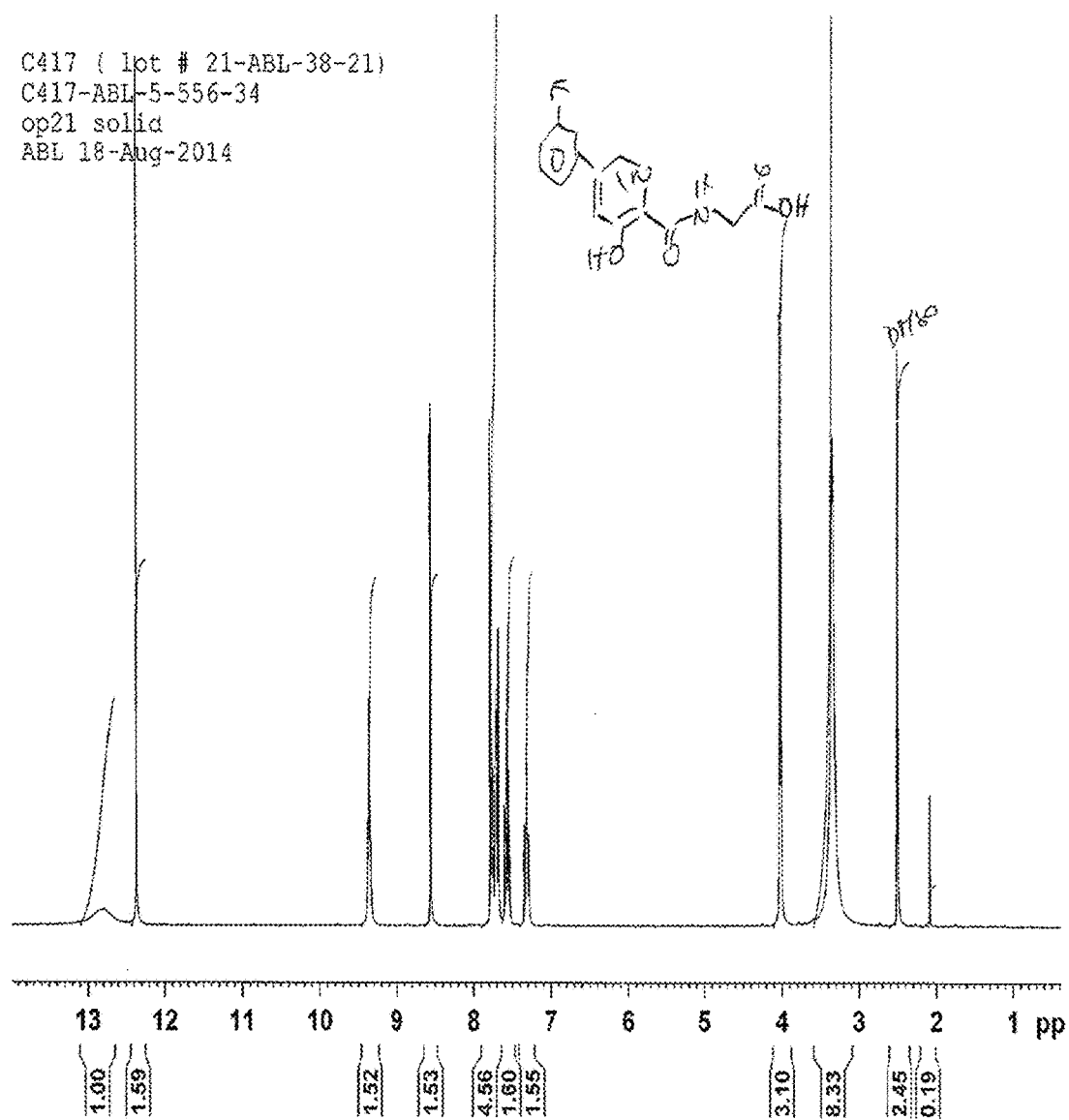
FIG. 80 depicts a ¹H NMR spectrum of N-carboxymethyl-5-(3-fluorophenyl)-3-hydroxypyridine-2-carboxamide.

The solid was dried under vacuum at 50° C. to give 1818.4 g N-carboxymethyl-5-(3-fluorophenyl)-3-hydroxypyridine-2-carboxamide (1) as a white to off white solid in 81% yield. FIG. 80 depicts the $^1$H NMR spectrum of N-carboxymethyl-5-(3-fluorophenyl)-3-hydroxypyridine-2-carboxamide (1).

What is claimed is:

1. A crystal form of Compound 1, or a tautomer thereof:

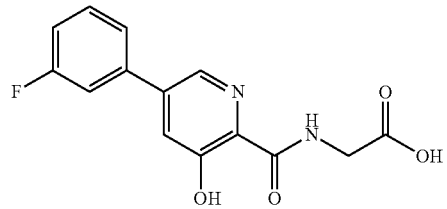

I which is Form A, and which has an X-ray powder diffraction pattern comprising peaks at approximately 12.1, 23.0 and 26.9° 2θ.

2. The crystal form of claim 1 which has a thermogravimetric analysis thermogram comprising no mass loss of the crystal form before about 155° C. when heated from about 25° C. to about 300° C.

3. The crystal form of claim 1 which has a differential scanning calorimetry thermogram comprising an endotherm event with a maximum at approximately 186° C. when heated from about 25° C. to about 300° C.

4. The crystal form of claim 1 which is anhydrous.

5. A pharmaceutical composition comprising the crystal form of claim 1.

6. The crystal form of claim 1, wherein the X-ray powder diffraction pattern further comprises peaks at approximately 13.1, 14.5, 16.6, 19.6, and 20.1° 2θ.

7. The crystal form of claim 6 which has a thermogravimetric analysis thermogram comprising no mass loss of the crystal form before about 155° C. when heated from about 25° C. to about 300° C.

8. The crystal form of claim 6 which has a differential scanning calorimetry thermogram comprising an endotherm event with a maximum at approximately 186° C. when heated from about 25° C. to about 300° C.

9. The crystal form of claim 6 which is anhydrous.

10. A pharmaceutical composition comprising the crystal form of claim 6.

11. A crystal form comprising Compound 1, or a tautomer thereof:

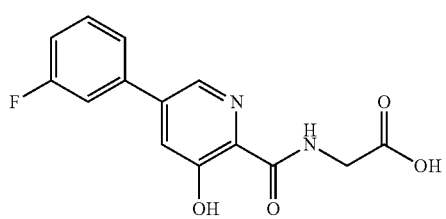

1 which Form B, and which has an X-ray powder diffraction pattern comprising peaks at approximately 4.3, 8.6, 15.5, and 25.3° 2θ.

12. A crystal form comprising Compound 1, or a tautomer thereof:

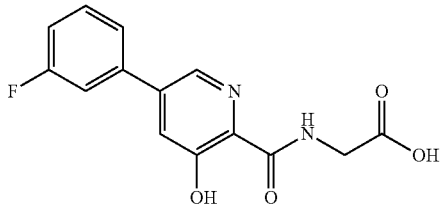

which is Form C, and which has an X-ray powder diffraction pattern comprising peaks at approximately 4.4, 8.6, 11.4 and 15.6° 2θ.

13. A crystal form comprising Compound 1, or a tautomer thereof:

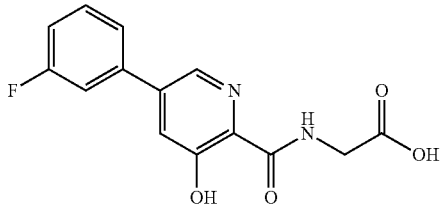

which is Form D and which has an X-ray powder diffraction pattern comprising peaks at approximately 4.3, 7.4, 8.6 and 15.5° 2θ.

14. A crystal form comprising Compound 1, or a tautomer thereof:

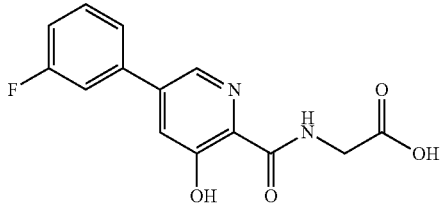

which is Form E, and which has an X-ray powder diffraction pattern comprising peaks at approximately 4.3, 8.6, 15.5 and 27.9° 2θ.

15. A crystal form comprising Compound 1, or a tautomer thereof:

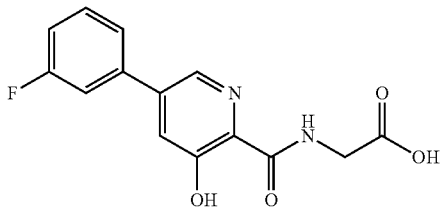

which is Form F and which has an X-ray powder diffraction pattern comprising peaks at approximately 4.0, 4.2 and 15.2° 2θ.

16. A crystal form comprising Compound 1, or a tautomer thereof:

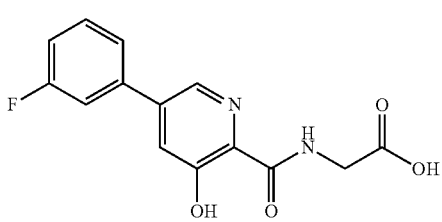

which is Form H, and which has an X-ray powder diffraction pattern comprising peaks at approximately 4.2, 8.3, 15.2 and 20.9° 2θ.

17. A crystal form comprising Compound 1, or a tautomer thereof:

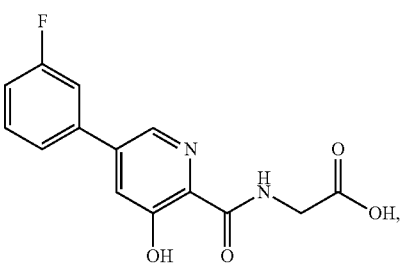

which Form H, and which has an X-ray powder diffraction pattern comprising peaks at approximately 14.1, 18.8 and 21.4° 2θ.

* * * * *